United States Patent
Hoffman et al.

(10) Patent No.: US 11,685,719 B2
(45) Date of Patent: Jun. 27, 2023

(54) PYRIDINONE MK2 INHIBITORS AND USES THEREOF

(71) Applicant: Xinthera, Inc., San Diego, CA (US)

(72) Inventors: Robert L. Hoffman, San Diego, CA (US); Lynnie Trzoss, San Diego, CA (US); Qing Dong, San Diego, CA (US); Stephen W. Kaldor, San Diego, CA (US)

(73) Assignee: XINTHERA, INC., San Diego, CA (US)

( * ) Notice: Subject to any disclaimer, the term of this patent is extended or adjusted under 35 U.S.C. 154(b) by 0 days.

(21) Appl. No.: 17/859,496

(22) Filed: Jul. 7, 2022

(65) Prior Publication Data

US 2023/0053465 A1 Feb. 23, 2023

Related U.S. Application Data

(60) Provisional application No. 63/340,079, filed on May 10, 2022, provisional application No. 63/220,322, filed on Jul. 9, 2021.

(51) Int. Cl.
| | | |
|---|---|---|
| *C07D 213/69* | (2006.01) | |
| *C07D 401/14* | (2006.01) | |
| *C07D 405/14* | (2006.01) | |

(52) U.S. Cl.
CPC ......... *C07D 213/69* (2013.01); *C07D 401/14* (2013.01); *C07D 405/14* (2013.01); *C07B 2200/05* (2013.01)

(58) Field of Classification Search
CPC ... C07D 213/69; C07D 401/14; C07D 405/14
USPC ....................................................... 514/256
See application file for complete search history.

(56) References Cited

U.S. PATENT DOCUMENTS

| | | | |
|---|---|---|---|
| 9,056,110 | B2 | 6/2015 | Selness et al. |
| 9,115,089 | B2 | 8/2015 | Hockerman et al. |
| 9,359,300 | B2 | 6/2016 | Selness et al. |
| 9,365,546 | B2 | 6/2016 | Selness et al. |
| 9,365,547 | B2 | 6/2016 | Selness et al. |
| 9,636,333 | B2 | 5/2017 | Hockerman et al. |
| 2007/0167621 | A1 | 7/2007 | Durley |
| 2012/0142709 | A1 | 6/2012 | Selness et al. |
| 2013/0143906 | A1 | 6/2013 | Selness et al. |
| 2022/0235025 | A1 | 7/2022 | DeCrescenzo et al. |
| 2022/0402892 | A1 | 12/2022 | Trzoss et al. |

FOREIGN PATENT DOCUMENTS

| | | |
|---|---|---|
| CN | 115636814 A | 1/2023 |
| WO | WO-03068230 A1 | 8/2003 |
| WO | WO-2004087677 A2 | 10/2004 |
| WO | WO-2005018557 A2 | 3/2005 |
| WO | WO-2007091176 A1 | 8/2007 |
| WO | WO-2008153942 A1 | 12/2008 |
| WO | WO-2010141538 A1 | 12/2010 |
| WO | WO-2012078684 A1 | 6/2012 |
| WO | WO-2013105676 A1 | 7/2013 |
| WO | WO-2014197846 A1 | 12/2014 |
| WO | WO-2021022186 A1 | 2/2021 |
| WO | WO-2022081573 A1 | 4/2022 |
| WO | WO-2022212489 A1 | 10/2022 |
| WO | WO-2023283338 A1 | 1/2023 |
| WO | WO-2023016535 A1 * | 2/2023 |

OTHER PUBLICATIONS

Co-pending U.S. Appl. No. 17/868,567, inventors Trzoss; Lynnie et al., filed Jul. 19, 2022.
PCT/US2022/036362 International Search Report and Written Opinion dated Sep. 20, 2022.
Masood et al., Lead Diversification 2: Application to P38, gMTP and lead compounds. Bioorg Med Chem Lett 22:1255-1262 (2012).
PCT/US2022/022525 International Search Report and Written Opinion dated Jul. 1, 2022.
Selness et al., Design, synthesis and activity of a potent, selective series of N-aryl pyridinone inhibitors of p38 kinase. Bioorg Med Chem Lett 21:4059-4065 (2011).
Selness et al., Discovery of PH-797804, a highly selective and potent inhibitor of p38 MAP kinase. Bioorg Med Chem Lett 21:4066-4071 (2011).
U.S. Appl. No. 63/139,533, filed Jan. 20, 2021 as filed with Filing Receipt.
U.S. Appl. No. 17/533,931 Granted Petition to Accept Unitentially Delayed Claim Under 35 U.S.C. 119(e) dated Mar. 20, 2023.
U.S. Appl. No. 17/868,567 3rd Party Submission dated Apr. 3, 2023.

* cited by examiner

*Primary Examiner* — Kahsay Habte
(74) *Attorney, Agent, or Firm* — Wilson Sonsini Goodrich & Rosati

(57) ABSTRACT

Described herein are MK2 inhibitors and pharmaceutical compositions comprising said inhibitors. The subject compounds and compositions are useful for the treatment of autoimmune disorders, chronic inflammatory disorders, acute inflammatory disorders, auto-inflammatory disorders, fibrotic disorders, metabolic disorders, neoplastic disorders, and cardiovascular or cerebrovascular disorders.

30 Claims, No Drawings

PYRIDINONE MK2 INHIBITORS AND USES THEREOF

CROSS-REFERENCE

This application claims the benefit of U.S. Provisional Application Ser. No. 63/220,322 filed Jul. 9, 2021 and U.S. Provisional Application Ser. No. 63/340,079 filed May 10, 2022, which are hereby incorporated by reference in their entirety.

BACKGROUND OF THE INVENTION

Mitogen-activated protein kinases (MAPK) are a conserved family of enzymes that relay and propagate external stimuli, using phosphorylation cascades to generate a coordinated cellular response to the environment. The MAPK are proline-directed serine/threonine-specific protein kinases that regulate cellular activities, such as gene expression, mitosis, differentiation, and cell survival/apoptosis. To date, four distinct classes of mammalian MAPK have been identified: the extracellular signaling kinases (ERK1 and 2), the c-jun N-terminal kinase-1 (JNK1-3), the p38 MAPK (p38α, β, γ, and δ), and ERK5. The MAPK are activated by the dual phosphorylation of Thr and Tyr residues within a TXY activation motif by coordinated dual-specificity MAPKK, where X is Glu, Pro, and Gly in ERK, JNK, and p38 MAPK, respectively. MAPK are 60-70% identical to each other, yet differ in their activation loop sequences and sizes. The activation loop is adjacent to the enzyme-active site, and its phosphorylation allows the enzyme to reposition active-site residues into the optimal orientation for substrate binding and catalysis. Downstream substrates of MAPK include mitogen-activated protein-kinase-activated protein (MAPKAP) kinases and transcription factors, the phosphorylation of which, either directly or indirectly, regulates gene expression at several points, including transcription, nuclear export, and mRNA stability and translation. The cellular consequences of MAPK activation include inflammation, apoptosis, differentiation, and proliferation.

Distinct genes encode four p38 MAPK in humans: p38α, β, γ, and δ. Significant amino acid sequence homology is observed among the 4 isoforms, with 60-75 overall sequence identity and >90% identity within the kinase domains. Tissue-selective expression is observed, with p38γ found predominantly in skeletal muscle, p38δ in the testes, pancreas, and small intestine. In contrast, p38a and β are more ubiquitously expressed.

p38 MAPK is the major isoform involved in the immune and inflammatory response. As such its function is critical for the production and activity of multiple proinflammatory cytokines, including TNFa, IL-1, IL-6, and IL-8, in cells such as macrophages, monocytes, synovial cells, and endothelial cells. p38 MAPK is also responsible for the induction of key inflammatory enzymes such as COX2 and iNOS, the major sources of eicosanoids and nitric oxide at sites of inflammation, respectively. Additionally, the p38 MAPK pathway regulates the expression of matrix metalloproteinases (MMP), including MMP2, MMP9, and MMP13.

The use of selective and potent inhibitors has facilitated the discovery of several families of p38 MAPK substrates, including transcription factors, MAPKAP kinases, and other enzymes. p38 MAPK can directly phosphorylate several transcription factors, such as myocyte—specific enhancer binding factor 2C (MEF2C), CHOP, peroxisome proliferator-activated receptor (PPAR) a, PPAR γ co-activator 1 and p53. These transcription factors are involved in cellular functions such as apoptosis, gluconeogenesis, and synthesis of enzymes involved in fatty acid oxidation. p38 MAPK is also involved in the direct or indirect phosphorylation of enzyme substrates, such as cytosolic phospholipase A2, and the Cdc25 phosphatases, which are involved in the activation of cyclin-dependent protein kinase activity and cell-cycle regulation. Therefore in addition to its role in the inflammatory response, p38 MAPK has other functions associated with normal and abnormal cell growth and survival as well as cellular function and homeostasis. The MAPKAP kinases (MK2, MK-3, and PRAK) are selectively phosphorylated by p38 MAPK, while the phosphorylation of MSK1/2, MNK1/2, and RSKb is catalyzed by both p38 MAPK and ERK.

MK-2, MK-3, and PRAK, once phosphorylated and activated by p38 MAPK, share similar substrate specificities. All of these kinases can phosphorylate the small heat-shock protein Hsp27. Studies have shown that the PRAK- and MK3-deficient mice do not display any resistance to endotoxic shock or a decrease in lipopolysaccharide-(LPS)-induced cytokine production. In contrast, MK-2-deficient mice show a resistance to endotoxic shock and an impaired inflammatory response, as well as a significantly decreased production of cytokines such as TNFa, IFNy and IL-6. Thus, the p38/MK2 axis is important for mediating pro-inflammatory responses.

The p38:MK2 complex is very stable with a Kd of 6 nM. The binding affinity of p38 for MK2 is driven by the C-terminal domain of MK2 containing several positively charged amino acid residues. Crystallographic studies of the p38:MK2 complex demonstrated that the C-terminal region of MK2 wraps around p38a and binds to the negatively charged ED binding site. The tight binding of p38 to MK2 may give rise to conformational changes providing additional binding pockets for inhibitors that would specifically be dependent upon the p38:MK2 interaction. Taken together, these two studies suggests that selective p38/MK2 axis blockade is achievable with small molecule inhibitors. In comparison to traditional p38 MAPK inhibitors these p38/MK2 inhibitors should retain or enhance potency and exhibit improved safety features in animal models of disease or in human clinical settings.

The p38/MK2 role in the regulation of inflammatory cytokines (TNFa, IL-Iβ, IL-6) and enzymes responsible for inflammation (COX-2, iNOS, and MMPs) makes it an attractive drug target. Several classical p38 MAPK inhibitors have progressed to testing in clinical trials. Some of these candidates have failed, for safety or other reasons, but several have reported clinical data in diseases such as rheumatoid arthritis, pain, Crohn's disease, acute coronary syndrome, multiple myeloma, and chronic obstructive pulmonary disease. In addition to these diseases several IL-Iβ mediated diseases could be impacted by a p38 inhibitor based upon the key role for the p38 MAPK pathway in the biosynthesis and activity of this cytokine. These diseases include the family of cryopyrin associated periodic disorders (CAPS), chronic gout, diabetes, Still's disease, Familial Mediterranean Fever, among others. There is a need for new safe and effective p38/MK2 inhibitors.

SUMMARY OF THE INVENTION

Disclosed herein is a compound of Formula (I), or a pharmaceutically acceptable salt, solvate, stereoisomer, or rotamer thereof:

Formula (I)

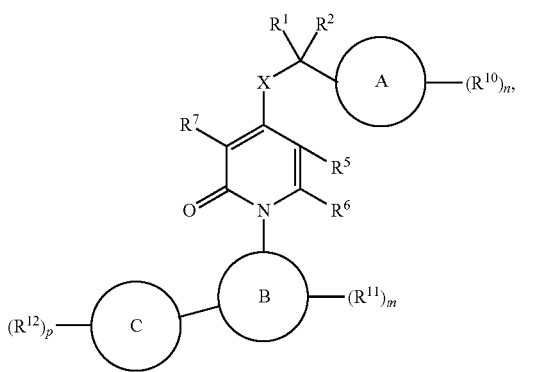

wherein:
Ring A is cycloalkyl, heterocycloalkyl, aryl, or heteroaryl;
each $R^{10}$ is independently hydrogen, deuterium, halogen, —CN, —NO$_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O)$_2$NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more $R^{10a}$;
or two $R^{10}$ on the same atom are taken together to form an oxo; each $R^{10a}$ is independently deuterium, halogen, —CN, —NO$_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O)$_2$NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;
or two $R^{10a}$ on the same atom are taken together to form an oxo; n is 1-4;
$R^1$ and $R^2$ are independently hydrogen, deuterium, halogen, —CN, —NO$_2$, —OH, —OR$^a$, —NR$^c$R$^d$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;
or $R^1$ and $R^2$ are taken together to form an oxo;
or $R^1$ and $R^2$ are taken together to form a cycloalkyl or heterocycloalkyl; wherein the cycloalkyl and heterocycloalkyl is optionally substituted with deuterium, halogen, —CN, —OH, —OCH$_3$, —NH$_2$, —NHCH$_3$, —N(CH$_3$)$_2$, —C(═O)CH$_3$, —C(═O)OH, —C(═O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;
X is —C(R$^3$)$_2$—, —NR$^4$—, —O—, or —S—;
each $R^3$ are independently hydrogen, deuterium, halogen, —CN, —NO$_2$, —OH, —OR$^a$, —NR$^c$R$^d$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;
or two $R^3$ are taken together to form an oxo;
$R^4$ is hydrogen, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;
$R^5$ is hydrogen, deuterium, halogen, —CN, —NO$_2$, —OH, —OR$^a$, —NR$^c$R$^d$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;
$R^6$ is hydrogen, deuterium, halogen, —CN, —NO$_2$, —OH, —OR$^a$, —NR$^c$R$^d$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;
$R^7$ is hydrogen, deuterium, halogen, C$_1$-C$_6$alkyl, C$_1$-C$_6$haloalkyl, or C$_1$-C$_6$deuteroalkyl;
Ring B is cycloalkyl, heterocycloalkyl, aryl, or heteroaryl;
each $R^{11}$ is independently hydrogen, deuterium, halogen, —CN, —NO$_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O)$_2$NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroayl is optionally and independently substituted with one or more $R^{11a}$;
or two $R^{11}$ on the same atom are taken together to form an oxo;
each $R^{11a}$ is independently deuterium, halogen, —CN, —NO$_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O)$_2$NR$^c$R$^d$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;
or two $R^{11a}$ on the same atom are taken together to form an oxo;
m is 1-4;
Ring C is N-linked pyridinone, N-linked pyrimidinone, N-linked pyrazinone, N-linked pyridazinone, N-linked dihydroimidazolone, N-linked tetrahydropyrimidinone, N-linked piperazinone, or N-linked tetrahydropyridazinone;
each $R^{12}$ is independently hydrogen, deuterium, halogen, —CN, —NO$_2$, —OH, —OR$^a$, —OC(═O)R$^a$, —OC(═O)OR$^b$, —OC(═O)NR$^c$R$^d$, —SH, —SR$^a$, —S(═O)R$^a$, —S(═O)$_2$R$^a$, —S(═O)$_2$NR$^c$R$^d$, —S(═O)(═NR$^b$)R$^a$, —SiR$^c$R$^d$OR$^b$, —NR$^c$R$^d$, —NR$^b$C(═O)NR$^c$R$^d$, —NR$^b$C(═O)R$^a$, —NR$^b$C(═O)OR$^b$, —NR$^b$S(═O)$_2$R$^a$, —C(═O)R$^a$, —C(═O)OR$^b$, —C(═O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroayl); wherein the alkyl, alkenyl, alkynyl, cycloalkyl, heterocycloalkyl, aryl, and heteroaryl is optionally and independently substituted with one or more $R^{12a}$;

each $R^{12a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)C(=O)R$^a$, —C(=O)OR$^b$, —C(=O)NR$^c$R$^d$, —C(=O)C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, or heteroaryl;

or two $R^{12a}$ on the same atom are taken together to form an oxo;

p is 1-4;

each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl; and each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^b$ and $R^c$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^a$ and $R^b$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^b$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Also disclosed herein is a pharmaceutical composition comprising a compound disclosed herein, or a pharmaceutically acceptable salt, solvate, stereoisomer, or rotamer thereof, and a pharmaceutically acceptable carrier.

Also disclosed herein is a method for treating a condition comprising administering to a subject in need thereof a therapeutically effective amount of a compound disclosed herein, or a pharmaceutically acceptable salt, solvate, stereoisomer, or rotamer thereof, wherein the condition is selected from the group consisting of an autoimmune disorder, a chronic inflammatory disorder, an acute inflammatory disorder, an auto-inflammatory disorder, a fibrotic disorder, a metabolic disorder, a neoplastic disorder, and a cardiovascular or a cerebrovascular disorder.

Also disclosed herein is a method of treating a p38 MAP kinase-mediated disease in a subject in need thereof comprising administering to the subject a therapeutically effective amount of a compound disclosed herein, or a pharmaceutically acceptable salt, solvate, stereoisomer, or rotamer thereof.

Also disclosed herein is a method of treating a MK2-mediated disease in a subject in need thereof comprising administering to the subject a therapeutically effective amount of a compound disclosed herein, or a pharmaceutically acceptable salt, solvate, stereoisomer, or rotamer thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Carboxyl" refers to —COOH.

"Alkyl" refers to a straight-chain, or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl(phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms (C$_3$-C$_{15}$ cycloalkyl or C$_3$-C$_{15}$ cycloalkenyl), from three to ten carbon atoms (C$_3$-C$_{10}$ cycloalkyl or C$_3$-C$_{10}$ cycloalkenyl), from three to eight carbon atoms (C$_3$-C$_8$ cycloalkyl or C$_3$-C$_8$ cycloalkenyl), from three to six carbon atoms (C$_3$-C$_6$ cycloalkyl or C$_3$-C$_6$ cycloalkenyl), from three to five carbon atoms (C$_3$-C$_5$ cycloalkyl or C$_3$-C$_5$ cycloalkenyl), or three to four carbon atoms (C$_3$-C$_4$ cycloalkyl or C$_3$-C$_4$ cycloalkenyl). In some embodiments, the cycloalkyl is a 3- to 10-membered cycloalkyl or a 3- to 10-membered cycloalkenyl. In some embodiments, the cycloalkyl is a 3- to 6-membered cycloalkyl or a 3- to 6-membered cycloalkenyl. In some embodiments, the cycloalkyl is a 5- to 6-membered cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, CD$_3$, CH$_2$D, CHD$_2$, CH$_2$CD$_3$, CD$_2$CD$_3$, CHDCD$_3$, CH$_2$CH$_2$D, or CH$_2$CHD$_2$. In some embodiments, the deuteroalkyl is CD$_3$.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (C$_2$-C$_{15}$ heterocycloalkyl or C$_2$-C$_{15}$ heterocycloalkenyl), from two to ten carbon atoms (C$_2$-C$_{10}$ heterocycloalkyl or C$_2$-C$_{10}$ heterocycloalkenyl), from two to eight carbon atoms (C$_2$-C$_8$ heterocycloalkyl or C$_2$-C$_8$ heterocycloalkenyl), from two to seven carbon atoms (C$_2$-C$_7$ heterocycloalkyl or C$_2$-C$_7$ heterocycloalkenyl), from two to six carbon atoms (C$_2$-C$_6$ heterocycloalkyl or C$_2$-C$_7$ heterocycloalkenyl), from two to five carbon atoms (C$_2$-C$_5$ heterocycloalkyl or C$_2$-C$_5$ heterocycloalkenyl), or two to four carbon atoms (C$_2$-C$_4$ heterocycloalkyl or C$_2$-C$_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroayl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroayl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroayl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

The term "one or more" when referring to an optional substituent means that the subject group is optionally substituted with one, two, three, four, or more substituents. In some embodiments, the subject group is optionally substituted with one, two, three, or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

"Synergy" or "synergize" refers to an effect of a combination that is greater than additive of the effects of each component alone at the same doses.

As used herein, a "disease or disorder associated with MK2" or, alternatively, "an MK2-mediated disease or disorder" means any disease or other deleterious condition in which MK2, or a mutant thereof, is known or suspected to play a role.

As used herein, a "disease or disorder associated with p38 MAP kinase" or, alternatively, "a p38 MAP kinase-mediated disease or disorder" means any disease or other deleterious condition in which p38 MAP kinase, or a mutant thereof, is known or suspected to play a role.

Compounds

Described herein are compounds of Formula (I)-(Ia)-(Ij), or a pharmaceutically acceptable salt, solvate, stereoisomer, or rotamer thereof useful in the treatment of autoimmune disorders, chronic inflammatory disorders, acute inflammatory disorders, auto-inflammatory disorders, fibrotic disorders, metabolic disorders, neoplastic disorders, or cardiovascular or cerebrovascular disorders.

Disclosed herein is a compound of Formula (I), or a pharmaceutically acceptable salt, solvate, stereoisomer, or rotamer thereof:

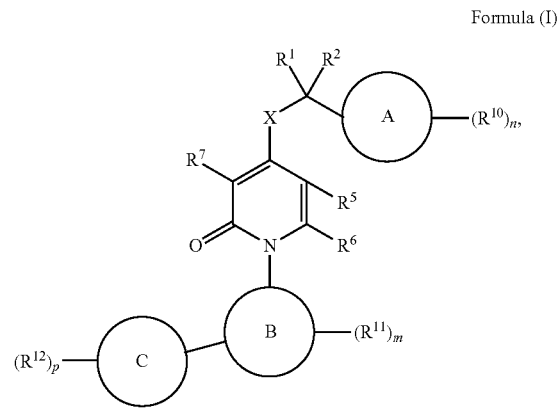

Formula (I)

wherein:

Ring A is cycloalkyl, heterocycloalkyl, aryl, or heteroaryl;

each $R^{10}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroayl is optionally and independently substituted with one or more $R^{10a}$;

or two $R^{10}$ on the same atom are taken together to form an oxo; each $R^{10a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two $R^{10a}$ on the same atom are taken together to form an oxo;

n is 1-4;

$R^1$ and $R^2$ are independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

or $R^1$ and $R^2$ are taken together to form an oxo;

or $R^1$ and $R^2$ are taken together to form a cycloalkyl or heterocycloalkyl; wherein the cycloalkyl and heterocycloalkyl is optionally substituted with deuterium, halogen, —CN, —OH, —OCH$_3$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

X is —C(R$^3$)$_2$—, —NR$^4$—, —O—, or —S—;

each R$^3$ are independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl; or two R$^3$ are taken together to form an oxo;

R$^4$ is hydrogen, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

R$^5$ is hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

R$^6$ is hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

R$^7$ is hydrogen, deuterium, halogen, C$_1$-C$_6$alkyl, C$_1$-C$_6$haloalkyl, or C$_1$-C$_6$deuteroalkyl;

Ring B is cycloalkyl, heterocycloalkyl, aryl, or heteroaryl;

each R$^{11}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more R$^{11a}$;

or two R$^1$ on the same atom are taken together to form an oxo;

each R$^{11a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{11a}$ on the same atom are taken together to form an oxo;

m is 1-4;

Ring C is N-linked pyridinone, N-linked pyrimidinone, N-linked pyrazinone, N-linked pyridazinone, N-linked dihydroimidazolone, N-linked tetrahydropyrimidinone, N-linked piperazinone, or N-linked tetrahydropyridazinone;

each R$^{12}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —S(=O)(=NR$^b$)R$^a$, —SiR$^c$R$^d$OR$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(ayl), or C$_1$-C$_6$alkylene(heteroaryl); wherein the alkyl, alkenyl, alkynyl, cycloalkyl, heterocycloalkyl, aryl, and heteroaryl is optionally and independently substituted with one or more R$^{12a}$;

each R$^{12a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, —C(=O)C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{12a}$ on the same atom are taken together to form an oxo;

p is 1-4;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, $C_1$-$C_6$aminoalkyl, $C_1$-$C_6$heteroalkyl, $C_2$-$C_6$alkenyl, $C_2$-$C_6$alkynyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^c$ and $R^d$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^b$ and $R^c$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or $R^a$ and $R^b$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl;

or two $R^b$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

Also disclosed herein is a compound of Formula (Ia), or a pharmaceutically acceptable salt, solvate, stereoisomer, or rotamer thereof:

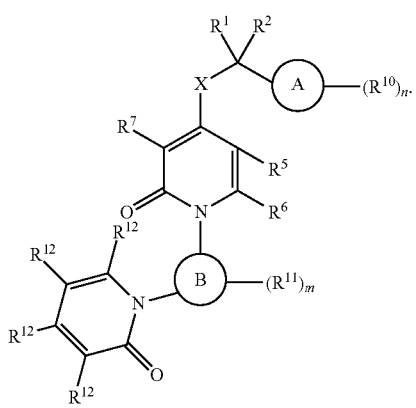

Formula (Ia)

Also disclosed herein is a compound of Formula (Ib), or a pharmaceutically acceptable salt, solvate, stereoisomer, or rotamer thereof:

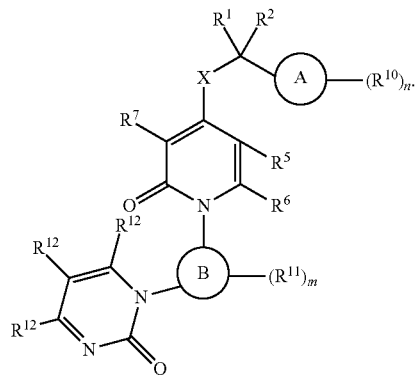

Formula (Ib)

Also disclosed herein is a compound of Formula (Ic), or a pharmaceutically acceptable salt, solvate, stereoisomer, or rotamer thereof:

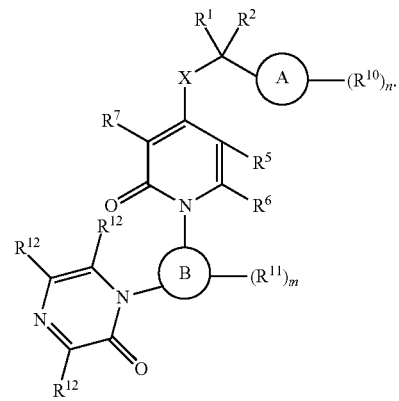

Formula (Ic)

Also disclosed herein is a compound of Formula (Id), or a pharmaceutically acceptable salt, solvate, stereoisomer, or rotamer thereof:

Formula (Id)

Also disclosed herein is a compound of Formula (Ie), or a pharmaceutically acceptable salt, solvate, stereoisomer, or rotamer thereof:

Formula (Ie)

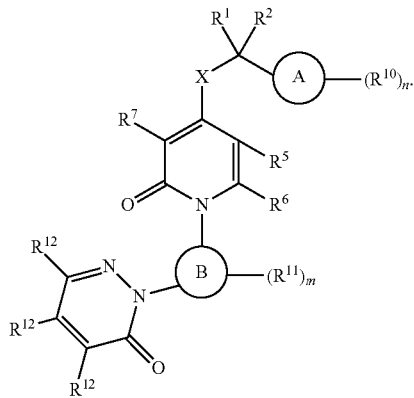

Also disclosed herein is a compound of Formula (If), or a pharmaceutically acceptable salt, solvate, stereoisomer, or rotamer thereof:

Formula (If)

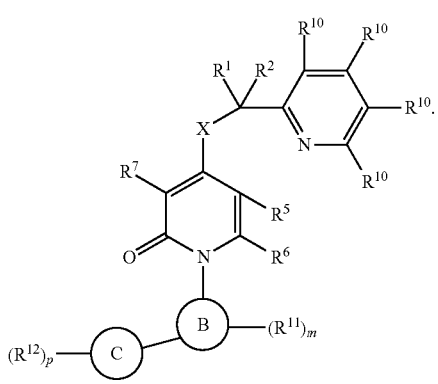

Also disclosed herein is a compound of Formula (Ig), or a pharmaceutically acceptable salt, solvate, stereoisomer, or rotamer thereof:

Formula (Ig)

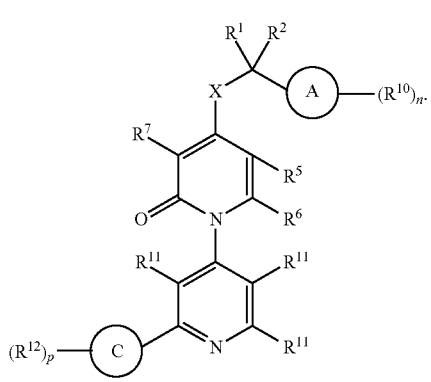

Also disclosed herein is a compound of Formula (Ih), or a pharmaceutically acceptable salt, solvate, stereoisomer, or rotamer thereof:

Formula (Ih)

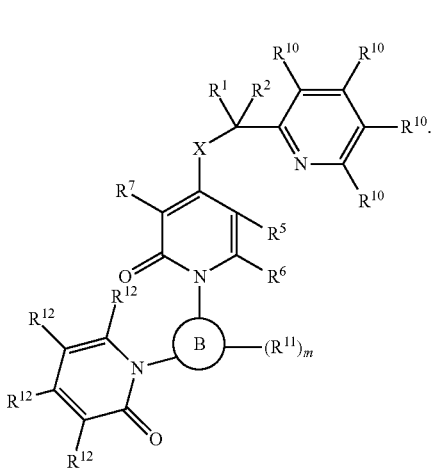

Also disclosed herein is a compound of Formula (Ii), or a pharmaceutically acceptable salt, solvate, stereoisomer, or rotamer thereof:

Formula (Ii)

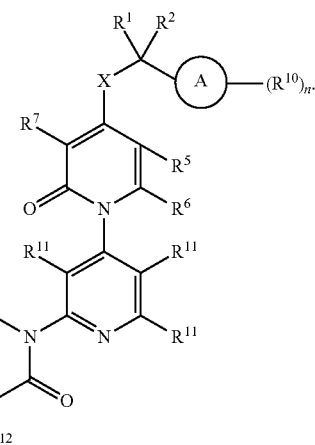

Also disclosed herein is a compound of Formula (Ij), or a pharmaceutically acceptable salt, solvate, stereoisomer, or rotamer thereof:

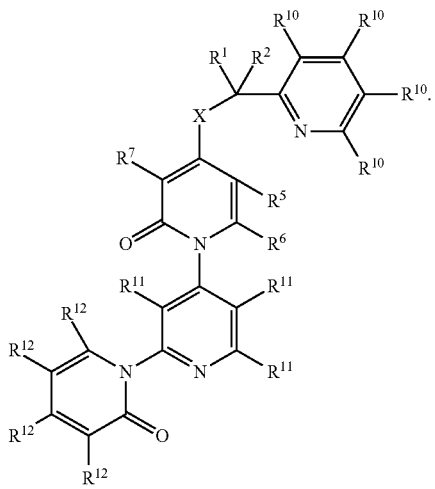

Formula (Ij)

In some embodiments of a compound of Formula (I), (Ia)-(Ie), (Ig), or (Ii), Ring A is heteroaryl. In some embodiments of a compound of Formula (I), (Ia)-(Ie), (Ig), or (Ii), Ring A is a 6-membered heteroaryl. In some embodiments of a compound of Formula (I), (Ia)-(Ie), (Ig), or (Ii), Ring A is pyridyl. In some embodiments of a compound of Formula (I), (Ia)-(Ie), (Ig), or (Ii), Ring A is phenyl.

In some embodiments of a compound of Formula (I), (Ia)-(Ij), each $R^{10}$ is independently hydrogen, deuterium, halogen, —CN, —OH, —OR$^a$, —NR$^c$R$^d$, $C_1$-$C_6$alkyl, $C_1$-$C_6$haloalkyl, or $C_1$-$C_6$deuteroalkyl. In some embodiments of a compound of Formula (I), (Ia)-(Ij), each $R^{10}$ is independently hydrogen, halogen, or $C_1$-$C_6$alkyl. In some embodiments of a compound of Formula (I), (Ia)-(Ij), each $R^{10}$ is independently hydrogen or halogen.

In some embodiments of a compound of Formula (I), (Ia)-(Ij), each $R^{10}$ is independently deuterium, halogen, —CN, —OH, —OR$^a$, —NR$^c$R$^d$, $C_1$-$C_6$alkyl, $C_1$-$C_6$haloalkyl, or $C_1$-$C_6$deuteroalkyl. In some embodiments of a compound of Formula (I), (Ia)-(Ij), each $R^{10}$ is independently halogen or $C_1$-$C_6$alkyl. In some embodiments of a compound of Formula (I), (Ia)-(Ij), each $R^{10}$ is independently halogen.

In some embodiments of a compound of Formula (I), (Ia)-(Ie), (Ig), or (Ii), n is 1 or 2. In some embodiments of a compound of Formula (I), (Ia)-(Ie), (Ig), or (Ii), n is 2 or 3. In some embodiments of a compound of Formula (I), (Ia)-(Ie), (Ig), or (Ii), n is 1. In some embodiments of a compound of Formula (I), (Ia)-(Ie), (Ig), or (Ii), n is 2. In some embodiments of a compound of Formula (I), (Ia)-(Ie), (Ig), or (Ii), n is 3.

In some embodiments of a compound of Formula (I), (Ia)-(Ij), $R^1$ and $R^2$ are independently hydrogen, deuterium, halogen, $C_1$-$C_6$alkyl, $C_1$-$C_6$haloalkyl, or $C_1$-$C_6$deuteroalkyl. In some embodiments of a compound of Formula (I), (Ia)-(Ij), $R^1$ and $R^2$ are independently hydrogen, deuterium, halogen, or $C_1$-$C_6$alkyl. In some embodiments of a compound of Formula (I), (Ia)-(Ij), $R^1$ and $R^2$ are hydrogen. In some embodiments of a compound of Formula (I), (Ia)-(Ij), $R^1$ and $R^2$ are deuterium.

In some embodiments of a compound of Formula (I), (Ia)-(Ij), X is —O—.

In some embodiments of a compound of Formula (I), (Ia)-(Ij), $R^1$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (I), (Ia)-(Ij), $R^5$ is hydrogen, deuterium, halogen, —CN, or $C_1$-$C_6$alkyl. In some embodiments of a compound of Formula (I), (Ia)-(Ij), $R^5$ is hydrogen. In some embodiments of a compound of Formula (I), (Ia)-(Ij), $R^6$ is hydrogen, deuterium, halogen, —CN, or $C_1$-$C_6$alkyl.

In some embodiments of a compound of Formula (I), (Ia)-(Ij), $R^6$ is hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (I), (Ia)-(Ij), $R^6$ is hydrogen, deuterium, halogen, —CN, or $C_1$-$C_6$alkyl. In some embodiments of a compound of Formula (I), (Ia)-(Ij), $R^6$ is $C_1$-$C_6$alkyl.

In some embodiments of a compound of Formula (I), (Ia)-(Ij), $R^7$ is hydrogen, deuterium, halogen, or $C_1$-$C_6$haloalkyl. In some embodiments of a compound of Formula (I), (Ia)-(Ij), $R^7$ is hydrogen, deuterium, or halogen. In some embodiments of a compound of Formula (I), (Ia)-(Ij), $R^7$ is halogen. In some embodiments of a compound of Formula (I), (Ia)-(Ij), $R^7$ is chloro. In some embodiments of a compound of Formula (I), (Ia)-(Ij), $R^7$ is bromo. In some embodiments of a compound of Formula (I), (Ia)-(Ij), $R^7$ is —CHF$_2$.

In some embodiments of a compound of Formula (I), (Ia)-(Ie), (Ig), or (Ih), Ring B is a phenyl or a 6-membered heteroaryl. In some embodiments of a compound of Formula (I), (Ia)-(Ie), (Ig), or (Ih), Ring B is pyridinyl. In some embodiments of a compound of Formula (I), (Ia)-(Ie), (Ig), or (Ih), Ring B is phenyl.

In some embodiments of a compound of Formula (I), (Ia)-(Ij), each $R^{11}$ is independently deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (I), (Ia)-(Ij), each $R^{11}$ is independently $C_1$-$C_6$alkyl.

In some embodiments of a compound of Formula (I), (Ia)-(Ij), each $R^{11}$ is independently hydrogen, deuterium, halogen, —CN, —OH, —OR$^a$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, $C_2$-$C_6$alkynyl, or cycloalkyl. In some embodiments of a compound of Formula (I), (Ia)-(Ij), each $R^{11}$ is independently hydrogen or $C_1$-$C_6$alkyl.

In some embodiments of a compound of Formula (I), (Ia)-(Ij), m is 1 or 2. In some embodiments of a compound of Formula (I), (Ia)-(Ij), m is 1-4. In some embodiments of a compound of Formula (I), (Ia)-(Ij), m is 2-4. In some embodiments of a compound of Formula (I), (Ia)-(Ij), m is 1. In some embodiments of a compound of Formula (I), (Ia)-(Ij), m is 2.

In some embodiments of a compound of Formula (I), (If), (Ig), Ring C is N-linked pyridinone, N-linked pyrimidinone, N-linked pyrazinone, or N-linked pyridazinone. In some embodiments of a compound of Formula (I), (If), (Ig), Ring C is N-linked pyridinone. In some embodiments of a compound of Formula (I), (If), (Ig), Ring C is N-linked pyrimidinone. In some embodiments of a compound of Formula (I), (If), (Ig), Ring C is N-linked pyrazinone. In some embodiments of a compound of Formula (I), (If), (Ig), Ring C is N-linked pyridazinone.

In some embodiments of a compound of Formula (I), (If), (Ig), Ring C is

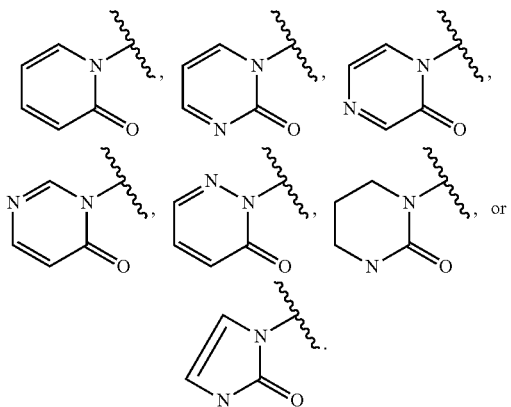

In some embodiments of a compound of Formula (I), (If), (Ig), Ring C is

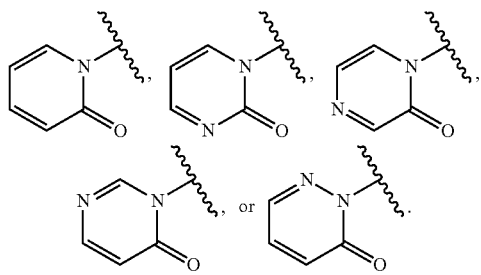

In some embodiment of a compound of Formula (I), (If), (Ig), Ring C is

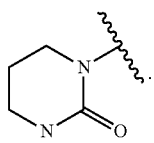 [SMILES: *N1CCCNC1=O]

In some embodiments of a compound of Formula (I), (If), (Ig), Ring C is

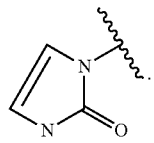 [SMILES: *n1cc[nH]c1=O]

In some embodiments of a compound of Formula (I), (If), (Ig), Ring C is

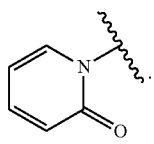

In some embodiments of a compound of Formula (I), (Ia)-(Ij), each $R^{12}$ is independently hydrogen, deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, cycloalkyl, heterocycloalkyl, aryl, and heteroaryl is optionally and independently substituted with one or more $R^{12a}$.

In some embodiments of a compound of Formula (I), (Ia)-(Ij), each $R^{12}$ is independently hydrogen, deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, heteroaryl, $C_1$-$C_6$alkylene(cycloalkyl), or $C_1$-$C_6$alkylene(heterocycloalkyl); wherein the alkyl, cycloalkyl, heterocycloalkyl, aryl, and heteroaryl is optionally and independently substituted with one or more $R^{12a}$.

In some embodiments of a compound of Formula (I), (Ia)-(Ij), each $R^{12}$ is independently hydrogen, deuterium, halogen, $C_1$-$C_6$alkyl, $C_1$-$C_6$haloalkyl, $C_1$-$C_6$hydroxyalkyl, cycloalkyl, heterocycloalkyl, $C_1$-$C_6$alkylene(cycloalkyl), or $C_1$-$C_6$alkylene(heterocycloalkyl); wherein the alkyl, cycloalkyl, and heterocycloalkyl is optionally and independently substituted with one or more $R^{12a}$.

In some embodiments of a compound of Formula (I), (Ia)-(Ij), each $R^{12}$ is independently hydrogen, deuterium, halogen, $C_1$-$C_6$alkyl, $C_1$-$C_6$haloalkyl, $C_1$-$C_6$hydroxyalkyl, cycloalkyl, or heterocycloalkyl; wherein the alkyl, cycloalkyl, and heterocycloalkyl is optionally and independently substituted with one or more $R^{12a}$.

In some embodiments of a compound of Formula (I), (Ia)-(Ij), each $R^{12}$ is independently hydrogen or $C_1$-$C_6$hydroxyalkyl.

In some embodiments of a compound of Formula (I), (Ia)-(Ij), each $R^{12}$ is independently deuterium, halogen, —CN, —OH, —$OR^a$, —$NR^cR^d$, —C(=O)$R^a$, —C(=O)$OR^b$, —C(=O)$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, heteroaryl, $C_1$-$C_6$alkylene(cycloalkyl), $C_1$-$C_6$alkylene(heterocycloalkyl), $C_1$-$C_6$alkylene(aryl), or $C_1$-$C_6$alkylene(heteroaryl); wherein the alkyl, cycloalkyl, heterocycloalkyl, aryl, and heteroaryl is optionally and independently substituted with one or more $R^{12a}$.

In some embodiments of a compound of Formula (I), (Ia)-(Ij), each $R^{12}$ is independently deuterium, halogen, —CN, —OH, —$OR^a$, —$NR^cR^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, cycloalkyl, heterocycloalkyl, aryl, heteroaryl, $C_1$-$C_6$alkylene(cycloalkyl), or $C_1$-$C_6$alkylene(heterocycloalkyl); wherein the alkyl, cycloalkyl, heterocycloalkyl, aryl, and heteroaryl is optionally and independently substituted with one or more $R^{12a}$.

In some embodiments of a compound of Formula (I), (Ia)-(Ij), each $R^{12}$ is independently deuterium, halogen, $C_1$-$C_6$alkyl, $C_1$-$C_6$haloalkyl, $C_1$-$C_6$hydroxyalkyl, cycloalkyl, heterocycloalkyl, $C_1$-$C_6$alkylene(cycloalkyl), or $C_1$-$C_6$alkylene(heterocycloalkyl); wherein the alkyl, cycloalkyl, and heterocycloalkyl is optionally and independently substituted with one or more $R^{12a}$.

In some embodiments of a compound of Formula (I), (Ia)-(Ij), each $R^{12}$ is independently deuterium, halogen, $C_1$-$C_6$alkyl, $C_1$-$C_6$haloalkyl, $C_1$-$C_6$hydroxyalkyl, cycloalkyl, or heterocycloalkyl; wherein the alkyl, cycloalkyl, and heterocycloalkyl is optionally and independently substituted with one or more $R^{12a}$.

In some embodiments of a compound of Formula (I), (Ia)-(Ij), each $R^{12}$ is independently $C_1$-$C_6$hydroxyalkyl.

In some embodiments of a compound of Formula (I), (Ia)-(Ij), each $R^{12a}$ is independently deuterium, halogen, —CN, —OH, —OR$^a$, —NR$^c$R$^d$, —C(=O)R$^a$, —C(=O)OR$^b$, —C(=O)NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, or heterocycloalkyl.

In some embodiments of a compound of Formula (I), (Ia)-(Ij), each $R^{12a}$ is independently deuterium, halogen, —CN, —OH, —OR$^a$, —NR$^c$R$^d$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl. In some embodiments of a compound of Formula (I), (Ia)-(Ij), each $R^{12a}$ is independently deuterium, halogen, —CN, —OH, —OR$^a$, $C_1$-$C_6$alkyl, or $C_1$-$C_6$haloalkyl.

In some embodiments of a compound of Formula (I), (If), or (Ig), p is 1 or 2. In some embodiments of a compound of Formula (I), (If), or (Ig), p is 1-3. In some embodiments of a compound of Formula (I), (If), or (Ig), p is 1. In some embodiments of a compound of Formula (I), (If), or (Ig), p is 2.

In some embodiments of a compound disclosed herein, each $R^a$ is independently $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^a$ is independently $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^a$ is independently $C_1$-$C_6$alkyl, $C_1$-$C_6$haloalkyl, cycloalkyl, or heterocycloalkyl. In some embodiments of a compound disclosed herein, each $R^a$ is independently $C_1$-$C_6$alkyl or $C_1$-$C_6$haloalkyl. In some embodiments of a compound disclosed herein, each $R^a$ is independently $C_1$-$C_6$alkyl.

In some embodiments of a compound disclosed herein, each $R^b$ is independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroaryl; wherein each alkyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^b$ is independently hydrogen, $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^b$ is independently hydrogen, $C_1$-$C_6$alkyl, $C_1$-$C_6$haloalkyl, cycloalkyl, or heterocycloalkyl. In some embodiments of a compound disclosed herein, each $R^b$ is independently hydrogen, $C_1$-$C_6$alkyl, or $C_1$-$C_6$haloalkyl. In some embodiments of a compound disclosed herein, each $R^b$ is independently hydrogen or $C_1$-$C_6$alkyl.

In some embodiments of a compound disclosed herein, each $R^c$ and $R^d$ are independently hydrogen, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl, cycloalkyl, heterocycloalkyl, aryl, or heteroayl; wherein each alkyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^c$ and $R^d$ are independently hydrogen, $C_1$-$C_6$alkyl, $C_1$-$C_6$haloalkyl, cycloalkyl, or heterocycloalkyl; wherein each alkyl, cycloalkyl, and heterocycloalkyl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, $C_1$-$C_6$heteroalkyl. In some embodiments of a compound disclosed herein, each $R^c$ and $R^d$ are independently hydrogen, $C_1$-$C_6$alkyl, $C_1$-$C_6$haloalkyl, cycloalkyl, or heterocycloalkyl. In some embodiments of a compound disclosed herein, each $R^c$ and $R^d$ are independently hydrogen, $C_1$-$C_6$alkyl, or $C_1$-$C_6$haloalkyl. In some embodiments of a compound disclosed herein, each $R^c$ and $R^d$ are independently hydrogen or $C_1$-$C_6$alkyl.

In some embodiments of a compound disclosed herein, $R^c$ and $R^d$ are taken together with the atom to which they are attached to form a heterocycloalkyl optionally substituted with one or more oxo, deuterium, halogen, —CN, —OH, —OCH$_3$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$haloalkyl, $C_1$-$C_6$deuteroalkyl, $C_1$-$C_6$hydroxyalkyl, $C_1$-$C_6$aminoalkyl, or $C_1$-$C_6$heteroalkyl.

In some embodiments of a compound disclosed herein, each $R^{10}$, $R^{11}$, $R^{12}$, $R^a$, $R^b$, $R^c$, $R^d$, the heterocycloalkyl formed when $R^c$ and $R^d$ are taken together, the heterocycloalkyl formed when $R^a$ and $R^b$ are taken together, and the heterocycloalkyl formed when $R^b$ and $R^c$ are taken together is independently substituted with one, two, three, four, or five substituents as defined herein. In some embodiments of a compound disclosed herein, each $R^{10}$, $R^{11}$, $R^{12}$, $R^a$, $R^b$, $R^c$, $R^d$, the heterocycloalkyl formed when $R^c$ and $R^d$ are taken together, the heterocycloalkyl formed when $R^a$ and $R^b$ are taken together, and the heterocycloalkyl formed when $R^b$ and $R^c$ are taken together is independently substituted with one, two, three, or four substituents as defined herein. In some embodiments of a compound disclosed herein, each $R^{10}$, $R^{11}$, $R^{12}$, $R^a$, $R^b$, $R^c$, $R^d$, the heterocycloalkyl formed when $R^c$ and $R^d$ are taken together, the heterocycloalkyl formed when $R^a$ and $R^b$ are taken together, and the heterocycloalkyl formed when $R^b$ and $R^c$ are taken together is independently substituted with one, two, or three substituents as defined herein. In some embodiments of a compound disclosed herein, each $R^{10}$, $R^{11}$, $R^{12}$, $R^a$, $R^b$, $R^c$, $R^d$, the heterocycloalkyl formed when $R^c$ and $R^d$ are taken together, the heterocycloalkyl formed when $R^a$ and $R^b$ are taken together, and the heterocycloalkyl formed when $R^b$ and $R^c$ are taken together is independently substituted with one or two substituents as defined herein. In some embodiments of a compound disclosed herein, each $R^{10}$, $R^1$, $R^{12}$, $R^a$, $R^b$, $R^c$, $R^d$, the heterocycloalkyl formed when $R^c$ and $R^d$ are taken together, the heterocycloalkyl formed when $R^a$ and $R^b$ are taken together, and the heterocycloalkyl formed when $R^b$ and $R^c$ are taken together is independently substituted with one substituent as defined herein.

Any combination of the groups described above for the various variables is contemplated herein. Throughout the specification, groups and substituents thereof are chosen by one skilled in the field to provide stable moieties and compounds.

In some embodiments the compound of Formula (I), or a pharmaceutically acceptable salt, solvate, stereoisomer, or rotamer thereof, is selected from:

| Ex. | Structure |
|---|---|
| 1A | 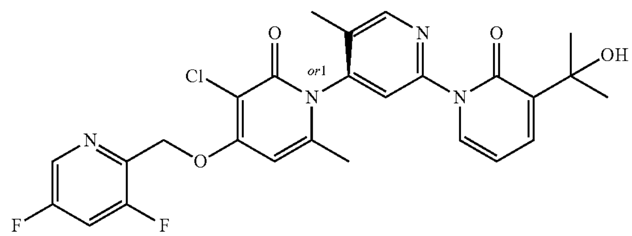 |
| 1B | 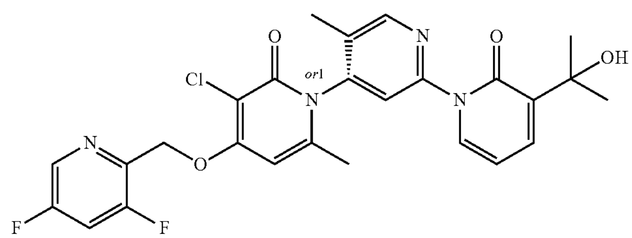 |
| 2A | 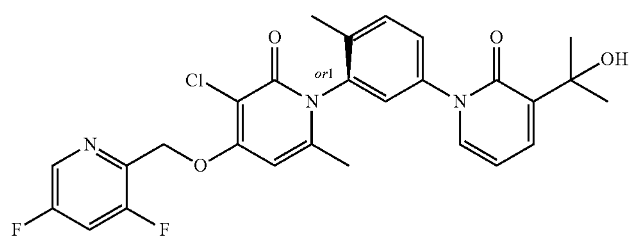 |
| 2B | 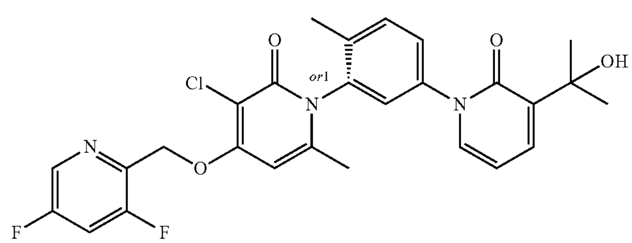 |
| 3A | 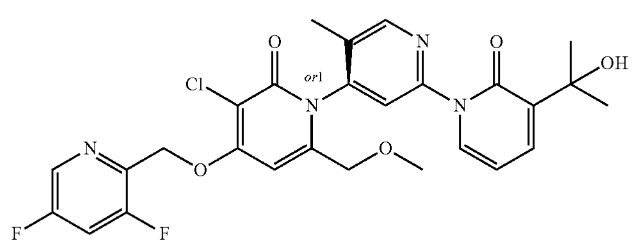 |

| Ex. | Structure |
|---|---|
| 3B | 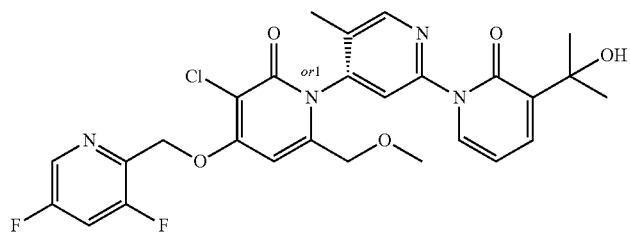 |
| 4A | 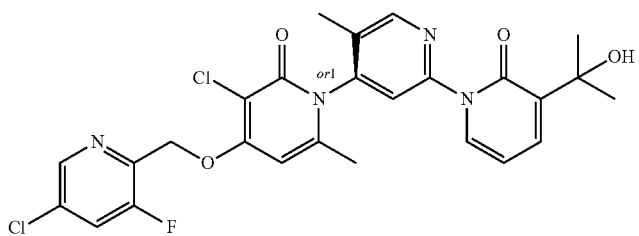 |
| 4B | 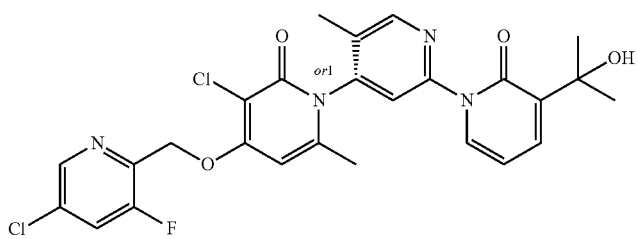 |
| 5A | 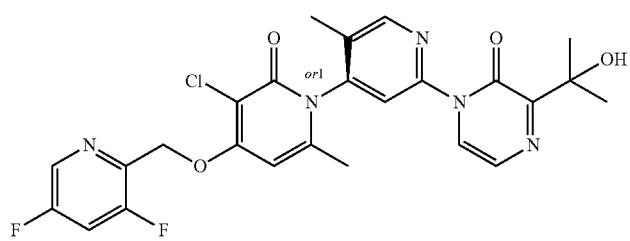 |
| 5B | 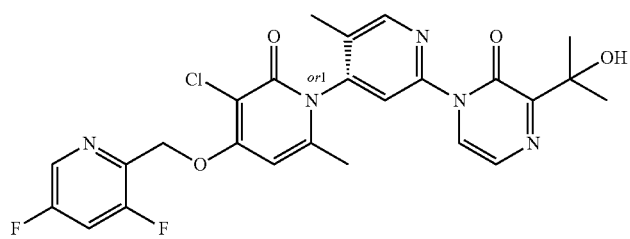 |
| 6 | 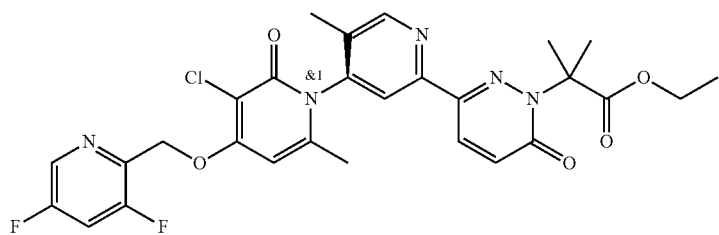 |

-continued
| Ex. | Structure |
|---|---|
| 7A | 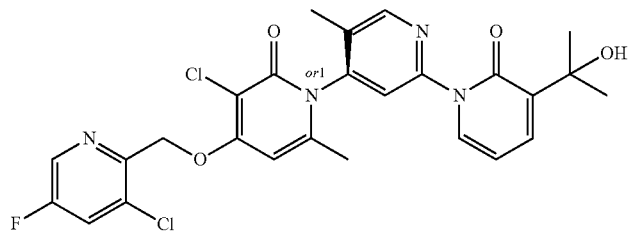 |
| 7B | 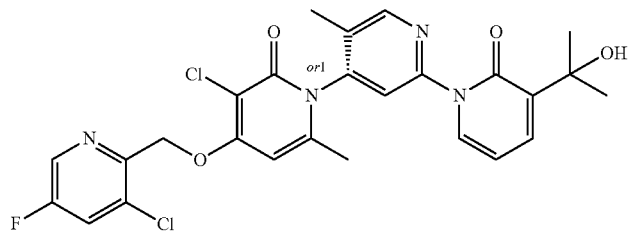 |
| 8A | 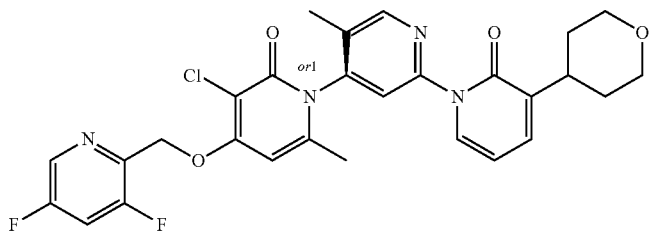 |
| 8B | 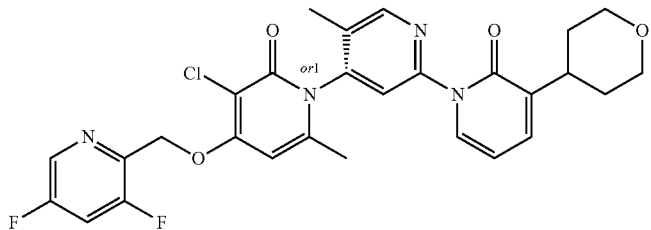 |
| 9A | 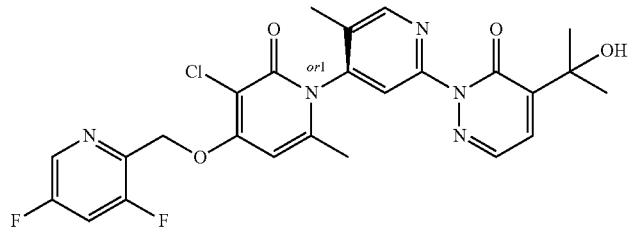 |
| 9B | 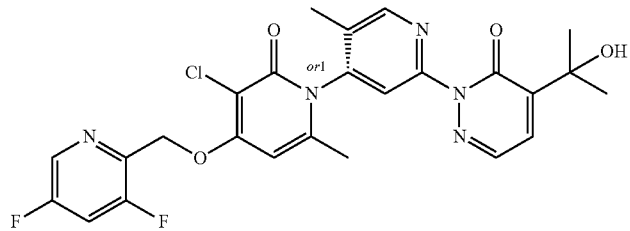 |

-continued
| Ex. | Structure |
|---|---|
| 10A | 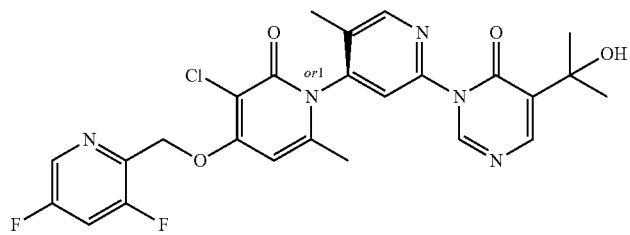 |
| 10B | 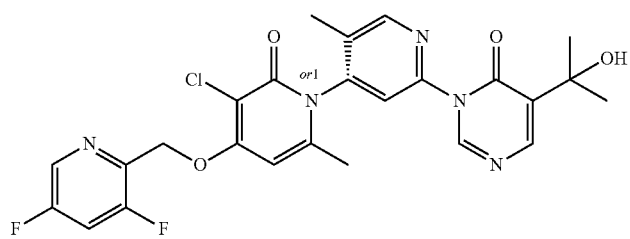 |
| 11A | 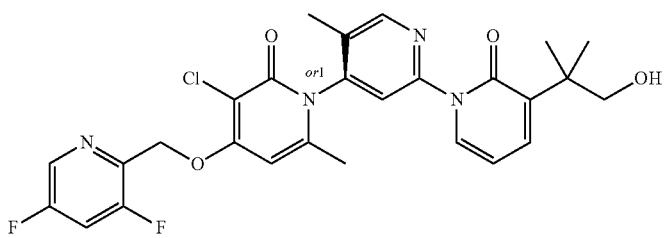 |
| 11B | 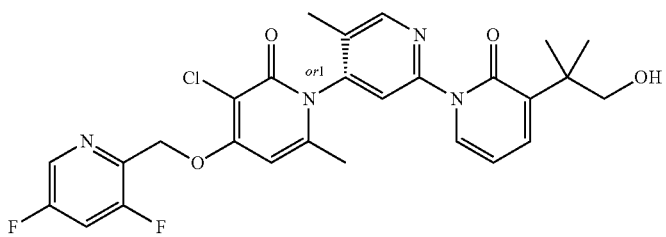 |
| 12A | 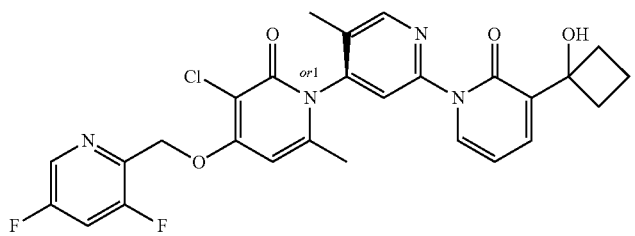 |
| 12B | 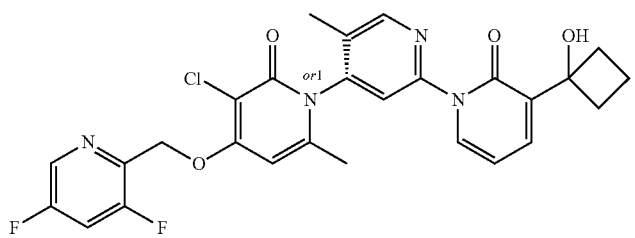 |

-continued
| Ex. | Structure |
|---|---|
| 13A | 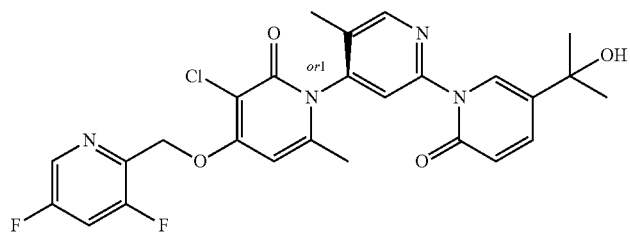 |
| 13B | 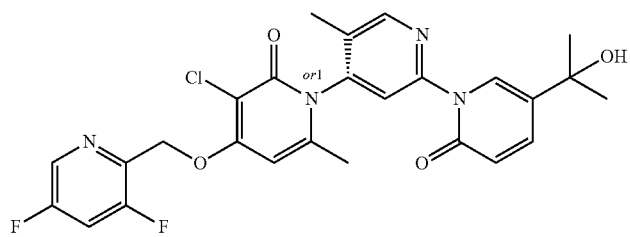 |
| 14A | 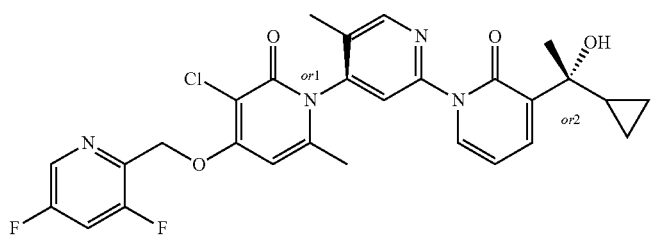 |
| 14B | 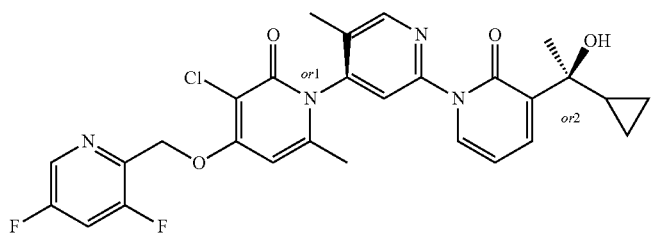 |
| 14C | 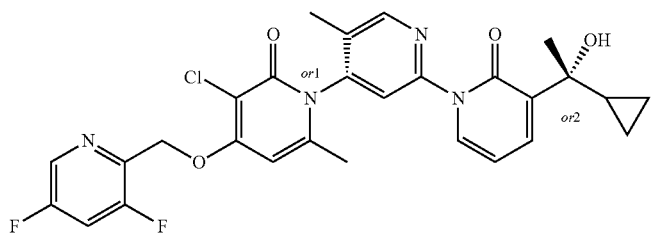 |
| 14D | 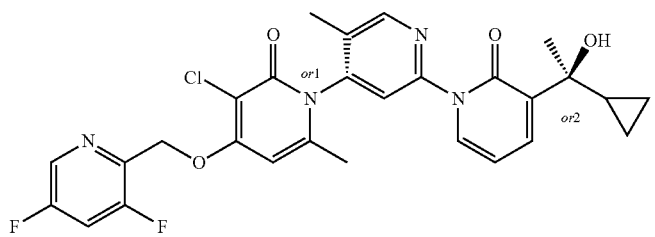 |

| Ex. | Structure |
|---|---|
| 15A | 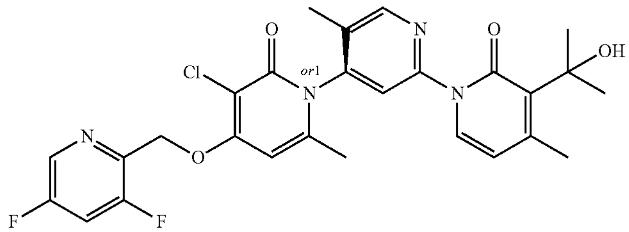 |
| 15B | 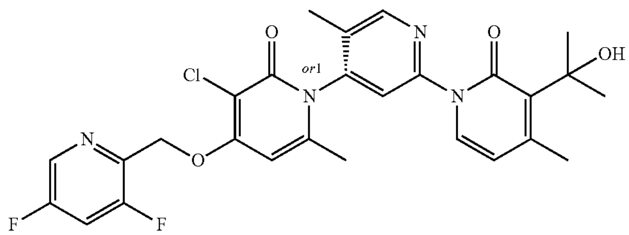 |
| 16A | 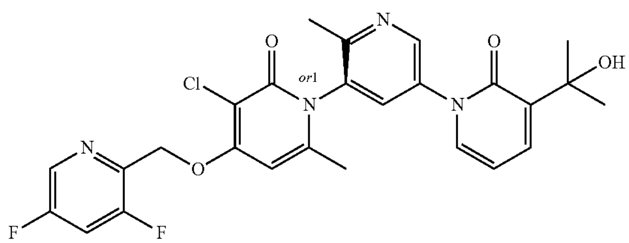 |
| 16B | 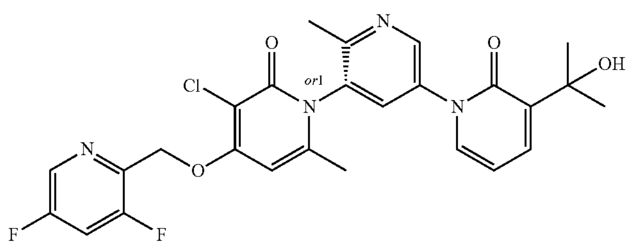 |
| 17A | 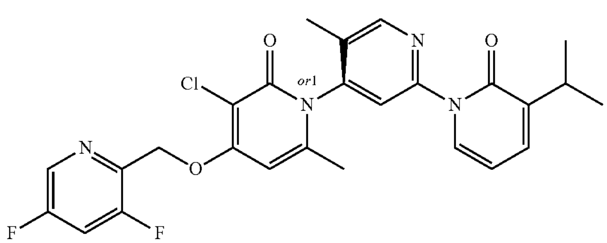 |
| 17B | 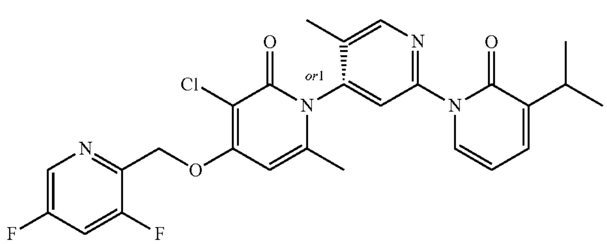 |

-continued
| Ex. | Structure |
|---|---|
| 18A | 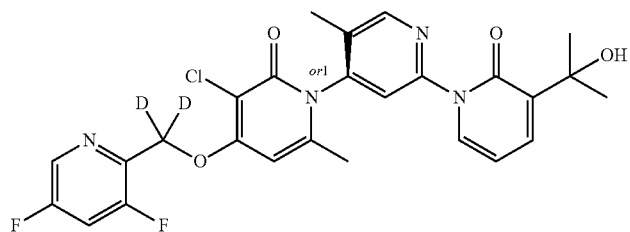 |
| 18B | 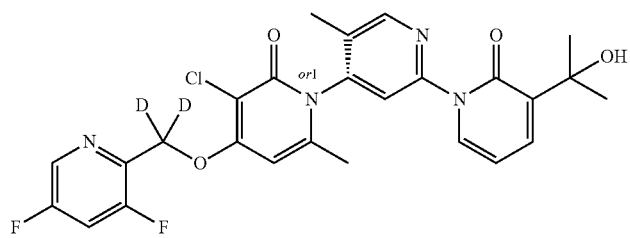 |
| 19A | 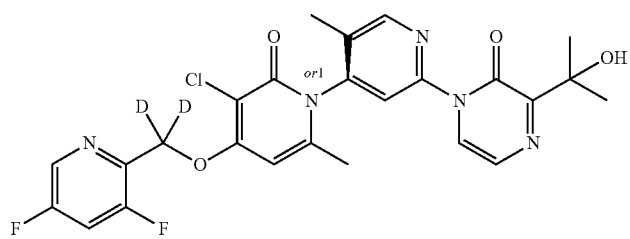 |
| 19B | 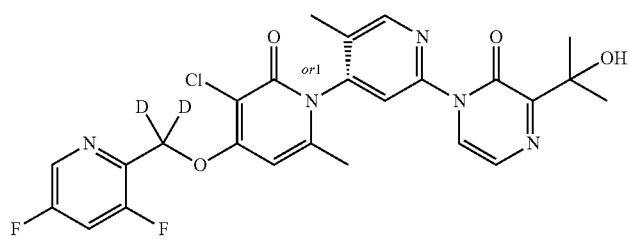 |
| 20A | 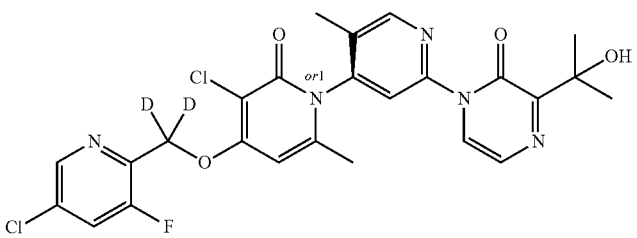 |
| 20B | 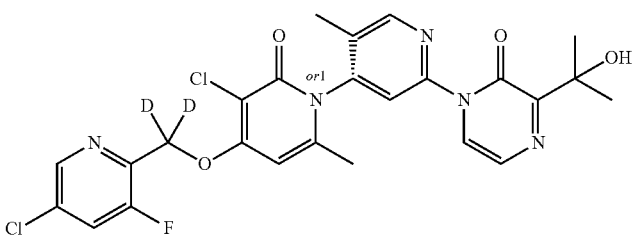 |

| Ex. | Structure |
|---|---|
| 21A | 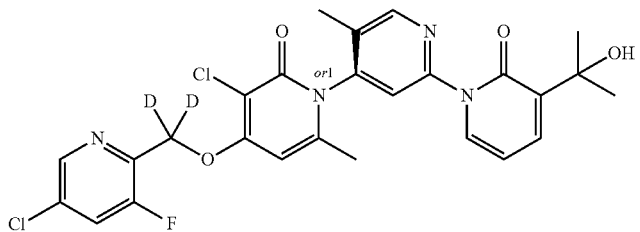 |
| 21B | 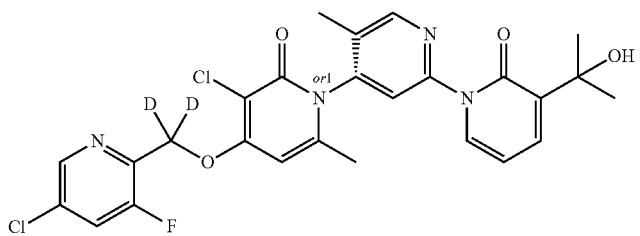 |
| 22A | 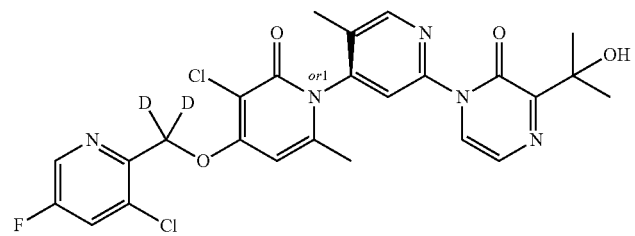 |
| 22B | 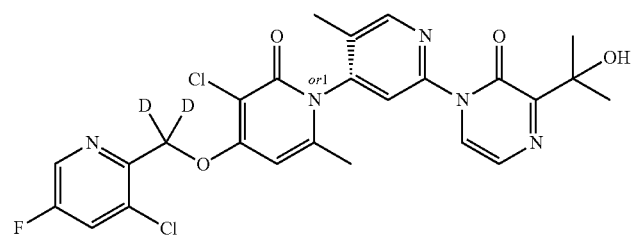 |
| 23A | 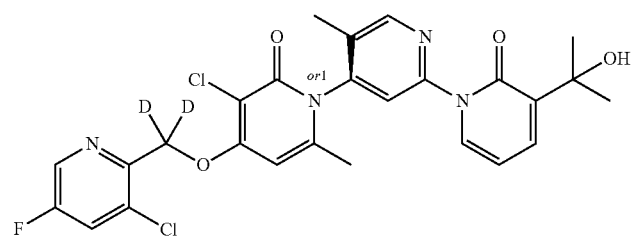 |
| 23B | 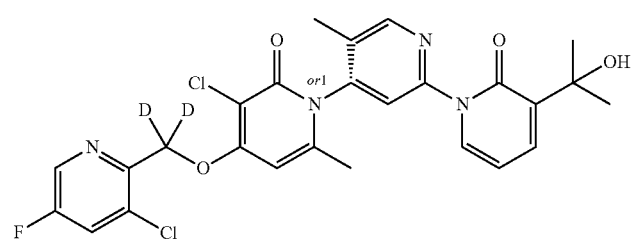 |

-continued
| Ex. | Structure |
|---|---|
| 24A | 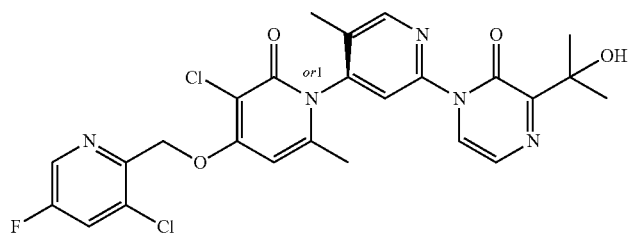 |
| 24B | 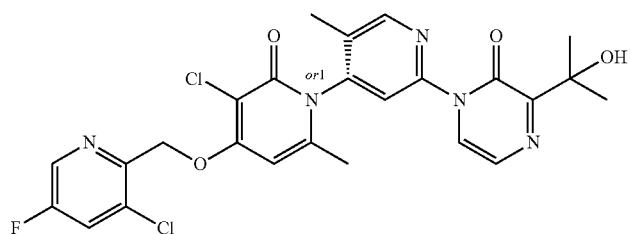 |
| 25A | 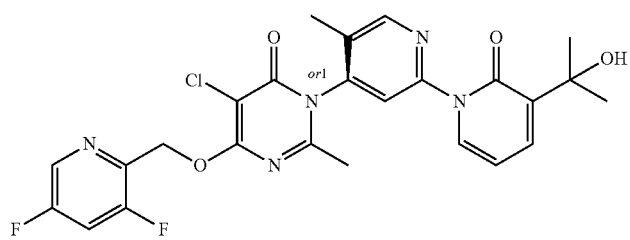 |
| 25B | 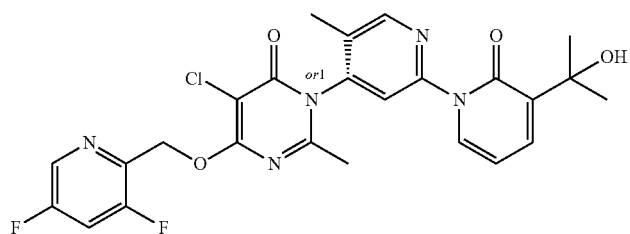 |
| 26A | 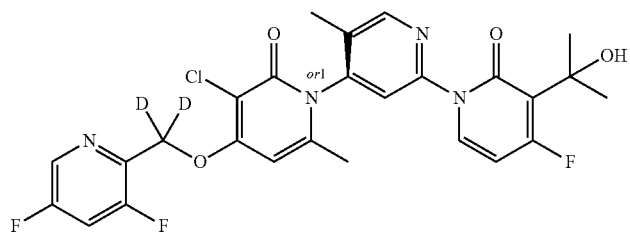 |
| 26B | 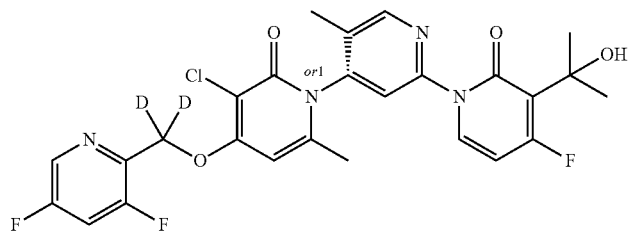 |

-continued
| Ex. | Structure |
|---|---|
| 27A | 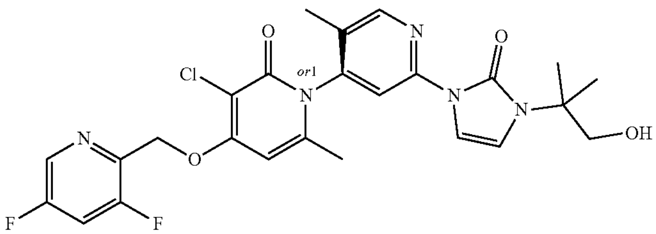 |
| 27B | 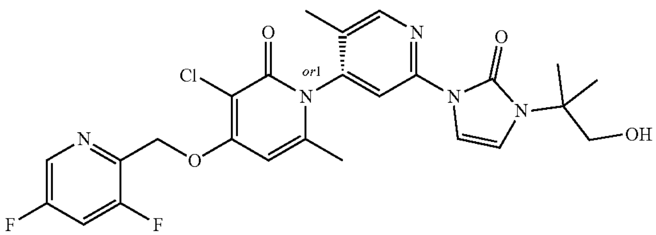 |
| 28A | 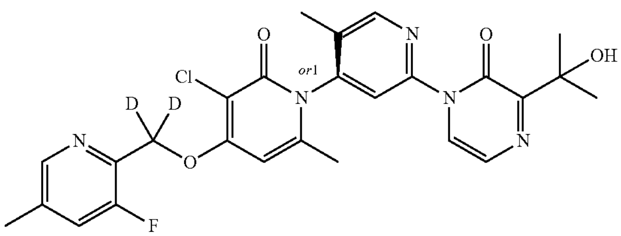 |
| 28B | 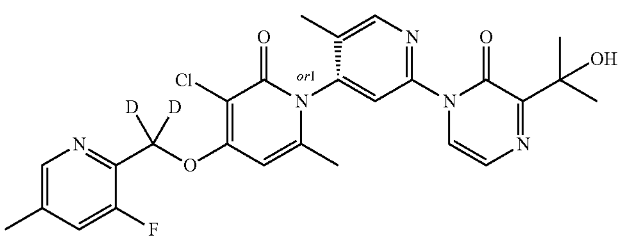 |
Note: all rotamers found in table 1 were arbitrarily assigned.
In some embodiments the compound of Formula (I) is selected from:
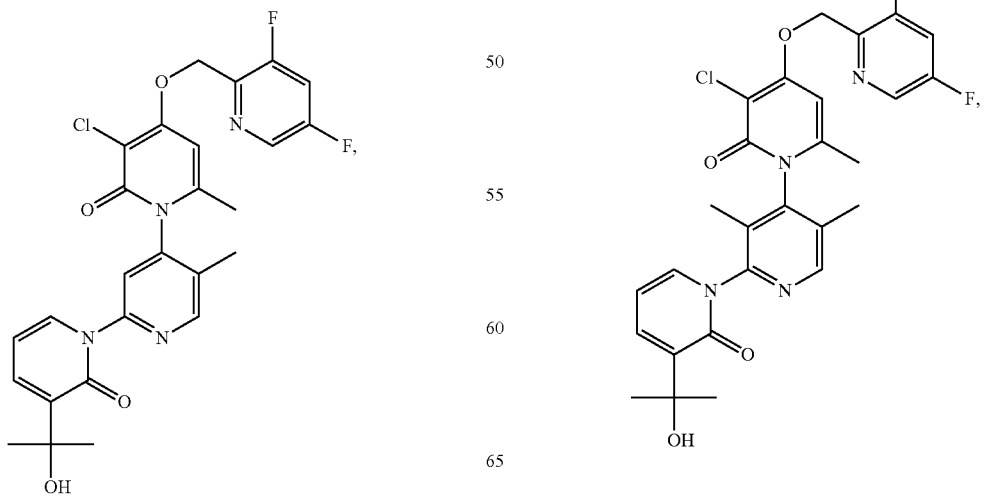

47
-continued
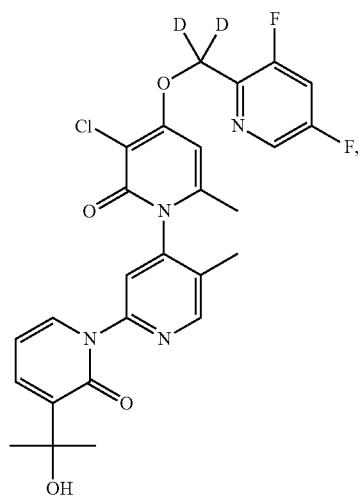
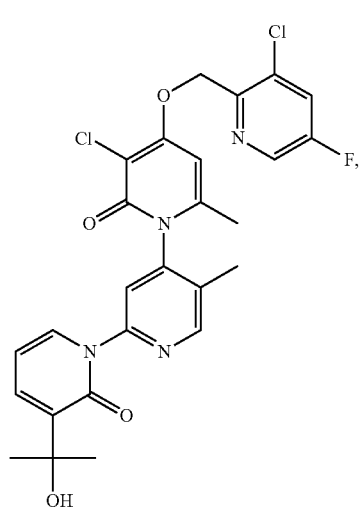
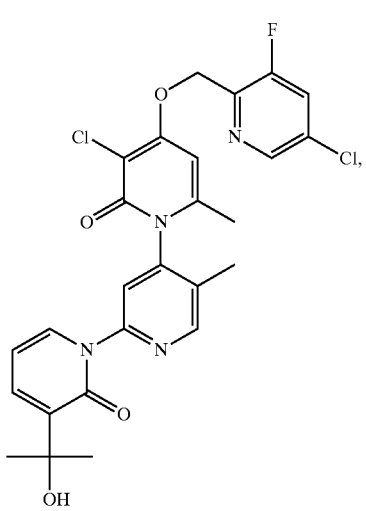
48
-continued
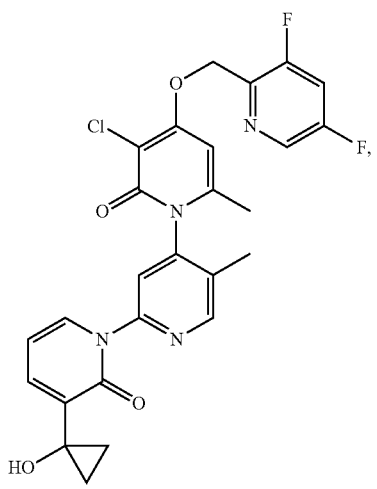
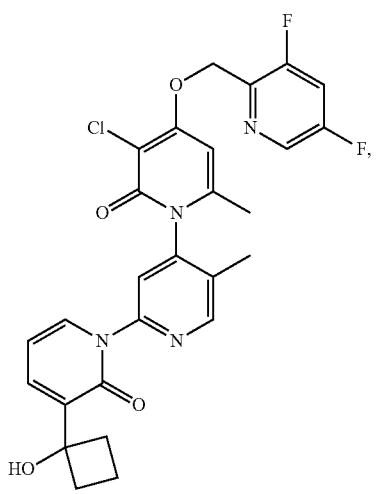
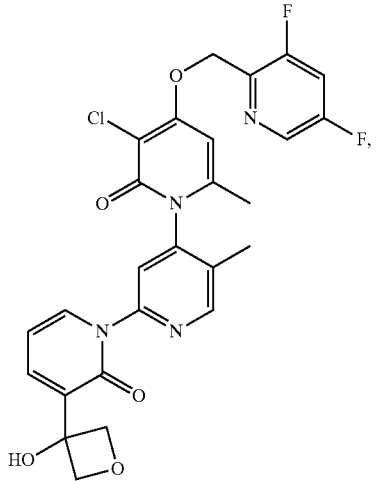

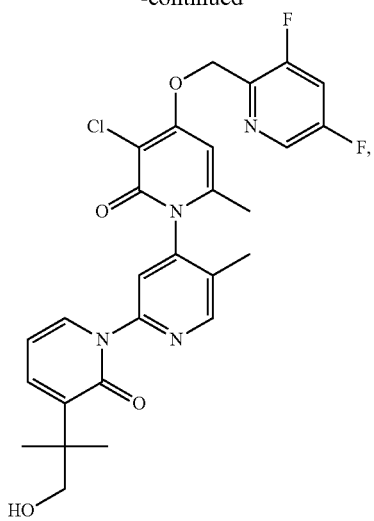
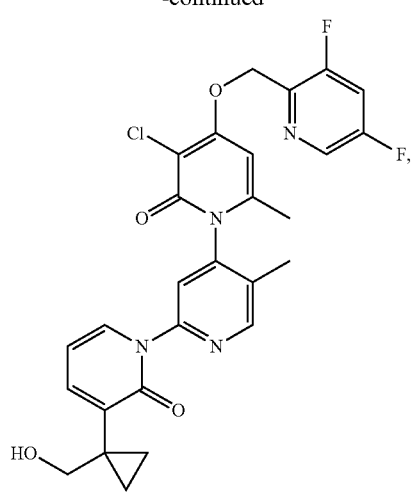

51 -continued
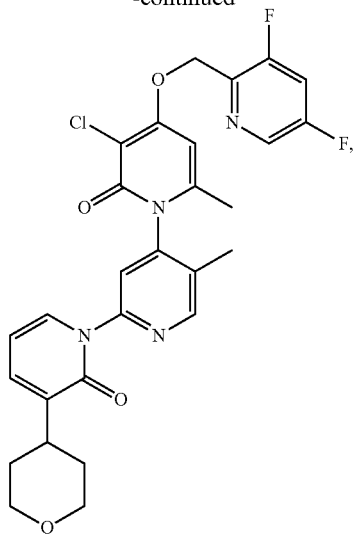
52 -continued
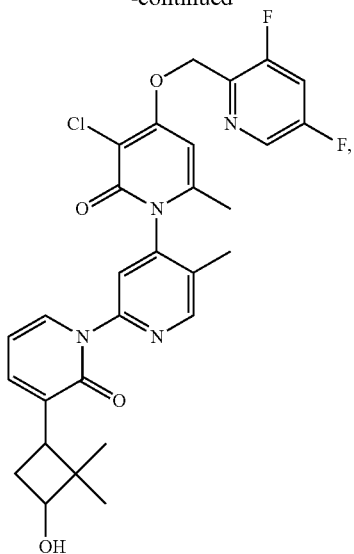
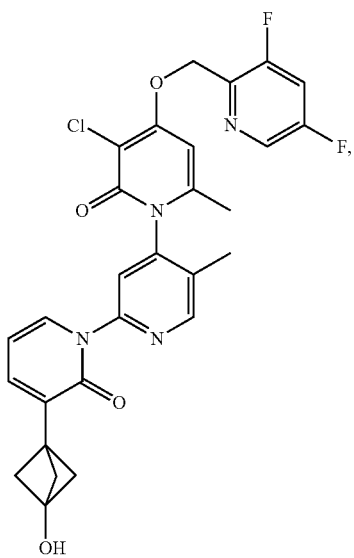

53 54
-continued -continued
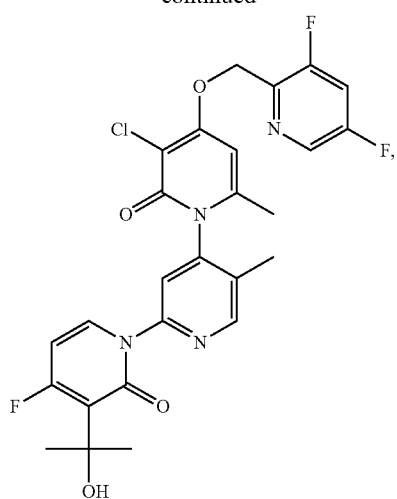
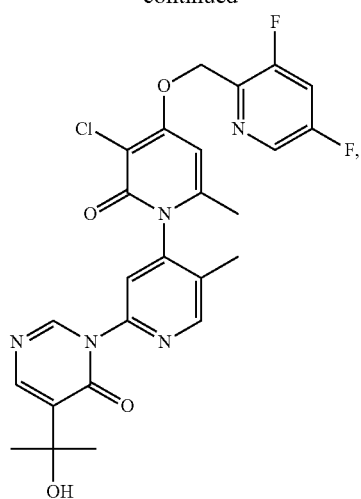

55
-continued
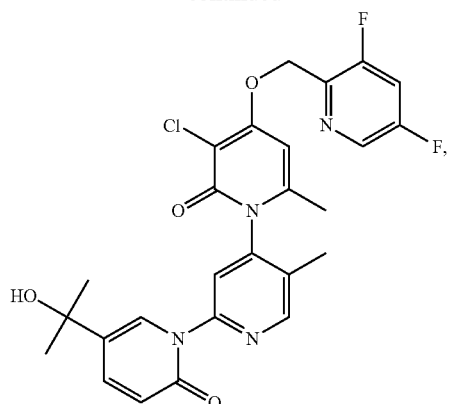
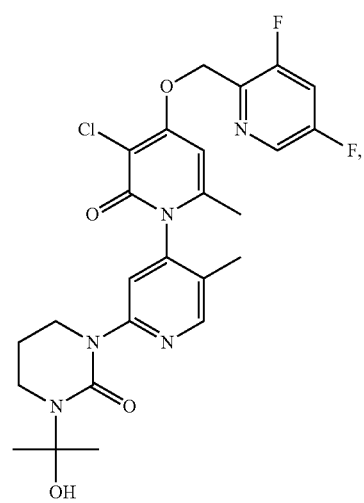
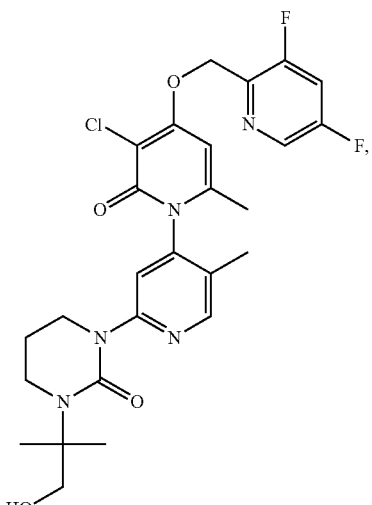
56
-continued
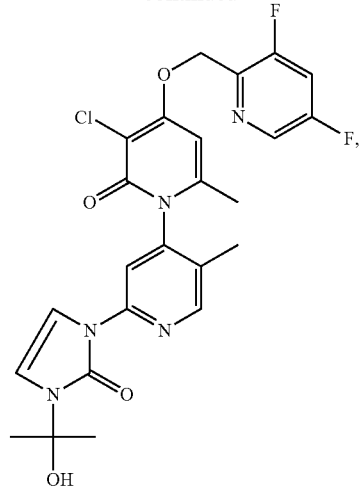
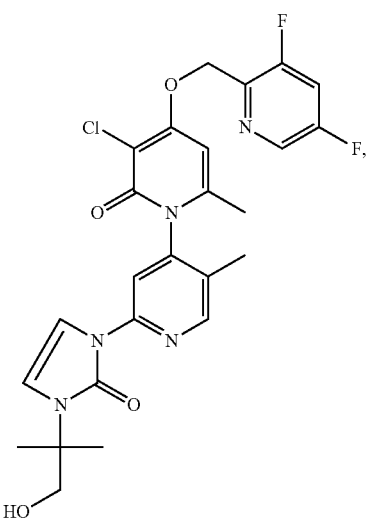
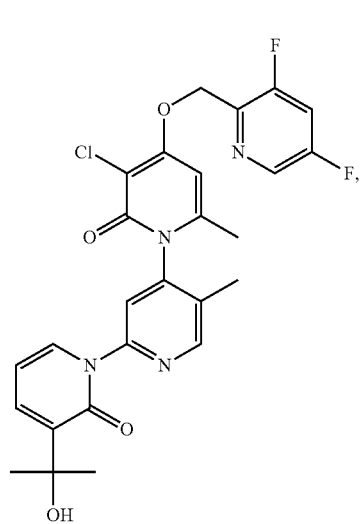

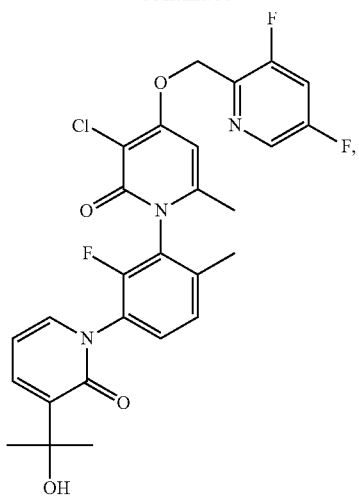

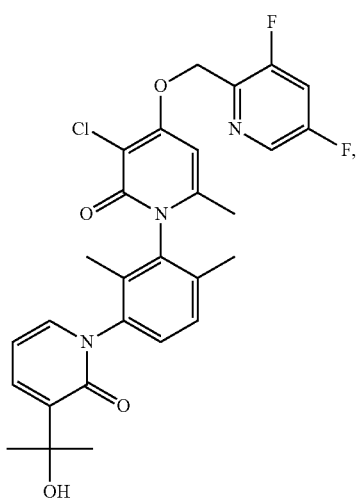

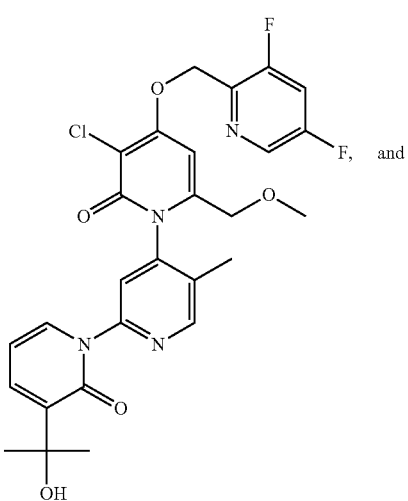

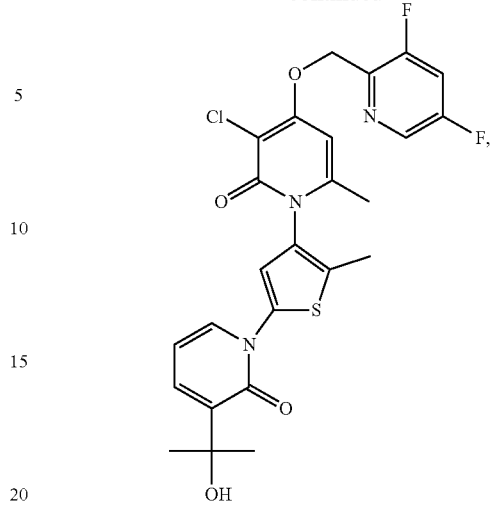

or a pharmaceutically acceptable salt, solvate, stereoisomer, or rotamer thereof.

Further Forms of Compounds Disclosed Herein

Isomers Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

In some embodiments, the compounds described herein exist as rotamers caused by the slow rotation of the N—C bond between the central pyridinone ring and Ring B.

In some embodiments,

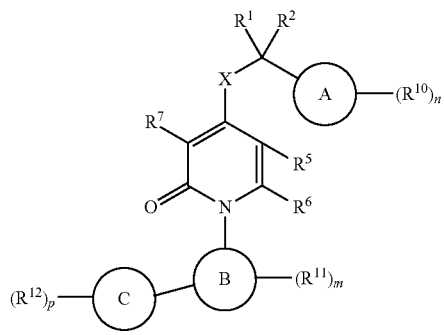

exists as

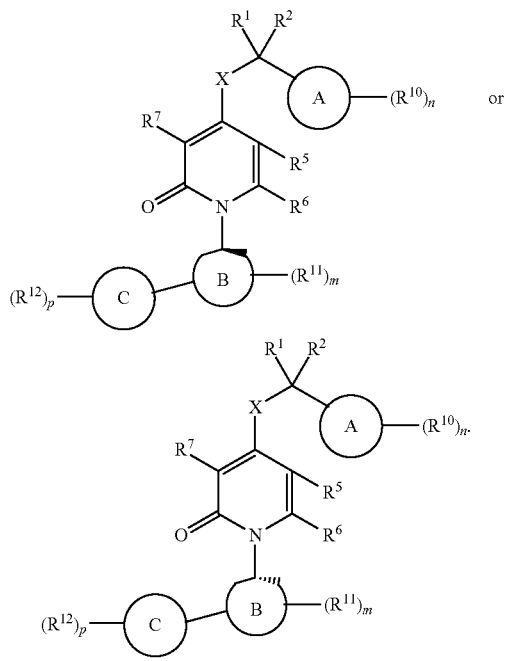

For example OH exists as OH or OH

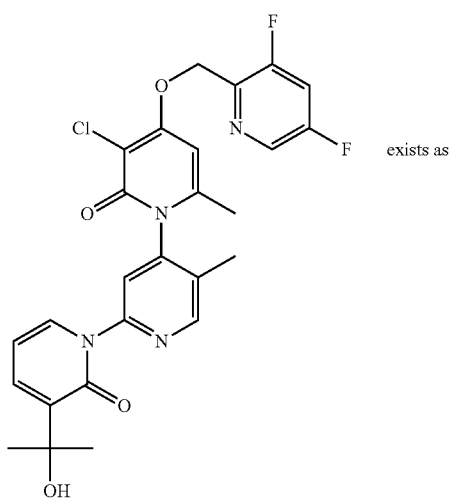

exists as

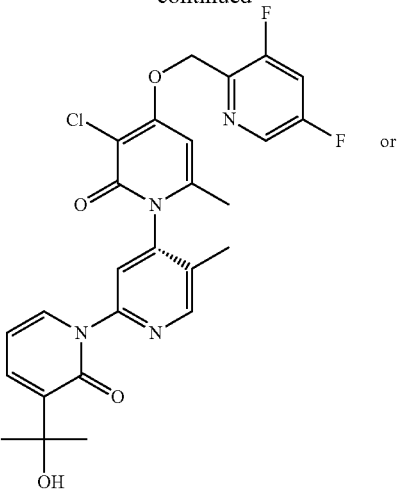

or

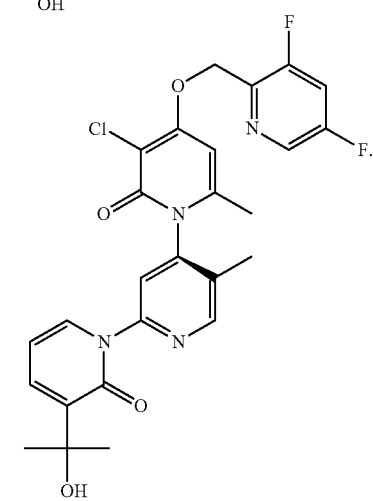

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, stereoisomers, or rotamers thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., 14C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, stereoisomer, or rotamers thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, stereoisomer, or rotamer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Described herein are compounds and compositions generally useful for the inhibition of kinase activity of one or more enzymes. Examples of kinases that are inhibited by the compounds and compositions described herein and against which the methods described herein are useful include p38 MAP kinase, MK2, or a mutant thereof.

MAP kinase-activated protein kinase 2 ("MK2") is an enzyme that in humans is encoded by the MAPKAPK2 gene. This gene encodes a member of the Ser/Thr protein kinase family. This kinase is regulated through direct phosphorylation by p38 MAP kinase. In conjunction with p38 MAP kinase, this kinase is known to be involved in many cellular processes including stress and inflammatory responses, nuclear export, gene expression regulation and cell proliferation. Heat shock protein HSP27 was shown to be one of the substrates of this kinase in vivo. Two transcript variants encoding two different isoforms have been found for this gene.

MK2 is a multi-domain protein consisting of an N-terminal proline-rich domain, a catalytic domain, an autoinhibitory domain and at the C-terminus a nuclear export signal (NES) and nuclear localization signal (NLS). Two isoforms of human MK2 have been characterized. One isoform consists of 400 amino acids and the other isoform 370 residues which is thought to be a splice variant missing the C-terminal NLS. MK2 is located in the nucleus of the cell and upon binding and phosphorylation by p38, the MK2 NES becomes functional and both kinases are co-transported out of the nucleus to the cytoplasm. Interestingly, transport of the MK2/p38 complex does not require catalytically active MK2, as the active site mutant, Asp207Ala, is still transported to the cytoplasm. Phosphorylation of human MK2 by p38 on residues T222, S272 and T334 is thought to activate the enzyme by inducing a conformational change of the autoinhibitory domain thus exposing the active site for substrate binding. Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity.

Diseases or disorders associated with MK2 that are treated by compounds disclosed herein include autoimmune disorders, chronic inflammatory disorders, acute inflammatory disorders, auto-inflammatory disorders, fibrotic disorders, metabolic disorders, neoplastic disorders, and cardiovascular or cerebrovascular disorders.

In some embodiments, the MK2-mediated disease or disorder is an autoimmune disorder, chronic and/or acute inflammatory disorder, and/or auto-inflammatory disorder. Exemplary autoimmune and/or inflammatory and/or auto-inflammatory disorders include: inflammatory bowel diseases (for example, ulcerative colitis or Crohn's disease), multiple sclerosis, psoriasis, arthritis, rheumatoid arthritis, osteoarthritis, juvenile arthritis, psoriatic arthritis, reactive arthritis, ankylosing spondylitis, cryopyrin associated periodic syndromes, Muckle-Wells syndrome, familial cold auto-inflammatory syndrome, neonatal-onset multisystem inflammatory disease, TNF receptor associated periodic syndrome, acute and chronic pancreatitis, atherosclerosis, gout, ankylosing spondylitis, fibrotic disorders (for example, hepatic fibrosis or idiopathic pulmonary fibrosis), nephropathy, sarcoidosis, scleroderma, anaphylaxis, diabetes (for example, diabetes mellitus type 1 or diabetes mellitus type 2), diabetic retinopathy, Still's disease, vasculitis, sarcoidosis, pulmonary inflammation, acute respiratory distress syndrome, wet and dry age-related macular degeneration, autoimmune hemolytic syndromes, autoimmune and inflammatory hepatitis, autoimmune neuropathy, autoimmune ovarian failure, autoimmune orchitis, autoimmune thrombocytopenia, silicone implant associated autoimmune disease, Sjogren's syndrome, familial Mediterranean fever, systemic lupus erythematosus, vasculitis syndromes (for example, temporal, Takayasu's and giant cell arteritis, Behçet's disease or Wegener's granulomatosis), vitiligo, secondary hematologic manifestation of autoimmune diseases (for example, anemias), drug-induced autoimmunity, Hashimoto's thyroiditis, hypophysitis, idiopathic thrombocytic purpura, metal-induced autoimmunity, myasthenia gravis, pemphigus, autoimmune deafness (for example, Meniere's disease), Goodpasture's syndrome, Graves' disease, HW-related autoimmune syndromes, Guillain-Barre disease, Addison's disease, anti-phospholipid syndrome, asthma, atopic dermatitis, Celiac disease, Cushing's syndrome, dermatomyositis, idiopathic adrenal atrophy, idiopathic thrombocytopenia, Kawasaki syndrome, Lambert-Eaton Syndrome, pernicious anemia, pollinosis, polyarteritis nodosa, primary biliary cirrhosis, primary sclerosing cholangitis, Raynaud's, Reiter's Syndrome, relapsing polychondritis, Schmidt's syndrome, thyrotoxidosis, sepsis, septic shock, endotoxic shock, exotoxin-induced toxic shock, gram negative sepsis, toxic shock syndrome, glomerulonephritis, peritonitis, interstitial cystitis, hyperoxia-induced inflammations, chronic obstructive pulmonay disease (COPD), vasculitis, graft vs. host reaction (for example, graft vs. host disease), allograft rejections (for example, acute allograft rejection or chronic allograft rejection), early transplantation rejection (for example, acute allograft rejection), reperfusion injury, pain (for example, acute pain, chronic pain, neuropathic pain, or fibromyalgia), chronic infections, meningitis, encephalitis, myocarditis, gingivitis, post-surgical trauma, tissue injury, traumatic brain injury, enterocolitis, sinusitis, uveitis, ocular inflammation, optic neuritis, gastric ulcers, esophagitis, peritonitis, periodontitis, dermatomyositis, gastritis, myositis, polymyalgia, pneumonia and bronchitis.

In some embodiments, the MK2-mediated disease or disorder is a fibrotic disorder. Exemplary fibrotic disorders include systemic sclerosis/scleroderma, lupus nephritis, connective tissue disease, wound healing, surgical scarring, spinal cord injury, CNS scarring, acute lung injury, pulmonary fibrosis (for example, idiopathic pulmonary fibrosis or cystic fibrosis), chronic obstructive pulmonary disease, adult respiratory distress syndrome, acute lung injury, drug-induced lung injury, glomerulonephritis, chronic kidney disease (for example, diabetic nephropathy), hypertension-induced nephropathy, alimentary track or gastrointestinal fibrosis, renal fibrosis, hepatic or biliary fibrosis, liver fibrosis (for example, nonalcoholic steatohepatitis, hepatitis C, or hepatocellular carcinoma), cirrhosis (for example, primary biliary cirrhosis or cirrhosis due to fatty liver disease (for example, alcoholic and nonalcoholic steatosis)), radiation-induced fibrosis (for example, head and neck, gastrointestinal or pulmonary), primary sclerosing cholangitis, restenosis, cardiac fibrosis (for example, endomyocardial fibrosis or atrial fibrosis), ophthalmic scarring, fibrosclerosis, fibrotic cancers, fibroids, fibroma, fibroadenomas, fibrosarcomas, transplant arteriopathy, keloid, mediastinal fibrosis, myelofibrosis, retroperitoneal fibrosis, progressive massive fibrosis, and nephrogenic systemic fibrosis.

In some embodiments, the MK2-mediated disease or disorder is a metabolic disorder. Exemplary metabolic disorders include obesity, steroid-resistance, glucose intolerance, and metabolic syndrome.

In some embodiments, the MK2-mediated disease or disorder is a neoplastic disease or disorder. Exemplary neoplastic diseases or disorders include cancers. In some embodiments, exemplary neoplastic diseases or disorders include angiogenesis disorders, multiple myeloma, leukemias (for example, acute lymphocytic leukemia, acute and chronic myelogenous leukemia, chronic lymphocytic leukemia, acute lymphoblastic leukemia, or promyelocytic leukemia), lymphomas (for example, B-cell lymphoma, T-cell lymphoma, mantle cell lymphoma, hairy cell lymphoma, Burkitt's lymphoma, mast cell tumors, Hodgkin's disease or non-Hodgkin's disease), myelodysplastic syndrome, fibrosarcoma, rhabdomyosarcoma; astrocytoma, neuroblastoma, glioma and schwannomas; melanoma, seminoma, teratocarcinoma, osteosarcoma, xenoderma pigmentosum, keratoctanthoma, thyroid follicular cancer, Kaposi's sarcoma, melanoma, teratoma, rhabdomyosarcoma, metastatic and bone disorders, as well as cancer of the bone, mouth/pharynx, esophagus, larynx, stomach, intestine, colon, rectum, lung (for example, non-small cell lung cancer or small cell lung cancer), liver, pancreas, nerve, brain (for example, glioma or glioblastoma multiforme), head and neck, throat, ovary, uterus, prostate, testis, bladder, kidney, breast, gall bladder, cervix, thyroid, prostate, and skin.

In some embodiments, the MK2-mediated disorder is a cardiovascular or cerebrovascular disorder. Exemplary cardiovascular disorders include atherosclerosis, restenosis of an atherosclerotic coronary artery, acute coronary syndrome, myocardial infarction, cardiac-allograft vasculopathy and stroke. Exemplary cerebrovascular diseases include central nervous system disorders with an inflammatory or apoptotic component, Alzheimer's disease, Parkinson's disease, Huntington's disease, amyotrophic lateral sclerosis, spinal cord injury, neuronal ischemia, and peripheral neuropathy.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage, or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage, or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the subject every 12 hours; (v) the compound is administered to the subject every 24 hours. In further or alternative embodiments, the method comprises a drug holiday, wherein the administration of the compound is temporarily suspended, or the dose of the compound being administered is temporarily reduced; at the end of the drug holiday, dosing of the compound is resumed. In one embodiment, the length of the drug holiday varies from 2 days to 1 year.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long-acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended-release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal, and topical routes of administration.

In another aspect, provided herein are pharmaceutical compositions comprising a compound described herein, or a pharmaceutically acceptable salt, solvate, stereoisomer, or rotamer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, stereoisomer, or rotamer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, stereoisomer, or rotamer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are methods of treating an autoimmune disorder, a chronic inflammatory disorder, an acute inflammatory disorder, an auto-inflammatory disorder, a fibrotic disorder, a metabolic disorder, a neoplastic disorder, or a cardiovascular or a cerebrovascular disorder using a compound disclosed herein, or a pharmaceutically acceptable salt, solvate, stereoisomer, or rotamer thereof, in combination with an additional therapeutic agent.

In some embodiments, the additional therapeutic agent is selected from the group consisting of anti-inflammatory drugs, anti-atherosclerotic drugs, immunosuppressive drugs, immunomodulatory drugs, cytostatic drugs, anti-proliferative agents, angiogenesis inhibitors, kinase inhibitors, cytokine blockers, and inhibitors of cell adhesion molecules.

In some embodiments, the additional therapeutic agent is selected from the group consisting of NSAIDs, immunosuppressive drugs, immunomodulatory drugs, cytostatic drugs, antiproliferative agents, angiogenesis inhibitors, biological agents, steroids, vitamin D3 analogs, retinoids, other kinase inhibitors, cytokine blockers, corticosteroids, and inhibitors of cell adhesion molecules. In some embodiments, the additional therapeutic agent is selected from the group consisting of torcetrapib, aspirin, niacin, HMG CoA reductase inhibitors (e.g., atorvastatin, fluvastatin, lovastatin, pravastatin, rosuvastatin and simvastatin), colesevelam, cholestyramine, colestipol, gemfibrozil, probucol, and clofibrate.

In some embodiments, the additional therapeutic agent is selected from the group consisting of corticosteroids, non-steroidal anti-inflammatory drugs (NSAID) (e.g. ibuprofen, naproxen, acetaminophen, aspirin, Fenoprofen (Nalfon), Flurbiprofen (Ansaid), Ketoprofen, Oxaprozin (Daypro), Diclofenac sodium (Voltaren), Diclofenac potassium (Cataflam), Etodolac (Lodine), Indomethacin (Indocin), Ketorolac (Toradol), Sulindac (Clinoril), Tolmetin (Tolectin), Meclofenamate (Meclomen), Mefenamic acid (Ponstel), Nabumetone (Relafen), Piroxicam (Feldene), cox-2 inhibitors (e.g., celecoxib (Celebrex))), immunosuppressants (e.g., methotrexate (Rheumatrex), leflunomide (Arava), azathioprine (Imuran), cyclosporine (Neoral, Sandimmune), tacrolimus and cyclophosphamide (Cytoxan), CD20 blockers (Rituximab), Tumor Necrosis Factor (TNF) blockers (e.g., etanercept (Enbrel), infliximab (Remicade) and adalimumab (Humira)), Abatacept (CTLA4-Ig) and interleukin-1 receptor antagonists (e.g. Anakinra (Kineret), interleukin 6 inhibitors (e.g., Actemra), interleukin 17 inhibitors (e.g., AIN457), Janus kinase inhibitors (e.g., Tasocitinib), syk inhibitors (e.g. R788), and chloroquine and its derivatives.

In some embodiments, the additional therapeutic agent is selected from the group consisting of an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-1R antibody, NFkB inhibitor, proteosome inhibitor, chemotherapy agent, and glucose reduction agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

EXAMPLE

Intermediate 1

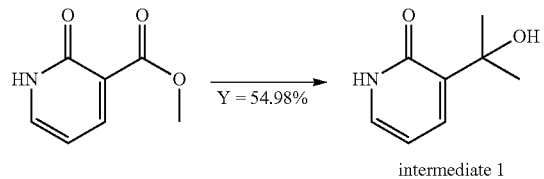

intermediate 1

Step 1: Preparation of
3-(2-hydroxypropan-2-yl)-1H-pyridin-2-one

To a stirred solution of methyl 2-oxo-1H-pyridine-3-carboxylate (2 g, 13.060 mmol, 1.00 equiv) in THF (20 mL)

was added MeMgBr in THF (32.65 mL, 65.300 mmol, 5.00 equiv) dropwise at 0° C. under nitrogen atmosphere. The resulting mixture was stirred for 2 h at room temperature under nitrogen atmosphere. The reaction was quenched with saturated NH₄Cl (aq.) (40 mL) at room temperature. The resulting mixture was extracted with EtOAc (3×20 mL). The combined organic layers were washed with brine (30 mL), dried over anhydrous Na₂SO₄. After filtration, the filtrate was concentrated under reduced pressure. The residue was purified by silica gel column chromatography to afford 3-(2-hydroxypropan-2-yl)-1H-pyridin-2-one (1.1 g, 54.98%) as a white solid. LC-MS: (ES+H, m/z): [M+H]⁺=154.1.

Intermediate 2-4

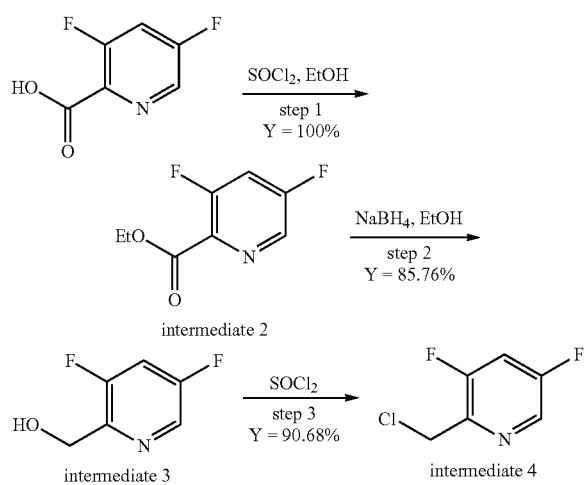

Step 1: Preparation of ethyl 3,5-difluoropicolinate

A solution of 3,5-difluoropyridine-2-carboxylic acid (50.00 g, 314.28 mmol, 1.00 equiv) in ethanol (200 ml) was cooled using an ice bath, followed by the addition of SOCl₂ (50 mL, 689.25 mmol, 2.20 equiv) dropwise at 0° C. The resulting mixture was stirred for 3 h at 60° C. under nitrogen atmosphere. The mixture was allowed to r.t. The resulting mixture was concentrated under vacuum. The residue was purified by silica gel column chromatography to afford ethyl 3,5-difluoropicolinate (59 g, 100%) as a colorless liquid. LC-MS: (ES+H, m/z): [M+H]⁺=188.1.

Step 2: Preparation of (3,5-difluoropyridin-2-yl)methanol

To a stirred solution of ethyl 3,5-difluoropyridine-2-carboxylate (40.00 g, 213.74 mmol, 1.00 equiv) in ethanol (300 ml) was added NaBH₄ (20.22 g, 534.34 mmol, 2.50 equiv) in portions at 0° C. under nitrogen atmosphere. The resulting mixture was stirred for 30 min at 0° C. under nitrogen atmosphere. The resulting mixture was stirred for additional 2 h at room temperature under nitrogen atmosphere. The reaction was quenched with sat. NH₄Cl (aq.) at 0° C. EtOH was removed under reduced pressure. The aqueous layer was basified to pH 10 with saturated Na₂CO₃ (aq., 300 mL), followed by extracted with EtOAc (3×300 mL). The combined organic layers were washed with brine, dried over anhydrous Na₂SO₄. After filtration, the filtrate was concentrated under vacuum to afford (3,5-difluoropyridin-2-yl)methanol (26.6 g, 85.76%) as a colorless liquid. LC-MS: (ES+H, m/z): [M+H]⁺=146.1.

Step 3: Preparation of 2-(chloromethyl)-3,5-difluoropyridine

To a stirred solution of (3,5-difluoropyridin-2-yl)methanol (34.00 g, 234.31 mmol, 1.00 equiv) in DCM (500 mL) was added DMF (160 mg), and then cooled using ice water bath. To the above mixture was added SOCl₂ (40 mL, 551.40 mmol, 2.35 equiv) dropwise under nitrogen atmosphere. The resulting mixture was stirred for 2 h at room temperature under nitrogen atmosphere. The resulting mixture was concentrated under vacuum to afford 2-(chloromethyl)-3,5-difluoropyridine (34.75 g, 90.68%) as a brown-yellow semi-solid. LC-MS: (ES+H, m/z): [M+H]⁺=164.0. ¹H NMR (400 MHz, Chloroform-d) δ 8.35 (d, 1H), 7.28 (td, 1H), 4.73 (d, 2H).

Intermediate 5-8

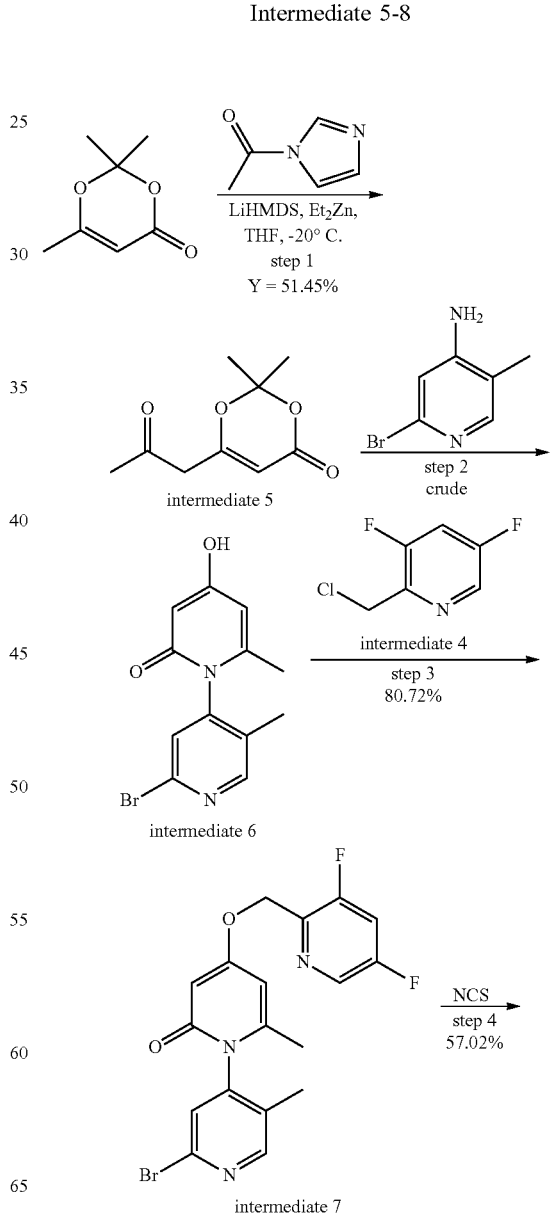

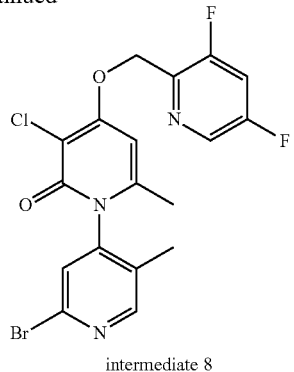

intermediate 8

Step 1: Preparation of 2,2-dimethyl-6-(2-oxopropyl)-1,3-dioxin-4-one

A solution of LiHMDS (3.16 L, 3.16 mol, 1.50 equiv, 1M in THF) in THF (1000 mL) was treated with 2,2,6-trimethyl-1,3-dioxin-4-one (300 g, 2.11 mol, 1.00 equiv) for 1 h at −20° C. under nitrogen atmosphere followed by the addition of ZnEt$_2$ (3.16 L, 3.16 mol, 1.50 equiv, 1M in hexane) dropwise over 2 h at −20° C. The resulting mixture was stirred for 30 min at −20° C. under nitrogen atmosphere. To the above mixture was added acetylimidazole (348.58 g, 3.16 mol, 1.50 equiv) at −10° C. The resulting mixture was stirred for additional overnight at room temperature. The reaction was quenched by the addition of 1 L Water/THF (1:1) at −10° C. The mixture was acidified to pH 1-2 with 2M HCl (aq.). The resulting mixture was extracted with EtOAc (3×5 L). The combined organic layers were washed with brine (3×5 L), dried over anhydrous Na$_2$SO$_4$. After filtration, the filtrate was concentrated under reduced pressure. The residue was purified by silica gel column chromatography to afford 2,2-dimethyl-6-(2-oxopropyl)-1,3-dioxin-4-one (200 g, 51.45%) as a Brown yellow crystal. LC-MS: (ES+H, m/z): [M+H]$^+$=185.0. $^1$H NMR (400 MHz, DMSO-d$_6$) δ 5.35 (s, 1H), 3.35 (s, 2H), 2.25 (s, 3H), 1.72 (d, 6H).

Step 2: Preparation of 2'-bromo-4-hydroxy-5',6-dimethyl-[1,4'-bipyridin]-2-one A mixture of 2,2-dimethyl-6-(2-oxopropyl)-1,3-dioxin-4-one (22.16 g, 120.296 mmol, 1.5 equiv) and 2-bromo-5-methylpyridin-4-amine (15 g, 80.197 mmol, 1.00 equiv) in 1,4-dioxane (200 mL) was stirred for 2 h at 90° C., to the above mixture was added H$_2$SO$_4$ (7.87 g, 80.197 mmol, 1 equiv) dropwise at room temperature under air atmosphere. The resulting mixture was stirred for additional 1 h at 90° C. The resulting mixture was concentrated under reduced pressure. To the resulting mixture was added H$_2$O (40 mL) and the slurry was stirred for 10 min. The precipitated solids were collected by filtration and washed with Et$_2$O (3×10 mL), then dried under vacuum to afford 2'-bromo-4-hydroxy-5',6-dimethyl-[1,4'-bipyridin]-2-one (22.7 g, crude) as a yellow solid. The crude resulting mixture was used in the next step directly without further purification. LC-MS: (ES+H, m/z): [M+H]$^+$=294.9.

Step 3: 2'-chloro-4-[(4-methoxyphenyl)methoxy]-5',6-dimethyl-[1,4'-bipyridin]-2-one To a stirred mixture of 2'-bromo-4-hydroxy-5',6-dimethyl-[1,4'-bipyridin]-2-one (42.00 g, 142.307 mmol, 1 equiv) and 2-(chloromethyl)-3,5-difluoropyridine (46.55 g, 284.614 mmol, 2 equiv) in DMF (450 mL) were added K$_2$CO$_3$ (98.34 g, 711.535 mmol, 5.00 equiv) and 18-Crown-6(3.76 g, 14.231 mmol, 0.10 equiv) at room temperature under nitrogen atmosphere. The resulting mixture was stirred for 2 h at 60° C. under nitrogen atmosphere. Desired product could be detected by LCMS. The reaction mixture was partitioned between EA (1000 mL) and water (500 mL). The organic layer was washed with water (500 mL) and brine (500 mL), and then dried over Na$_2$SO$_4$. The solution was concentrated under reduced pressure. The residue was purified by silica gel column chromatography to afford 2'-bromo-4-[(3,5-difluoropyridin-2-yl)methoxy]-5',6-dimethyl-[1,4'-bipyridin]-2-one (48.5 g, 80.72%) as a yellow oil. LC-MS: (ES+H, m/z): [M+H]$^+$=424.0.

Step 4: Preparation of 2'-bromo-3-chloro-4-[(3,5-difluoropyridin-2-yl)methoxy]-5',6-dimethyl-[1,4'-bipyridin]-2-one To a stirred mixture of 2'-bromo-4-[(3,5-difluoropyridin-2-yl)methoxy]-5',6-dimethyl-[1,4'-bipyridin]-2-one (12 g, 28.421 mmol, 1 equiv) and NCS (3.79 g, 28.421 mmol, 1 equiv) in 2-Propanol (21 mL) were added 2,2-dichloroacetic acid (1.2 mL, 2.870 mmol, 0.10 equiv) dropwise at room temperature under nitrogen atmosphere. The resulting mixture was stirred for 2 h at 60° C. under nitrogen atmosphere. The precipitated solids were collected by filtration and washed with 2-propanol to afford 2'-bromo-3-chloro-4-[(3,5-difluoropyridin-2-yl)methoxy]-5',6-dimethyl-[1,4'-bipyridin]-2-one (7.40 g, 57.02%) as a white solid. LC-MS: (ES+H, m/z): [M+H]$^+$=457.9. $^1$H NMR (300 MHz, DMSO-d$_6$) δ 8.60 (d, J=2.4 Hz, 1H), 8.52 (s, 1H), 8.10 (ddd, J=10.0, 8.9, 2.4 Hz, 1H), 7.81 (s, 1H), 6.80 (s, 1H), 5.48 (d, J=2.0 Hz, 2H), 1.98-1.94 (m, 6H).

Intermediate 9-11

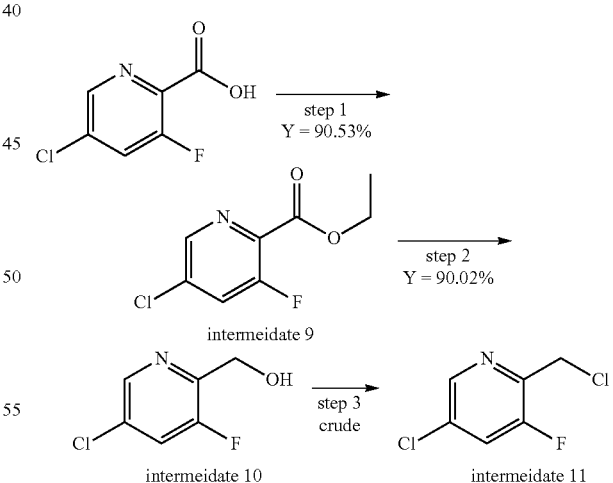

Step 1: Preparation of ethyl 5-chloro-3-fluoropyridine-2-carboxylate

A solution of 5-chloro-3-fluoropyridine-2-carboxylic acid (2.00 g, 11.39 mmol, 1.00 equiv) in EtOH (4 mL) was cooled using an ice bath, followed by the addition of H$_2$SO$_4$ (2.00 mL) dropwise at 0° C. The resulting mixture was stirred overnight at 50° C. under nitrogen atmosphere. The mixture was allowed to r.t. The resulting mixture was diluted with H₂O (10 mL). The mixture was basified to pH 9 with Na₂CO₃. The resulting mixture was extracted with EA (3×50 mL). The combined organic layers were washed with brine (2×50 mL), dried over anhydrous Na₂SO₄. After filtration, the filtrate was concentrated under reduced pressure to afford ethyl 5-chloro-3-fluoropyridine-2-carboxylate (2.10 g, 90.53%) as a yellow liquid. LC-MS: (ES+H, m/z): [M+H]⁺=204.1.

Step 2: Preparation of (5-chloro-3-fluoropyridin-2-yl)methanol

To a stirred solution of ethyl 5-chloro-3-fluoropyridine-2-carboxylate (2.10 g, 10.31 mmol, 1.00 equiv) in EtOH (4 mL) was added NaBH₄ (0.98 g, 25.90 mmol, 2.51 equiv) in portions at 0° C. under nitrogen atmosphere. The resulting mixture was stirred for 30 min at 0° C. under nitrogen atmosphere. The resulting mixture was stirred for additional 2 h at room temperature under nitrogen atmosphere. The reaction was quenched with sat. NH₄Cl (aq.) at 0° C. EtOH was removed under reduced pressure. The aqueous layer was basified to pH 10 with saturated Na₂CO₃ (aq.), followed by extracted with EA (3×100 mL). The combined organic layers were washed with brine, dried over anhydrous Na₂SO₄. After filtration, the filtrate was concentrated under vacuum to afford (5-chloro-3-fluoropyridin-2-yl)methanol (1.50 g, 90.02%) as a yellow solid. LC-MS: (ES+H, m/z): [M+H]⁺=162.1.

Step 3: Preparation of 5-chloro-2-(chloromethyl)-3-fluoropyridine

To a stirred solution of (5-chloro-3-fluoropyridin-2-yl)methanol (1.45 g, 8.97 mmol, 1.00 equiv) in DCM (2 mL) was added DMF (0.66 g, 8.97 mmol, 1.00 equiv), and then cooled using ice water bath. To the above mixture was added SOCl₂ (1.00 mL, 13.78 mmol, 1.54 equiv) dropwise under nitrogen atmosphere. The resulting mixture was stirred for 2 h at room temperature under nitrogen atmosphere. The resulting mixture was concentrated under vacuum to afford 5-chloro-2-(chloromethyl)-3-fluoropyridine (2.00 g, crude) as a brown yellow semi-solid. The crude product was used in the next step directly without further purification. LC-MS: (ES+H, m/z): [M+H]⁺=180.1.

Intermediate 12-14

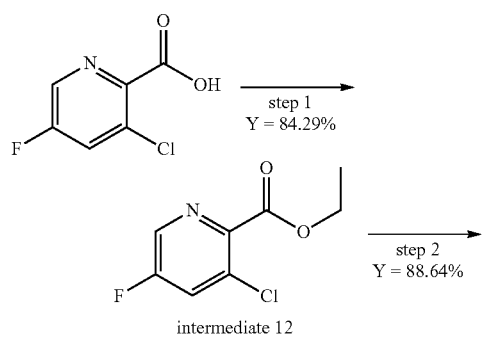

intermediate 12

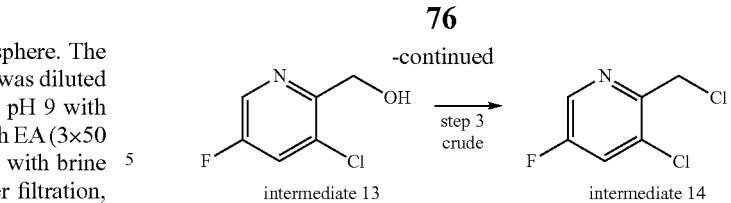

Step 1: Preparation of ethyl 3-chloro-5-fluoropyridine-2-carboxylate

A solution of 3-chloro-5-fluoropyridine-2-carboxylic acid (4.50 g, 25.63 mmol, 1.00 equiv) in EtOH (100 mL) was cooled with an ice bath. To the above mixture was added SOCl₂ (6.13 g, 51.53 mmol, 2.01 equiv) dropwise over 3 min at 0° C. The resulting mixture was stirred for additional 3 h at room temperature. The mixture was allowed to r.t. The resulting mixture was concentrated under vacuum. The residue was purified by silica gel column chromatography to afford ethyl 3-chloro-5-fluoropyridine-2-carboxylate (4.40 g, 84.29%) as a colorless liquid. LC-MS: (ES+H, m/z): [M+H]⁺=203.9.

Step 2: Preparation of (3-chloro-5-fluoropyridin-2-yl)methanol

To a stirred solution of ethyl 3-chloro-5-fluoropyridine-2-carboxylate (2.10 g, 10.31 mmol, 1.00 equiv) in EtOH (30 mL) was added NaBH₄ (0.98 g, 25.90 mmol, 2.51 equiv) in portions at 0° C. under nitrogen atmosphere. The resulting mixture was stirred for 30 min at 0° C. under nitrogen atmosphere. The resulting mixture was stirred for additional 2 h at room temperature under nitrogen atmosphere. The reaction was quenched with sat. NH₄Cl (aq.) at 0° C. The resulting mixture was concentrated under reduced pressure to remove EtOH, then extracted with EA (3×30 mL). The combined organic layers were washed with brine, dried over anhydrous Na₂SO₄. After filtration, the filtrate was concentrated under vacuum to afford (3-chloro-5-fluoropyridin-2-yl)methanol (2 g, 95.24%) as a yellow oil. LC-MS: (ES+H, m/z): [M+H]⁺=162.0.

Step 3: Preparation of 3-chloro-2-(chloromethyl)-5-fluoropyridine

To a stirred solution of (3-chloro-5-fluoropyridin-2-yl)methanol (2.10 g, 12.99 mmol, 1.00 equiv) in DCM (30 mL) was added DMF (0.1 mL, 1.30 mmol, 0.10 equiv) at 0 under nitrogen atmosphere. The SOCl₂ (2.3 mL, 32.49 mmol, 2.50 equiv) was added dropwise under nitrogen atmosphere. The resulting mixture was stirred for 2 h at room temperature. The resulting mixture was concentrated under vacuum, to afford 3-chloro-2-(chloromethyl)-5-fluoropyridine (2.00 g, crude) as a brown yellow oil. The crude product was used in the next step directly without further purification. LC-MS: (ES+H, m/z): [M+H]⁺=179.90.

Intermediate 15-18

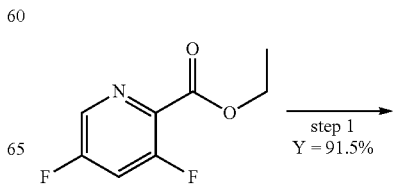

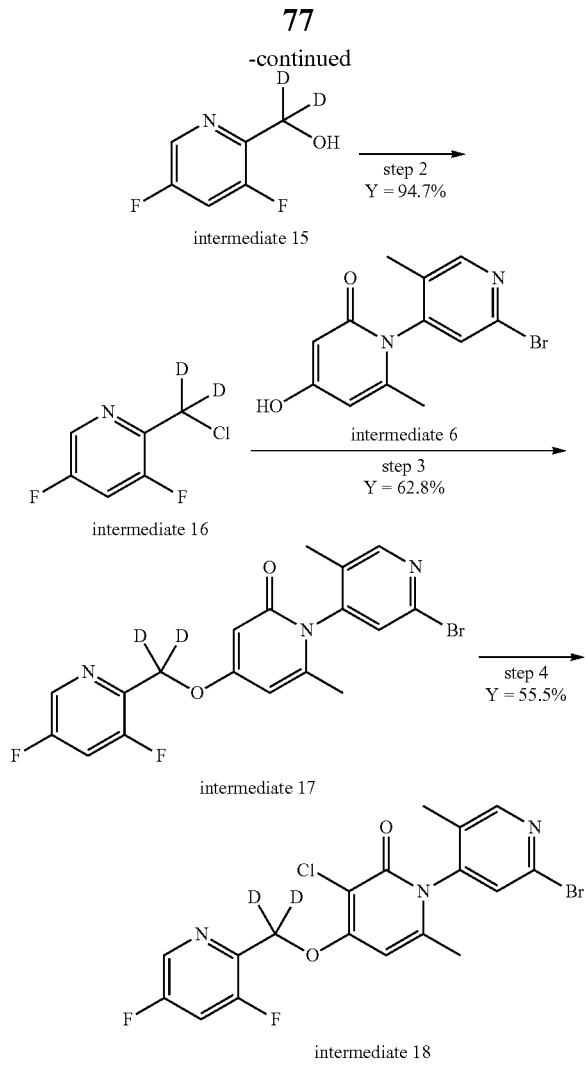

Step 1: Preparation of (3,5-difluoropyridin-2-yl)methan-d2-ol

To a stirred solution of ethyl 5-chloro-3-fluoropyridine-2-carboxylate (500.00 g, 2671.71 mmol, 1.00 equiv) in $CD_3OD$ (500 mL) and THF (1000 mL) was added sodium (H)boranuide (111.84 g, 2671.71 mmol, 1.00 equiv) in portions at 0° C. under nitrogen air. The resulting mixture was stirred for 2 hours at room temperature under nitrogen atmosphere. The resulting mixture was quenched by the addition of $D_2O$ (200 mL) at 0° C. and stirred for 30 min at 0° C. The mixture was diluted with EtOAc (2000 mL) and washed with water (2000 ml) and brine (2000 ml). The organic layers were dried over anhydrous $Na_2SO_4$. After filtration, the filtrate was concentrated under reduced pressure, to afford (3,5-difluoropyridin-2-yl)methan-d2-ol methanol (360.00 g, 91.5%) as a yellow oil. LC-MS: (ES+H, m/z): [M+H]$^+$=148.1. $^1$H NMR (300 MHz, DMSO-d$_6$) δ 8.44 (d, 1H), 7.88 (ddd, 1H), 5.37 (s, 1H).

Step 2: Preparation of 2-(chloromethyl-d2)-3,5-difluoropyridine

To a stirred solution of (3,5-difluoropyridin-2-yl)methan-d2-ol (300.00 g, 2039.13 mmol, 1.00 equiv) in DCM (1000 mL) was added DMF (14.91 g, 203.91 mmol, 0.10 equiv) and $SOCl_2$ (606.44 g, 5097.84 mmol, 2.50 equiv) dropwise under nitrogen atmosphere at 0. The resulting mixture was stirred for 2 h at room temperature under nitrogen atmosphere. The resulting mixture was concentrated under vacuum to afford 2-(chloromethyl-d2)-3,5-difluoropyridine (320.00 g, 94.7%) as a yellow oil which was used directly in next step without further purification. LC-MS: (ES+H, m/z): [M+H]$^+$=166.1. $^1$H NMR (300 MHz, DMSO-d$_6$) δ 8.48 (d, 1H), 8.04-7.93 (m, 1H).

Step 3: Preparation of 2'-bromo-4-((3,5-difluoropyridin-2-yl)methoxy-d2)-5',6-dimethyl-2H-[1,4'-bipyridin]-2-one To a stirred mixture of 2'-bromo-4-hydroxy-5',6-dimethyl-[1,4'-bipyridin]-2-one (100.00 g, 338.82 mmol, 1.00 equiv), 18-Crown-6 (5.37 g, 3.00 mmol, 0.40 equiv) and $K_2CO_3$ (42.14 g, 304.94 mmol, 3.00 equiv) in DMF (200 mL) was added 2-(chloromethyl-d2)-3,5-difluoropyridine (27.75 g, 152.47 mmol, 1.50 equiv) at r.t. The resulting mixture was stirred for 2.5 h at 60° C. under nitrogen atmosphere. The resulting mixture was filtered, the filter cake was washed with EtOAc (3×500 mL). The filtrate was diluted with EA (3000 mL). The resulting mixture was washed with brine (3×2000 mL) and water (5×2000 mL). The organic layer was dried over anhydrous $Na_2SO_4$. After filtration, the filtrate was concentrated under reduced pressure. The residue was purified by trituration with $Et_2O$ (3×250 ml) and dried under reduced pressure to afford 2'-bromo-4-((3,5-difluoropyridin-2-yl)methoxy-d2)-5',6-dimethyl-2H-[1,4'-bipyridin]-2-one (90 g, 62.8%) as a white solid. LC-MS: (ES+H, m/z): [M+H]$^+$=424.0. $^1$H NMR (300 MHz, DMSO-d$_6$) δ 8.59 (d, 1H), 8.48 (s, 1H), 8.08 (ddd, 1H), 7.73 (s, 1H), 6.13 (dd, 1H), 6.03 (d, 1H), 1.97 (s, 3H), 1.85 (s, 3H).

Step 4: Preparation of 2'-bromo-3-chloro-4-((3,5-difluoropyridin-2-yl)methoxy-d2)-5',6-dimethyl-2H-[1,4'-bipyridin]-2-one To a stirred solution of 2'-bromo-4-((3,5-difluoropyridin-2-yl)methoxy-d2)-5',6-dimethyl-2H-[1,4'-bipyridin]-2-one (100.00 g, 235.71 mmol, 1.00 equiv) and NCS (37.77 g, 282.85 mmol, 1.20 equiv) in IPA (500 mL) was added 2,2-dichloroacetic acid (3.04 g, 23.57 mmol, 0.10 equiv) dropwise at room temperature. The resulting mixture was stirred for 1 h at 60° C. under nitrogen atmosphere. The mixture was allowed to cool down to r.t. The precipitated solids were collected by filtration and washed with cold IPA (4×30 mL), to afford 2'-bromo-3-chloro-4-((3,5-difluoropyridin-2-yl)methoxy-d2)-5',6-dimethyl-2H-[1,4'-bipyridin]-2-one (60.00 g, 55.5%) as a white solid. LC-MS: (ES+H, m/z): [M+H]$^+$=458.0. $^1$H NMR 300 MHz, DMSO-d$_6$) δ 8.60 (d, 1H), 8.52 (s, 1H), 8.10 (ddd, 1H), 7.81 (s, 1H), 6.80 (d, 1H), 1.96 (s, 6H).

Intermediate 19

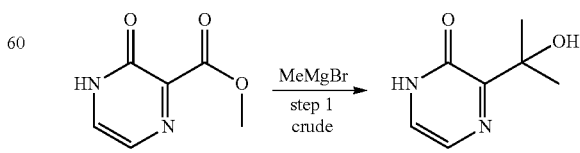

intermediate 19

Step 1: Preparation of 3-(2-hydroxypropan-2-yl)-1H-pyrazin-2-one

To a stirred solution of methyl 3-oxo-4H-pyrazine-2-carboxylate (500 mg, 3.24 mmol, 1.00 equiv) in THF (30 mL) was added bromo(methyl)magnesium (32 mL, 32.44 mmol, 10.00 equiv) dropwise at −5° C. under N2 atmosphere. The resulting mixture was stirred for 2 h at r.t. under $N_2$ atmosphere. The reaction was quenched by the addition of saturated $NH_4Cl$ (10 mL) at 0° C. The resulting mixture was extracted with EtOAc (3×50 mL). The combined organic layers were washed with brine, dried over anhydrous $Na_2SO_4$. After filtration, the filtrate was concentrated under reduced pressure to afford 3-(2-hydroxypropan-2-yl)-1H-pyrazin-2-one (350 mg, crude) as a yellow solid. LC-MS: (ES+H, m/z): [M+H]$^+$=155.3.

Intermediate 20-23

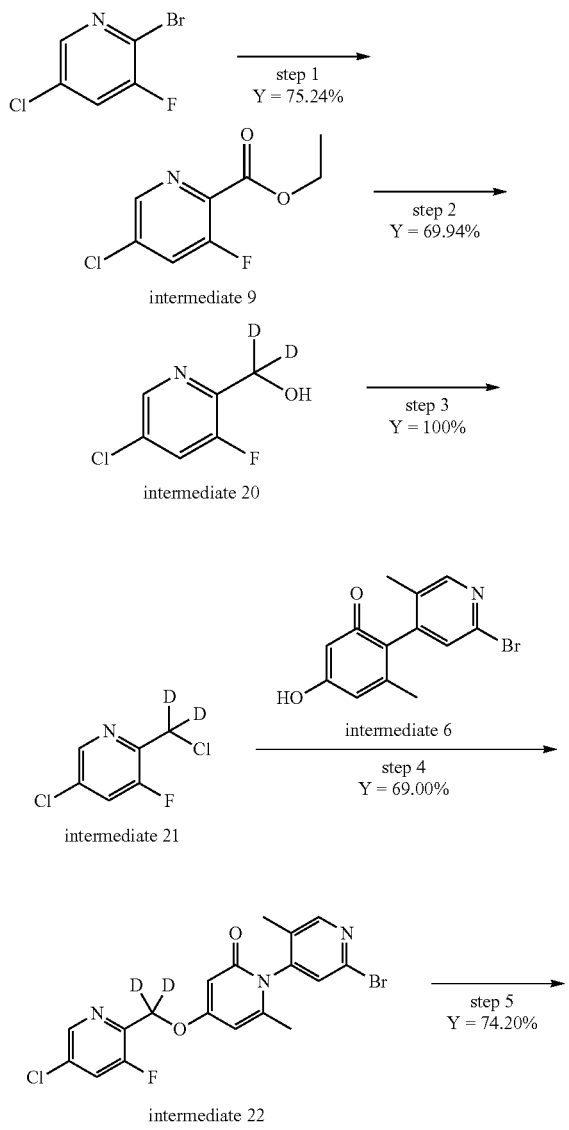

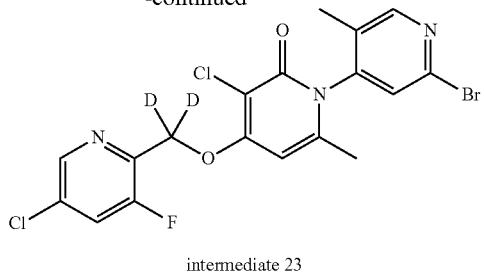

intermediate 23

Step 1: Preparation of ethyl 5-chloro-3-fluoropyridine-2-carboxylate

To a stirred mixture of 2-bromo-5-chloro-3-fluoropyridine (50.00 g, 237.60 mmol, 1.00 equiv) and Pd(dppf)Cl$_2$ (8.69 g, 11.88 mmol, 0.05 equiv) in EtOH (250 ml) were added NEt$_3$ (72.13 g, 712.82 mmol, 3.00 equiv) at room temperature. The resulting mixture was stirred for 6 h at 80° C. under carbon monoxide atmosphere (50 atm). The mixture was allowed to room temperature. The resulting mixture was concentrated under reduced pressure. The residue was purified by silica gel column chromatography to afford ethyl 5-chloro-3-fluoropyridine-2-carboxylate (36.40 g, 75.24%) as a yellow green liquid. LC-MS: (ES+H, m/z): [M+H]$^+$=204.2. $^1$H NMR (300 MHz, DMSO-d$_6$) δ 8.63 (dd, 1H), 8.24 (dd, 1H), 4.36 (q, 2H), 1.32 (t, 3H).

Step 2: Preparation of 5-chloro-3-fluoropyridin-2-yl)(2H2)methanol

To a stirred solution of ethyl 5-chloro-3-fluoropyridine-2-carboxylate (42.00 g, 206.28 mmol, 1.00 equiv) and CaCl$_2$ (68.68 g, 618.85 mmol, 3.00 equiv) in solution of CD$_3$OD (200 mL) and THF (400 mL) were added sodium borodeuteride (17.27 g, 412.57 mmol, 2.00 equiv) in portions at 0° C. under nitrogen atmosphere. The resulting mixture was stirred for 3 h at room temperature under nitrogen atmosphere. The resulting mixture was diluted with EtOAc (500 mL). Diatomaceous earth (100 g) was added to the reaction solvent and the resulting mixture was stirred for 10 min. The resulting mixture was filtered, the filter cake was washed with EtOAc (3×1 L). The filtrate was quenched by the addition of D$_2$O (35 mL) at 0° C. And washed with brine (2×500 ml). The organic layers were dried over anhydrous Na$_2$SO$_4$. After filtration, the filtrate was concentrated under reduced pressure. To afford (5-chloro-3-fluoropyridin-2-yl)(2H2)methanol (23.60 g, 69.94%) as a white solid. LC-MS: (ES+H, m/z): [M+H]$^+$=164.2. $^1$H NMR (300 MHz, DMSO-d$_6$) δ 8.48 (dd, 1H), 8.06 (dd, 1H), 5.41 (s, 1H).

Step 3: Preparation of 5-chloro-2-[chloro($^2$H2)methyl]-3-fluoropyridine

To a stirred solution of (5-chloro-3-fluoropyridin-2-yl)(2H2)methanol (23.60 g, 144.28 mmol, 1.00 equiv) and DMF (1.05 g, 14.42 mmol, 0.10 equiv) in DCM (200 mL) were added SOCl$_2$ (42.91 g, 360.70 mmol, 2.50 equiv) dropwise at 0° C. under nitrogen atmosphere. The resulting mixture was stirred for 2 h at room temperature under nitrogen atmosphere. The resulting mixture was concentrated under vacuum. To afford 5-chloro-2-[chloro(2H2)methyl]-3-fluoropyridine (26.30 g, 100%) as a brown oil.

LC-MS: (ES+H, m/z): [M+H]⁺=182.1. ¹H NMR (300 MHz, DMSO-d₆) δ 8.53 (dd, 1H), 8.18 (dd, 1H).

Step 4: Preparation of 2'-bromo-4-[(5-chloro-3-fluoropyridin-2-yl)(2H2)methoxy]-5',6-dimethyl-[1,4'-bipyridin]-2-one To a stirred mixture of 2'-bromo-4-hydroxy-5',6-dimethyl-[1,4'-bipyridin]-2-one (30.00 g, 101.64 mmol, 1.00 equiv), 5-chloro-2-[chloro(2H2)methyl]-3-fluoropyridine (27.75 g, 152.47 mmol, 1.50 equiv), 18-Crown-6 (5.37 g, 20.33 mmol, 0.20 equiv) and K₂CO₃ (42.14 g, 304.94 mmol, 3.00 equiv) in DMF (200 mL). The resulting mixture was stirred for 2.5 h at 60° C. under nitrogen atmosphere. The mixture was allowed to room temperature. The resulting mixture was diluted with EA (2 L). The resulting mixture was washed with water (5×100 mL), and brine (500 mL). The organic layer dried over anhydrous Na₂SO₄. After filtration, the filtrate was concentrated under reduced pressure. The residue was purified by silica gel column chromatography to afford 2'-bromo-4-[(5-chloro-3-fluoropyridin-2-yl)(2H2)methoxy]-5',6-dimethyl-[1,4'-bipyridin]-2-one (30.91 g, 69.00%) as a white solid. LC-MS: (ES+H, m/z): [M+H]⁺=440.1/442.1. ¹H NMR (400 MHz, DMSO-d₆) δ 8.60 (dd, 1H), 8.47 (s, 1H), 8.22 (dd, 1H), 7.72 (s, 1H), 6.13 (s, 1H), 6.01 (d, 1H), 1.96 (s, 3H), 1.85 (s, 3H).

Step 5: Preparation of 2'-bromo-3-chloro-4-[(5-chloro-3-fluoropyridin-2-yl)(2H2)methoxy]-5',6-dimethyl-[1,4'-bipyridin]-2-one To a stirred solution of 2'-bromo-4-[(5-chloro-3-fluoropyridin-2-yl)(2H2)methoxy]-5',6-dimethyl-[1,4'-bipyridin]-2-one (30.00 g, 68.07 mmol, 1.00 equiv) and NCS (10.91 g, 81.69 mmol, 1.20 equiv) in IPA (200 mL) was added 2,2-dichloroacetic acid (0.88 g, 6.80 mmol, 0.10 equiv) dropwise at room temperature under air atmosphere. The resulting mixture was stirred for 1 h at 60° C. under nitrogen atmosphere. The mixture was allowed to cool down to 0° C. The precipitated solids were collected by filtration and washed with cold IPA (3×20 mL). To afford 2'-bromo-3-chloro-4-[(5-chloro-3-fluoropyridin-2-yl)(2H2)methoxy]-5',6-dimethyl-[1,4'-bipyridin]-2-one (24.00 g, 74.20%) as a white solid. LC-MS: (ES+H, m/z): [M+H]⁺=474.0/476.0. ¹H NMR (400 MHz, DMSO-d₆) δ 8.60 (dd, 1H), 8.52 (s, 1H), 8.23 (dd, 1H), 7.80 (s, 1H), 6.78 (d, 1H), 1.97 (s, 3H), 1.96 (s, 3H).

Intermediate 24-27

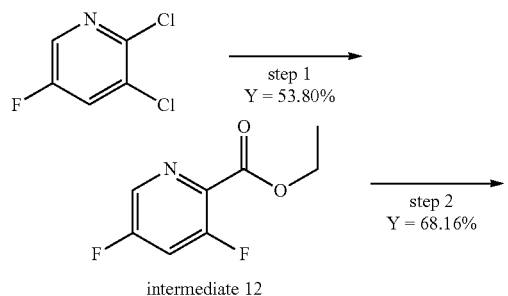

intermediate 12

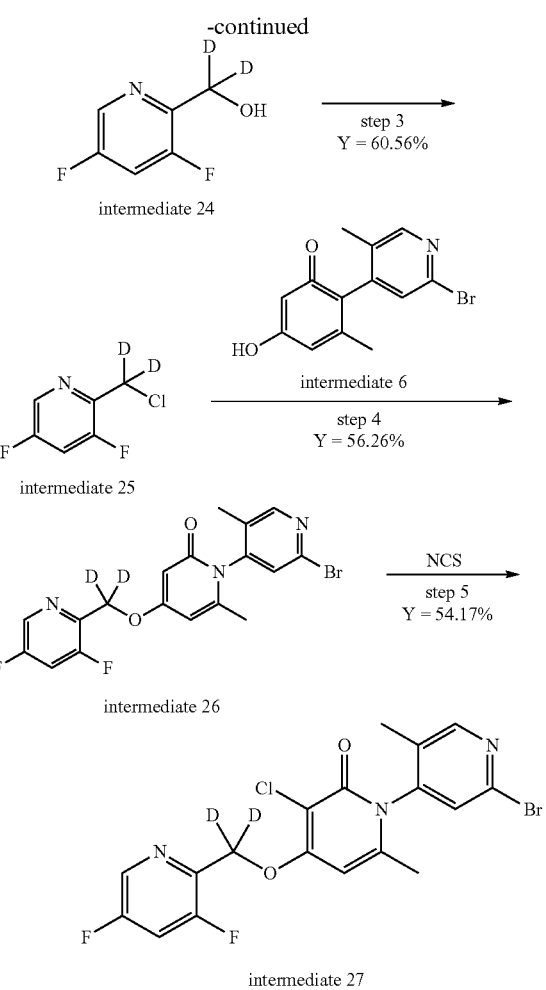

Step 1: Preparation of ethyl 3-chloro-5-fluoropyridine-2-carboxylate

To a stirred mixture of 2,3-dichloro-5-fluoropyridine (50.00 g, 301.24 mmol, 1.00 equiv) and Pd(dppf)Cl₂ (4.41 g, 6.02 mmol, 0.02 equiv) in EtOH (250 ml) were added Et₃N (72.13 g, 712.82 mmol, 3.00 equiv) dropwise at room temperature. The resulting mixture was stirred for 18 h at 100° C. under carbon monoxide atmosphere (50 atm). The mixture was allowed to room temperature. The resulting mixture was concentrated under reduced pressure. The residue was purified by silica gel column chromatography to afford ethyl 3-chloro-5-fluoropyridine-2-carboxylate (33.00 g, 53.80%) as a colorless liquid. LC-MS: (ES+H, m/z): [M+H]⁺=204.0. ¹H NMR (400 MHz, DMSO-d₆) δ 8.70 (d, 1H), 8.29 (dd, 1H), 4.42 (q, 2H), 1.36 (t, 3H).

Step 2: Preparation of (3-chloro-5-fluoropyridin-2-yl)methan-d2-ol

To a stirred solution of ethyl 3-chloro-5-fluoropyridine-2-carboxylate (84.00 g, 412.57 mmol, 1.00 equiv) and CaCl₂ (91.57 g, 825.14 mmol, 2.00 equiv) in solution of CD₃OD (500 mL) and THF (500 mL) were added Sodium borodeuteride (51.81 g, 1237.72 mmol, 3.00 equiv) in portions at 0° C. under nitrogen atmosphere. The resulting mixture was stirred for 2 h at r.t. under nitrogen atmosphere. The resulting mixture was diluted with EtOAc (500 mL). Diatomaceous earth (100 g) was added to the reaction solvent. The resulting mixture was filtered, the filter cake was washed with EtOAc (3×1 L). The filtrate was quenched by the addition of D₂O (50 mL) at 0° C. and washed with brine (500 ml). The organic layers were dried over anhydrous Na₂SO₄. After filtration, the filtrate was concentrated under reduced pressure, to afford (3-chloro-5-fluoropyridin-2-yl)methan-d2-ol (46.00 g, 68.16%) as a colorless liquid. LC-MS: (ES+H, m/z): [M+H]⁺=164.0. ¹H NMR (300 MHz, DMSO-d₆) δ 8.53 (d, 1H), 8.01 (dd, 1H), 5.22 (br, 1H).

Step 3: Preparation of 3-chloro-2-(chloromethyl-d2)-5-fluoropyridine

To a stirred solution of (3-chloro-5-fluoropyridin-2-yl) methan-d2-ol (46.00 g, 281.22 mmol, 1.00 equiv) and DMF (2.18 mL, 28.12 mmol, 0.1 equiv) in DCM (200 mL) were added SOCl₂ (40.80 mL, 562.45 mmol, 2.00 equiv) dropwise at 0° C. under nitrogen atmosphere. The resulting mixture was stirred for 2 h at r.t. under nitrogen atmosphere. The resulting mixture was concentrated under vacuum to afford 3-chloro-2-(chloromethyl-d2)-5-fluoropyridine (31.00 g, 60.56%) as a brown yellow liquid. LC-MS: (ES+H, m/z): [M+H]⁺=182.0. ¹H NMR (300 MHz, DMSO-d₆) δ 8.59 (d, 1H), 8.16 (dd, 1H).

Step 4: Preparation of 2'-bromo-4-((3-chloro-5-fluoropyridin-2-yl)methoxy-d2)-5',6-dimethyl-2H-[1,4'-bipyridin]-2-one To a stirred mixture of 2'-bromo-4-hydroxy-5',6-dimethyl-[1,4'-bipyridin]-2-one (25.00 g, 84.70 mmol, 1.00 equiv), 18-Crown-6 (4.48 g, 16.94 mmol, 0.2 equiv) and K₂CO₃ (58.53 g, 423.53 mmol, 5.00 equiv) in DMF (250 mL) was added 3-chloro-2-(chloromethyl-d2)-5-fluoropyridine (30.84 g, 169.41 mmol, 2.00 equiv) at r.t. The resulting mixture was stirred for 2 h at 60° C. under nitrogen atmosphere. The mixture was allowed to room temperature. The resulting mixture was diluted with EA (2000 mL). The resulting mixture was washed with brine (5×500 mL). The organic layer dried over anhydrous Na₂SO₄. After filtration, the filtrate was concentrated under reduced pressure. The residue was purified by silica gel column chromatography to afford 2'-bromo-4-((3-chloro-5-fluoropyridin-2-yl)methoxy-d2)-5',6-dimethyl-2H-[1,4'-bipyridin]-2-one (30.00 g, 56.26%) as a white solid. LC-MS: (ES+H, m/z): [M+H]⁺=440.0. ¹H NMR (300 MHz, DMSO-d₆) δ 8.67 (d, 1H), 8.48 (s, 1H), 8.23 (dd, 1H), 7.73 (s, 1H), 6.14 (dd, 1H), 6.01 (d, 1H), 1.97 (s, 3H), 1.86 (s, 3H).

Step 5: Preparation of 2'-bromo-3-chloro-4-((3-chloro-5-fluoropyridin-2-yl)methoxy-d2)-5',6-dimethyl-2H-[1,4'-bipyridin]-2-one To a stirred solution of 2'-bromo-4-((3-chloro-5-fluoropyridin-2-yl)methoxy-d2)-5',6-dimethyl-2H-[1,4'-bipyridin]-2-one (30.00 g, 68.07 mmol, 1.00 equiv) and NCS (11.82 g, 88.49 mmol, 1.30 equiv) in IPA (300 mL) was added 2,2-dichloroacetic acid (0.88 g, 6.80 mmol, 0.10 equiv) dropwise at room temperature. The resulting mixture was stirred for 1 h at 60° C. under nitrogen atmosphere. The mixture was allowed to cool down to r.t. The precipitated solids were collected by filtration and washed with cold IPA (3×40 mL), to afford 2'-bromo-3-chloro-4-((3-chloro-5-fluoropyridin-2-yl)methoxy-d2)-5',6-dimethyl-2H-[1,4'-bipyridin]-2-one (17.52 g, 54.17%) as a white solid. LC-MS: (ES+H, m/z): [M+H]⁺=476.05. ¹H NMR (300 MHz, DMSO-d₆) δ 8.68 (d, 1H), 8.55-8.50 (m, 1H), 8.25 (dd, 1H), 7.81 (s, intel H), 6.77 (d, 1H), 1.97 (s, 3H), 1.95 (s, 3H).

Example 1A, 1B

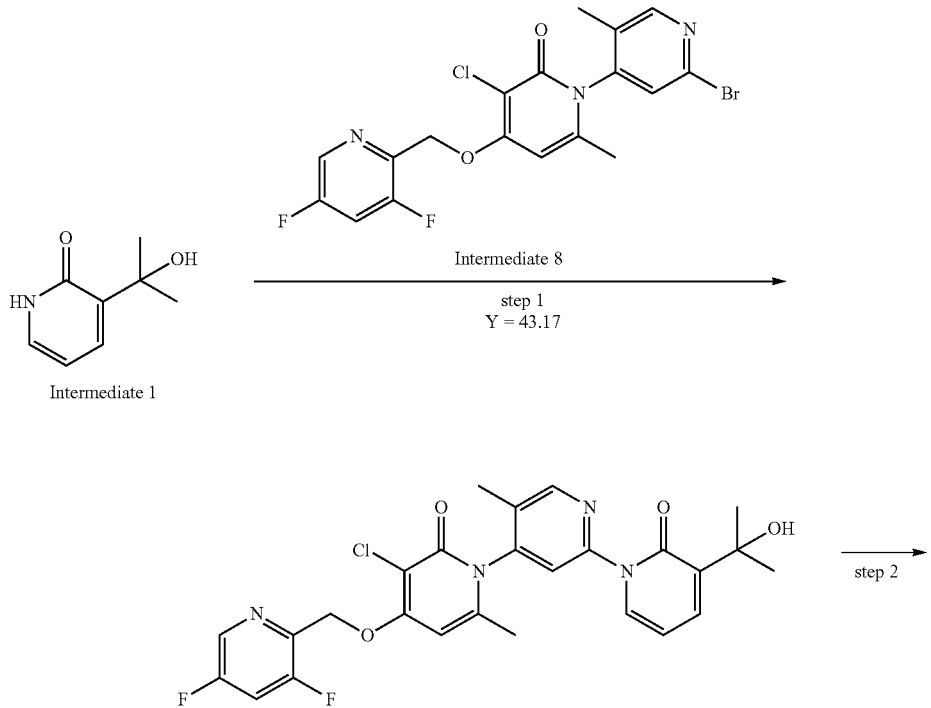

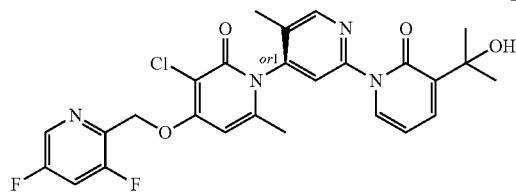

Example 1A

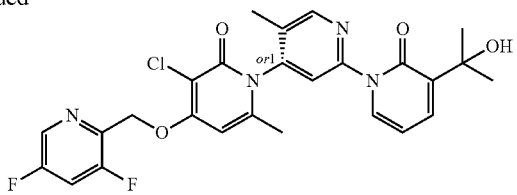

Example 1B

Step 1: Preparation of 3-chloro-4-[(3,5-difluoropyridin-2-yl)methoxy]-2'-[3-(2-hydroxypropan-2-yl)-2-oxopyridin-1-yl]-5',6-dimethyl-[1,4'-bipyridin]-2-one To a stirred mixture of 2'-bromo-3-chloro-4-[(3,5-difluoropyridin-2-yl)methoxy]-5',6-dimethyl-[1,4'-bipyridin]-2-one (500 mg, 1.095 mmol, 1 equiv), (1R,2R)—N1,N2-dimethylcyclohexane-1,2-diamine (311.49 mg, 2.190 mmol, 2 equiv) and CuI (417.04 mg, 2.190 mmol, 2 equiv) in dioxane (20 mL) were added $K_2CO_3$ (302.64 mg, 2.190 mmol, 2 equiv) at room temperature under nitrogen atmosphere. The resulting mixture was stirred for overnight at 80° C. under nitrogen atmosphere. The mixture was allowed to cool down to room temperature. The reaction was quenched with saturating $NH_4Cl$ (aq.) (50 mL) at room temperature. The resulting mixture was extracted with EtOAc (3×25 mL). The combined organic layers were washed with brine (40 mL), dried over anhydrous $Na_2SO_4$. After filtration, the filtrate was concentrated under reduced pressure. The residue was purified by silica gel column chromatography to afford 3-chloro-4-[(3,5-difluoropyridin-2-yl)methoxy]-2'-[3-(2-hydroxypropan-2-yl)-2-oxopyridin-1-yl]-5',6-dimethyl-[1,4'-bipyridin]-2-one (250 mg, 43.17%) as a white solid. LC-MS: (ES+H, m/z): [M+H]$^+$ =529.1. $^1$H NMR (300 MHz, DMSO-$d_6$) δ 8.69 (s, 1H), 8.60 (d, 1H), 8.64-8.00 (m, 1H), 7.86 (d, 1H), 7.79 (s, 1H), 7.69 (s, 1H), 6.81 (s, 1H), 6.43 (t, 1H), 5.48 (s, 2H), 5.23 (s, 1H), 2.08 (s, 3H), 2.01 (s, 3H), 1.47 (d, 6H).

Step 2: Preparation of rel-3-chloro-4-[(3,5-difluoropyridin-2-yl)methoxy]-2'-[3-(2-hydroxypropan-2-yl)-2-oxopyridin-1-yl]-5',6-dimethyl-[1,4'-bipyridin]-2-one and rel-3-chloro-4-[(3,5-difluoropyridin-2-yl)methoxy]-2'-[3-(2-hydroxypropan-2-yl)-2-oxopyridin-1-yl]-5',6-dimethyl-[1,4'-bipyridin]-2-one 3-chloro-4-[(3,5-difluoropyridin-2-yl)methoxy]-2'-[3-(2-hydroxypropan-2-yl)-2-oxopyridin-1-yl]-5',6-dimethyl-[1,4'-bipyridin]-2-one (250 mg, 0.473 mmol, 1 equiv) was separated by Prep-HPLC to afford rel-3-chloro-4-[(3,5-difluoropyridin-2-yl)methoxy]-2'-[3-(2-hydroxypropan-2-yl)-2-oxopyridin-1-yl]-5',6-dimethyl-[1,4'-bipyridin]-2-one (Example 1A, 48.0 mg, 97.6%, ee=100.0%) and rel-3-chloro-4-[(3,5-difluoropyridin-2-yl)methoxy]-2'-[3-(2-hydroxypropan-2-yl)-2-oxopyridin-1-yl]-5',6-dimethyl-[1,4'-bipyridin]-2-one (Example 1B, 51.4 mg, 98.7%, ee=99.6%) as a white solid.

Example 1A: LC-MS: (ES+H, m/z): [M+H]$^+$=529.00. $^1$H NMR (300 MHz, DMSO-$d_6$) δ 8.69 (s, 1H), 8.61 (d, 1H), 8.17-8.03 (m, 1H), 7.86 (m, 1H), 7.79 (s, 1H), 7.70 (m, 1H), 6.81 (m, 1H), 6.43 (t, 1H), 5.48 (d, 2H), 5.23 (s, 1H), 2.08 (s, 3H), 2.01 (s, 3H), 1.47 (S, 3H), 1.46 (S, 3H). $^{19}$F NMR (377 MHz, DMSO-$d_6$) δ−120.16, −120.18, −122.36, −122.38. [a]$_D^{25}$=−171 (C=1, MeOH).

Example 1B: LC-MS: (ES+H, m/z): [M+H]$^+$=529.10. $^1$H NMR (400 MHz, DMSO-$d_6$) δ 8.68 (s, 1H), 8.60 (d, 1H), 8.09 (m, 1H), 7.85 (m, 1H), 7.78 (s, 1H), 7.69 (m, 1H), 6.82-6.77 (m, 1H), 6.42 (t, 1H), 5.48 (d, 2H), 5.22 (s, 1H), 2.07 (s, 3H), 2.01 (s, 3H), 1.47 (S, 3H), 1.46 (S, 3H). $^{19}$F NMR (377 MHz, DMSO-$d_6$) δ−120.16, −120.18, −122.35, −122.37. [a]$_D^{25}$=+174.8 (C=1, MeOH).

Example 2A, 2B

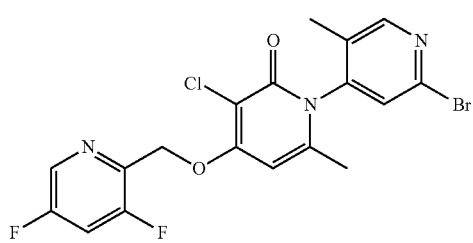

Intermediate 8

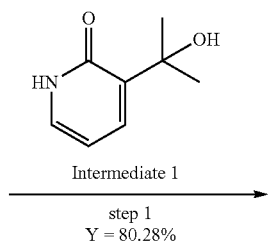

Intermediate 1 step 1
Y = 80.28%

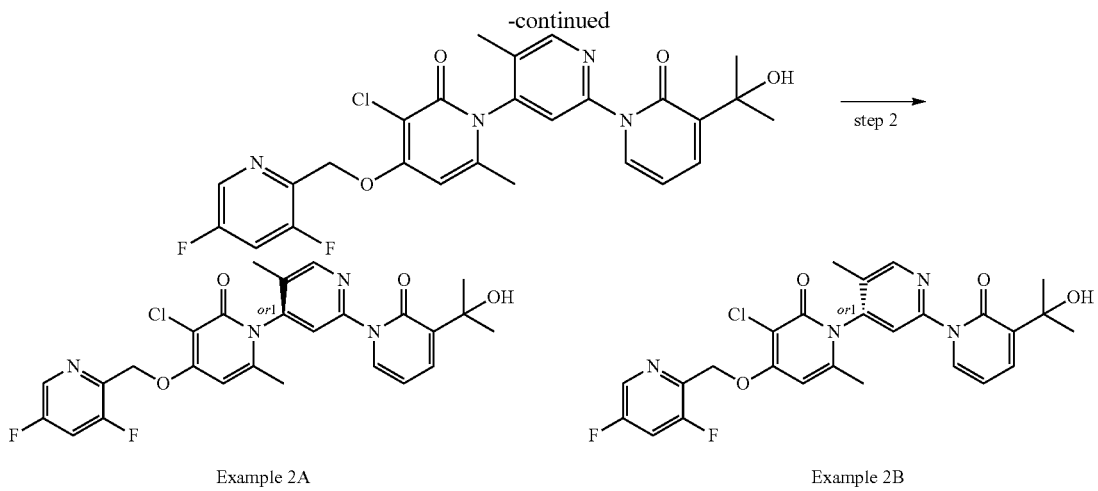

Example 2A

Example 2B

Step 1: Preparation of 3-chloro-4-[(3,5-difluoropyridin-2-yl)methoxy]-1-{5-[3-(2-hydroxypropan-2-yl)-2-oxopyridin-1-yl]-2-methylphenyl}-6-methylpyridin-2-one To a stirred mixture of 1-(5-bromo-2-methylphenyl)-3-chloro-4-[(3,5-difluoropyridin-2-yl)methoxy]-6-methylpyridin-2-one (300 mg, 0.65 mmol, 1.00 equiv), 3-(2-hydroxypropan-2-yl)-1H-pyridin-2-one (200 mg, 1.31 mmol, 2.00 equiv), CuI (250.77 mg, 1.31 mmol, 2.00 equiv) and (1R,2R)-1-N,2-N-dimethylcyclohexane-1,2-diamine (187.29 mg, 1.31 mmol, 2.00 equiv) in 1,4-dioxane (5 mL) was added $K_2CO_3$ (181.98 mg, 1.31 mmol, 2.00 equiv) at room temperature under nitrogen atmosphere. The resulting mixture was stirred for 3 h at 80° C. under nitrogen atmosphere. The mixture was allowed to cool down to room temperature. The reaction was quenched with sat. $NH_4Cl$ (aq.) (50 mL) at room temperature. The resulting mixture was extracted with EtOAc (2×25 mL). The combined organic layers were washed with brine (30 mL), dried over anhydrous $Na_2SO_4$. After filtration, the filtrate was concentrated under reduced pressure. The residue was purified by reverse combi-flash chromatography to afford 3-chloro-4-[(3,5-difluoropyridin-2-yl)methoxy]-1-{5-[3-(2-hydroxypropan-2-yl)-2-oxopyridin-1-yl]-2-methylphenyl}-6-methylpyridin-2-one (140 mg, 40.28%) as alight yellow solid. LC-MS: (ES+H, m z): [M+H]$^+$=528.1. $^1$H NMR (400 MHz, DMSO-$d_6$) δ 8.59 (d, 1H), 8.12-8.06 (m, 1H), 7.66-7.64 (m, 1H), 7.63-7.60 (m, 1H), 7.54 (d, 1H), 7.48-7.44 (m, 1H), 7.37 (d, 1H), 6.77-6.72 (m, 1H), 6.39-6.34 (m, 1H), 5.46 (d, 2H), 5.29 (s, 1H), 2.03 (s, 3H), 2.16 (s, 3H), 1.46 (s, 6H).

Step 5: Preparation of rel-3-chloro-4-[(3,5-difluoropyridin-2-yl)methoxy]-1-{5-[3-(2-hydroxypropan-2-yl)-2-oxopyridin-1-yl]-2-methylphenyl}-6-methylpyridin-2-one and rel-3-chloro-4-[(3,5-difluoropyridin-2-yl)methoxy]-1-{5-[3-(2-hydroxypropan-2-yl)-2-oxopyridin-1-yl]-2-methylphenyl}-6-methylpyridin-2-one The race-mixture (140 mg) was separated by Prep-HPLC to afford rel-3-chloro-4-[(3,5-difluoropyridin-2-yl)methoxy]-1-{5-[3-(2-hydroxypropan-2-yl)-2-oxopyridin-1-yl]-2-methylphenyl}-6-methylpyridin-2-one (Example 2A, 68.7 mg, ee=100.00%) as alight yellow solid. and rel-3-chloro-4-[(3,5-difluoropyridin-2-yl)methoxy]-1-{5-[3-(2-hydroxypropan-2-yl)-2-oxopyridin-1-yl]-2-methylphenyl}-6-methylpyridin-2-one (Example 2B, 38.8 mg, ee=100.00%) as alight yellow solid.

Example 2A: LC-MS: (ES+H, m z): [M+H]$^+$=528.25. $^1$H NMR (300 MHz, DMSO-$d_6$) δ 8.60 (d, 1H), 8.15-8.05 (m, 1H), 7.70-7.60 (m, 2H), 7.55 (d, 1H), 7.49-7.44 (m, 1H), 7.38 (d, 1H), 6.75 (s, 1H), 6.40-6.34 (m, 1H), 5.47 (d, 2H), 5.30 (s, 1H), 2.03 (s, 3H), 2.16 (s, 3H), 1.47 (s, 3H), 1.46 (s, 3H). $^{19}$F NMR (377 MHz, DMSO-$d_6$) δ−120.15, −120.17, −122.39, −122.41.

Example 2B: LC-MS: (ES+H, m z): [M+H]$^+$=528.25. $^1$H NMR (300 MHz, DMSO-$d_6$) δ 8.60 (d, 1H), 8.15-8.05 (m, 1H), 7.70-7.60 (m, 2H), 7.55 (d, 1H), 7.49-7.44 (m, 1H), 7.38 (d, 1H), 6.75 (s, 1H), 6.40-6.34 (m, 1H), 5.47 (d, 2H), 5.30 (s, 1H), 2.03 (s, 3H), 2.16 (s, 3H), 1.47 (s, 3H), 1.46 (s, 3H). $^{19}$F NMR (377 MHz, DMSO-$d_6$) δ−120.15, −120.17, −122.39, −122.41.

Example 3A, 3B

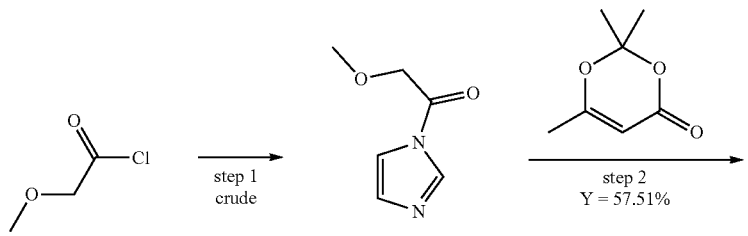

-continued
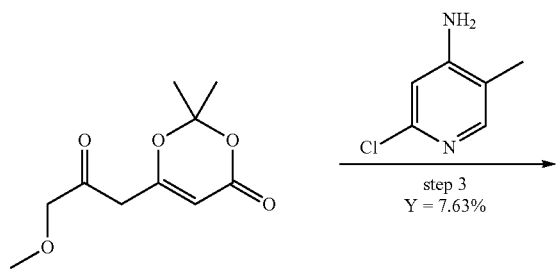
step 3
Y = 7.63%
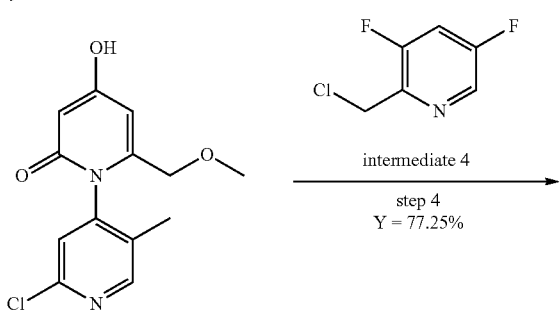
intermediate 4
step 4
Y = 77.25%
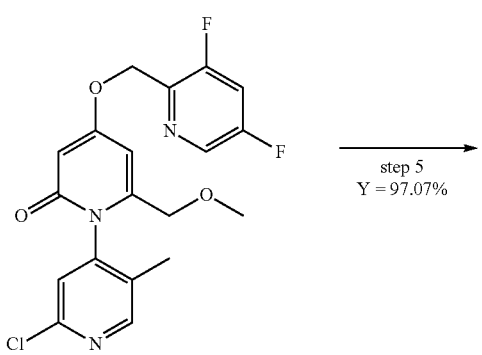
step 5
Y = 97.07%
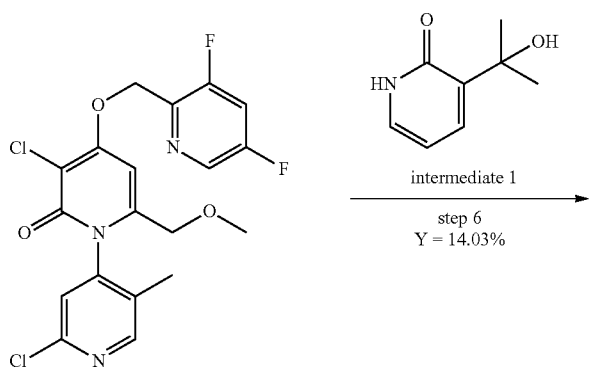
intermediate 1
step 6
Y = 14.03%
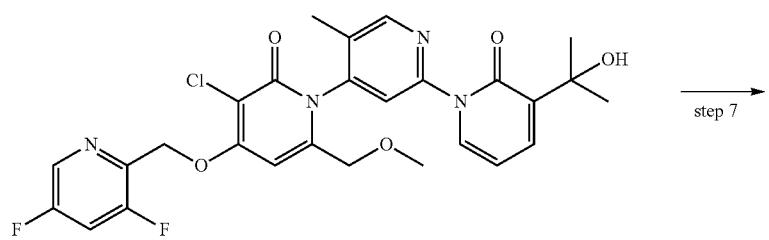
step 7

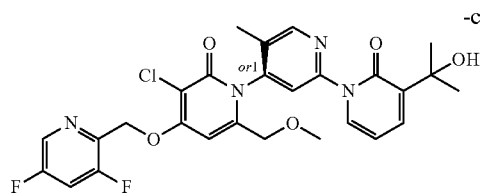

Example 3A

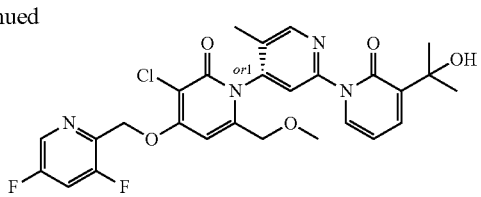

Example 3B

Step 1: Preparation of 1-(imidazol-1-yl)-2-methoxyethanone

To a stirred solution of imidazole (25.09 g, 368.60 mmol, 2.00 equiv) in THF (200 mL) was added methoxyacetyl chloride (20.00 g, 184.30 mmol, 1.00 equiv) dropwise at 0° C. under nitrogen atmosphere. The resulting mixture was stirred for 3 h at 0° C. under nitrogen atmosphere. The reaction was monitored by LCMS. The resulting mixture was filtered, the filter cake was washed with THF (3×50 mL). The filtrate was concentrated under reduced pressure to afford product 1-(imidazol-1-yl)-2-methoxyethanone (16.00 g, 61.95%) as yellow oil. $^1$H NMR (300 MHz, Chloroform-d) δ7.52 (t, 1H), 7.22 (d, 1H), 7.15-7.05 (m, 1H), 4.55 (s, 2H), 3.51 (s, 3H).

Step 2: Preparation of 6-(3-methoxy-2-oxopropyl)-2,2-dimethyl-1,3-dioxin-4-one Into a 1 L 3-necked round-bottom flask were added THF (50 mL) at room temperature, then LiHMDS (56.98 mL, 1M in THF, 56.98 mmol, 1.50 equiv) at −20° C. under nitrogen atmosphere. To the above solution was added 2,2,6-trimethyl-1,3-dioxin-4-one (5.40 g, 37.99 mmol, 1.00 equiv) dropwise at −20° C. under nitrogen atmosphere. The resulting mixture was stirred for 1 h at −20° C. To the stirred mixture was added diethylzinc (56.98 mL, 56.98 mmol, 1.50 equiv) dropwise at −20° C. under nitrogen atmosphere. Slowly raise the temperature of the reaction to −10 and stir for 10 min. 1-(imidazol-1-yl)-2-methoxyethanone (7.99 g, 56.98 mmol, 1.50 equiv) was then added to the above mixture at −10° C. under nitrogen atmosphere. The resulting mixture was stirred for additional 2 h at room temperature. The reaction was quenched by the addition of water (50 mL) at −20° C. The mixture was acidified to pH 6 with HCl (aq.). The resulting mixture was diluted with EtOAc (200 mL). The resulting mixture was washed with brine (200 mL). The organic layers were dried over anhydrous Na$_2$SO$_4$. After filtration, the filtrate was concentrated under reduced pressure. The residue was purified by silica gel column chromatography to afford 6-(3-methoxy-2-oxopropyl)-2,2-dimethyl-1,3-dioxin-4-one (4.68 g, 57.51%) as a yellow liquid. LC-MS: (ES+H, m/z): [M+H]$^+$=215.1. $^1$H NMR (300 MHz, DMSO-d$_6$) δ 5.47 (s, 1H), 4.14 (s, 2H), 3.53 (s, 2H), 3.30 (s, 3H), 1.64 (s, 6H).

Step 3: Preparation of 2'-chloro-4-hydroxy-6-(methoxymethyl)-5'-methyl-[1,4'-bipyridin]-2-one To a stirred mixture of 6-(3-methoxy-2-oxopropyl)-2,2-dimethyl-1,3-dioxin-4-one (4.00 g, 18.67 mmol, 1.00 equiv) in 1,4-dioxane (40 mL) were added 2-chloro-5-methylpyridin-4-amine (2.66 g, 18.67 mmol, 1.00 equiv) at room temperature under nitrogen atmosphere. The resulting mixture was stirred for 3 h at 90° C. under nitrogen atmosphere. The resulting mixture were added H$_2$SO$_4$ (1.83 g, 18.67 mmol, 1.00 equiv) dropwise at room temperature under nitrogen atmosphere. The resulting mixture was stirred for 1 h at 90° C. under nitrogen atmosphere. Desired product could be detected. The mixture was allowed to cool down to room temperature. To the above mixture was added H$_2$O (3 mL), followed by addition of a large amount of ethyl ether and then stirred for 15 min at room temperature, The precipitated solids were collected by filtration and washed with diethyl ether. The resulting mixture was concentrated under reduced pressure to afford 2'-chloro-4-hydroxy-6-(methoxymethyl)-5'-methyl-[1,4'-bipyridin]-2-one (400 mg, 7.63%) as a white solid. LC-MS: (ES+H, m/z): [M+H]$^+$=281.2.

Step 4: Preparation of 2'-chloro-4-[(3,5-difluoropyridin-2-yl)methoxy]-6-(methoxymethyl)-5'-methyl-[1,4'-bipyridin]-2-one To a stirred mixture of 2'-chloro-4-hydroxy-6-(methoxymethyl)-5'-methyl-[1,4'-bipyridin]-2-one (417 mg, 1.49 mmol, 1.00 equiv) and 2-(chloromethyl)-3,5-difluoropyridine (486 mg, 2.92 mmol, 2.00 equiv) in DMF (5 mL) were added K$_2$CO$_3$ (1.02 g, 7.43 mmol, 5.00 equiv) and 18-Crown-6(39 mg, 0.15 mmol, 0.10 equiv) at room temperature under nitrogen atmosphere. The resulting mixture was stirred for 2 h at 60° C. under nitrogen atmosphere. The resulting mixture was diluted with EtOAc (50 mL). The resulting mixture was washed with brine (50 mL). The organic layers were dried over anhydrous Na$_2$SO$_4$. After filtration, the filtrate was concentrated under reduced pressure. The residue was purified by silica gel column chromatography to afford 2'-chloro-4-[(3,5-difluoropyridin-2-yl)methoxy]-6-(methoxymethyl)-5'-methyl-[1,4'-bipyridin]-2-one (468 mg, 77.25%) as a white solid. LC-MS: (ES+H, m/z): [M+H]$^+$=408.0.

Step 5: Preparation of 2',3-dichloro-4-[(3,5-difluoropyridin-2-yl)methoxy]-6-(methoxymethyl)-5'-methyl-[1,4'-bipyridin]-2-one To a stirred mixture of 2'-chloro-4-[(3,5-difluoropyridin-2-yl)methoxy]-6-(methoxymethyl)-5'-methyl-[1,4'-bipyridin]-2-one (418 mg, 1.03 mmol, 1.00 equiv) and NCS (137 mg, 1.03 mmol, 1.00 equiv) in 2-Propanol (2 mL) was added 2,2-dichloroacetic acid (0.01 mL, 0.10 mmol, 0.10 equiv) dropwise at room temperature under nitrogen atmosphere. The resulting mixture was stirred for 2 h at 60° C. under nitrogen atmosphere. Desired product could be detected by LCMS. The resulting mixture was diluted with EtOAc (50 mL). The resulting mixture was washed with NaHCO$_3$ (50 mL). The organic layers were dried over anhydrous Na$_2$SO$_4$. After filtration, the filtrate was concentrated under reduced pressure to afford 2',3-dichloro-4-[(3,5-difluoropyridin-2-yl)

methoxy]-6-(methoxymethyl)-5'-methyl-[1,4'-bipyridin]-2-one (440 mg, 97.07%) as a white solid. LC-MS: (ES+H, m/z): [M+H]⁺=441.9.

Step 6: Preparation of 3-chloro-4-[(3,5-difluoropyridin-2-yl)methoxy]-2'-[3-(2-hydroxypropan-2-yl)-2-oxopyridin-1-yl]-6-(methoxymethyl)-5'-methyl-[1,4'-bipyridin]-2-one To a stirred mixture of 2',3-dichloro-4-[(3,5-difluoropyridin-2-yl)methoxy]-6-(methoxymethyl)-5'-methyl-[1,4'-bipyridin]-2-one (450 mg, 1.02 mmol, 1.00 equiv) and 3-(2-hydroxypropan-2-yl)-1H-pyridin-2-one (312 mg, 2.04 mmol, 2.00 equiv) in 1,4-dioxane (4 mL) were added K₂CO₃ (281 mg, 2.04 mmol, 2.00 equiv), CuI (388 mg, 2.04 mmol, 2.00 equiv), NaI (305 mg, 2.04 mmol, 2.00 equiv) and (1S,2S)—N1,N2-dimethylcyclohexane-1,2-diamine (289 mg, 2.04 mmol, 2.00 equiv) at room temperature under nitrogen atmosphere. The resulting mixture was stirred overnight at 100° C. under nitrogen atmosphere. The resulting mixture was diluted with EtOAc (50 mL). The resulting mixture was washed with water (3×50 mL). The organic layers were dried over anhydrous Na₂SO₄. After filtration, the filtrate was concentrated under reduced pressure to afford the crude product (230 mg), which was purified by Prep-HPLC to afford 3-chloro-4-[(3,5-difluoropyridin-2-yl)methoxy]-2'-[3-(2-hydroxypropan-2-yl)-2-oxopyridin-1-yl]-6-(methoxymethyl)-5'-methyl-[1,4'-bipyridin]-2-one (130 mg, 22.86%) as a white solid. LC-MS: (ES+H, m/z): [M+H]⁺=559.2.

Step 7: Preparation of rel-3-chloro-4-[(3,5-difluoropyridin-2-yl)methoxy]-2'-[3-(2-hydroxypropan-2-yl)-2-oxopyridin-1-yl]-6-(methoxymethyl)-5'-methyl-[1,4'-bipyridin]-2-one and rel-3-chloro-4-[(3,5-difluoropyridin-2-yl)methoxy]-2'-[3-(2-hydroxypropan-2-yl)-2-oxopyridin-1-yl]-6-(methoxymethyl)-5'-methyl-[1,4'-bipyridin]-2-one The racemate (130 mg) was separated by Prep-Chiral-HPLC to afford Example 3A (47.1 mg, 99.1%, ee=100%) as a white solid and Example 3B (45.1 mg, 99.1%, ee=97.24%) as a white solid.

Example 3A: LC-MS: (ES+H, m/z): [M+H]⁺=559.1. ¹H NMR (300 MHz, DMSO-d6) δ 8.65 (s, 1H), 8.60 (d, 1H), 8.14-8.06 (m, 1H), 7.87-7.82 (m, 1H), 7.79 (s, 1H), 7.72-7.67 (m, 1H), 6.87 (s, 1H), 6.42 (t, 1H), 5.53 (s, 2H), 5.23 (s, 1H), 4.12-3.95 (m, 2H), 3.07 (s, 3H), 2.06 (s, 3H), 1.47 (s, 6H). ¹⁹F NMR (282 MHz, DMSO-d₆) δ−120.09, −120.11, −122.31, −122.35.

Example 3B: LC-MS: (ES+H, m/z): [M+H]⁺=559.1. ¹H NMR (300 MHz, DMSO-d₆) δ 8.65 (s, 1H), 8.60 (d, 1H), 8.14-8.06 (m, 1H), 7.87-7.82 (m, 1H), 7.79 (s, 1H), 7.72-7.67 (m, 1H), 6.87 (s, 1H), 6.42 (t, 1H), 5.53 (s, 3H), 5.23 (s, 1H), 4.12-3.95 (m, 2H), 3.07 (s, 3H), 2.06 (s, 3H), 1.47 (s, 6H). ¹⁹F NMR (282 MHz, DMSO-d₆) δ−120.09, −120.11, −122.31, −122.35.

Example 4A, Example 4B

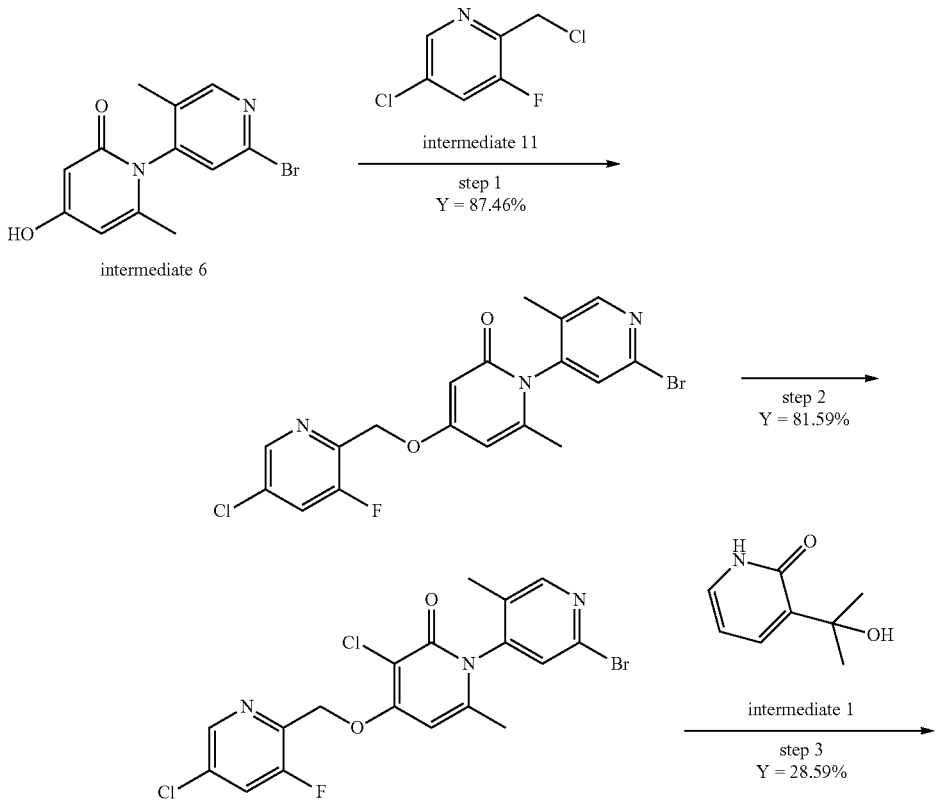

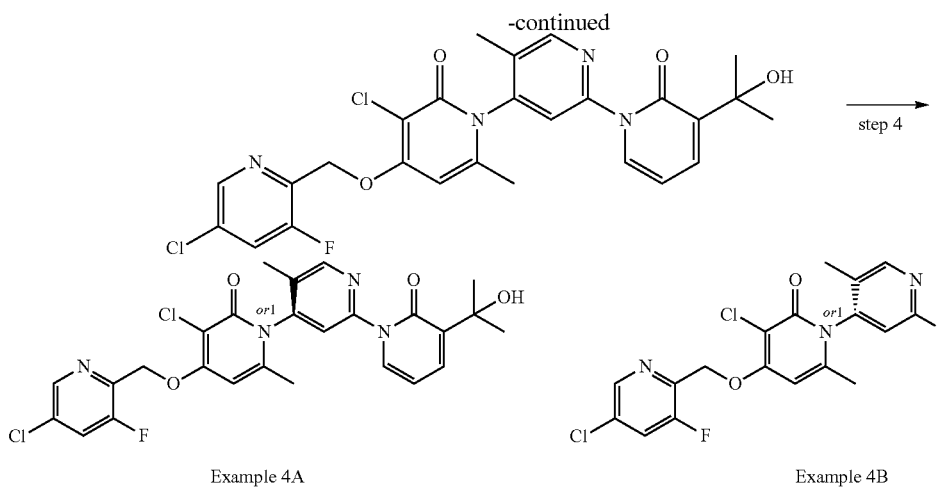

Example 4A

Example 4B

Step 1: Preparation of 2'-bromo-4-[(5-chloro-3-fluoropyridin-2-yl)methoxy]-5',6-dimethyl-[1,4'-bipyridin]-2-one To a stirred solution of 2'-bromo-4-hydroxy-5',6-dimethyl-[1,4'-bipyridin]-2-one (1.00 g, 3.38 mmol, 1.00 equiv) and 5-chloro-2-(chloromethyl)-3-fluoropyridine (914 mg, 5.08 mmol, 1.50 equiv) in DMF (10 mL) were added 18-Crown-6 (89 mg, 0.33 mmol, 0.10 equiv) and $K_2CO_3$ (1.40 g, 10.16 mmol, 3.00 equiv) at room temperature under nitrogen atmosphere. The resulting mixture was stirred overnight at 60° C. under nitrogen atmosphere. The mixture was allowed to cool down to r.t. The reaction was poured into water (50 mL) at room temperature. The resulting mixture was extracted with EtOAc (3×50 mL). The combined organic layers were washed with brine (5×100 mL), dried over anhydrous $Na_2SO_4$. After filtration, the filtrate was concentrated under reduced pressure. The residue was purified by silica gel column chromatography to afford 2'-bromo-4-[(5-chloro-3-fluoropyridin-2-yl)methoxy]-5',6-dimethyl-[1,4'-bipyridin]-2-one (1.30 g, 87.46%) as an off-white solid. LC-MS: (ES+H, m/z): $[M+H]^+$=439.9.

Step 2: Preparation of 2'-bromo-3-chloro-4-[(5-chloro-3-fluoropyridin-2-yl)methoxy]-5',6-dimethyl-[1,4'-bipyridin]-2-one To a stirred solution of 2'-bromo-4-[(5-chloro-3-fluoropyridin-2-yl)methoxy]-5',6-dimethyl-[1,4'-bipyridin]-2-one (500 mg, 1.14 mmol, 1.00 equiv) and NCS (152 mg, 1.00 equiv) in IPA (2.5 mL) was added 2,2-dichloroacetic acid (14 mg, 0.11 mmol, 0.10 equiv) dropwise at room temperature under nitrogen atmosphere. The resulting mixture was stirred for 2 h at 60° C. under nitrogen atmosphere. The mixture was allowed to cool down to r.t. The precipitated solids were collected by filtration and washed with cool IPA (2×10 mL), to afford 2'-bromo-3-chloro-4-[(5-chloro-3-fluoropyridin-2-yl)methoxy]-5',6-dimethyl-[1,4'-bipyridin]-2-one (440 mg, 81.59%) as a white solid. LC-MS: (ES+H, m/z): $[M+H]^+$=473.9.

Step 3: Preparation of 3-chloro-4-[(5-chloro-3-fluoropyridin-2-yl)methoxy]-2'-[3-(2-hydroxypropan-2-yl)-2-oxopyridin-1-yl]-5',6-dimethyl-[1,4'-bipyridin]-2-one A mixture of 2'-bromo-3-chloro-4-[(5-chloro-3-fluoropyridin-2-yl)methoxy]-5',6-dimethyl-[1,4'-bipyridin]-2-one (440 mg, 0.93 mmol, 1.00 equiv), 3-(2-hydroxypropan-2-yl)-1H-pyridin-2-one (285 mg, 1.86 mmol, 2.00 equiv), (1R,2R)—N1,N2-dimethylcyclohexane-1,2-diamine (264 mg, 1.86 mmol, 2.00 equiv), CuI (44 mg, 0.23 mmol, 0.25 equiv) and $K_2CO_3$ (257 mg, 1.86 mmol, 2.00 equiv) in super dry 1,4-dioxane (5 mL) was stirred for 3 h at 100° C. under nitrogen atmosphere. The reaction was poured into water (50 mL) at room temperature. The resulting mixture was extracted with EtOAc (3×50 mL). The combined organic layers were washed with brine (100 mL), dried over anhydrous $Na_2SO_4$. After filtration, the filtrate was concentrated under reduced pressure. The crude product (220 mg) was purified by Prep-HPLC, the pure fraction was concentrated under reduced pressure to afford 3-chloro-4-[(5-chloro-3-fluoropyridin-2-yl)methoxy]-2'-[3-(2-hydroxypropan-2-yl)-2-oxopyridin-1-yl]-5',6-dimethyl-[1,4'-bipyridin]-2-one (145 mg, 28.59%) as an off-white solid. LC-MS: (ES+H, m/z): $[M+H]^+$=544.8.

Step 4: Preparation of rel-3-chloro-4-[(5-chloro-3-fluoropyridin-2-yl)methoxy]-2'-[3-(2-hydroxypropan-2-yl)-2-oxopyridin-1-yl]-5',6-dimethyl-[1,4'-bipyridin]-2-one and rel-3-chloro-4-[(5-chloro-3-fluoropyridin-2-yl)methoxy]-2'-[3-(2-hydroxypropan-2-yl)-2-oxopyridin-1-yl]-5',6-dimethyl-[1,4'-bipyridin]-2-one)

The racemate 3-chloro-4-[(5-chloro-3-fluoropyridin-2-yl)methoxy]-2'-[3-(2-hydroxypropan-2-yl)-2-oxopyridin-1-yl]-5',6-dimethyl-[1,4'-bipyridin]-2-one (190 mg) was separated by prep-chiral-HPLC, the pure fraction was concentrated under vacuum and was lyophilized to afford Example 4A (45.1 mg, 98.6% purity, ee=100%) as an off-white solid and Example 4B (50.0 mg, 98.9% purity, ee=100%) as an off-white solid.

Example 4A: LC-MS: (ES+H, m/z): $[M+H]^+$=545.10. $^1$H NMR (400 MHz, DMSO-$d_6$) δ 8.68 (d, 1H), 8.63-8.60 (m, 1H), 8.27-8.21 (m, 1H), 7.88-7.83 (m, 1H), 7.78 (s, 1H), 7.72-7.68 (m, 1H), 6.81-6.75 (m, 1H), 6.45-6.39 (m, 1H), 5.50 (d, 2H), 5.22 (s, 1H), 2.07 (s, 3H), 1.99 (s, 3H), 1.47 (s, 3H), 1.46 (s, 3H). $^{19}$F NMR (377 MHz, DMSO-$d_6$) δ−121.60.

Example 4B: LC-MS: (ES+H, m/z): $[M+H]^+$=545.10. $^1$H NMR (400 MHz, DMSO-$d_6$) δ 8.68 (d, 1H), 8.62-8.60 (m, 1H), 8.26-8.21 (m, 1H), 7.88-7.83 (m, 1H), 7.78 (s, 1H), 7.72-7.68 (m, 1H), 6.79-6.76 (m, 1H), 6.45-6.40 (m, 1H), 5.50 (d, 2H), 5.22 (s, 1H), 2.07 (s, 3H), 1.99 (s, 3H), 1.47 (s, 3H), 1.46 (s, 3H). $^{19}$F NMR (377 MHz, DMSO-$d_6$) δ−121.60.

Example 5A, Example 5B

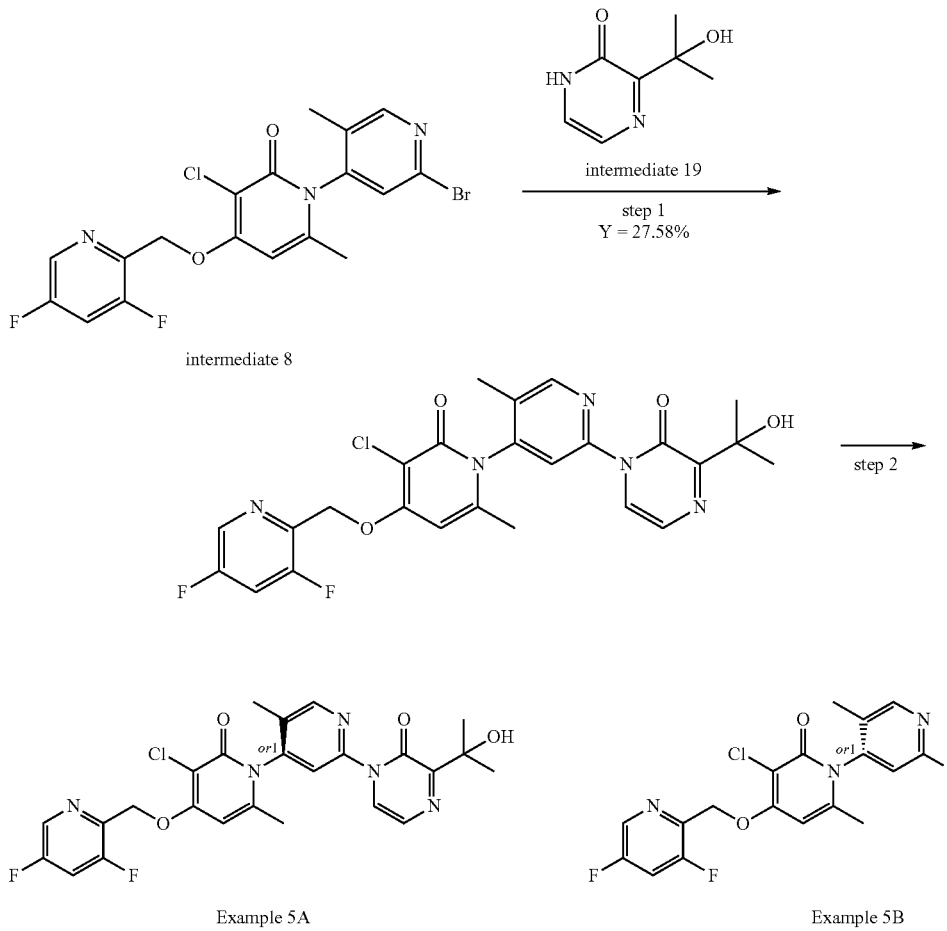

Step 1: Preparation of racemate 3-chloro-4-[(3,5-difluoropyridin-2-yl)methoxy]-2'-[3-(2-hydroxypropan-2-yl)-2-oxopyrazin-1-yl]-5',6-dimethyl-[1,4'-bipyridin]-2-one A mixture of 2'-bromo-3-chloro-4-[(3,5-difluoropyridin-2-yl)methoxy]-5',6-dimethyl-[1,4'-bipyridin]-2-one (500 mg, 1.09 mmol, 1.00 equiv), 3-(2-hydroxypropan-2-yl)-1H-pyrazin-2-one (337 mg, 2.19 mmol, 2.00 equiv), (1R,2R)—N1,N2-dimethylcyclohexane-1,2-diamine (311 mg, 2.19 mmol, 2.00 equiv), $K_2CO_3$ (302 mg, 2.19 mmol, 2.00 equiv) and CuI (417 mg, 2.19 mmol, 2.00 equiv) in 1,4-dioxane (5 mL) was stirred for 2 h at 80° C. under nitrogen atmosphere. The resulting mixture was cooled down to r.t. and poured into 10 mL of water. The resulting mixture was extracted with EtOAc (3×20 mL). The combined organic layers were washed with brine (50 mL), dried over anhydrous $Na_2SO_4$. After filtration, the filtrate was concentrated under reduced pressure. The residue was purified by silica gel column chromatography to afford crude product, which was further purified by Prep-HPLC to afford 3-chloro-4-[(3,5-difluoropyridin-2-yl)methoxy]-2'-[3-(2-hydroxypropan-2-yl)-2-oxopyrazin-1-yl]-5',6-dimethyl-[1,4'-bipyridin]-2-one (160 mg, 27.58%) as a white solid. LC-MS: (ES+H, m/z): $[M+H]^+=530.0$.

Step 2: Preparation of rel-3-chloro-4-[(3,5-difluoropyridin-2-yl)methoxy]-2'-[3-(2-hydroxypropan-2-yl)-2-oxopyrazin-1-yl]-5',6-dimethyl-[1,4'-bipyridin]-2-one and rel-3-chloro-4-[(3,5-difluoropyridin-2-yl)methoxy]-2'-[3-(2-hydroxypropan-2-yl)-2-oxopyrazin-1-yl]-5',6-dimethyl-[1,4'-bipyridin]-2-one The racemate (160 mg) was separated by Prep-Chiral-HPLC to afford Example 5A (69.5 mg, 98.2% purity, ee=100%) as white solid and Example 5B (56.2 mg, 99.5% purity, ee=100%) as white solid.

Example 5A: LC-MS: (ES+H, m/z): $[M+H]^+=530.2$. $^1H$ NMR (400 MHz, DMSO-$d_6$) δ 8.74 (s, 1H), 8.60 (d, 1H), 8.15-8.05 (m, 1H), 8.00 (d, 1H), 7.94 (s, 1H), 7.47 (d, 1H), 6.81 (s, 1H), 5.49 (d, 2H), 5.12 (s, 1H), 2.10 (s, 3H), 2.00 (s, 3H), 1.50 (s, 6H). $^{19}F$ NMR (377 MHz, DMSO-$d_6$) δ −120.17, −120.19, −122.36, −122.38.

Example 5B: LC-MS: (ES+H, m/z): $[M+H]^+=530.2$. $^1H$ NMR (400 MHz, DMSO-$d_6$) δ 8.74 (s, 1H), 8.60 (d, 1H), 8.13-8.06 (m, 1H), 8.00 (d, 1H), 7.94 (s, 1H), 7.47 (d, 1H), 6.81 (s, 1H), 5.49 (d, 2H), 5.12 (s, 1H), 2.10 (s, 3H), 2.00 (s, 3H), 1.50 (s, 6H). $^{19}F$ NMR (377 MHz, DMSO-$d_6$) δ −120.17, −120.19, −122.36, −122.38.

Example 6

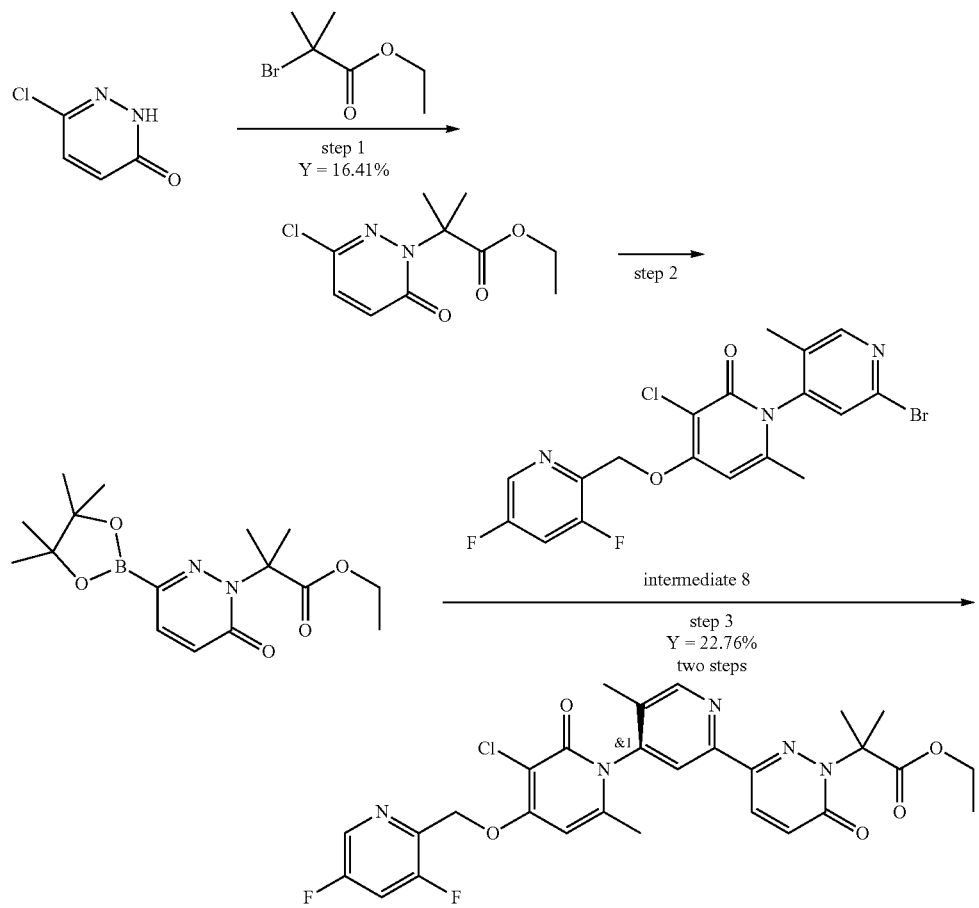

Example 6

Step 1: Preparation of ethyl 2-(3-chloro-6-oxopyridazin-1-yl)-2-methylpropanoate To a stirred solution of 6-chloro-2H-pyridazin-3-one (2.60 g, 19.91 mmol, 1.00 equiv) in DMF (50 mL) were added LiHMDS (19.92 mL, 1 mol/L in THF, 19.91 mmol, 1.00 equiv) dropwise at room temperature under nitrogen atmosphere. The resulting mixture was stirred for 1 h at room temperature under nitrogen atmosphere. To the above mixture was added ethyl α-bromoisobutyrate (7.77 g, 39.83 mmol, 2.00 equiv) dropwise at room temperature. The resulting mixture was stirred overnight at 80° C. The mixture was allowed to cool down to room temperature. The reaction was quenched with sat. NH$_4$Cl (aq.) at 0° C., The mixture was acidified to pH 6 with CH$_3$COOH. The resulting mixture was extracted with EtOAc (3×100 mL). The combined organic layers were washed with brine (5×100 mL), dried over anhydrous Na$_2$SO$_4$. After filtration, the filtrate was concentrated under reduced pressure. The residue was purified by silica gel column chromatography, the pure fraction was concentrated under vacuum to afford ethyl 2-(3-chloro-6-oxopyridazin-1-yl)-2-methylpropanoate (800 mg, 16.41%) as a yellow liquid. $^1$H NMR (300 MHz, Chloroform-d) δ 7.21 (d, 1H), 6.87 (d, 1H), 4.18 (q, 2H), 1.67 (s, 6H), 1.22 (t, 3H).

Step 2-3: Preparation of ethyl 2-(3-{3-chloro-4-[(3,5-difluoropyridin-2-yl)methoxy]-5',6-dimethyl-2-oxo-[1,4'-bipyridin]-2'-yl}-6-oxopyridazin-1-yl)-2-methylpropanoate To a stirred mixture of ethyl 2-(3-chloro-6-oxopyridazin-1-yl)-2-methylpropanoate (280 mg, 1.14 mmol, 1.00 equiv) and bis(pinacolato)diboron (581 mg, 2.28 mmol, 2.00 equiv) in 1,4-dioxane (5 mL) were added XPhos (54 mg, 0.11 mmol, 0.10 equiv), Pd(AcO)$_2$ (12 mg, 0.05 mmol, 0.05 equiv) and AcOK (336 mg, 3.43 mmol, 3.00 equiv) at room temperature under nitrogen atmosphere. The resulting mixture was stirred for 2 h at 80° C. under nitrogen atmosphere. The mixture was allowed to cool down to room temperature. The resulting mixture was used in the next step directly without further purification.

To the above mixture was added 2'-bromo-3-chloro-4-[(3,5-difluoropyridin-2-yl)methoxy]-5',6-dimethyl-[1,4'-bipyridin]-2-one (439 mg, 0.96 mmol, 0.84 equiv), K$_2$CO$_3$ (474 mg, 3.43 mmol, 3.00 equiv) and Pd(dppf)Cl$_2$CH$_2$Cl$_2$ (46 mg, 0.05 mmol, 0.05 equiv) and H$_2$O (1 mL) at room temperature under nitrogen atmosphere. The resulting mixture was stirred for 2 h at 80° C. under nitrogen atmosphere. The mixture was allowed to cool down to room temperature. The resulting mixture was poured into water (100 mL) at room temperature. The resulting mixture was extracted with EtOAc (3×50 mL). The combined organic layers were washed with brine (3×50 mL), dried over anhydrous Na$_2$SO$_4$. After filtration, the filtrate was concentrated under reduced pressure. The residue was purified by silica gel column chromatography, the pure fraction was concentrated under vacuum to afford crude product (270 mg). The crude product (100 mg) was purified by Prep-HPLC, the pure fraction was concentrated under reduced pressure and then lyophilized to afford ethyl 2-(3-{3-chloro-4-[(3,5-difluoropyridin-2-yl)methoxy]-5',6-dimethyl-2-oxo-[1,4'-bipyridin]-2'-yl}-6-oxopyridazin-1-yl)-2-methylpropanoate (56.6 mg, 22.76%) as a white solid. LC-MS: (ES+H, m/z): [M+H]$^+$=586.1. $^1$H NMR (300 MHz, DMSO-d$_6$) δ 8.78 (s, 1H), 8.61 (d, 1H), 8.38 (d, 1H), 8.17-8.04 (m, 2H), 7.13 (d, 1H), 6.82 (s, 1H), 5.49 (s, 2H), 4.08 (q, 2H), 2.06 (s, 3H), 1.98 (s, 3H), 1.68 (s, 3H), 1.67 (s, 3H), 1.13 (t, 3H). $^{19}$F NMR (282 MHz, DMSO-d$_6$) δ−120.11, −120.14, −122.29, −122.32.

Example 7A, 7B

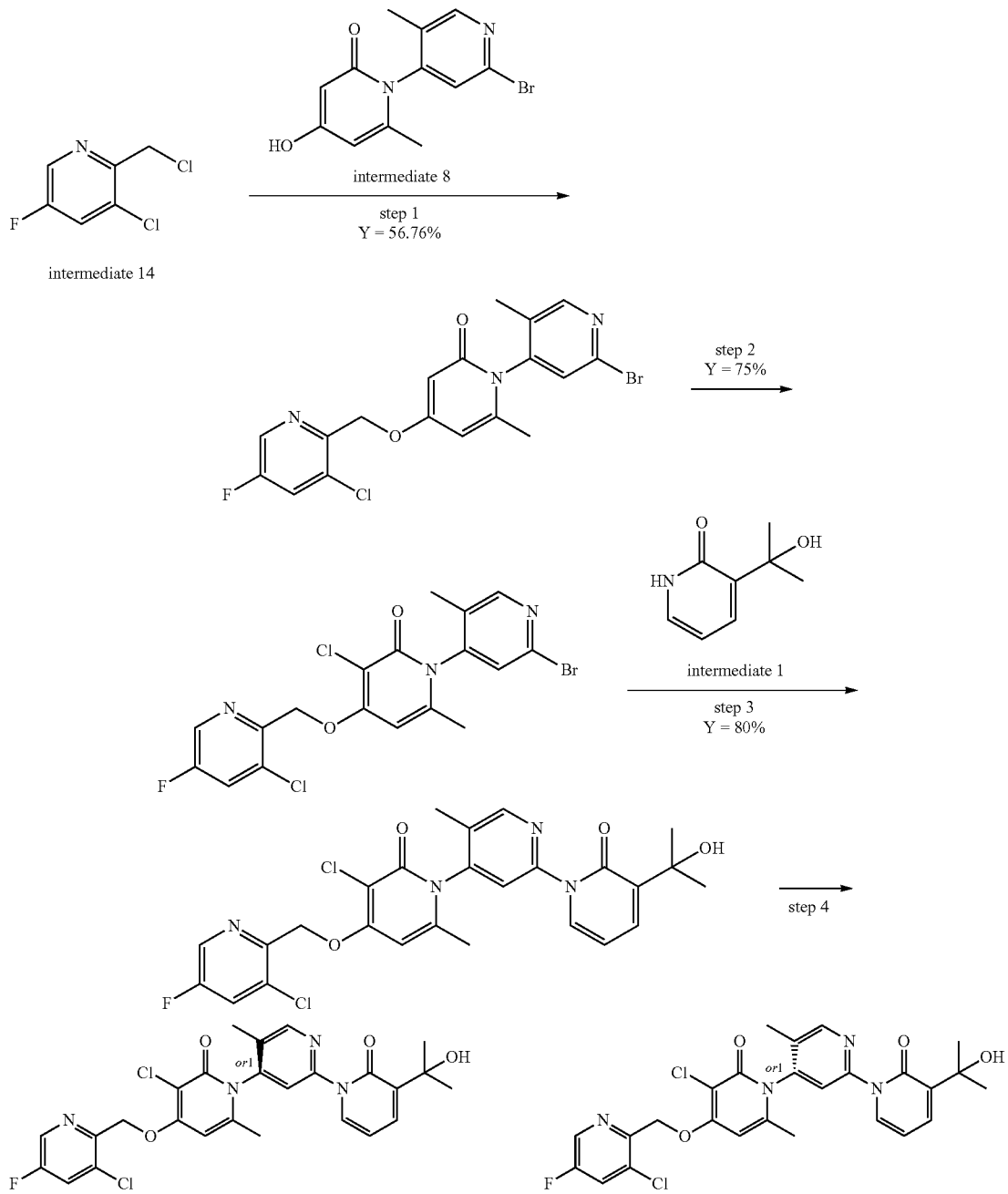

Step 1: Preparation of 2'-bromo-4-[(3-chloro-5-fluoropyridin-2-yl)methoxy]-5',6-dimethyl-[1,4'-bipyridin]-2-one To a stirred mixture of 2'-bromo-4-hydroxy-5',6-dimethyl-[1,4'-bipyridin]-2-one (3.00 g, 10.16 mmol, 1.00 equiv) and 3-chloro-2-(chloromethyl)-5-fluoropyridine (3.64 g, 20.22 mmol, 1.99 equiv) in DMF (0.79 mL, 10.16 mmol, 1.00 equiv) were added $K_2CO_3$ (7.02 g, 50.82 mmol, 5.00 equiv) and 18-Crown-6 (806 mg, 3.04 mmol, 0.30 equiv) at room temperature under nitrogen atmosphere. The resulting mixture was stirred for 1 h at 60° C. under nitrogen atmosphere. The mixture was allowed to cool down to room temperature. The reaction mixture was diluted with ethyl acetate (100 mL). The organic layer was washed with water (100 mL) and brine (100 mL), and then dried over $Na_2SO_4$. The solution was concentrated under reduced pressure. The residue was purified by silica gel column chromatography to afford 2'-bromo-4-[(3-chloro-5-fluoropyridin-2-yl)methoxy]-5',6-dimethyl-[1,4'-bipyridin]-2-one (2.00 g, 66.67%) as an off-white solid. LC-MS: (ES+H, m/z): $[M+H]^+=439.9$.

Step 2: Preparation of 2'-bromo-3-chloro-4-[(3-chloro-5-fluoropyridin-2-yl)methoxy]-5',6-dimethyl-[1,4'-bipyridin]-2-one To a stirred mixture of 2'-bromo-4-[(3-chloro-5-fluoropyridin-2-yl)methoxy]-5',6-dimethyl-[1,4'-bipyridin]-2-one (2.00 g, 4.55 mmol, 1.00 equiv) and 2,2-dichloroacetic acid (0.06 mL, 0.45 mmol, 0.10 equiv) in i-PrOH (10 mL) was added NCS (608 mg, 4.55 mmol, 1.00 equiv) at room temperature under nitrogen atmosphere. The resulting mixture was stirred for 2 h at 60° C. under nitrogen atmosphere. The mixture was allowed to cool down to room temperature. The precipitated solids were collected by filtration and washed with cool IPA (2×5 mL), to afford 2'-bromo-3-chloro-4-[(3-chloro-5-fluoropyridin-2-yl)methoxy]-5',6-dimethyl-[1,4'-bipyridin]-2-one (1.50 g, 75%) as a white solid. LC-MS: (ES+H, m/z): $[M+H]^+=473.9$.

Step 3: Preparation of 3-chloro-4-[(3-chloro-5-fluoropyridin-2-yl)methoxy]-2'-[3-(2-hydroxypropan-2-yl)-2-oxopyridin-1-yl]-5',6-dimethyl-[1,4'-bipyridin]-2-one To a stirred solution of 2'-bromo-3-chloro-4-[(3-chloro-5-fluoropyridin-2-yl)methoxy]-5',6-dimethyl-[1,4'-bipyridin]-2-one (750 mg, 1.58 mmol, 1.00 equiv), 3-(2-hydroxypropan-2-yl)-1H-pyridin-2-one (485.65 mg, 3.17 mmol, 2 equiv), (1R,2R)—N1,N2-dimethylcyclohexane-1,2-diamine (450 mg, 3.17 mmol, 2.00 equiv) and CuI (603 mg, 3.17 mmol, 2.00 equiv) in dioxane (15 mL) were added $K_2CO_3$ (438 mg, 3.17 mmol, 2.00 equiv) at room temperature under nitrogen atmosphere. The resulting mixture was stirred overnight at 80° C. under nitrogen atmosphere. The resulting mixture was diluted with ethyl acetate (100 mL), then washed with water (2×50 mL) and brine (50 mL), dried over anhydrous $Na_2SO_4$. After filtration, The resulting mixture was concentrated under reduced pressure. The residue was purified by reverse flash chromatography to afford 3-chloro-4-[(3-chloro-5-fluoropyridin-2-yl)methoxy]-2'-[3-(2-hydroxypropan-2-yl)-2-oxopyridin-1-yl]-5',6-dimethyl-[1,4'-bipyridin]-2-one (600 mg, 80%) as a white solid. LC-MS: (ES+H, m/z): $[M+H]^+=545.0$.

Step 4: Preparation of rel-3-chloro-4-[(3-chloro-5-fluoropyridin-2-yl)methoxy]-2'-[3-(2-hydroxypropan-2-yl)-2-oxopyridin-1-yl]-5',6-dimethyl-[1,4'-bipyridin]-2-one and rel-3-chloro-4-[(3-chloro-5-fluoropyridin-2-yl)methoxy]-2'-[3-(2-hydroxypropan-2-yl)-2-oxopyridin-1-yl]-5',6-dimethyl-[1,4'-bipyridin]-2-one The 3-chloro-4-[(3-chloro-5-fluoropyridin-2-yl)methoxy]-2'-[3-(2-hydroxypropan-2-yl)-2-oxopyridin-1-yl]-5',6-dimethyl-[1,4'-bipyridin]-2-one (190 mg) was isolated by prep-chiral-HPLC, the pure fraction was concentrated under vacuum and was lyophilized to afford rel-3-chloro-4-[(3-chloro-5-fluoropyridin-2-yl)methoxy]-2'-[3-(2-hydroxypropan-2-yl)-2-oxopyridin-1-yl]-5',6-dimethyl-[1,4'-bipyridin]-2-one (Example 7A, 76.3 mg, 96.7% purity, ee=100%) as an off-white solid and rel-3-chloro-4-[(3-chloro-5-fluoropyridin-2-yl)methoxy]-2'-[3-(2-hydroxypropan-2-yl)-2-oxopyridin-1-yl]-5',6-dimethyl-[1,4'-bipyridin]-2-one (Example 7B, 67.2 mg, 98.4% purity, ee=100%) as an off-white solid.

Example 7A: LC-MS: (ES+H, m/z): $[M+H]^+=545.0$. $^1$H NMR (300 MHz, DMSO-$d_6$) δ 8.72-8.65 (m, 2H), 8.25 (dd, 1H), 7.86 (dd, 1H), 7.79 (s, 1H), 7.70 (dd, 1H), 6.77 (s, 1H), 6.43 (t, 1H), 5.50 (s, 2H), 5.23 (s, 1H), 2.08 (s, 3H), 2.00 (s, 3H), 1.48 (s, 3H), 1.47 (s, 3H). $^{19}$F NMR (282 MHz, DMSO-$d_6$) δ −124.21.

Example 7B: LC-MS: (ES+H, m/z): $[M+H]^+=545.0$. $^1$H NMR (300 MHz, DMSO-$d_6$) δ 8.72-8.64 (m, 2H), 8.25 (dd, 1H), 7.86 (dd, 1H), 7.79 (s, 1H), 7.70 (dd, 1H), 6.77 (s, 1H), 6.43 (t, 1H), 5.50 (s, 2H), 5.24 (s, 1H), 2.08 (s, 3H), 2.00 (s, 3H), 1.48 (s, 3H), 1.47 (s, 3H). $^{19}$F NMR (282 MHz, DMSO-$d_6$) δ −124.19.

Example 8A, 8B

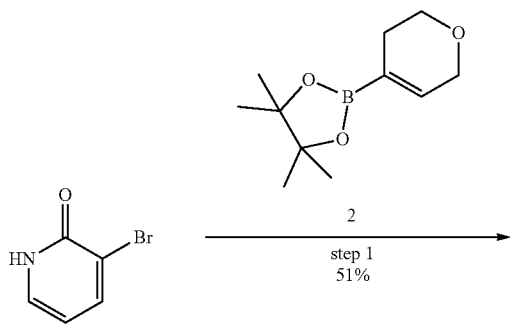

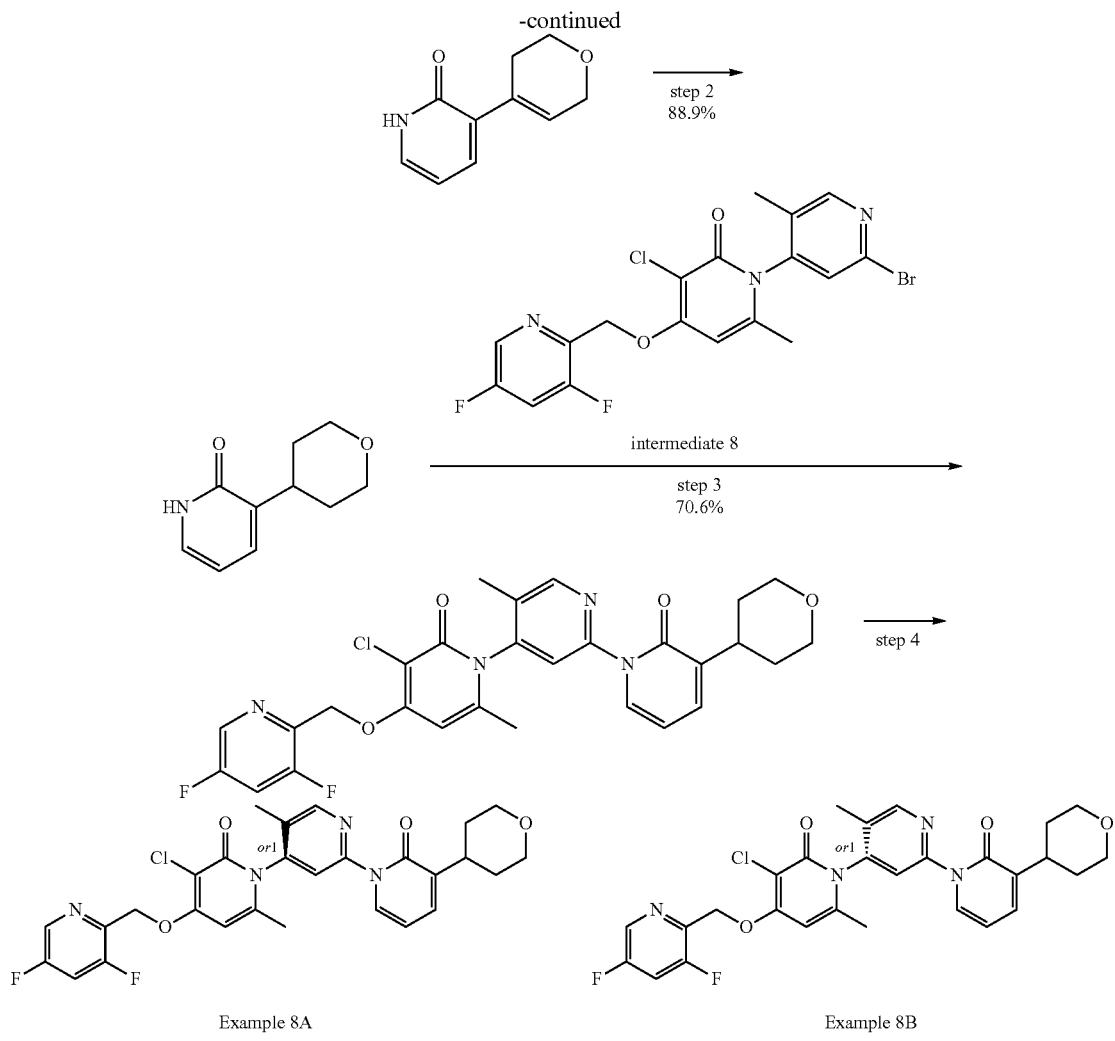

Example 8A

Example 8B

Step 1: Preparation of 3-(3,6-dihydro-2H-pyran-4-yl)-1H-pyridin-2-one

To a stirred mixture of 3-bromo-1H-pyridin-2-one (5.00 g, 28.73 mmol, 1.00 equiv) and 2-(3,6-dihydro-2H-pyran-4-yl)-4,4,5,5-tetramethyl-1,3,2-dioxaborolane (18.11 g, 86.20 mmol, 3.00 equiv) in dioxane (150 mL) and H$_2$O (30 mL) were added AcOK (8.46 g, 86.20 mmol, 3.00 equiv), Pd(dppf)Cl$_2$ (4.21 g, 5.74 mmol, 0.20 equiv), the resulting mixture was stirred overnight at 110° C. under nitrogen atmosphere. The reaction was allowed to cool down to room atmosphere. The resulting mixture was filtered, the filter cake was washed with EtOAc (3×100 mL). The filtrate was concentrated under reduced pressure. The residue was purified by silica gel column chromatography to afford 3-(3,6-dihydro-2H-pyran-4-yl)-1H-pyridin-2-one) (2.60 g, 51.0%) as a yellow solid. LC-MS: (ES+H, m/z): [M+H]$^+$=177.9.

Step 2: Preparation of 3-(oxan-4-yl)-1H-pyridin-2-one

A mixture of 3-(3,6-dihydro-2H-pyran-4-yl)-1H-pyridin-2-one (2.00 g, 11.28 mmol, 1.00 equiv) and Pd/C (158 mg, 1.12 mmol, 0.10 equiv) in MeOH (100 mL) was stirred for 3 h at room temperature under hydrogen atmosphere. The resulting mixture was filtered, the filter cake was washed with MeOH (3×50 mL). The filtrate was concentrated under reduced pressure. This resulted in 3-(oxan-4-yl)-1H-pyridin-2-one) (1.80 g, 88.9%) as a yellow solid. LC-MS: (ES+H, m/z): [M+H]$^+$=180.2.

Step 3: Preparation of 3-chloro-4-[(3,5-difluoropyridin-2-yl)methoxy]-5',6-dimethyl-2'-[3-(oxan-4-yl)-2-oxopyridin-1-yl]-[1,4'-bipyridin]-2-one To a stirred mixture of 3-(oxan-4-yl)-1H-pyridin-2-one (500 mg, 2.79 mmol, 2.00 equiv) and 2'-bromo-3-chloro-4-[(3,5-difluoropyridin-2-yl)methoxy]-5',6-dimethyl-[1,4'-bipyridin]-2-one (637 mg, 1.39 mmol, 1.00 equiv) in dioxane (15 mL) were added CuI (531 mg, 2.79 mmol, 2.00 equiv), N1,N2-dimethylcyclohexane-1,2-diamine (396 mg, 2.79 mmol, 2.00 equiv) and K$_2$CO$_3$ (386 mg, 2.79 mmol, 2.00 equiv), the resulting mixture was stirred at 80° C. for 3 h under nitrogen atmosphere. The resulting mixture was filtered, the filter cake was washed with EtOAc (3×10 mL). The filtrate was extracted with EtOAc (3×30 mL). The combined organic layers were washed with brine (60 mL), dried over anhydrous Na$_2$SO$_4$. After filtration, the filtrate was concentrated under reduced pressure. The residue was purified by Prep-HPLC. This resulted in 3-chloro-4-[(3,5- difluoropyridin-2-yl)methoxy]-5',6-dimethyl-2'-[3-(oxan-4-yl)-2-oxopyridin-1-yl]-[1,4'-bipyridin]-2-one (547 mg, 70.6%) as a white solid. LC-MS: (ES+H, m/z): [M+H]⁺=555.1.

Step 4: Preparation of rel-3-chloro-4-[(3,5-difluoro-pyridin-2-yl)methoxy]-5',6-dimethyl-2'-[3-(oxan-4-yl)-2-oxopyridin-1-yl]-[1,4'-bipyridin]-2-one and rel-3-chloro-4-[(3,5-difluoropyridin-2-yl)methoxy]-5',6-dimethyl-2'-[3-(oxan-4-yl)-2-oxopyridin-1-yl]-[1,4'-bipyridin]-2-one 3-chloro-4-[(3,5-difluoropyridin-2-yl)methoxy]-5',6-dimethyl-2'-[3-(oxan-4-yl)-2-oxopyridin-1-yl]-[1,4'-bipyridin]-2-one (260 mg) was separated by prep-chiral-HPLC to afford Example 8A (68.5 mg, 98.5% purity, ee=100.0%) and Example 8B (56.6 mg, 99.2% purity, ee=100.0%) as a white solid.

Example 8A: LC-MS: (ES+H, m/z): [M+H]⁺=555.05. ¹H NMR (300 MHz, DMSO-d₆) δ 8.68 (s, 1H), 8.61 (d, 1H), 8.13-8.10 (m, 1H), 7.86 (dd, 1H), 7.80 (s, 1H), 7.40-7.34 (m, 1H), 6.81 (s, 1H), 6.39 (t, 1H), 5.49 (d, 2H), 3.94 (d, 2H), 3.47-3.37 (m, 2H), 2.99-2.92 (m, 1H), 2.08 (s, 3H), 2.02 (s, 3H), 1.69-1.81 (m, 2H), 1.62-1.52 (m, 2H). ¹⁹F NMR (282 MHz, DMSO-d₆) δ−120.16, −120.19, −122.36, −122.38.

Example 8B: LC-MS: (ES+H, m/z): [M+H]⁺=555.00. ¹H NMR (300 MHz, DMSO-d₆) δ 8.68 (s, 1H), 8.60 (d, 1H), 8.13-8.06 (m, 1H), 7.87 (dd, 1H), 7.80 (s, 1H), 7.38-7.36 (m, 1H), 6.81 (s, 1H), 6.39 (t 1H), 5.49 (d, 2H), 3.94 (d, 2H), 3.51-3.33 (m, 2H), 2.95 (t, 1H), 2.08 (s, 3H), 2.01 (s, 3H), 1.82-1.39 (m, 4H). ¹⁹F NMR (282 MHz, DMSO-d₆) δ−120.16, −120.19, −122.36, −122.38.

Example 9A, 9B

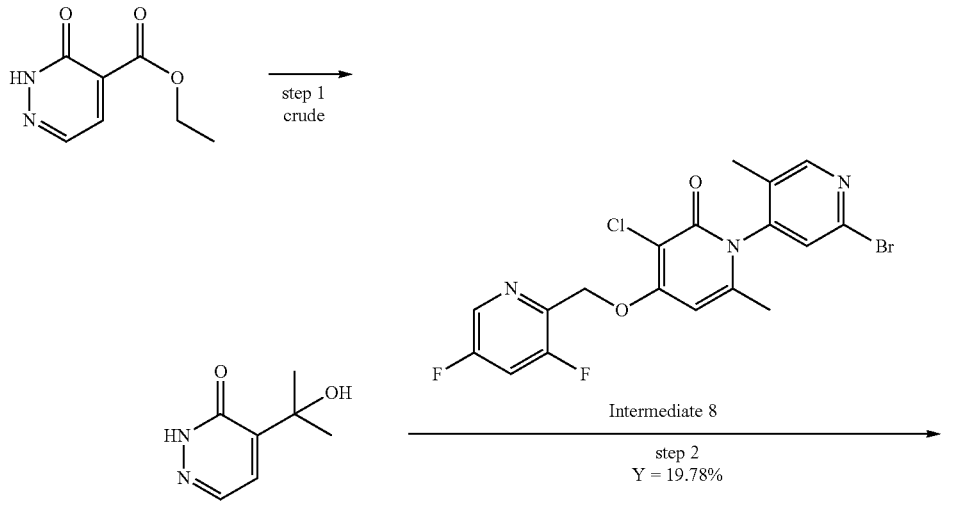

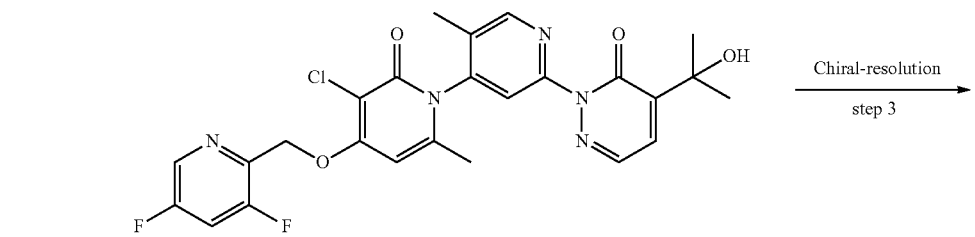

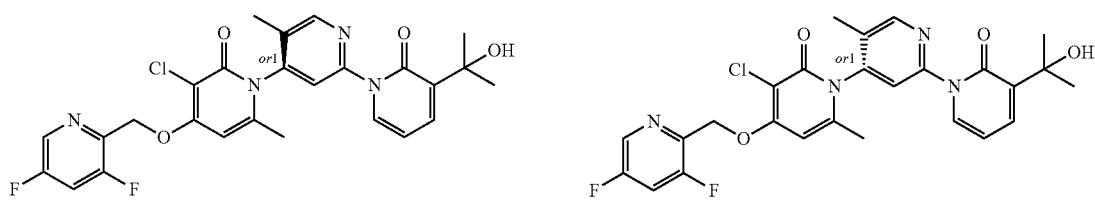

Example 9A

Example 9B

Step 1: Preparation of
4-(2-hydroxypropan-2-yl)-2H-pyridazin-3-one

To a stirred solution of ethyl 3-oxo-2H-pyridazine-4-carboxylate (1.00 g, 5.94 mmol, 1.00 equiv) in THF (10 ml) were added CH₃MgBr (19.80 mL, 3 M in 2-MeTHF, 59.40 mmol, 10.00 equiv) dropwise at 0° C. under nitrogen atmosphere. The resulting mixture was stirred for 2 h at 0° C. under nitrogen atmosphere. The reaction was quenched with sat. NH₄Cl (aq.) at 0° C. The resulting mixture was extracted with EtOAc (3×100 mL). The combined organic layers were washed with brine (50 mL), dried over anhydrous Na₂SO₄. The filtrate was concentrated under reduced pressure. The crude product was used in the next step directly without further purification. LC-MS: (ES+H, m/z): [M+H]⁺=155.3.

Step 2: Preparation of bis(3-chloro-4-[(3,5-difluoro-pyridin-2-yl)methoxy]-2'-[5-(2-hydroxypropan-2-yl)-6-oxopyridazin-1-yl]-5',6-dimethyl-[1,4'-bipyridin]-2-one)

To a mixture of 4-(2-hydroxypropan-2-yl)-2H-pyridazin-3-one (1.00 g, 6.49 mmol, 1.00 equiv), 2'-bromo-3-chloro-4-[(3,5-difluoropyridin-2-yl)methoxy]-5',6-dimethyl-[1,4'-bipyridin]-2-one (3.26 g, 7.12 mmol, 1.10 equiv), (1R,2R)—N1,N2-dimethylcyclohexane-1,2-diamine (0.92 g, 6.48 mmol, 1.00 equiv), CuI (1.24 g, 6.48 mmol, 1.00 equiv) and K₂CO₃ (1.80 g, 12.98 mmol, 2.00 equiv) in dioxane (20 mL) at room temperature. The mixture was heated at 80° C. for 3 h. The mixture was allowed to cool down to room temperature. The resulting mixture was diluted with water (100 mL). Then extracted with EtOAc (3×100 mL). The combined organic layers were washed with brine (100 mL), dried over anhydrous Na₂SO₄. After filtration, the filtrate was concentrated under reduced pressure. The residue was purified by silica gel column chromatography to afford 3-chloro-4-[(3,5-difluoropyridin-2-yl)methoxy]-2'-[5-(2-hydroxypropan-2-yl)-6-oxopyridazin-1-yl]-5',6-dimethyl-[1,4'-bipyridin]-2-one (0.68 g, 19.78%) as a white solid. LC-MS: (ES+H, m/z): [M+H]⁺=529.9. ¹H NMR (400 MHz, Chloroform-d) δ 8.68 (s, 1H), 8.40 (d, 1H), 8.00 (d, 1H), 7.55 (s, 1H), 7.36-7.27 (m, 1H), 7.25 (d, 1H), 6.41 (d, 1H), 5.41 (d, 2H), 5.14-4.43 (m, 1H), 2.19 (s, 3H), 2.07 (s, 3H), 1.60 (s, 3H), 1.59 (s, 3H).

Step 3: Preparation of rel-3-chloro-4-[(3,5-difluoro-pyridin-2-yl)methoxy]-2'-[5-(2-hydroxypropan-2-yl)-6-oxopyridazin-1-yl]-5',6-dimethyl-[1,4'-bipyridin]-2-one and rel-3-chloro-4-[(3,5-difluoropyridin-2-yl)methoxy]-2'-[5-(2-hydroxypropan-2-yl)-6-oxopyridazin-1-yl]-5',6-dimethyl-[1,4'-bipyridin]-2-one The rac-mixture (150 mg) was separated by Prep-Chiral HPLC to afford rel-3-chloro-4-[(3,5-difluoropyridin-2-yl)methoxy]-2'-[5-(2-hydroxypropan-2-yl)-6-oxopyridazin-1-yl]-5',6-dimethyl-[1,4'-bipyridin]-2-one (Example 9A, 45.9 mg, ee=100%) as an off-white solid and rel-3-chloro-4-[(3,5-difluoropyridin-2-yl)methoxy]-2'-[5-(2-hydroxypropan-2-yl)-6-oxopyridazin-1-yl]-5',6-dimethyl-[1,4'-bipyridin]-2-one (Example 9B, 50.8 mg, ee=99.32%)

Example 9A: LC-MS: (ES+H, m/z): [M+H]⁺=530.0. ¹H NMR (300 MHz, DMSO-d₆) δ 8.69 (s, 1H), 8.60 (d, 1H), 8.15-8.08 (m, 1H), 8.07 (d, 1H), 7.69 (s, 1H), 7.59 (d, 1H), 6.81 (d, 1H), 5.48 (d, 2H), 5.40 (s, 1H), 2.09 (s, 3H), 1.98 (s, 3H), 1.50 (s, 3H), 1.49 (s, 3H). ¹⁹F NMR (282 MHz, DMSO-d₆) δ −120.15, −120.18, −122.35, −122.37.

Example 9B: LC-MS: (ES+H, m/z): [M+H]⁺=530.0. ¹H NMR (300 MHz, DMSO-d₆) δ 8.69 (s, 1H), 8.60 (d, 1H), 8.15-8.08 (m, 1H), 8.07 (d, 1H), 7.69 (s, 1H), 7.59 (d, 1H), 6.81 (d, 1H), 5.48 (d, 2H), 5.40 (s, 1H), 2.09 (s, 3H), 1.98 (s, 3H), 1.50 (s, 3H), 1.49 (s, 3H). ¹⁹F NMR (282 MHz, DMSO-d₆) δ −120.15, −120.18, −122.35, −122.37.

Example 10A, 10B

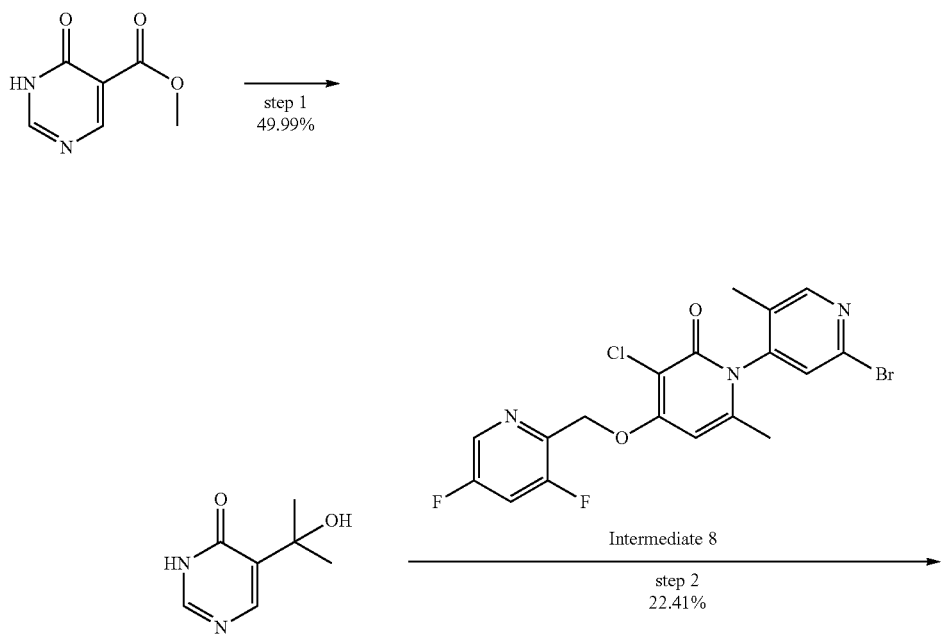

-continued

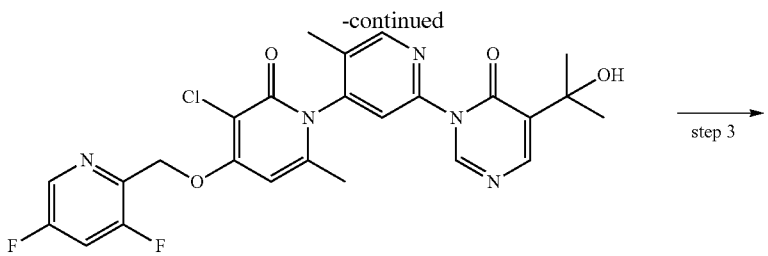

step 3

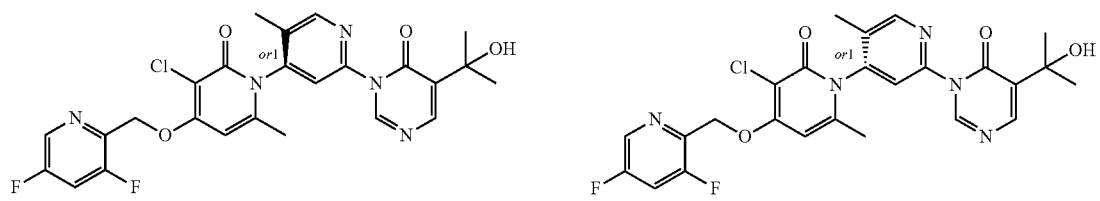

Example 10A                                                   Example 10B

Step 1: Preparation of 5-(2-hydroxypropan-2-yl)-3H-pyrimidin-4-one

To a stirred solution of methyl 4-oxo-3H-pyrimidine-5-carboxylate (3.00 g, 19.46 mmol, 1.00 equiv) in THF (200 mL) was added MeMgBr (64 mL, 3 Min 2-MeTHF, 194.65 mmol, 10.00 equiv) dropwise at 0° C. under nitrogen atmosphere. The resulting mixture was stirred for 1 h at 0° C. under nitrogen atmosphere. The reaction was quenched by the addition of sat. $NH_4Cl$ (aq.) (100 mL) at 0° C. The resulting mixture was extracted with EtOAc (3×100 mL). The combined organic layers were washed with brine (100 mL), dried over anhydrous $Na_2SO_4$. After filtration, the filtrate was concentrated under reduced pressure. This resulted in 5-(2-hydroxypropan-2-yl)-3H-pyrimidin-4-one (1.50 g, 49.99%) as a white solid. The crude product was used in the next step directly without further purification. LC-MS: (ES+H, m/z): $[M+H]^+$=155.3.

Step 2: Preparation of 3-chloro-4-[(3,5-difluoropyridin-2-yl)methoxy]-2'-[5-(2-hydroxypropan-2-yl)-6-oxopyrimidin-1-yl]-5',6-dimethyl-[1,4'-bipyridin]-2-one To a stirred mixture of 5-(2-hydroxypropan-2-yl)-3H-pyrimidin-4-one (337 mg, 2.19 mmol, 2.00 equiv) and 2'-bromo-3-chloro-4-[(3,5-difluoropyridin-2-yl)methoxy]-5',6-dimethyl-[1,4'-bipyridin]-2-one (500 mg, 1.09 mmol, 1.00 equiv) in dioxane (20 mL) were added CuI (417 mg, 2.19 mmol, 2.00 equiv), $K_2CO_3$ (302 mg, 2.19 mmol, 2.00 equiv) and (1S,2S)—N1,N2-dimethylcyclohexane-1,2-diamine (311 mg, 2.19 mmol, 2.00 equiv) at room temperature under nitrogen atmosphere. The resulting mixture was stirred overnight at 80° C. under nitrogen atmosphere. The reaction was monitored by LCMS. The mixture was allowed to cool down to room temperature. The resulting mixture was filtered, the filter cake was washed with EtOAc (3×20 mL). The resulting mixture was poured into water (100 mL), extracted with EtOAc (100 mL). The combined organic layers were washed with brine (200 mL), dried over anhydrous $Na_2SO_4$. After filtration, the filtrate was concentrated under reduced pressure. The residue was purified by Prep HPLC. This resulted in 3-chloro-4-[(3,5-difluoropyridin-2-yl)methoxy]-2'-[5-(2-hydroxypropan-2-yl)-6-oxopyrimidin-1-yl]-5',6-dimethyl-[1,4'-bipyridin]-2-one (130 mg, 22.41%) as a white solid. LC-MS: (ES+H, m/z): $[M+H]^+$=530.2.

Step 3: Preparation of rel-3-chloro-4-[(3,5-difluoropyridin-2-yl)methoxy]-2'-[5-(2-hydroxypropan-2-yl)-6-oxopyrimidin-1-yl]-5',6-dimethyl-[1,4'-bipyridin]-2-one & rel-3-chloro-4-[(3,5-difluoropyridin-2-yl)methoxy]-2'-[5-(2-hydroxypropan-2-yl)-6-oxopyrimidin-1-yl]-5',6-dimethyl-[1,4'-bipyridin]-2-one)

The 3-chloro-4-[(3,5-difluoropyridin-2-yl)methoxy]-2'-[5-(2-hydroxypropan-2-yl)-6-oxopyrimidin-1-yl]-5',6-dimethyl-[1,4'-bipyridin]-2-one (260 mg) was separated by prep-chiral-HPLC to afford Example 10A (93.1 mg, 99.2% purity, ee=100%) and Example 10B (73.9 mg, 99.6% purity, ee=100%) as a white solid.

Example 10A: LC-MS: (ES+H, m/z): $[M+H]^+$=530.05. $^1$H NMR (400 MHz, DMSO-$d_6$) δ 8.73 (s, 1H), 8.61 (s, 1H) 8.59 (d, 1H), 8.14 (s, 1H), 8.09-8.06 (m, 1H), 7.79 (s, 1H), 6.81 (s, 1H), 5.49 (d, 2H), 5.22 (s, 1H), 2.10 (s, 3H), 2.00 (s, 3H), 1.48 (s, 3H), 1.47 (s, 3H). $^{19}$F NMR (377 MHz, DMSO-$d_6$) δ −120.16, −120.18, −122.34, −122.36.

Example 10B: LC-MS: (ES+H, m/z): $[M+H]^+$=530.05. $^1$H NMR (400 MHz, DMSO-$d_6$) δ 8.73 (s, 1H), 8.61 (s, 1H) 8.59 (d, 1H), 8.14 (s, 1H), 8.09-8.06 (m, 1H), 7.80 (s, 1H), 6.81 (s, 1H), 5.49 (d, 2H), 5.23 (s, 1H), 2.10 (s, 3H), 2.00 (s, 3H), 1.48 (s, 3H), 1.47 (s, 3H). $^{19}$F NMR (377 MHz, DMSO-$d_6$) δ−120.15, −120.17, −122.33, −122.35.

Example 11A, 11B

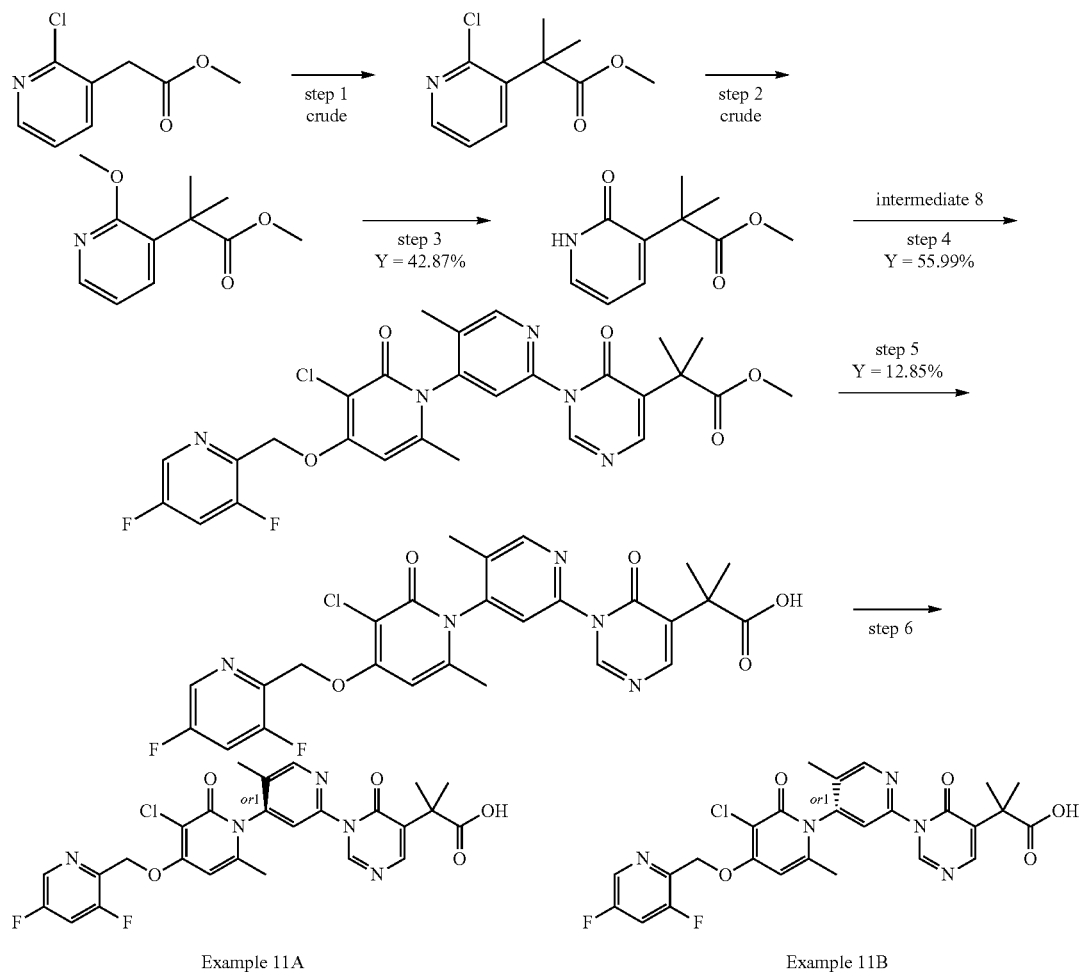

Example 11A

Example 11B

Step 1: Preparation of methyl 2-(2-chloropyridin-3-yl)-2-methylpropanoate

To a stirred mixture of methyl 2-(2-chloropyridin-3-yl) acetate (5.00 g, 26.93 mmol, 1.00 equiv) in THF (50 mL) was added LiHMDS (80.81 mL, 1 Min THF, 80.81 mmol, 3.00 equiv) dropwise at −78° C. under nitrogen atmosphere. The resulting mixture was stirred for 30 min at −78° C. under nitrogen atmosphere. MeI (11.47 g, 80.81 mmol, 3.00 equiv) was added dropwise to the above solution at −78° C. under nitrogen atmosphere. The resulting mixture was stirred for 1 h at −78° C. under nitrogen atmosphere. Desired product could be detected by LCMS. The mixture was allowed to warm up room temperature. The reaction was quenched with sat. $NH_4Cl$ (aq.) (500 mL) at room temperature. The resulting mixture was extracted with $CH_2Cl_2$ (3×500 mL). The combined organic layers were dried over anhydrous $Na_2SO_4$. After filtration, the filtrate was concentrated under reduced pressure to afford methyl 2-(2-chloropyridin-3-yl)-2-methylpropanoate (5.7 g, crude) as a colorless oil. LC-MS: (ES+H, m/z): $[M+H]^+$=214.1.

Step 2: Preparation of methyl 2-(2-methoxypyridin-3-yl)-2-methylpropanoate

To a mixture of methyl 2-(2-chloropyridin-3-yl)-2-methylpropanoate (3.00 g, 14.04 mmol, 1.00 equiv), $Cs_2CO_3$ (6.86 g, 21.06 mmol, 1.50 equiv), t-BuXPhos (0.36 g, 0.84 mmol, 0.06 equiv) and MeOH (20.00 mL, 493.97 mmol, 35.18 equiv) in Toluene (20.00 mL) was added $Pd(OAc)_2$ (0.19 g, 0.84 mmol, 0.06 equiv) at room temperature. The resulting mixture was stirred overnight at 80° C. under nitrogen atmosphere. The mixture was allowed to cool down to room temperature. The reaction was poured into water (400 mL), extracted with EtOAc (3×400 mL). The combined organic layers were dried over anhydrous $Na_2SO_4$. After filtration, the filtrate was concentrated under reduced pressure to afford methyl 2-(2-methoxypyridin-3-yl)-2-methylpropanoate (2.40 g, crude) as a white solid. LC-MS: (ES+H, m/z): $[M+H]^+$=210.2.

Step 3: Preparation of methyl 2-methyl-2-(2-oxo-1H-pyridin-3-yl)propanoate

To a mixture of methyl 2-(2-methoxypyridin-3-yl)-2-methylpropanoate (2.00 g, 9.55 mmol, 1.00 equiv) in MeCN (50 mL) was added TMSI (7.65 g, 38.23 mmol, 4.00 equiv) at room temperature. The resulting mixture was stirred for 2 h at 50° C. under nitrogen atmosphere. The resulting mixture was concentrated under reduced pressure. The residue was purified by silica gel column chromatography to afford methyl 2-methyl-2-(2-oxo-1H-pyridin-3-yl)propanoate (800 mg, 42.87%) as a white solid. LC-MS: (ES+H, m/z): [M+H]$^+$=196.1. $^1$H NMR (300 MHz, Chloroform-d) δ 7.44 (dd, 1H), 7.38 (dd, 1H), 6.33 (t, 1H), 3.66 (s, 3H), 1.52 (s, 6H).

Step 4: Preparation of methyl 2-(1-{3-chloro-4-[(3,5-difluoropyridin-2-yl)methoxy]-5',6-dimethyl-2-oxo-[1,4'-bipyridin]-2'-yl}-2-oxopyridin-3-yl)-2-methylpropanoate To a mixture of methyl 2-methyl-2-(2-oxo-1H-pyridin-3-yl)propanoate (0.85 g, 4.38 mmol, 1.00 equiv), K$_2$CO$_3$ (1.21 g, 8.76 mmol, 2.00 equiv), (1S,2S)—N1,N2-dimethylcyclohexane-1,2-diamine (0.25 g, 1.75 mmol, 0.40 equiv) and 2'-bromo-3-chloro-4-[(3,5-difluoropyridin-2-yl)methoxy]-5',6-dimethyl-[1,4'-bipyridin]-2-one (2.00 g, 4.38 mmol, 1.00 equiv) in 1,4-dioxane (30.00 mL) was added CuI (0.17 g, 0.87 mmol, 0.20 equiv) at room temperature. The resulting mixture was stirred for 2 h at 80° C. under nitrogen atmosphere. The mixture was allowed to cool down to room temperature. The reaction was poured into water (300 mL), extracted with EtOAc (3×300 mL). The combined organic layers were dried over anhydrous Na$_2$SO$_4$. After filtration, the filtrate was concentrated under reduced pressure. The residue was purified by silica gel column chromatography to afford methyl 2-(1-{3-chloro-4-[(3,5-difluoropyridin-2-yl)methoxy]-5',6-dimethyl-2-oxo-[1,4'-bipyridin]-2'-yl}-2-oxopyridin-3-yl)-2-methylpropanoate (1.40 g, 55.99%) as a white solid. LC-MS: (ES+H, m/z): [M+H]$^+$=571.1. $^1$H NMR (400 MHz, DMSO-d$_6$) δ 8.69 (s, 1H), 8.60 (d, 1H), 8.14-8.05 (m, 1H), 7.97-7.90 (m, 1H), 7.77 (s, 1H), 7.55-7.48 (m, 1H), 6.80 (s, 1H), 6.43 (t, 1H), 5.54-5.44 (m, 2H), 3.49 (s, 3H), 2.07 (s, 3H), 1.99 (s, 3H), 1.42 (s, 3H), 1.40 (s, 3H).

Step 5: Preparation of 3-chloro-4-[(3,5-difluoropyridin-2-yl)methoxy]-2'-[3-(1-hydroxy-2-methylpropan-2-yl)-2-oxopyridin-1-yl]-5',6-dimethyl-[1,4'-bipyridin]-2-one To a stirred mixture of methyl 2-(1-{3-chloro-4-[(3,5-difluoropyridin-2-yl)methoxy]-5',6-dimethyl-2-oxo-[1,4'-bipyridin]-2'-yl}-2-oxopyridin-3-yl)-2-methylpropanoate (900 mg, 1.57 mmol, 1.00 equiv) in THF (12.00 mL) was added LiAlH$_4$ (0.63 mL, 2.5 M in THF, 1.57 mmol, 1.00 equiv) dropwise at 0° C. under nitrogen atmosphere. The resulting mixture was stirred for 1 h at 0° C. under nitrogen atmosphere. The reaction was quenched with 15% sodium hydroxide (aq.) at 0° C. The resulting mixture was filtered, the filtrate was concentrated under reduced pressure. The crude product was purified by Prep-HPLC to afford 3-chloro-4-[(3,5-difluoropyridin-2-yl)methoxy]-2'-[3-(1-hydroxy-2-methylpropan-2-yl)-2-oxopyridin-1-yl]-5',6-dimethyl-[1,4'-bipyridin]-2-one (110 mg, 12.85%) as a white solid. LC-MS: (ES+H, m/z): [M+H]$^+$=543.3.

Step 6: Preparation of rel-3-chloro-4-[(3,5-difluoropyridin-2-yl)methoxy]-2'-[3-(1-hydroxy-2-methylpropan-2-yl)-2-oxopyridin-1-yl]-5',6-dimethyl-[1,4'-bipyridin]-2-one and rel-3-chloro-4-[(3,5-difluoropyridin-2-yl)methoxy]-2'-[3-(1-hydroxy-2-methylpropan-2-yl)-2-oxopyridin-1-yl]-5',6-dimethyl-[1,4'-bipyridin]-2-one The racemate 3-chloro-4-[(3,5-difluoropyridin-2-yl)methoxy]-2'-[3-(1-hydroxy-2-methylpropan-2-yl)-2-oxopyridin-1-yl]-5',6-dimethyl-[1,4'-bipyridin]-2-one (110 mg, 0.20 mmol) was purified by Prep-chiral-HPLC to afford rel-3-chloro-4-[(3,5-difluoropyridin-2-yl)methoxy]-2'-[3-(1-hydroxy-2-methylpropan-2-yl)-2-oxopyridin-1-yl]-5',6-dimethyl-[1,4'-bipyridin]-2-one (Example 11A, 33.7 mg, ee=100.00%) as a white solid and rel-3-chloro-4-[(3,5-difluoropyridin-2-yl)methoxy]-2'-[3-(1-hydroxy-2-methylpropan-2-yl)-2-oxopyridin-1-yl]-5',6-dimethyl-[1,4'-bipyridin]-2-one (Example 11B, 31.5 mg, ee=100.00%) as a white solid.

Example 11A: LC-MS: (ES+H, m/z): [M+H]$^+$=543.3. $^1$H NMR (300 MHz, DMSO-d$_6$) δ 8.68 (s, 1H), 8.61 (d, 1H), 8.15-8.05 (m, 1H), 7.86-7.80 (m, 1H), 7.75 (s, 1H), 7.43-7.35 (m, 1H), 6.81 (s, 1H), 6.35 (t, 1H), 5.53-5.44 (m, 2H), 4.49 (t, 1H), 3.74-3.56 (m, 2H), 2.08 (s, 3H), 2.02 (s, 3H), 1.23 (s, 3H), 1.23 (s, 3H). $^{19}$F NMR (377 MHz, DMSO-d$_6$) δ−120.15, −120.18, −122.35, −122.37.

Example 11B: LC-MS: (ES+H, m/z): [M+H]$^+$=543.3. $^1$H NMR (300 MHz, DMSO-d$_6$) δ 8.68 (s, 1H), 8.61 (d, 1H), 8.15-8.05 (m, 1H), 7.88-7.80 (m, 1H), 7.75 (s, 1H), 7.44-7.34 (m, 1H), 6.81 (s, 1H), 6.35 (t, 1H), 5.53-5.44 (m, 2H), 4.49 (t, 1H), 3.73-3.55 (m, 2H), 2.08 (s, 3H), 2.02 (s, 3H), 1.23 (s, 3H), 1.23 (s, 3H). $^{19}$F NMR (377 MHz, DMSO-d$_6$) δ−120.15, −120.18, −122.35, −122.37.

Example 12A, 12B

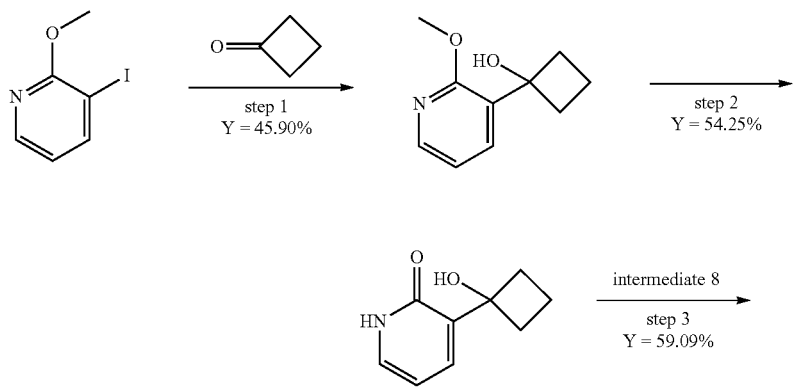

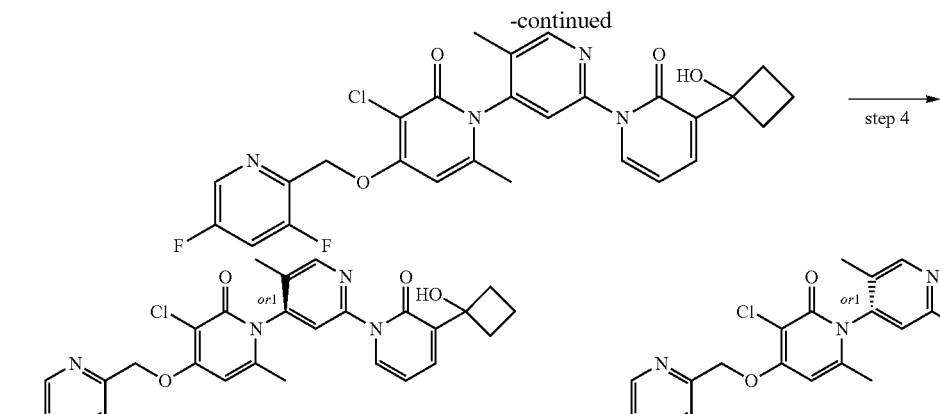

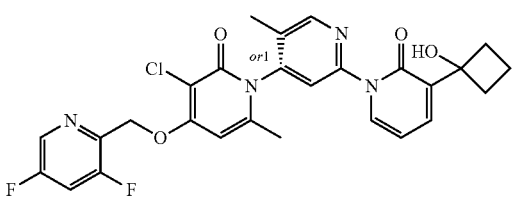

Example 12A

Example 12B

Step 1: Preparation of 1-(2-methoxypyridin-3-yl)cyclobutan-1-ol

To a stirred solution of 3-iodo-2-methoxypyridine (5.00 g, 21.27 mmol, 1.00 equiv) in Toluene (100.00 mL) was added i-PrMgCl (2.84 g, 27.65 mmol, 1.30 equiv) dropwise at 0° C. under nitrogen atmosphere. The resulting mixture was stirred for 0.5 h at 0° C. under nitrogen atmosphere. To the above mixture was added cyclobutanone (2.24 g, 31.91 mmol, 1.50 equiv) dropwise at 0° C. The resulting mixture was stirred for additional 1 h at 0° C. The reaction was quenched with water at 0° C. The resulting mixture was extracted with EtOAc (3×200 mL). The combined organic layers were washed with brine (100 mL), dried over anhydrous $Na_2SO_4$. After filtration, the filtrate was concentrated under reduced pressure. The residue was purified by silica gel column chromatography to afford 1-(2-methoxypyridin-3-yl)cyclobutan-1-ol (1.75 g, 45.90%) as a yellow oil. LC-MS: (ES+H, m/z): $[M+H]^+$=180.1. $^1$H NMR (400 MHz, DMSO-$d_6$) δ 8.08-8.02 (m, 1H), 7.68-7.63 (m, 1H), 6.97-6.92 (m, 1H), 5.20 (s, 1H), 3.88 (s, 3H), 2.61-2.48 (m, 2H), 2.22-2.13 (m, 2H), 2.02-1.93 (m, 1H), 1.67-1.54 (m, 1H).

Step 2: Preparation of 3-(1-hydroxycyclobutyl)-1H-pyridin-2-one

To a mixture of 1-(2-methoxypyridin-3-yl)cyclobutan-1-ol (400 mg, 2.23 mmol, 1.00 equiv) in DMF (10.00 mL) was added (ethylsulfanyl)sodium (1877 mg, 22.32 mmol, 10.00 equiv) at room temperature. The resulting mixture was stirred overnight at 100° C. under nitrogen atmosphere. The mixture was allowed to cool down to room temperature. The mixture was neutralized to pH 7 with AcOH. The resulting mixture was filtered, the filtrate was concentrated under reduced pressure. The residue was purified by silica gel column chromatography to afford 3-(1-hydroxycyclobutyl)-1H-pyridin-2-one (200 mg, 54.25%) as a white solid. LC-MS: (ES+H, m/z): $[M+H]^+$=166.1. $^1$H NMR (400 MHz, DMSO-$d_6$) δ 11.76 (s, 1H), 7.49 (dd, 1H), 7.32 (dd, 1H), 6.24 (t, 1H), 5.81-5.55 (m, 1H), 2.48-2.41 (m, 2H), 2.13-2.02 (m, 2H), 1.93-1.81 (m, 1H), 1.65-1.53 (m, 1H).

Step 3: Preparation of 3-chloro-4-[(3,5-difluoropyridin-2-yl)methoxy]-2'-[3-(1-hydroxycyclobutyl)-2-oxopyridin-1-yl]-5',6-dimethyl-[1,4'-bipyridin]-2-one To a mixture of 3-(1-hydroxycyclobutyl)-1H-pyridin-2-one (173 mg, 1.05 mmol, 1.20 equiv), (1S,2S)—N1,N2-dimethylcyclohexane-1,2-diamine (49 mg, 0.35 mmol, 0.40 equiv), $K_2CO_3$ (242 mg, 1.75 mmol, 2.00 equiv) and 2'-bromo-3-chloro-4-[(3,5-difluoropyridin-2-yl)methoxy]-5',6-dimethyl-[1,4'-bipyridin]-2-one (400 mg, 0.87 mmol, 1.00 equiv) in 1,4-dioxane (8.00 mL) was added CuI (33 mg, 0.17 mmol, 0.20 equiv) at room temperature. The resulting mixture was stirred for 2 h at 80° C. under nitrogen atmosphere. The reaction was poured into water (150 mL), extracted with EtOAc (3×150 mL). The combined organic layers were dried over anhydrous $Na_2SO_4$. After filtration, the filtrate was concentrated under reduced pressure. The resulting mixture was concentrated under reduced pressure. The residue was purified by reverse flash chromatography to afford 3-chloro-4-[(3,5-difluoropyridin-2-yl)methoxy]-2'-[3-(1-hydroxycyclobutyl)-2-oxopyridin-1-yl]-5',6-dimethyl-[1,4'-bipyridin]-2-one (280 mg, 59.09%) as a white solid. LC-MS: (ES+H, m/z): $[M+H]^+$=541.1.

Step 3: Preparation of rel-3-chloro-4-[(3,5-difluoropyridin-2-yl)methoxy]-2'-[3-(1-hydroxycyclobutyl)-2-oxopyridin-1-yl]-5',6-dimethyl-[1,4'-bipyridin]-2-one and rel-3-chloro-4-[(3,5-difluoropyridin-2-yl)methoxy]-2'-[3-(1-hydroxycyclobutyl)-2-oxopyridin-1-yl]-5',6-dimethyl-[1,4'-bipyridin]-2-one The racemate 3-chloro-4-[(3,5-difluoropyridin-2-yl)methoxy]-2'-[3-(1-hydroxycyclobutyl)-2-oxopyridin-1-yl]-5',6-dimethyl-[1,4'-bipyridin]-2-one (280 mg, 0.51 mmol) was purified by Prep-chiral-HPLC to afford rel-3-chloro-4-[(3,5-difluoropyridin-2-yl)methoxy]-2'-[3-(1-hydroxycyclobutyl)-2-oxopyridin-1-yl]-5',6-dimethyl-[1,4'-bipyridin]-2-one (Example 12A, 100.8 mg, ee=100.00%) as a white solid and rel-3-chloro-4-[(3,5-difluoropyridin-2-yl)methoxy]-2'-[3-(1-hydroxycyclobutyl)-2-oxopyridin-1-yl]-5',6-dimethyl-[1,4'-bipyridin]-2-one (Example 12B, 103.2 mg, ee=99.32%) as a white solid.

Example 12A: LC-MS: (ES+H, m/z): $[M+H]^+$=541.2. $^1$H NMR (400 MHz, DMSO-$d_6$) δ 8.70 (s, 1H), 8.60 (d, 1H), 8.15-8.05 (m, 1H), 7.95-7.90 (m, 1H), 7.84 (s, 1H), 7.59 (dd, 1H), 6.81 (s, 1H), 6.44 (t 1H), 5.48 (s, 2H), 5.31 (s, 1H), 2.64-2.54 (m, 2H), 2.13-2.09 (m, 1H), 2.08 (s, 3H), 2.07-2.03 (m, 1H), 2.01 (s, 3H), 1.98-1.85 (m, 1H), 1.72-1.59 (m, 1H). $^{19}$F NMR (377 MHz, DMSO-$d_6$) δ−120.15, −120.17, −122.34, −122.36.

Example 12B: LC-MS: (ES+H, m/z): $[M+H]^+$=541.2. $^1$H NMR (400 MHz, DMSO-$d_6$) δ 8.70 (s, 1H), 8.60 (d, 1H), 8.14-8.06 (m, 1H), 7.95-7.89 (m, 1H), 7.84 (s, 1H), 7.62-7.56 (m, 1H), 6.81 (s, 1H), 6.43 (t, 1H), 5.48 (s, 2H), 5.31 (s, 1H), 2.64-2.54 (m, 2H), 2.12-2.09 (m, 1H), 2.08 (s, 3H), 2.07-2.03 (m, 1H), 2.01 (s, 3H), 1.98-1.84 (m, 1H), 1.72-1.57 (m, 1H). $^{19}$F NMR (377 MHz, DMSO-d$_6$) δ −120.16, −120.18, −122.34, −122.36.

Example 13A, Example 13B

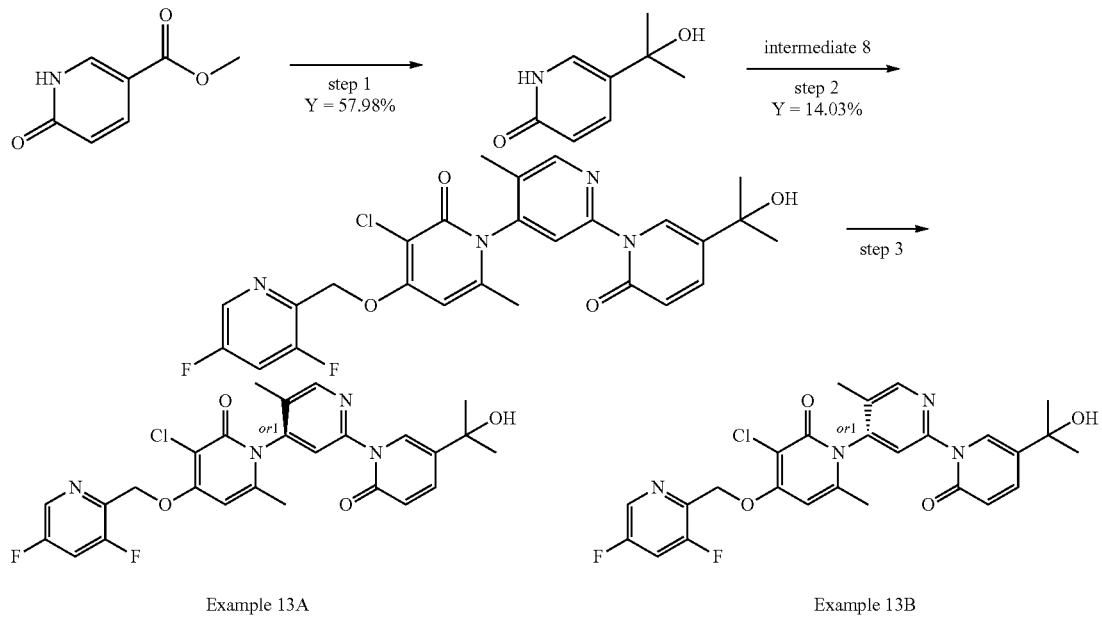

Example 13A

Example 13B

Step 1: Preparation of 5-(2-hydroxypropan-2-yl)-1H-pyridin-2-one

To a stirred solution of methyl 6-oxo-1H-pyridine-3-carboxylate (1.00 g, 6.53 mmol, 1.00 equiv) in THF (50 mL) was added MeMgBr (21.77 mL, 3 Min 2-MeTHF, 65.30 mmol, 10.00 equiv) dropwise at −10° C. The resulting mixture was stirred for additional 1 h at room temperature. The reaction was monitored by LCMS. The reaction was quenched by the addition of sat. NH$_4$Cl (aq.) (150 mL) at 0° C. The resulting mixture was extracted with EtOAc (4×300 mL). The combined organic layers were washed with brine (400 mL), dried over anhydrous Na$_2$SO$_4$. After filtration, the filtrate was concentrated under reduced pressure, to afford 5-(2-hydroxypropan-2-yl)-1H-pyridin-2-one (580 mg, 57.98%) as a white solid. LC-MS: (ES+H, m/z): [M+H]$^+$=154.3.

Step 2: Preparation of 3-chloro-4-[(3,5-difluoropyridin-2-yl)methoxy]-2'-[5-(2-hydroxypropan-2-yl)-2-oxopyridin-1-yl]-5',6-dimethyl-[1,4'-bipyridin]-2-one To a stirred mixture of 5-(2-hydroxypropan-2-yl)-1H-pyridin-2-one (537 mg, 3.50 mmol, 2.00 equiv) and 2'-bromo-3-chloro-4-[(3,5-difluoropyridin-2-yl)methoxy]-5',6-dimethyl-[1,4'-bipyridin]-2-one (800 mg, 1.75 mmol, 1.00 equiv) in 1,4-dioxane (6 mL) were added K$_2$CO$_3$ (484 mg, 3.50 mmol, 2.00 equiv), CuI (667 mg, 3.50 mmol, 2.00 equiv) and (1S,2S)—N1,N2-dimethylcyclohexane-1,2-diamine (498 mg, 3.50 mmol, 2.00 equiv) at room temperature under nitrogen atmosphere. The resulting mixture was stirred for 3 h at 80° C. under nitrogen atmosphere. The residue was diluted with H$_2$O (50 mL), and the mixture was extracted with EtOAc (2×100 mL). The combined organic phase was washed with brine (100 mL), dried over Na$_2$SO$_4$. The crude product was purified by Prep-HPLC to afford 3-chloro-4-[(3,5-difluoropyridin-2-yl)methoxy]-2'-[5-(2-hydroxypropan-2-yl)-2-oxopyridin-1-yl]-5',6-dimethyl-[1, 4'-bipyridin]-2-one (130 mg, 14.03%) as a white solid. LC-MS: (ES+H, m/z): [M+H]$^+$=529.05. $^1$H NMR (400 MHz, DMSO-d$_6$) δ 8.70 (s, 1H), 8.60 (d, 1H), 8.13-8.05 (m, 1H), 7.93 (d, 1H), 7.85 (s, 1H), 7.70-7.65 (m, 1H), 6.81 (s, 1H), 6.51 (d, 1H), 5.50 (d, 2H), 5.18 (s, 1H), 2.09 (s, 3H), 2.02 (s, 3H), 1.41 (s, 3H), 1.40 (s, 3H).

Step 3: Preparation of rel-3-chloro-4-[(3,5-difluoropyridin-2-yl)methoxy]-2'-[5-(2-hydroxypropan-2-yl)-2-oxopyridin-1-yl]-5',6-dimethyl-[1,4'-bipyridin]-2-one and rel-3-chloro-4-[(3,5-difluoropyridin-2-yl)methoxy]-2'-[5-(2-hydroxypropan-2-yl)-2-oxopyridin-1-yl]-5',6-dimethyl-[1,4'-bipyridin]-2-one 3-chloro-4-[(3,5-difluoropyridin-2-yl)methoxy]-2'-[5-(2-hydroxypropan-2-yl)-2-oxopyridin-1-yl]-5',6-dimethyl-[1, 4'-bipyridin]-2-one (130 mg, 0.233 mmol, 1.00 equiv) was separated by Prep-Chiral-HPLC to afford Example 13A (43.9 mg, 98.2% purity, ee=100%) as a white solid and Example 13B (33.6 mg, 98.3% purity, ee=100%) as a white solid.

Example 13A: LC-MS: (ES+H, m/z): [M+H]$^+$=529.0. $^1$H NMR (300 MHz, DMSO-d$_6$) δ 8.70 (s, 1H), 8.60 (d, 1H), 8.14-8.05 (m, 1H), 7.90 (d, 1H), 7.84 (s, 1H), 7.70-7.64 (m, 1H), 6.81 (s, 1H), 6.50 (d, 1H), 5.49 (d, 2H), 5.17 (s, 1H), 2.08 (s, 3H), 2.01 (s, 3H), 1.41 (s, 3H), 1.40 (s, 3H). $^{19}$F NMR (282 MHz, DMSO-d$_6$) δ−120.15, −120.17, −122.35, −122.38.

Example 13B: LC-MS: (ES+H, m/z): [M+H]$^+$=529.0. $^1$H NMR (300 MHz, DMSO-d$_6$) δ 8.70 (s, 1H), 8.60 (d, 1H), 8.14-8.05 (m, 1H), 7.90 (d, 1H), 7.84 (s, 1H), 7.70-7.64 (m, 1H), 6.81 (s, 1H), 6.50 (d, 1H), 5.49 (d, 2H), 5.17 (s, 1H), 2.08 (s, 3H), 2.01 (s, 3H), 1.41 (s, 3H), 1.40 (s, 3H). $^{19}$F NMR (282 MHz, DMSO-d$_6$) δ −120.15, −120.17, −122.35, −122.38.

Example 14A, 14B, 14C, 14D

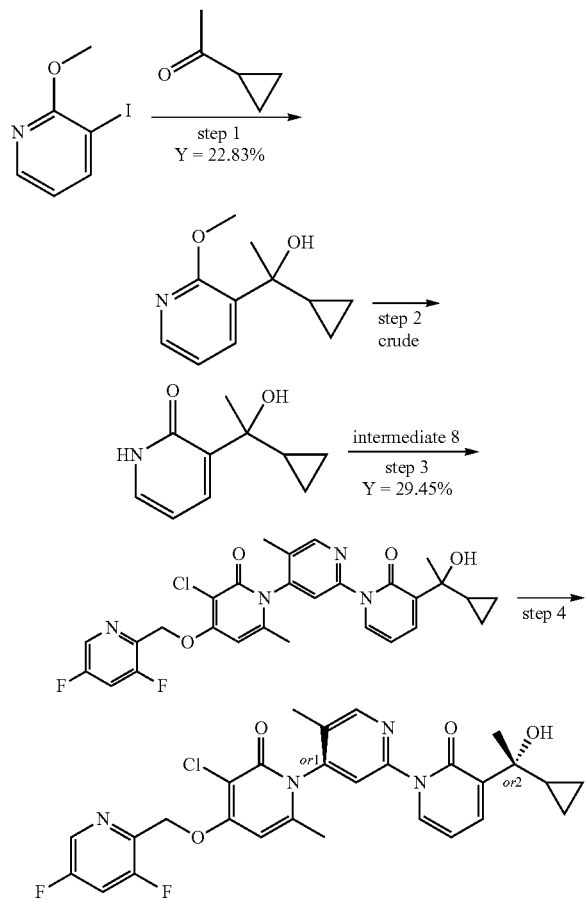

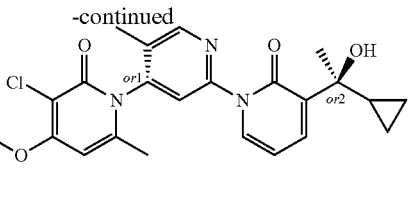

Example 14D

Step 1: Preparation of 1-cyclopropyl-1-(2-methoxypyridin-3-yl)ethanol

To a stirred solution of 3-iodo-2-methoxypyridine (4.00 g, 17.02 mmol, 1.00 equiv) in Toluene (100 mL) was added i-PrMgCl (11.06 mL, 2 M in THF, 22.12 mmol, 1.30 equiv) dropwise at 0° C. under nitrogen atmosphere. The resulting mixture was stirred for 30 min at 0° C. under nitrogen atmosphere. To the above mixture was added cyclopropyl methyl ketone (2.15 g, 25.55 mmol, 1.50 equiv) dropwise over 20 min at 0° C. The resulting mixture was stirred for additional 1 h at 0° C. The reaction was quenched with water at room temperature. The resulting mixture was extracted with EtOAc (3×200 mL). The combined organic layers were washed with brine (2×100 mL), dried over anhydrous Na$_2$SO$_4$. After filtration, the filtrate was concentrated under reduced pressure. The residue was purified by reverse combi-flash chromatography to afford 1-cyclopropyl-1-(2-methoxypyridin-3-yl)ethanol (751 mg, 22.83%) as a yellow oil. LC-MS: (ES+H, m/z): [M+H]$^+$=194.1. $^1$H NMR (300 MHz, DMSO-d$_6$) δ 8.02 (dd, 1H), 7.81 (dd, 1H), 6.95 (dd, 1H), 4.65 (s, 1H), 3.89 (s, 3H), 1.66-1.56 (m, 1H), 1.54 (s, 3H), 0.58-0.41 (m, 1H), 0.35-0.12 (m, 2H), 0.11--0.04 (m, 1H).

Step 2: Preparation of product 3-(1-cyclopropyl-1-hydroxyethyl)-1H-pyridin-2-one A mixture of 1-cyclopropyl-1-(2-methoxypyridin-3-yl)ethanol (1.14 g, 5.88 mmol, 1.00 equiv) and (ethylsulfanyl)sodium (4.95 g, 58.84 mmol, 10.0 equiv) in DMF (20 mL) was stirred for 3 h at 100° C. under nitrogen atmosphere. The mixture was allowed to r.t. The resulting mixture was diluted with water (100 mL). The mixture was acidified to pH=4-5 with conc. HCl. The resulting mixture was extracted with CHCl$_3$:IPA=3:1 (3×100 mL). The combined organic layers were concentrated under reduced pressure. The residue was purified by silica gel column chromatography to afford crude product 3-(1-cyclopropyl-1-hydroxyethyl)-1H-pyridin-2-one (1.40 g) as a yellow oil. The crude product was used in the next step directly without further purification. LC-MS: (ES+H, m/z): [M+H]$^+$=180.0. $^1$H NMR (300 MHz, DMSO-d$_6$) δ 12.07-11.10 (m, 1H), 7.52 (dd, 1H), 7.29 (dd, 1H), 6.23 (t, 1H), 5.56 (s, 1H), 1.54-1.46 (m, 1H), 1.44 (s, 3H), 0.50-0.30 (m, 1H), 0.34-0.20 (m, 2H), 0.20-0.07 (m, 1H).

Step 3: Preparation of 3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one A mixture of 3-(1-cyclopropyl-1-hydroxyethyl)-1H-pyridin-2-one (1.30 g, 7.25 mmol, 1.50 equiv), 2'-bromo-3-chloro-4-[(3,5-difluoropyridin-2-yl)methoxy]-5',6-dimethyl-[1,4'-bipyridin]-2-one (2.21 g, 4.83 mmol, 1.00 equiv), K₂CO₃ (1.34 g, 9.67 mmol, 2.00 equiv), CuI (1.84 g, 9.67 mmol, 2.00 equiv) and (1R,2R)-1-N,2-N-dimethylcyclohexane-1,2-diamine (1.38 g, 9.67 mmol, 2.00 equiv) in 1,4-dioxane(10 ml) was stirred for 2 h at 80° C. The mixture was allowed to cool down to r.t. The resulting mixture was diluted with water (100 mL). The resulting mixture was extracted with EtOAc (3×150 mL). The combined organic layers were washed with brine (150 mL), dried over anhydrous Na₂SO₄. After filtration, the filtrate was concentrated under reduced pressure. The residue was purified by silica gel column chromatography to afford 3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one (0.79 g, 29.40%) as a white solid. LC-MS: (ES+H, m/z): [M+H]⁺=555.0. ¹H NMR (400 MHz, DMSO-d₆) δ 8.69 (s, 1H), 8.60 (d, 1H), 8.15-8.03 (m, 1H), 7.86 (dd, 1H), 7.79 (d, 1H), 7.70-7.61 (m, 1H), 6.80 (t, 1H), 6.43 (t, 1H), 5.48 (d, 2H), 4.94 (d, 1H), 2.08 (s, 3H), 2.00 (s, 3H), 1.72-1.62 (m, 1H), 1.53 (d, 3H), 0.52-0.43 (m, 1H), 0.30-0.21 (m, 2H), 0.16-0.05 (m, 1H).

Step 4: Preparation of rel-3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one, rel-3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one, rel-3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one and rel-3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one The rac-mixture (570 mg) was separated by Prep-Chiral HPLC to afford a mixture of Example 14A and Example 14B (270 mg), rel-3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one (Example 14C, 100.1 mg, 97.8% purity, de=100%) as an off-white solid, rel-3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one (Example 14D, 84.0 mg, 97.0% purity, de=98.2%).

The mixture of Example 14A and Example 14B (270 mg) was further separated by Prep-Chiral HPLC to afford rel-3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one (Example 14A, 104.2 mg, 97.5% purity, de=100%) as an off-white solid and rel-3-chloro-2'-[3-(1-cyclopropyl-1-hydroxyethyl)-2-oxopyridin-1-yl]-4-[(3,5-difluoropyridin-2-yl)methoxy]-5',6-dimethyl-[1,4'-bipyridin]-2-one (Example 14B, 116.2 mg, 96.6% purity, de=100%)

Example 14A: LC-MS: (ES+H, m/z): [M+H]⁺=555.00. ¹H NMR (300 MHz, DMSO-d₆) δ 8.69 (s, 1H), 8.60 (d, 1H), 8.16-8.04 (m, 1H), 7.87 (dd, 1H), 7.80 (s, 1H), 7.66 (dd, 1H), 6.80 (s, 1H), 6.43 (t, 1H), 5.48 (d, 2H), 4.96 (s, 1H), 2.08 (s, 3H), 2.01 (s, 3H), 1.73-1.61 (m, 1H), 1.53 (s, 3H), 0.54-0.42 (m, 1H), 0.32-0.19 (m, 2H), 0.18-0.07 (m, 1H). ¹⁹F NMR (282 MHz, DMSO-d₆) δ−120.16, −120.18, −122.35, −122.37.

Example 14B: LC-MS: (ES+H, m/z): [M+H]⁺=555.00. ¹H NMR (300 MHz, DMSO-d₆) δ 8.69 (s, 1H), 8.60 (d, 1H), 8.16-8.03 (m, 1H), 7.87 (dd, 1H), 7.80 (s, 1H), 7.66 (dd, 1H), 6.80 (s, 1H), 6.43 (t, 1H), 5.48 (d, 2H), 4.96 (s, 1H), 2.08 (s, 3H), 2.01 (s, 3H), 1.73-1.61 (m, 1H), 1.53 (s, 3H), 0.53-0.43 (m, 1H), 0.32-0.20 (m, 2H), 0.18-0.06 (m, 1H). ¹⁹F NMR (282 MHz, DMSO-d₆) δ−120.16, −120.18, −122.35, −122.37.

Example 14C: LC-MS: (ES+H, m/z): [M+H]⁺=555.00. ¹H NMR (300 MHz, DMSO-d₆) δ 8.69 (s, 1H), 8.61 (d, 1H), 8.17-8.03 (m, 1H), 7.87 (dd, 1H), 7.79 (s, 1H), 7.66 (dd, 1H), 6.81 (s, 1H), 6.43 (t, 1H), 5.48 (d, 2H), 4.94 (s, 1H), 2.08 (s, 3H), 2.01 (s, 3H), 1.72-1.62 (m, 1H), 1.54 (s, 3H), 0.54-0.44 (m, 1H), 0.30-0.21 (m, 2H), 0.16-0.05 (m, 1H). ¹⁹F NMR (282 MHz, DMSO-d₆) δ−120.16, −120.18, −122.35, −122.37.

Example 14D: LC-MS: (ES+H, m/z): [M+H]⁺=554.95. ¹H NMR (300 MHz, DMSO-d₆) δ 8.69 (s, 1H), 8.60 (d, 1H), 8.16-8.03 (m, 1H), 7.87 (dd, 1H), 7.80 (s, 1H), 7.66 (dd, 1H), 6.80 (s, 1H), 6.43 (t, 1H), 5.48 (d, 2H), 4.96 (s, 1H), 2.08 (s, 3H), 2.01 (s, 3H), 1.73-1.62 (m, 1H), 1.53 (s, 3H), 0.52-0.42 (m, 1H), 0.31-0.21 (m, 2H), 0.17-0.07 (m, 1H). ¹⁹F NMR (282 MHz, DMSO-d₆) δ−120.16, −120.18, −122.35, −122.37.

Example 15A, 15B

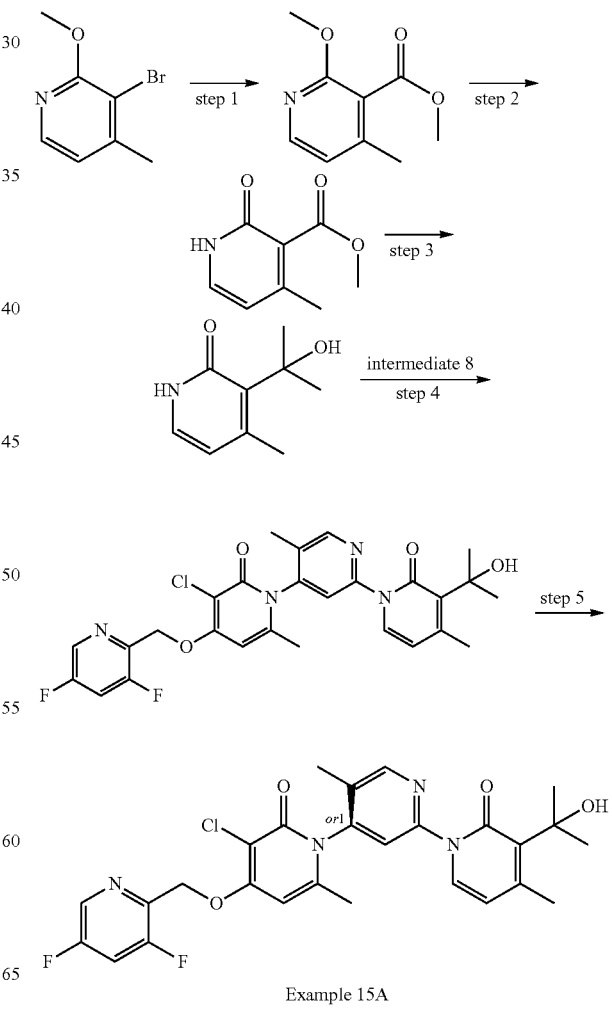

Example 15A

-continued

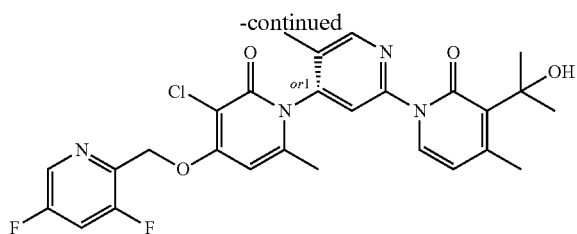

Example 15B

Step 1: Preparation of methyl 2-methoxy-4-methylpyridine-3-carboxylate

To a stirred mixture of 3-bromo-2-methoxy-4-methylpyridine (2.00 g, 9.89 mmol, 1.00 equiv) in MeOH (5 ml) was added Pd(dppf)Cl$_2$ (0.72 g, 0.99 mmol, 0.10 equiv) and DIEA (3.84 g, 29.69 mmol, 3.00 equiv) at room temperature under carbon monoxide (20 atm) atmosphere. The resulting mixture was stirred for 24 h at 110° C. The reaction was poured into water at room temperature. The aqueous layer was extracted with CH$_2$Cl$_2$ (3×20 mL). The combined organic layers were washed with brine (50 mL), dried over anhydrous Na$_2$SO$_4$. The resulting mixture was concentrated under reduced pressure. The residue was purified by silica gel column chromatography to afford methyl 2-methoxy-4-methylpyridine-3-carboxylate (480 mg, 26.76%) as a yellow oil. LC-MS: (ES+H, m z): [M+H]$^+$=181.9. $^1$H NMR (300 MHz, DMSO-d$_6$) δ 8.12 (d, 1H), 6.97-6.92 (m, 1H), 3.85 (s, 3H), 3.83 (s, 3H), 2.23 (s, 3H).

Step 2: Preparation of methyl 2-oxo-1H-pyridine-3-carboxylate

To a stirred mixture of methyl 2-methoxy-4-methylpyridine-3-carboxylate (710 mg, 3.91 mmol, 1.00 equiv) in MeCN was added TMSI (1.57 g, 7.83 mmol, 2.00 equiv) dropwise at room temperature. The resulting mixture was stirred for additional 4 h at 50° C. The reaction was poured into water at room temperature. The aqueous layer was extracted with EtOAc (3×20 mL). The combined organic layers were washed with brine (50 mL), dried over anhydrous Na$_2$SO$_4$. The resulting mixture was concentrated under reduced pressure. The residue was purified by silica gel column chromatography to afford methyl 2-oxo-1H-pyridine-3-carboxylate (540 mg, 89.99%) as a yellow solid. LC-MS: (ES+H, m z): [M+H]$^+$=168.1. $^1$H NMR (400 MHz, DMSO-d$_6$) δ 11.80 (s, 1H), 7.36 (d, 1H), 6.10 (d, 1H), 3.75 (s, 3H), 2.10 (s, 3H).

Step 3: Preparation of 3-(2-hydroxypropan-2-yl)-4-methyl-1H-pyridin-2-one

To a stirred mixture of methyl 4-methyl-2-oxo-1H-pyridine-3-carboxylate (440 mg, 2.63 mmol, 1.00 equiv) in THF (5 mL) was added bromo(methyl)magnesium 1 M in THF (26 mL, 26.32 mmol, 10.00 equiv) dropwise at 0° C. under nitrogen atmosphere. The resulting mixture was stirred for additional 2 h at 80° C. The reaction was quenched with sat. NH$_4$Cl (aq.) at 0° C. The aqueous layer was extracted with EtOAc (3×20 mL). The combined organic layers were washed with brine (50 mL), dried over anhydrous Na$_2$SO$_4$. The resulting mixture was concentrated under reduced pressure. The residue was purified by silica gel column chromatography to afford 3-(2-hydroxypropan-2-yl)-4-methyl-1H-pyridin-2-one (300 mg, 68.16%) as a white solid. LC-MS: (ES+H, m/z): [M+H]$^+$=168.3. $^1$H NMR (300 MHz, DMSO-d$_6$) δ 11.68 (s, 1H), 7.42 (s, 1H), 7.20 (d, 1H), 6.08 (d, 1H), 2.31 (s, 3H), 1.47 (s, 6H).

Step 4: Preparation of 3-chloro-4-[(3,5-difluoropyridin-2-yl)methoxy]-2'-[3-(2-hydroxypropan-2-yl)-4-methyl-2-oxopyridin-1-yl]-5',6-dimethyl-[1,4'-bipyridin]-2-one To a stirred mixture of 3-(2-hydroxypropan-2-yl)-4-methyl-1H-pyridin-2-one (300 mg, 1.79 mmol, 1.50 equiv) and (2E)-3-{3-chloro-4-[(3,5-difluoropyridin-2-yl)methoxy]-6-methyl-2-oxopyridin-1-yl}pent-2-enecarbonimidoyl bromide (534 mg, 1.19 mmol, 1.00 equiv) in 1,4-dioxane(8 ml) were added (1R,2R)—N1,N2-dimethylcyclohexane-1,2-diamine (68 mg, 0.47 mmol, 0.40 equiv), K$_2$CO$_3$ (330 mg, 2.39 mmol, 2.00 equiv) and CuI (45 mg, 0.23 mmol, 0.20 equiv) at room temperature under nitrogen atmosphere. The resulting mixture was stirred for additional 2 h at 100° C. The reaction was poured into water at room temperature. The aqueous layer was extracted with EtOAc (4×30 mL). The resulting mixture was concentrated under reduced pressure. The crude product was purified by Prep-HPLC to afford 3-chloro-4-[(3,5-difluoropyridin-2-yl)methoxy]-2'-[3-(2-hydroxypropan-2-yl)-4-methyl-2-oxopyridin-1-yl]-5',6-dimethyl-[1,4'-bipyridin]-2-one (380 mg, 58.51%) as a white solid. LC-MS: (ES+H, m z): [M+2+H]$^+$=545.2.

Step 5: Preparation of rel-3-chloro-4-[(3,5-difluoropyridin-2-yl)methoxy]-2'-[3-(2-hydroxypropan-2-yl)-4-methyl-2-oxopyridin-1-yl]-5',6-dimethyl-[1,4'-bipyridin]-2-one and rel-3-chloro-4-[(3,5-difluoropyridin-2-yl)methoxy]-2'-[3-(2-hydroxypropan-2-yl)-4-methyl-2-oxopyridin-1-yl]-5',6-dimethyl-[1,4'-bipyridin]-2-one The racemate (300 mg) was separated by Prep-Chiral-HPLC to afford Example 15A (130.3 mg, 97.7% purity, ee=100%) as a white solid and Example 15B (130.0 mg, 98.3% purity, ee=100%) as a white solid.

Example 15A: LC-MS: (ES+H, m/z): [M+H]$^+$=543.0. $^1$H NMR(400 MHz, DMSO-d$_6$) δ 8.66 (s, 1H), 8.60 (d, 1H), 8.11-8.06 (m, 1H), 7.77-7.71 (m, 2H), 6.80 (s, 1H), 6.21 (d, 1H), 5.89 (s, 1H), 5.48 (d, 2H), 2.45 (s, 3H), 2.07 (s, 3H), 1.99 (s, 3H), 1.54 (s, 3H), 1.53 (s, 3H). $^{19}$F NMR (377 MHz, DMSO-d$_6$) δ −120.16, −120.18, −122.36, −122.38.

Example 15B: LC-MS: (ES+H, m/z): [M+H]$^+$=543.1. $^1$H NMR(400 MHz, DMSO-d$_6$) δ 8.66 (s, 1H), 8.60 (d, 1H), 8.11-8.06 (m, 1H), 7.77-7.71 (m, 2H), 6.80 (s, 1H), 6.21 (d, 1H), 5.89 (s, 1H), 5.48 (d, 2H), 2.45 (s, 3H), 2.07 (s, 3H), 1.99 (s, 3H), 1.54 (s, 3H), 1.53 (s, 3H). $^{19}$F NMR (377 MHz, DMSO-d$_6$) δ −120.16, −120.18, −122.35, −122.37.

Example 16A, 16B

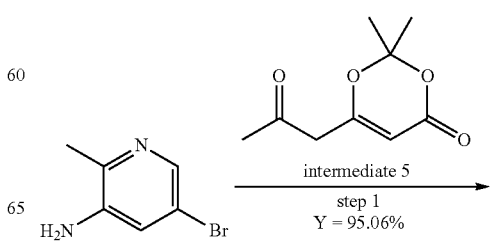

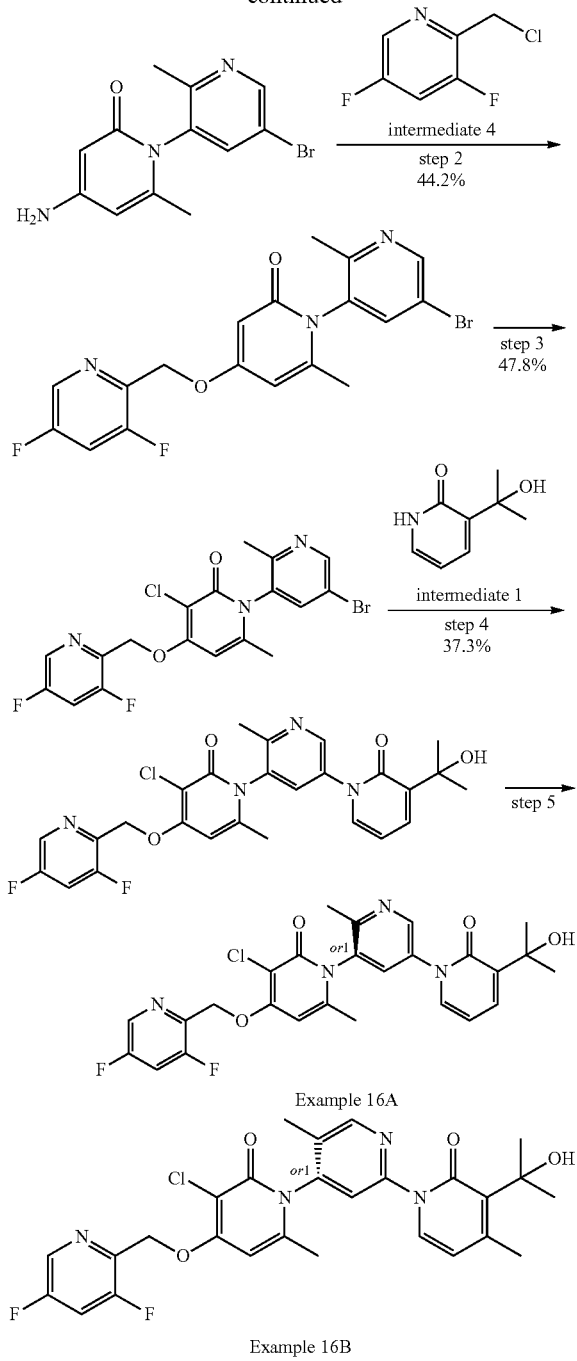

Example 16A

Example 16B

Step 1: Preparation of 5'-bromo-4-hydroxy-2',6-dimethyl-[1,3'-bipyridin]-2-one

A solution of 5-bromo-2-methylpyridin-3-amine (10.00 g, 53.46 mmol, 1.00 equiv) and 2,2-dimethyl-6-(2-oxopropyl)-1,3-dioxin-4-one (19.70 g, 106.92 mmol, 2.00 equiv) in 1,4-dioxane (100 mL) was stirred for 2 h at 80° C. under nitrogen atmosphere. To the above mixture was added $H_2SO_4$ (3.99 mL, 74.85 mmol, 1.40 equiv) dropwise at 0° C. The resulting mixture was stirred for another 2 h at 80° C. under nitrogen atmosphere. The mixture was allowed to r.t. The resulting mixture was concentrated under reduced pressure. The residue was dissolved in water (50 mL) and $Et_2O$ (100 mL). The precipitated solids were collected by filtration and washed with $Et_2O$ (3×10 mL), to afford 5'-bromo-4-hydroxy-2',6-dimethyl-[1,3'-bipyridin]-2-one (15.00 g, 95.06%) as a white solid. LC-MS: (ES+H, m/z): $[M+H]^+$=294.9.

Step 2: Preparation of 5'-bromo-4-[(3,5-difluoropyridin-2-yl)methoxy]-2',6-dimethyl-[1,3'-bipyridin]-2-one To a stirred mixture of 5'-bromo-4-hydroxy-2',6-dimethyl-[1,3'-bipyridin]-2-one (3.00 g, 10.16 mmol, 1.00 equiv) and 2-(chloromethyl)-3,5-difluoropyridine (3.32 g, 20.33 mmol, 2.00 equiv) in DMF (70 mL) were added 18-Crown-6 (0.81 g, 3.06 mmol, 0.30 equiv) and $K_2CO_3$ (7.02 g, 50.79 mmol, 5.00 equiv) at r.t. The result mixture was stirred for 3 h at 60° C. under nitrogen atmosphere. The mixture was allowed to cool down to room temperature. The resulting mixture was filtered, the filter cake was washed with DCM (3×50 mL). The filtrate was concentrated under reduced pressure. The residue was purified by silica gel column chromatography to afford 5'-bromo-4-[(3,5-difluoropyridin-2-yl)methoxy]-2',6-dimethyl-[1,3'-bipyridin]-2-one (1.90 g, 44.27%) as a light yellow solid. LC-MS: (ES+H, m/z): $[M+H]^+$=422.0.

Step 3: Preparation of 5'-bromo-3-chloro-4-[(3,5-difluoropyridin-2-yl) methoxy]-2',6-dimethyl-[1,3'-bipyridin]-2-one To a stirred mixture of 5'-bromo-4-[(3,5-difluoropyridin-2-yl)methoxy]-2',6-dimethyl-[1,3'-bipyridin]-2-one (1.70 g, 4.02 mmol, 1.00 equiv) and NCS (537 mg, 4.02 mmol, 1.00 equiv) in i-PrOH (9 mL) was added 2,2-dichloroacetic acid (51 mg, 0.40 mmol, 0.10 equiv) dropwise at room temperature. The resulting mixture was stirred for 2 h at 60° C. under nitrogen atmosphere. The mixture was allowed to cool down to room temperature. The precipitated solids were collected by filtration and washed with hexane (3×10 mL). This resulted in 5'-bromo-3-chloro-4-[(3,5-difluoropyridin-2-yl) methoxy]-2',6-dimethyl-[1,3'-bipyridin]-2-one (880 mg, 47.86%) as a white solid. LC-MS: (ES+H, m/z): $[M+H]^+$=457.9.

Step 4: Preparation of 5'-{3-chloro-4-[(3,5-difluoropyridin-2-yl) methoxy]-6-methyl-2-oxopyridin-1-yl}-3-(2-hydroxypropan-2-yl)-6'-methyl-[1,3'-bipyridin]-2-one To a stirred mixture of 5'-bromo-3-chloro-4-[(3,5-difluoropyridin-2-yl) methoxy]-2',6-dimethyl-[1,3'-bipyridin]-2-one (700 mg, 1.53 mmol, 1.00 equiv) and 3-(2-hydroxypropan-2-yl)-1H-pyridin-2-one (469 mg, 3.06 mmol, 2.00 equiv) in 1,4-dioxane (14 mL) were added CuI (58 mg, 0.30 mmol, 0.20 equiv), $K_2CO_3$ (423 mg, 3.06 mmol, 2.00 equiv) and N1,N2-dimethylcyclohexane-1,2-diamine (87 mg, 0.61 mmol, 0.40 equiv). The resulting mixture was stirred for 3 h at 90° C. under nitrogen atmosphere. The mixture was allowed to cool down to room temperature. The resulting mixture was filtered, the filter cake was washed with EtOAc (3×15 mL). The filtrate was poured into water (60 mL) and extracted with EtOAc (3×30 mL). The combined organic layers were washed with brine (80 mL), dried over anhydrous $Na_2SO_4$. After filtration, the filtrate was concentrated under reduced pressure. The residue was purified by PREP HPLC to afford 5'-{3-chloro-4-[(3,5-difluoropyridin-2-yl)

methoxy]-6-methyl-2-oxopyridin-1-yl}-3-(2-hydroxypropan-2-yl)-6'-methyl-[1,3'-bipyridin]-2-one (303 mg, 37.3%) as a white solid. LC-MS: (ES+H, m/z): [M+H]$^+$=529.3.

Step 5: Preparation of rel-5'-{3-chloro-4-[(3,5-difluoropyridin-2-yl)methoxy]-6-methyl-2-oxopyridin-1-yl}-3-(2-hydroxypropan-2-yl)-6'-methyl-[1,3'-bipyridin]-2-one & rel-5'-{3-chloro-4-[(3,5-difluoropyridin-2-yl)methoxy]-6-methyl-2-oxopyridin-1-yl}-3-(2-hydroxypropan-2-yl)-6'-methyl-[1,3'-bipyridin]-2-one 5'-{3-chloro-4-[(3,5-difluoropyridin-2-yl)methoxy]-6-methyl-2-oxopyridin-1-yl}-3-(2-hydroxypropan-2-yl)-6'-methyl-[1,3'-bipyridin]-2-one (290 mg) was separated by Prep-Chiral-HPLC to afford Example 16A (90.1 mg, 97.1% purity, ee=100.0%) and Example 16B (66.3 mg, 98.6% purity, ee=100.0%) as a white solid.

Example 16A: LC-MS: (ES+H, m/z): [M+H]$^+$=529.0. $^1$H NMR (300 MHz, DMSO-d$_6$) δ 8.67 (d, 1H), 8.60 (d, 1H), 8.15-8.05 (m, 1H), 8.02 (d, 1H), 7.76-7.65 (m, 2H), 6.80 (s, 1H), 6.42 (t, 1H), 5.49 (d, 2H), 5.25 (s, 1H), 2.26 (s, 3H), 2.01 (s, 3H), 1.47 (s, 3H), 1.46 (s, 3H). $^{19}$F NMR (282 MHz, DMSO-d$_6$) δ −120.13, −120.16, −122.34, −122.37.

Example 16B: LC-MS: (ES+H, m/z): [M+H]$^+$=529.0. $^1$H NMR (300 MHz, DMSO-d$_6$) δ 8.67 (d, 1H), 8.60 (d, 1H), 8.16-8.05 (m, 1H), 8.02 (d, 1H), 7.77-7.66 (m, 2H), 6.81 (s, 1H), 6.42 (t, 1H), 5.49 (d, 2H), 5.26 (s, 1H), 2.26 (s, 3H), 2.01 (s, 3H), 1.47 (s, 3H), 1.46 (s, 3H). $^{19}$F NMR (282 MHz, DMSO-d$_6$) δ −120.13, −120.15, −122.33, −122.36.

Example 17A, 17B

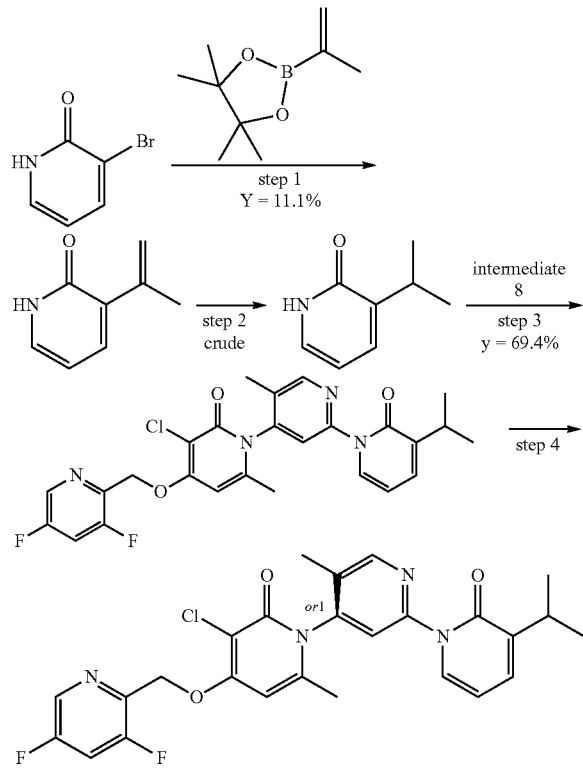

Example 17A

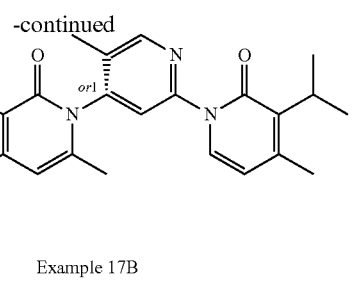

Example 17B

Step 1: Preparation of 3-(prop-1-en-2-yl)-1H-pyridin-2-one

To a stirred mixture of 3-bromo-1H-pyridin-2-one (6.00 g, 34.48 mmol, 1.00 equiv) and 4,4,5,5-tetramethyl-2-(prop-1-en-2-yl)-1,3,2-dioxaborolane (23.18 g, 137.93 mmol, 4.00 equiv) in 1,4-dioxane (60 mL) and H$_2$O (10 mL) were added K$_2$CO$_3$ (9.53 g, 68.96 mmol, 2.00 equiv), Pd(dppf)Cl$_2$ (3.78 g, 5.17 mmol, 0.15 equiv) at room temperature under nitrogen atmosphere. The resulting mixture was stirred for 2 h at 100° C. The reaction mixture was poured into water and the aqueous layer was extracted with EtOAc (3×100 mL), dried over anhydrous Na$_2$SO$_4$. After filtration, the filtrate was concentrated under reduced pressure. The residue was purified by silica gel column chromatography to afford 3-(prop-1-en-2-yl)-1H-pyridin-2-one (1.2 g, 11.1%, 50% purity) as a yellow solid. LC-MS: (ES+H, m/z): [M+H]$^+$=135.9.

Step 2: Preparation of 3-(prop-1-en-2-yl)-1H-pyridin-2-one

To a stirred mixture of 3-(prop-1-en-2-yl)-1H-pyridin-2-one (1.00 g) in DCM (10 ml) was added TFA (10 mL) and SiH(Et)$_3$ (5 mL) at room temperature under nitrogen atmosphere. The resulting mixture was stirred for 24 h at r.t. under nitrogen atmosphere. The resulting mixture was concentrated under reduced pressure to afford 3-(prop-1-en-2-yl)-1H-pyridin-2-one (2.00 g, crude). The crude product was used in the next step directly without further purification. LC-MS: (ES+H, m/z): [M+H]$^+$=138.1.

Step 3: Preparation of 3-chloro-4-[(3,5-difluoropyridin-2-yl)methoxy]-2'-(3-isopropyl-2-oxopyridin-1-yl)-5',6-dimethyl-[1,4'-bipyridin]-2-one To a stirred mixture of 3-isopropyl-1H-pyridin-2-one (600 mg, 4.38 mmol, 2.00 equiv) and 2'-bromo-3-chloro-4-[(3,5-difluoropyridin-2-yl)methoxy]-5',6-dimethyl-[1,4'-bipyridin]-2-one (1.00 g, 2.19 mmol, 1.00 equiv) in 1,4-dioxane (6 mL) were added (1R,2R)—N1,N2-dimethylcyclohexane-1,2-diamine (624 mg, 4.38 mmol, 2.00 equiv), CuI (835 mg, 4.38 mmol, 2.00 equiv) and K$_2$CO$_3$ (597 mg, 4.38 mmol, 2.00 equiv) at room temperature under nitrogen atmosphere. The resulting mixture was stirred for 2 h at 80° C. The mixture was allowed to cool down to room temperature. The reaction mixture was poured into water (30 mL) aqueous layer was extracted with EtOAc (3×50 mL), dried over anhydrous Na$_2$SO$_4$. After filtration, the filtrate was concentrated under reduced pressure. The residue was purified by silica gel column chromatography to afford crude product, which was further purified by Prep-HPLC to afford 3-chloro-4-[(3,5-difluoropyridin-2-yl)methoxy]-2'-(3-isopropyl-2-oxopyridin-1-yl)-5',6-dimethyl-

[1,4'-bipyridin]-2-one (220 mg, 69.4%) as a white solid. LC-MS: (ES+H, m/z): [M+H]⁺=513.2.

Step 4: Preparation of rel-3-chloro-4-[(3,5-difluoro-pyridin-2-yl)methoxy]-2'-(3-isopropyl-2-oxopyridin-1-yl)-5',6-dimethyl-[1,4'-bipyridin]-2-one & rel-3-chloro-4-[(3,5-difluoropyridin-2-yl)methoxy]-2'-(3-isopropyl-2-oxopyridin-1-yl)-5',6-dimethyl-[1,4'-bipyridin]-2-one The racemate (180 mg) was separated by prep-chiral-HPLC to afford Example 17A (63.2 mg, 99.7% purity, ee=100%) and Example 17B (62.0 mg, 96.3% purity, ee=100%) as a white solid.

Example 17A: LC-MS: (ES+H, m/z): [M+H]⁺=513.1. ¹H NMR (300 MHz, DMSO-d₆) δ 8.68 (s, 1H), 8.60 (d, 1H), 8.12-8.06 (m, 1H), 7.84-7.81 (m, 2H), 7.38-7.36 (m, 1H), 6.81 (s, 1H), 6.40-6.35 (m, 1H), 5.49 (d, 2H), 3.09-3.00 (m, 1H), 2.07 (s, 3H), 2.01 (s, 3H), 1.16-1.13 (m, 6H). ¹⁹F NMR (282 MHz, DMSO-d₆) δ −120.16, −120.18, −122.36, −122.38.

Example 17B: LC-MS: (ES+H, m/z): [M+H]⁺=512.95. ¹H NMR (300 MHz, DMSO-d₆) δ 8.68 (s, 1H), 8.60 (d, 1H), 8.13-8.06 (m, 1H), 7.84-7.81 (m, 2H), 7.38-7.36 (m, 1H), 6.80 (s, 1H), 6.40-6.35 (m, 1H), 5.49 (d, 2H), 3.09-3.00 (m, 1H), 2.07 (s, 3H), 2.01 (s, 3H), 1.16-1.13 (m, 6H). ¹⁹F NMR (282 MHz, DMSO-d₆) δ −120.16, −120.18, −122.36, −122.38.

Example 18A, 18B

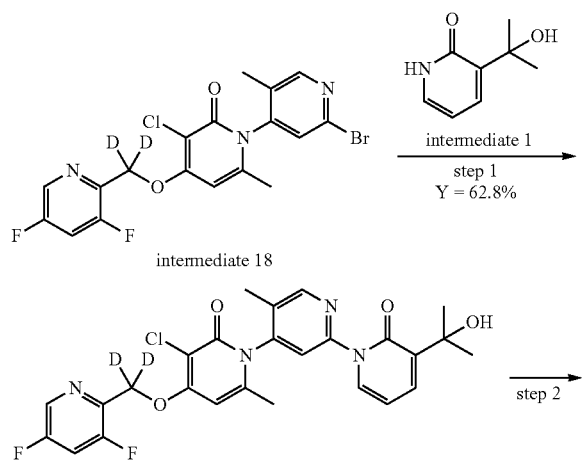

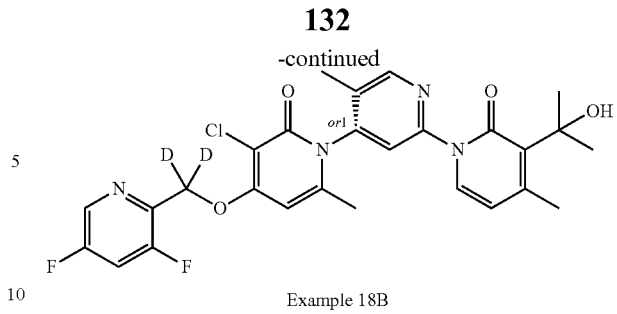

Example 18B

Step 1: Preparation of 3"-chloro-4"-((3,5-difluoropyridin-2-yl)methoxy-d2)-3-(2-hydroxypropan-2-yl)-5',6"-dimethyl-2H,2"H-[1,2':4',1"-terpyridine]-2,2"-dione To a stirred solution of 2'-bromo-3-chloro-4-[(3,5-difluoropyridin-2-yl)(2H2)methoxy]-5',6-dimethyl-[1,4'-bipyridin]-2-one (25.00 g, 54.50 mmol, 1.00 equiv), (1R,2R)—N1,N2-dimethylcyclohexane-1,2-diamine (3.10 g, 21.79 mmol, 0.40 equiv), K₂CO₃ (15.07 g, 109.00 mmol, 2.00 equiv) and CuI (2.08 g, 10.90 mmol, 0.20 equiv) in dioxane (210 mL) was added 3-(2-hydroxypropan-2-yl)-1H-pyridin-2-one (26.72 g, 174.43 mmol, 2.00 equiv) at room temperature under nitrogen atmosphere. The resulting mixture was stirred for 3 h at 80° C. under nitrogen atmosphere. The mixture was allowed to cool to room temperature. The resulting mixture was filtered, the filter cake was washed with ethyl acetate (3×100 mL). The filtrate was diluted with ethyl acetate (2 L) and washed with water (10% NH₃, 3×1 L). The organic layer was concentrated under reduced pressure. The residue was purified by silica gel column chromatography to afford crude product (23.88 g) as a light yellow solid, which was further purified by recrystallization from ACN, the materials were dissolved in ACN at 80° C., then cooled to r.t. for 2 h, and kept at 4° C. overnight. The precipitated solids were collected by filtration and washed with cold ACN (4×20 mL), to afford 3-chloro-4-[(3,5-difluoropyridin-2-yl)(2H2)methoxy]-2'-[3-(2-hydroxypropan-2-yl)-2-oxopyridin-1-yl]-5',6-dimethyl-[1,4'-bipyridin]-2-one (18.21 g, 62.8% yield, 97.2% purity) as a white solid. LC-MS: (ES+H, m/z): [M+H]⁺=531.1. ¹H NMR (300 MHz, DMSO-d₆) δ 8.69 (s, 1H), 8.60 (d, 1H), 8.09 (ddd, 1H), 7.86 (dd, 1H), 7.80 (s, 1H), 7.70 (dd, 1H), 6.81 (d, 1H), 6.43 (t 1H), 5.24 (s, 1H), 2.08 (s, 3H), 2.01 (s, 3H), 1.48 (s, 3H), 1.47 (s, 3H).

Step 2: Preparation of rel-3"-chloro-4"-((3,5-difluoropyridin-2-yl)methoxy-d2)-3-(2-hydroxypropan-2-yl)-5',6"-dimethyl-2H,2"H-[1,2':4',1"-terpyridine]-2,2"-dione (Example 18A)

The racemate (65.00 g) was separated by Prep-Chiral-SFC. The pure fraction was concentrated under reduced pressure to afford the solid, which was re-dissolved in ACN and then concentrated to dryness. The product was suspended in water (120 mL) at 50° C. for 30 min and then allowed to r.t. and kept at 4° C. for 20 min, the precipitated solid was collected to afford rel-3"-chloro-4"-((3,5-difluoropyridin-2-yl)methoxy-d2)-3-(2-hydroxypropan-2-yl)-5', 6"-dimethyl-2H,2"H-[1,2':4',1"-terpyridine]-2,2"-dione (Example 18A: 29.42 g, 98.4% purity, 97.8% deuterium purity, ee=100%) as a white solid and Example 18B (~30.40 g).

30 g of the isomer 2 (Example 18B) in dioxane (200 mL) was heated for 24 h at 100° C., the resulting mixture was concentrated to afford the racemate (~30 g), which was combined with another 6 g from previous mother liquor and then further separated by Prep-Chiral-SFC. The pure fraction was concentrated under reduced pressure to afford the solid, which was re-dissolved in ACN and then concentrated to dryness, to afford rel-3"-chloro-4"-((3,5-difluoropyridin-2-yl)methoxy-d2)-3-(2-hydroxypropan-2-yl)-5',6"-dimethyl-2H,2"H-[1,2':4',1"-terpyridine]-2,2"-dione (Example 18A: 15.10 g, 99.2% purity, 97.8% deuterium purity) as a white solid and Example 18B (~15.40 g, white solid).

2"H-[1,2':4',1"-terpyridine]-2,2"-dione (Example 18A: 41.62 g 99.3% purity, 97.9% deuterium purity, ee=100%).

Example 18A: LC-MS: (ES+H, m/z): [M+H]⁺=531.15. $^1$H NMR (300 MHz, DMSO-d$_6$) δ 8.69 (s, 1H), 8.61 (d, 1H), 8.16-8.03 (m, 1H), 7.86 (dd, 2.1 Hz, 1H), 7.80 (s, 1H), 7.70 (dd, 1H), 6.81 (s, 1H), 6.43 (t, 1H), 5.24 (s, 1H), 2.08 (s, 3H), 2.01 (s, 3H), 1.47 (d, 6H). $^{19}$F NMR (282 MHz, DMSO-d$_6$) δ -120.22, -120.24, -122.28, -122.31.

Example 19A, 19B

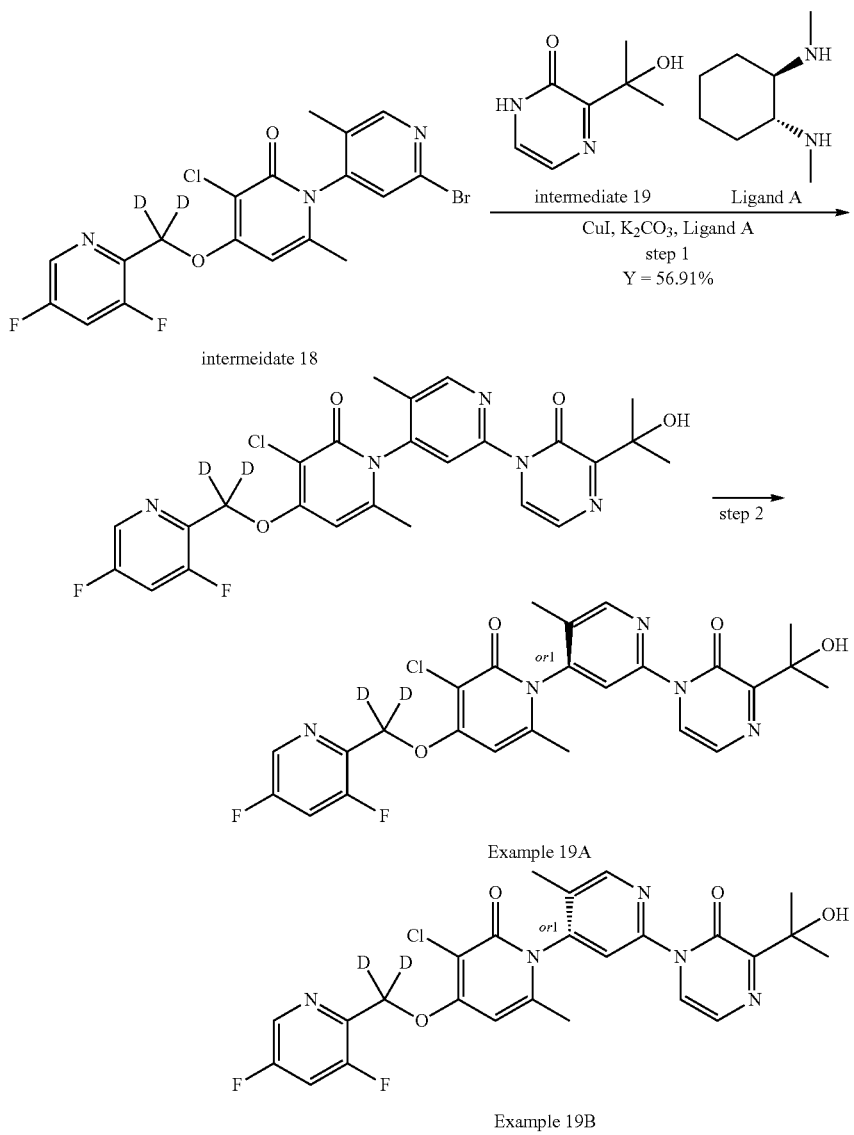

The 2 batches of Example 18A was combined (44.52 g) and then suspended in a co-solvent of IPA and water (440 mL, V$_{IPA}$/V$_{H2O}$=1:6), the slurry was stirred at room temperature for 30 min an then the seed was added, the resulting mixture was stirred for additional 48 hours before storage at 4° C. for 30 min, the precipitated solid was collected and dried to afford rel-3"-chloro-4"-((3,5-difluoropyridin-2-yl)methoxy-d2)-3-(2-hydroxypropan-2-yl)-5',6"-dimethyl-2H, Step 1: Preparation of 3-chloro-4-((3,5-difluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one A mixture of 2'-bromo-3-chloro-4-((3,5-difluoropyridin-2-yl)methoxy-d2)-5',6-dimethyl-2H-[1,4'-bipyridin]-2-one (25.00 g, 54.50 mmol, 1.00 equiv), 3-(2-hydroxypropan-2- yl)-1H-pyrazin-2-one (25.21 g, 163.51 mmol, 3.00 equiv), (1R,2R)—N1,N2-dimethylcyclohexane-1,2-diamine (1.55 g, 10.90 mmol, 0.20 equiv), K$_2$CO$_3$ (15.07 g, 109.00 mmol, 2.00 equiv) and CuI (1.04 g, 5.45 mmol, 0.10 equiv) in dioxane (250 ml) was stirred for 2 h at 80° C. under nitrogen atmosphere. The mixture was allowed to cool down to room temperature. The resulting mixture was diluted with EtOAc (500 mL). The resulting mixture was washed with water (10% NH$_3$.H$_2$O, 5×300 mL). The combined organic layers were washed with brine (500 mL), dried over anhydrous Na$_2$SO$_4$. After filtration, the filtrate was concentrated under reduced pressure. The residue was purified by silica gel column chromatography, the pure fraction was concentrated under reduced pressure to afford crude product (21.5 g) as a yellow solid. The crude product was recrystallized from ACN (150 mL) to afford 3-chloro-4-((3,5-difluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one (16.50 g, 56.91%) as alight yellow solid. LC-MS: (ES+H, m/z): [M+H]$^+$=532.3.

Step 2: Preparation of rel-3-chloro-4-((3,5-difluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one & rel-3-chloro-4-((3,5-difluoropyridin-2-yl)methoxy-d2)-2'-(3-(2-hydroxypropan-2-yl)-2-oxopyrazin-1(2H)-yl)-6-methyl-2H-[1,4'-bipyridin]-2-one The racemate (80.00 g) was separated by Prep-Chiral-SFC. The pure fraction was concentrated under reduced pressure to afford the crude product and Example 19B (~35.00 g). The crude product was re-dissolved in ACN and then concentrated to dryness. The solid was suspended in water (150 mL), stirred for 30 min at 50° C. and then allowed to r.t., the precipitated solid was collected and dried to afford Example 19A (33.60 g, 98.2% purity, 98.1% deuterium purity, ee=99.8%) as a light yellow solid.

35 g of the isomer 2 (Example 19B) in dioxane (200 mL) was heated for 24 h at 100° C., the resulting mixture was concentrated to afford the racemate (~35 g) and then further separated by Prep-Chiral-SFC. The pure fraction was concentrated under reduced pressure to afford the solid, which was re-dissolved in ACN and then concentrated to dryness, to afford rel-3"-chloro-4"-((3,5-difluoropyridin-2-yl)methoxy-d2)-3-(2-hydroxypropan-2-yl)-5',6"-dimethyl-2H,2"H-[1,2':4',1"-terpyridine]-2,2"-dione (Example 19A: 16.1 g, 98.0% purity, 97.7% deuterium purity, ee=100.0%) as a white solid and Example 19B (~15.20 g, yellow solid).

The 2 batches of Example 19A was combined (49.51 g). The product was re-dissolved in ACN and then concentrated to dryness. The product was suspended in water (150 mL), stirred for 30 min at 50° C. and then allowed to r.t., the precipitated solid was collected to afford (Example 19A: 98.0% purity, 97.7% deuterium purity, ee=100.0%) as a light yellow solid.

Example 19A: LC-MS: (ES+H, m/z): [M+H]$^+$=532.25. $^1$H NMR (400 MHz, DMSO-d$_6$) δ 8.75 (s, 1H), 8.60 (d, 1H), 8.13-8.07 (m, 1H), 8.00 (d, 1H), 7.94 (s, 1H), 7.48 (d, 1H), 6.82 (d, 1H), 5.13 (s, 1H), 2.11 (s, 3H), 2.01 (s, 3H), 1.51 (s, 6H). $^{19}$F NMR (377 MHz, DMSO-d$_6$) δ−120.25, −120.27, −122.32, −122.34.

Example 19B: LC-MS: (ES+H, m/z): [M+H]$^+$=532.3. $^1$H NMR (400 MHz, DMSO-d6) δ 8.75 (s, 1H), 8.60 (d, 1H), 8.13-8.07 (m, 1H), 8.00 (d, 1H), 7.94 (s, 1H), 7.48 (d, 1H), 6.82 (d, 1H), 5.13 (s, 1H), 2.11 (s, 3H), 2.01 (s, 3H), 1.51 (s, 6H). 19F NMR (377 MHz, DMSO-d6) δ−120.25, −120.27, −122.32, −122.34.

Example 20A, 20B

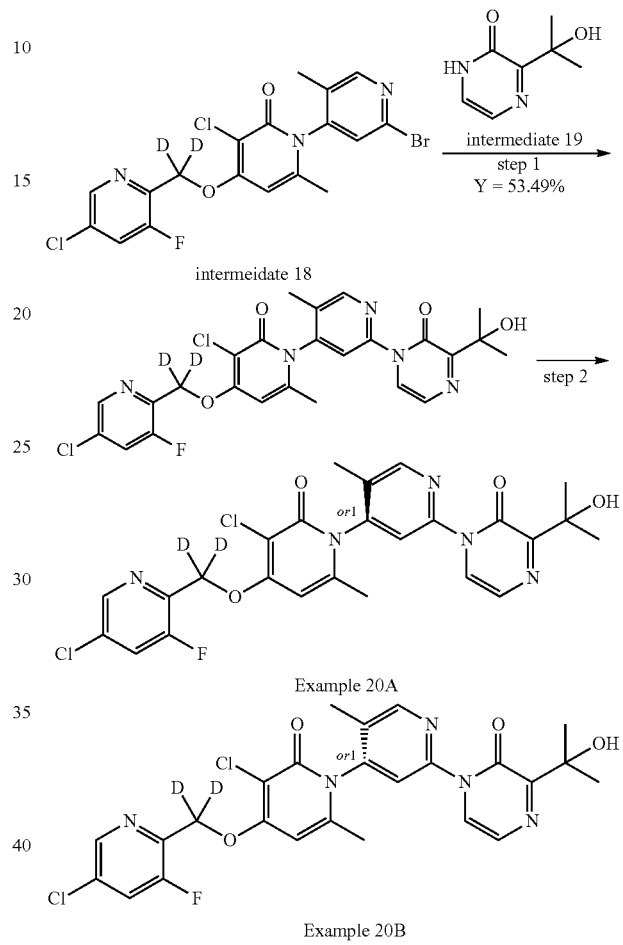

Step 1: Preparation of 3-chloro-4-[(5-chloro-3-fluoropyridin-2-yl)(2H2)methoxy]-2'-[3-(2-hydroxypropan-2-yl)-2-oxopyrazin-1-yl]-5',6-dimethyl-[1,4'-bipyridin]-2-one A mixture of 2'-bromo-3-chloro-4-[(5-chloro-3-fluoropyridin-2-yl)(2H2)methoxy]-5',6-dimethyl-[1,4'-bipyridin]-2-one (15.00 g, 31.57 mmol, 1.00 equiv), 3-(2-hydroxypropan-2-yl)-1H-pyrazin-2-one (9.73 g, 63.14 mmol, 2.00 equiv), K$_2$CO$_3$ (8.73 g, 63.14 mmol, 2.00 equiv), CuI (1.20 g, 6.31 mmol, 0.20 equiv) and (1R,2R)—N1,N2-dimethylcyclohexane-1,2-diamine (1.80 g, 12.62 mmol, 0.40 equiv) in dioxane (120 mL) was stirred for 2 h at 80° C. under nitrogen atmosphere. The mixture was allowed to room temperature. The resulting mixture was diluted with ethyl acetate (1500 mL) and washed with water (10% NH$_3$, 3×500 mL). The organic layer was concentrated under reduced pressure. The residue was purified by silica gel column chromatography to afford crude product (13 g) as a white solid. The crude product was recrystallized from DCM (20 mL) and ACN (40 mL) to afford 3-chloro-4-[(5-chloro-3- fluoropyridin-2-yl)(2H2)methoxy]-2'-[3-(2-hydroxypropan-2-yl)-2-oxopyrazin-1-yl]-5',6-dimethyl-[1,4'-bipyridin]-2-one (9.26 g, 53.49%) as a white solid. LC-MS: (ES+H, m/z): [M+H]$^+$=548.2. $^1$H NMR (400 MHz, DMSO-d$_6$) δ 8.74 (s, 1H), 8.61 (dd, 1H), 8.24 (dd, 1H), 8.00 (d, 1H), 7.94 (s, 1H), 7.47 (d, 1H), 6.79 (d, 1H), 5.12 (s, 1H), 2.10 (s, 3H), 2.00 (s, 3H), 1.50 (s, 6H).

Step 2: Preparation of rel-3-chloro-4-((5-chloro-3-fluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one and rel-3-chloro-4-((5-chloro-3-fluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one The racemate (9.20 g) was separated by Prep-SFC to afford rel-3-chloro-4-((5-chloro-3-fluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one (Example 20A: 3.47 g, 98.6% purity, 96.5% deuterium purity, ee=100%) as a white solid and rel-3-chloro-4-((5-chloro-3-fluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one (Example 20B: 3.55 g, 97.2% purity, 96.3% deuterium purity, ee=100%) as a white solid.

Example 20A: LC-MS: (ES+H, m/z): [M+H]$^+$=548.1. $^1$H NMR (400 MHz, DMSO-d$_6$) δ 8.74 (s, 1H), 8.61 (dd, 1H), 8.24 (dd, 1H), 8.00 (d, 1H), 7.94 (s, 1H), 7.47 (d, 1H), 6.79 (s, 1H), 5.12 (s, 1H), 2.10 (s, 3H), 2.00 (s, 3H), 1.51 (s, 6H). $^{19}$F NMR (377 MHz, DMSO-d$_6$) δ−121.68.

Example 20B: LC-MS: (ES+H, m/z): [M+H]$^+$=548.0. $^1$H NMR (400 MHz, DMSO-d$_6$) δ 8.74 (s, 1H), 8.61 (dd, 1H), 8.24 (dd, 1H), 8.00 (d, 1H), 7.95 (s, 1H), 7.47 (d, 1H), 6.79 (s, 1H), 5.13 (s, 1H), 2.10 (s, 3H), 2.00 (s, 3H), 1.51 (s, 6H). $^{19}$F NMR (377 MHz, DMSO-d$_6$) δ−121.68.

Example 21A, 21B

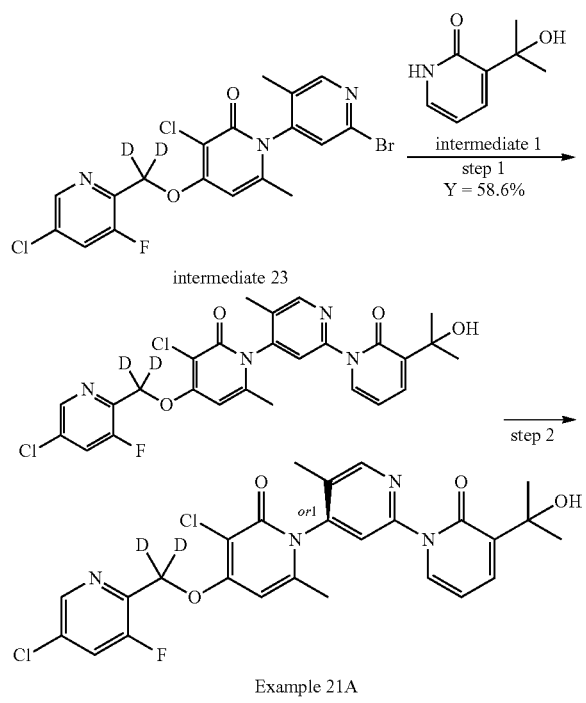

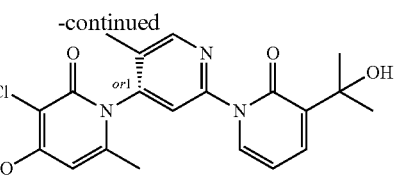

Example 21B

Step 1: Preparation of 3-chloro-4-[(5-chloro-3-fluoropyridin-2-yl)(2H2)methoxy]-2'-[3-(2-hydroxypropan-2-yl)-2-oxopyridin-1-yl]-5',6-dimethyl-[1,4'-bipyridin]-2-one A mixture of 2'-bromo-3-chloro-4-[(5-chloro-3-fluoropyridin-2-yl)(2H2)methoxy]-5',6-dimethyl-[1,4'-bipyridin]-2-one (1.00 g, 2.10 mmol, 1.00 equiv), 3-(2-hydroxypropan-2-yl)-1H-pyridin-2-one (0.64 g, 4.21 mmol, 2.00 equiv), (1R,2R)—N1,N2-dimethylcyclohexane-1,2-diamine (0.20 g, 1.05 mmol, 1.00 equiv), K$_2$CO$_3$ (0.58 g, 4.21 mmol, 2.00 equiv) and CuI (0.30 g, 2.10 mmol, 0.50 equiv) in dioxane (10 mL) was stirred for 2 h at 80° C. under nitrogen atmosphere. The mixture was allowed to cool down to room temperature. The resulting mixture was diluted with EtOAc (20 mL). The resulting mixture was washed with water (10% NH$_3$.H$_2$O, 3×20 mL). The combined organic layers were washed with brine (50 mL), dried over anhydrous Na$_2$SO$_4$. After filtration, the filtrate was concentrated under reduced pressure. The crude product was purified by Prep-HPLC to afford 3-chloro-4-[(5-chloro-3-fluoropyridin-2-yl) (2H2) methoxy]-2'-[3-(2-hydroxypropan-2-yl)-2-oxopyridin-1-yl]-5',6-dimethyl-[1,4'-bipyridin]-2-one (680 mg, 58.6%) as a white solid. LC-MS: (ES+H, m/z): [M+H]$^+$=547.1.

Step 2: Preparation of rel-3-chloro-4-[(5-chloro-3-fluoropyridin-2-yl)(2H2)methoxy]-2'-[3-(2-hydroxypropan-2-yl)-2-oxopyridin-1-yl]-5',6-dimethyl-[1,4'-bipyridin]-2-one & rel-3-chloro-4-[(5-chloro-3-fluoropyridin-2-yl)(2H2)methoxy]-2'-[3-(2-hydroxypropan-2-yl)-2-oxopyridin-1-yl]-5',6-dimethyl-[1,4'-bipyridin]-2-one The racemate (680 mg) was separated by prep-SFC to afford Example 21A (103.8 mg, 98.1% purity, 97.6% deuterium purity, ee=100.0%) and Example 21B (75.4 mg, 95.3% purity, 97.0% deuterium purity, ee=100.0%) as a white solid.

Example 21A: LC-MS: (ES+H, m/z): [M+H]$^+$=547.2. $^1$H NMR (300 MHz, DMSO-d$_6$) δ 8.69 (s, 1H), 8.61 (s, 1H), 8.30-8.20 (m, 1H), 7.91-7.82 (m, 1H), 7.79 (s, 1H), 7.75-7.66 (m, 1H), 6.78 (s, 1H), 6.43 (t, 1H), 5.24 (s, 1H), 2.08 (s, 3H), 2.00 (s, 3H), 1.47 (s, 3H), 1.46 (s, 3H). $^{19}$F NMR (282 MHz, DMSO-d$_6$) δ−121.66.

Example 21B: LC-MS: (ES+H, m/z): [M+H]$^+$=547.3. $^1$H NMR (300 MHz, DMSO-d$_6$) δ 8.69 (s, 1H), 8.61 (d, 1H), 8.32-8.19 (m, 1H), 7.91-7.82 (m, 1H), 7.79 (s, 1H), 7.75-7.66 (m, 1H), 6.78 (s, 1H), 6.43 (t, 1H), 5.23 (s, 1H), 2.08 (s, 3H), 2.00 (s, 3H), 1.47 (s, 3H), 1.46 (s, 3H). $^{19}$F NMR (282 MHz, DMSO-d$_6$) δ−121.67.

Example 22A, 22B

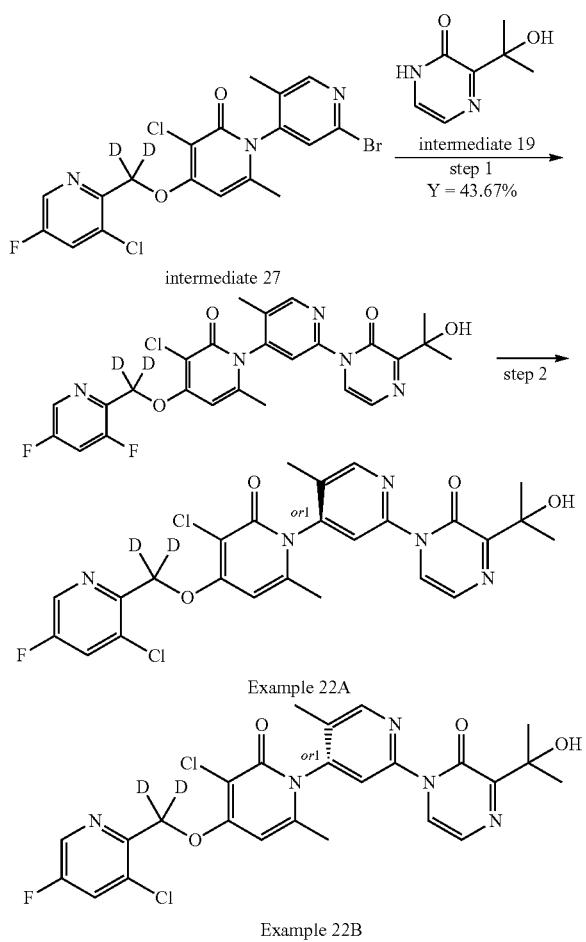

Example 22A

Example 22B

Step 1: Preparation of 3-chloro-4-((3-chloro-5-fluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one A mixture of 2'-bromo-3-chloro-4-((3-chloro-5-fluoropyridin-2-yl)methoxy-d2)-5',6-dimethyl-2H-[1,4'-bipyridin]-2-one (16.00 g, 33.67 mmol, 1 equiv), 3-(2-hydroxypropan-2-yl)-1H-pyrazin-2-one (454.26 mg, 2.94 mmol, 2.00 equiv), (1S,2S)—N1,N2-dimethylcyclohexane-1,2-diamine (83.83 mg, 0.58 mmol, 0.40 equiv), CuI (0.80 g, 4.20 mmol, 0.20 equiv) and $K_2CO_3$ (407.22 mg, 2.94 mmol, 2.00 equiv) in 1,4-dioxane (100 ml) was stirred for 2 h at 80° C. under nitrogen atmosphere. The mixture was allowed to room temperature. The resulting mixture was diluted with ethyl acetate (1000 mL) and washed with water (10% $NH_3$, 3×500 mL). The organic layer was concentrated under reduced pressure. The residue was purified by silica gel column chromatography to afford crude product (9.8 g). The crude product was recrystallized from ACN (50 ml) to afford 3-chloro-4-((3-chloro-5-fluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one (8.4 g, 43.67%) as a white solid. LC-MS: (ES+H, m/z): [M+H]⁺=548.0. ¹H NMR (400 MHz, DMSO-$d_6$) δ8.75 (s, 1H), 8.68 (d, 1H), 8.25 (dd, 1H), 8.00 (d, 1H), 7.95 (s, 1H), 7.47 (d, 1H), 6.78 (d, 1H), 5.13 (s, 1H), 2.10 (s, 3H), 2.00 (s, 3H), 1.51 (s, 6H).

Step 2: Preparation of rel-3-chloro-4-((3-chloro-5-fluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one and rel-3-chloro-4-((3-chloro-5-fluoropyridin-2-yl)methoxy-d2)-2'-(3-(2-hydroxypropan-2-yl)-2-oxopyrazin-1(2H)-yl)-5',6-dimethyl-2H-[1,4'-bipyridin]-2-one The racemate (8.40 g) was separated by Prep-Chiral-SFC to afford Example 22A (3.23 g, 98.2% purity, ee=100%, $[a]^{25}_D$ (c=1.075, MeOH): −136.93) as a white solid and Example 22B (3.13 g, 95.0% purity, ee=100%, $[a]^{25}_D$ (c=1.075, MeOH): +127.53) as a white solid.

Example 22A: LC-MS: (ES+H, m/z): [M+H]⁺=548.2. ¹H NMR (300 MHz, DMSO-$d_6$) δ 8.75 (s, 1H), 8.68 (d, 1H), 8.25 (dd, 1H), 8.00 (d, 1H), 7.95 (s, 1H), 7.48 (d, 1H), 6.79 (s, 1H), 5.13 (s, 1H), 2.11 (s, 3H), 2.00 (s, 3H), 1.51 (s, 6H). ¹⁹F NMR (282 MHz, DMSO-$d_6$) δ−124.18, −124.20.

Example 22B: LC-MS: (ES+H, m/z): [M+H]⁺=548.2. ¹H NMR (300 MHz, DMSO-$d_6$) δ 8.75 (s, 1H), 8.68 (d, 1H), 8.25 (dd, 1H), 8.00 (d, 1H), 7.96 (s, 1H), 7.48 (d, 1H), 6.79 (s, 1H), 5.13 (s, 1H), 2.11 (s, 3H), 2.00 (s, 3H), 1.51 (s, 6H). ¹⁹F NMR (282 MHz, DMSO-$d_6$) δ−124.18, −124.20.

Example 23A, 23B

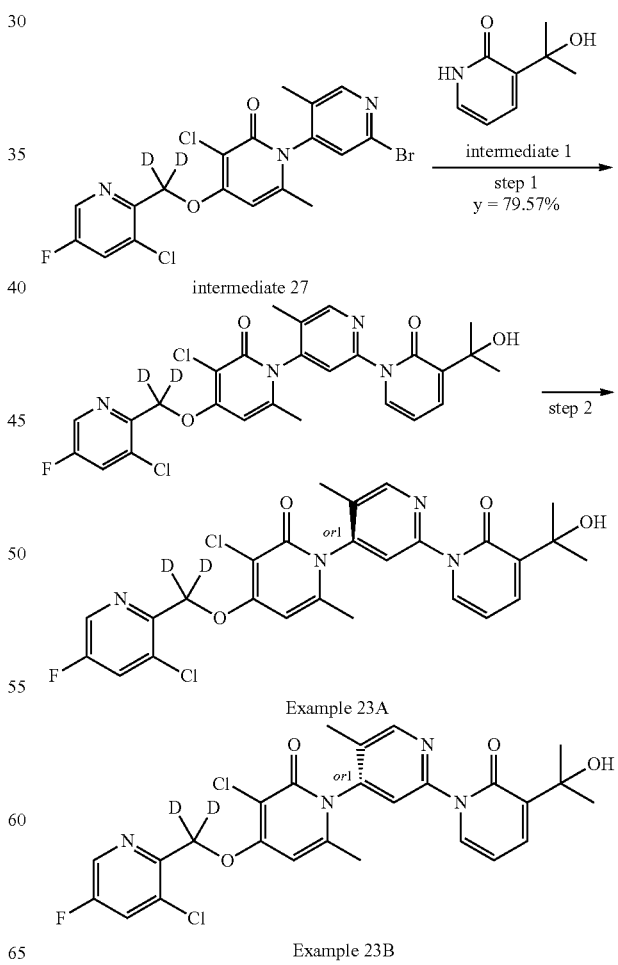

Example 23A

Example 23B

Step 1: Preparation of 4'-{3-chloro-4-[(3-chloro-5-fluoropyridin-2-yl)(2H2)methoxy]-6-methyl-2-oxopyridin-1-yl}-3-(2-hydroxypropan-2-yl)-5'-methyl-[1,2'-bipyridin]-2-one A mixture of 2'-bromo-3-chloro-4-[(3-chloro-5-fluoropyridin-2-yl)(2H2)methoxy]-5',6-dimethyl-[1,4'-bipyridin]-2-one (600 mg, 1.26 mmol, 1.00 equiv), 3-(2-hydroxypropan-2-yl)-1H-pyridin-2-one (386 mg, 2.52 mmol, 2.00 equiv), (1R,2R)—N1,N2-dimethylcyclohexane-1,2-diamine (71 mg, 0.50 mmol, 0.40 equiv), K$_2$CO$_3$ (349 mg, 2.52 mmol, 2.00 equiv) and CuI (48 mg, 0.25 mmol, 0.20 equiv) in dioxane (6 ml) was stirred for 2 h at 80° C. under nitrogen atmosphere. The mixture was allowed to cool down to room temperature. The resulting mixture was diluted with EtOAc (20 mL). The resulting mixture was washed with water (10% NH$_3$.H$_2$O, 3×20 mL). The combined organic layers were washed with brine (50 mL), dried over anhydrous Na$_2$SO$_4$. After filtration, the filtrate was concentrated under reduced pressure. The crude product (550 mg) was purified by Prep-HPLC to afford 4'-{3-chloro-4-[(3-chloro-5-fluoropyridin-2-yl)(2H2)methoxy]-6-methyl-2-oxopyridin-1-yl}-3-(2-hydroxypropan-2-yl)-5'-methyl-[1,2'-bipyridin]-2-one (550 mg, 79.57%) as a white solid. LC-MS: (ES+H, m/z): [M+H]$^+$=547.0.

Step 2: Preparation of rel-4'-{3-chloro-4-[(3-chloro-5-fluoropyridin-2-yl)(2H2)methoxy]-6-methyl-2-oxopyridin-1-yl}-3-(2-hydroxypropan-2-yl)-5'-methyl-[1,2'-bipyridin]-2-one & rel-4'-{3-chloro-4-[(3-chloro-5-fluoropyridin-2-yl)(2H2)methoxy]-6-methyl-2-oxopyridin-1-yl}-3-(2-hydroxypropan-2-yl)-5'-methyl-[1,2'-bipyridin]-2-one The racemate (500 mg) was separated by prep-SFC to afford Example 23A (192.8 mg, 98.4% purity, 95.9% deuterium purity, ee=100.0%) as a white solid and Example 23B (201.8 mg, 98.4% purity, 96.0% deuterium purity, ee=100.0%) as a white solid.

Example 23A: LC-MS: (ES+H, m/z): [M+H]$^+$=547.00. $^1$H NMR (400 MHz, DMSO-d$_6$) δ 8.70-8.64 (m, 2H), 8.25 (dd, 1H), 7.86 (dd, 1H), 7.79 (s, 1H), 7.70 (dd, 1H), 6.77 (s, 1H), 6.42 (t, 1H), 5.22 (s, 1H), 2.08 (s, 3H), 2.00 (s, 3H), 1.47 (s, 3H), 1.46 (s, 3H). $^{19}$F NMR (282 MHz, DMSO-d$_6$) δ−124.16.

Example 23B: LC-MS: (ES+H, m/z): [M+H]$^+$=547.05. $^1$H NMR (400 MHz, DMSO-d$_6$) δ 8.71-8.65 (m, 2H), 8.25 (dd, 1H), 7.86 (dd, 1H), 7.79 (s, 1H), 7.70 (dd, 1H), 6.77 (s, 1H), 6.42 (t, 1H), 5.23 (s, 1H), 2.08 (s, 3H), 2.00 (s, 3H), 1.47 (s, 3H), 1.46 (s, 3H). $^{19}$F NMR (282 MHz, DMSO-d$_6$) δ−124.16.

Example 24A, 24B

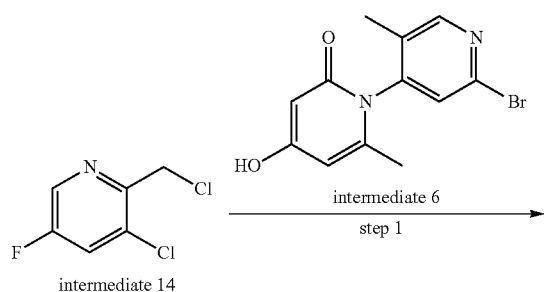

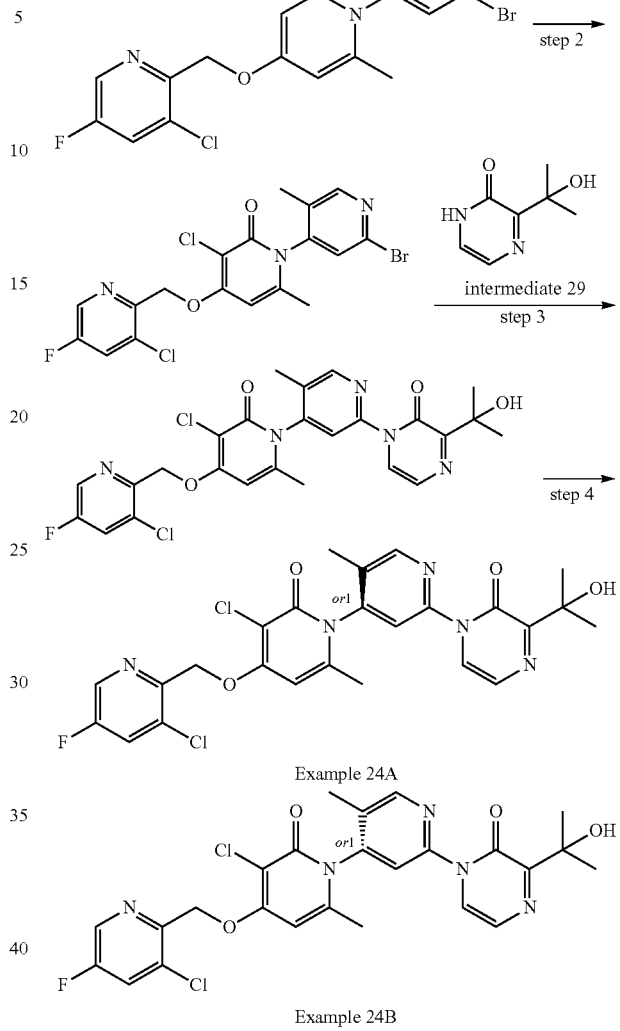

Example 24A

Example 24B

Step 1: Preparation of 2'-bromo-4-[(3-chloro-5-fluoropyridin-2-yl)methoxy]-5',6-dimethyl-[1,4'-bipyridin]-2-one A mixture of 2'-bromo-4-hydroxy-5',6-dimethyl-[1,4'-bipyridin]-2-one (1.32 g, 4.40 mmol, 1.00 equiv), 3-chloro-2-(chloromethyl)-5-fluoropyridine (2.43 g, 13.21 mmol, 3.00 equiv), 18-crown-6 (349 mg, 1.32 mmol, 0.30 equiv) and K$_2$CO$_3$ (3.71 g, 26.43 mmol, 6.00 equiv) in DMF (8 mL) was stirred for 1 h at 60° C. under nitrogen atmosphere. The resulting mixture was diluted with ethyl acetate (300 mL), washed with 3×100 mL of H$_2$O. The organic layers were concentrated under reduced pressure and purified by silica gel column chromatography to afford 2'-bromo-4-[(3-chloro-5-fluoropyridin-2-yl)methoxy]-5',6-dimethyl-[1,4'-bipyridin]-2-one (1.30 g, 66.2%) as a yellow oil. LC-MS: (ES+H, m/z): [M+H]$^+$=440.1. $^1$H NMR (400 MHz, DMSO-d$_6$) δ 8.68-8.65 (m, 1H), 8.48 (s, 1H), 8.25-8.20 (m, 1H), 7.74 (s, 1H), 6.16-6.12 (m, 1H), 6.02 (d, 1H), 5.26 (s, 2H), 1.97 (s, 3H), 1.86 (s, 3H).

Step 2: Preparation of 2'-bromo-3-chloro-4-[(3-chloro-5-fluoropyridin-2-yl)methoxy]-5',6-dimethyl-[1,4'-bipyridin]-2-one 2'-bromo-4-[(3-chloro-5-fluoropyridin-2-yl)methoxy]-5',6-dimethyl-[1,4'-bipyridin]-2-one (1.10 g, 2.50 mmol, 1.00 equiv), NCS (401 mg, 3.01 mmol, 1.20 equiv), 2,2-dichloroacetic acid (323 mg, 2.50 mmol, 1.00 equiv) was added to the IPA (5 mL) at room temperature. The resulting mixture was stirred for 2 h at 60° C. under nitrogen atmosphere. The mixture was allowed to r.t. The resulting mixture was filtered, the filter cake was washed with IPA (3×5 mL). The filtrate was concentrated under reduced pressure. This resulted in 2'-bromo-3-chloro-4-[(3-chloro-5-fluoropyridin-2-yl)methoxy]-5',6-dimethyl-[1,4'-bipyridin]-2-one (810 mg, 68.2%) as a white solid. LC-MS: (ES+H, m/z): [M+H]$^+$=474.0. $^1$H NMR (400 MHz, DMSO-$d_6$) δ 8.67 (d, 1H), 8.52 (s, 1H), 8.25 (dd, 1H), 7.81 (s, 1H), 6.76 (s, 1H), 5.48 (d, 2H), 1.96 (s, 3H), 1.94 (s, 3H).

Step 3: Preparation of 3-chloro-4-[(3-chloro-5-fluoropyridin-2-yl)methoxy]-2'-[3-(2-hydroxypropan-2-yl)-2-oxopyrazin-1-yl]-5',6-dimethyl-[1,4'-bipyridin]-2-one A mixture of 2'-bromo-3-chloro-4-[(3-chloro-5-fluoropyridin-2-yl)methoxy]-5',6-dimethyl-[1,4'-bipyridin]-2-one (725 mg, 1.53 mmol, 1.00 equiv), 3-(2-hydroxypropan-2-yl)-1H-pyrazin-2-one (708 mg, 4.59 mmol, 3.00 equiv), (1S,2S)—N1,N2-dimethylcyclohexane-1,2-diamine (87 mg, 0.61 mmol, 0.40 equiv), CuI (58 mg, 0.30 mmol, 0.20 equiv), K$_2$CO$_3$ (423 mg, 3.06 mmol, 2.00 equiv) in dioxane (5 mL) was stirred for 3 h at 80° C. under nitrogen atmosphere. The resulting mixture was diluted with ethyl acetate (150 mL), washed with 3×50 mL of 10% NH$_3$.H$_2$O. The organic layers were concentrated under reduced pressure and the residue was purified by silica gel column chromatography to afford crude product, which was further purified by PREP-HPLC. This resulted in 3-chloro-4-[(3-chloro-5-fluoropyridin-2-yl)methoxy]-2'-[3-(2-hydroxypropan-2-yl)-2-oxopyrazin-1-yl]-5',6-dimethyl-[1,4'-bipyridin]-2-one (140 mg, 16.7%) as a white solid. LC-MS: (ES+H, m/z): [M+H]$^+$=546.2.

Step 4: Preparation of rel-3-chloro-4-[(3-chloro-5-fluoropyridin-2-yl)methoxy]-2'-[3-(2-hydroxypropan-2-yl)-2-oxopyrazin-1-yl]-5',6-dimethyl-[1,4'-bipyridin]-2-one & rel-3-chloro-4-[(3-chloro-5-fluoropyridin-2-yl)methoxy]-2'-[3-(2-hydroxypropan-2-yl)-2-oxopyrazin-1-yl]-5',6-dimethyl-[1,4'-bipyridin]-2-one 3-chloro-4-[(3-chloro-5-fluoropyridin-2-yl)methoxy]-2'-[3-(2-hydroxypropan-2-yl)-2-oxopyrazin-1-yl]-5',6-dimethyl-[1,4'-bipyridin]-2-one (140 mg) was separated by prep-chiral-HPLC to afford Example 24A (57.6 mg, 99.7% purity, ee=100.0%) and Example 24B (42.6 mg, 99.6% purity, ee=100%) as a white solid.

Example 24A: LC-MS: (ES+H, m/z): [M+H]$^+$=546.00. $^1$H NMR (300 MHz, DMSO-$d_6$) δ 8.75 (s, 1H), 8.68 (d, 1H), 8.26 (dd, 1H), 8.00 (d, 1H), 7.95 (s, 1H), 7.48 (d, 1H), 6.79 (s, 1H), 5.51 (s, 2H), 5.13 (s, 1H), 2.10 (s, 3H), 2.00 (s, 3H), 1.51 (s, 6H). $^{19}$F NMR (282 MHz, DMSO-$d_6$) δ−124.24.

Example 24B: LC-MS: (ES+H, m/z): [M+H]$^+$=546.00. $^1$H NMR (300 MHz, DMSO-$d_6$) δ 8.75 (s, 1H), 8.68 (d, 1H), 8.26 (dd, 1H), 8.00 (d, 1H), 7.95 (s, 1H), 7.48 (d, 1H), 6.79 (s, 1H), 5.51 (s, 2H), 5.13 (s, 1H), 2.10 (s, 3H), 2.00 (s, 3H), 1.51 (s, 6H). $^{19}$F NMR (282 MHz, DMSO-$d_6$) δ−124.24.

Example 25A, 25B

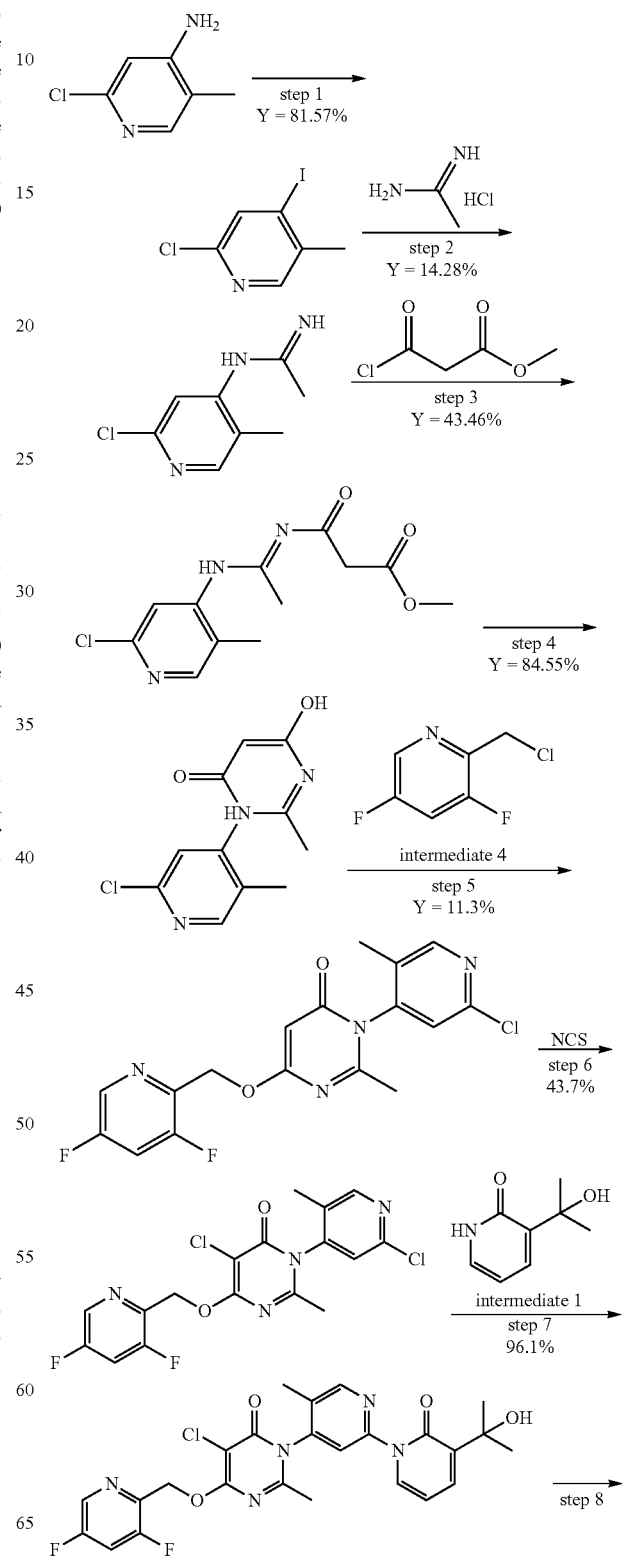

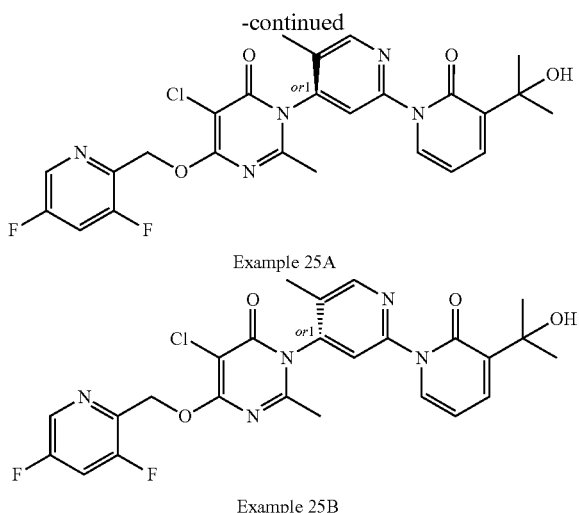

Example 25A

Example 25B

Step 1: Preparation of 2-chloro-4-iodo-5-methylpyridine

To a stirred mixture of 2-chloro-5-methylpyridin-4-amine (20 g, 140.26 mmol, 1.00 equiv) and triiodomethane (82.84 g, 210.39 mmol, 1.5 equiv) in THF (200 mL) was added tBuONO (21.7 g, 210.39 mmol, 1.5 equiv) dropwise at 0° C. under nitrogen atmosphere. The mixture was stirred for 1 h at room temperature. And the mixture was stirred for additional 3 h at 50° C. under nitrogen atmosphere. The mixture was allowed to cool down to r.t. The resulting mixture was concentrated under reduced pressure. The residue was purified by silica gel column chromatography to afford 2-chloro-4-iodo-5-methylpyridine (29 g, 81.57%) as a yellow solid. LC-MS: (ES+H, m/z): [M+H]$^+$=253.9. $^1$H NMR (400 MHz, DMSO-d$_6$) δ 8.26 (s, 1H), 8.01 (s, 1H), 2.33 (s, 3H).

Step 2: Preparation of N-(2-chloro-5-methylpyridin-4-yl)acetimidamide

A mixture of 2-chloro-4-iodo-5-methylpyridine (29 g, 114.412 mmol, 1.00 equiv), acetimidamide hydrochloride (32.27 g, 343.236 mmol, 3 equiv), K$_2$CO$_3$(55.34 g, 400.442 mmol, 3.5 equiv) and CuI (43.58 g, 228.82 mmol, 2 equiv) in DMF (70 mL) was stirred for overnight at 80° C. under nitrogen atmosphere. The mixture was allowed to cool down to r.t. The resulting mixture was diluted with EtOAc (1000 mL). The organic layers were washed with sat. NaCl (aq.) (3×500 mL), dried over anhydrous Na$_2$SO$_4$. After filtration, the filtrate was concentrated under reduced pressure. The residue was purified by silica gel column chromatography to afford N-(2-chloro-5-methylpyridin-4-yl)acetimidamide (3 g, 14.28%) as a brown solid. LC-MS: (ES+H, m/z): [M+H]$^+$ =184.0. $^1$H NMR (400 MHz, DMSO-d$_6$) δ 8.03 (s, 1H), 6.68 (s, 1H), 6.66-6.03 (m, 2H), 1.97 (s, 3H), 1.86 (s, 3H).

Step 3: Preparation of methyl (E)-3-((1-((2-chloro-5-methylpyridin-4-yl)amino)ethylidene)amino)-3-oxopropanoate To a stirred solution of N-(2-chloro-5-methylpyridin-4-yl)acetimidamide (700 mg, 3.812 mmol, 1.00 equiv) and 4-methylmorpholine (771.10 mg, 7.624 mmol, 2 equiv) in DCM (10 mL) were added methyl 3-chloro-3-oxopropanoate (1040.85 mg, 7.624 mmol, 2 equiv) dropwise at 0° C. under nitrogen atmosphere. The resulting mixture was stirred for 2 h at room temperature. The reaction was quenched by the addition of sat. NaHCO$_3$ (aq.) (10 mL) at room temperature. The resulting mixture was poured into water (50 mL). And the resulting mixture was extracted with EtOAc (3×50 mL). The combined organic layers were washed with sat. NaCl (aq.) (50 mL), then concentrated under reduced pressure. The residue was purified by silica gel column chromatography to afford methyl (E)-3-((1-((2-chloro-5-methylpyridin-4-yl)amino)ethylidene)amino)-3-oxopropanoate (470 mg, 43.46%) as a brown solid. LC-MS: (ES+H, m/z): [M+H]$^+$=283.8. $^1$H NMR (400 MHz, DMSO-d$_6$) δ 10.68 (s, 1H), 8.14 (s, 1H), 6.85 (s, 1H), 3.63 (s, 3H), 3.61 (s, 2H), 2.05 (s, 3H), 1.99 (s, 3H).

Step 4: Preparation of 3-(2-chloro-5-methylpyridin-4-yl)-6-hydroxy-2-methylpyrimidin-4(3H)-one To a stirred solution of methyl (E)-3-((1-((2-chloro-5-methylpyridin-4-yl)amino)ethylidene)amino)-3-oxopropanoate (2.8 g, 9.869 mmol, 1.00 equiv) in dioxane (20 mL) were added DBU (4.51 g, 29.607 mmol, 3 equiv) dropwise at 0° C. under nitrogen atmosphere. The resulting mixture was stirred for 4 h at 80° C. under nitrogen atmosphere. The mixture was allowed to cool down to r.t. The resulting mixture was concentrated under vacuum. The residue was purified by silica gel column chromatography to afford 3-(2-chloro-5-methylpyridin-4-yl)-6-hydroxy-2-methylpyrimidin-4(3H)-one (2.1 g, 84.55%) as a brown solid. LC-MS: (ES+H, m/z): [M+H]$^+$=252.0.

Step 5: Preparation of 3-(2-chloro-5-methylpyridin-4-yl)-6-[(3,5-difluoropyridin-2-yl)methoxy]-2-methylpyrimidin-4-one To a stirred mixture of 3-(2-chloro-5-methylpyridin-4-yl)-6-hydroxy-2-methylpyrimidin-4-one (3.80 g, 15.10 mmol, 1.00 equiv) and 2-(chloromethyl)-3,5-difluoropyridine (2.96 g, 18.12 mmol, 1.20 equiv) in DMF was added K$_2$CO$_3$ (6.26 g, 45.30 mmol, 3.00 equiv) and 18-Crown-6 (399 mg, 1.51 mmol, 0.10 equiv) at room temperature under nitrogen atmosphere. The resulting mixture was stirred for 3 h at 60° C. under nitrogen atmosphere. The mixture was allowed to cool down to room temperature. The resulting mixture was concentrated under vacuum. The residue was purified by silica gel column chromatography to afford 3-(2-chloro-5-methylpyridin-4-yl)-6-[(3,5-difluoropyridin-2-yl)methoxy]-2-methylpyrimidin-4-one (650 mg, 11.3%) as a yellow solid. LC-MS: (ES+H, m/z): [M+H]$^+$=379.0.

Step 6: Preparation of 5-chloro-3-(2-chloro-5-methylpyridin-4-yl)-6-[(3,5-difluoropyridin-2-yl)methoxy]-2-methylpyrimidin-4-one To a stirred mixture of 3-(2-chloro-5-methylpyridin-4-yl)-6-[(3,5-difluoropyridin-2-yl)methoxy]-2-methylpyrimidin-4-one (650 mg, 1.72 mmol, 1.00 equiv) and NCS (275 mg, 2.06 mmol, 1.20 equiv) in i-PrOH (2 ml) was added 2,2-dichloroacetic acid (22 mg, 0.17 mmol, 0.10 equiv) dropwise at room temperature under nitrogen atmosphere. The resulting mixture was stirred for 2 h at 60° C. under nitrogen atmosphere. The mixture was allowed to cool down to room temperature. The precipitated solids were collected by filtration and washed with i-PrOH (3×5 mL) to afford 5-chloro-3-(2-chloro-5-methylpyridin-4-yl)-6-[(3,5-difluoropyridin-2-yl)methoxy]-2-methylpyrimidin-4-one (310 mg, 43.7%) as a white solid. LC-MS: (ES+H, m/z): [M+H]⁺=414.9.

Step 7: Preparation of 4'-{5-chloro-4-[(3,5-difluoro-pyridin-2-yl)methoxy]-2-methyl-6-oxopyrimidin-1-yl}-3-(2-hydroxypropan-2-yl)-5'-methyl-[1,2'-bipyridin]-2-one To a stirred solution of 5-chloro-3-(2-chloro-5-methylpyridin-4-yl)-6-[(3,5-difluoropyridin-2-yl)methoxy]-2-methylpyrimidin-4-one (297 mg, 0.72 mmol, 1.00 equiv) and 3-(2-hydroxypropan-2-yl)-1H-pyridin-2-one (330 mg, 2.16 mmol, 3.00 equiv) in 1,4-dioxane (10 ml) was added CuI (137 mg, 0.72 mmol, 1.00 equiv), (1S,2S)—N1,N2-dimethylcyclohexane-1,2-diamine (205 mg, 1.44 mmol, 2.00 equiv), NaI (215 mg, 1.44 mmol, 2.00 equiv) and K₂CO₃ (298 mg, 2.16 mmol, 3.00 equiv) at room temperature under nitrogen atmosphere. The resulting mixture was stirred for 24 h at 100° C. under nitrogen atmosphere. The resulting mixture was diluted with EtOAc (50 mL). The resulting mixture was washed with 5% NH₃.H₂O (3×50 mL). The combined organic layer was washed with brine (50 mL), and then dried over Na₂SO₄. The solution was concentrated under reduced pressure. The residue was purified by PREP-HPLC. This resulted in 4'-{5-chloro-4-[(3,5-difluoropyridin-2-yl)methoxy]-2-methyl-6-oxopyrimidin-1-yl}-3-(2-hydroxypropan-2-yl)-5'-methyl-[1,2'-bipyridin]-2-one (55 mg, 14.4%) as a white solid. LC-MS: (ES+H, m/z): [M+H]⁺=530.1.

Step 8: Preparation of rel-4'-{5-chloro-4-[(3,5-difluoropyridin-2-yl)methoxy]-2-methyl-6-oxopyrimidin-1-yl}-3-(2-hydroxypropan-2-yl)-5'-methyl-[1,2'-bipyridin]-2-one & rel-4'-{5-chloro-4-[(3,5-difluoropyridin-2-yl)methoxy]-2-methyl-6-oxopyrimidin-1-yl}-3-(2-hydroxypropan-2-yl)-5'-methyl-[1,2'-bipyridin]-2-one 4'-{5-chloro-4-[(3,5-difluoropyridin-2-yl)methoxy]-2-methyl-6-oxopyrimidin-1-yl}-3-(2-hydroxypropan-2-yl)-5'-methyl-[1,2'-bipyridin]-2-one (55 mg) was separated by prep-chiral-HPLC to afford Example 25A (23.5 mg, 99.1% purity, ee=100%) and Example 25B (19.6 mg, 98.7% purity, ee=98.7%) as a white solid.

Example 25A: LC-MS: (ES+H, m/z): [M+H]⁺=530.10. ¹H NMR (400 MHz, DMSO-d₆) δ 8.71 (s, 1H), 8.57 (d, 1H), 8.08-8.02 (m, 1H), 7.98 (s, 1H), 7.85 (d, 1H), 7.70 (d, 1H), 6.43 (t, 1H), 5.63-5.59 (m, 2H), 5.22 (s, 1H), 2.15 (s, 3H), 2.12 (s, 3H), 1.47 (s, 3H), 1.46 (s, 3H). ¹⁹F NMR (400 MHz, DMSO-d₆) δ−120.38, −120.40, −123.00, −123.03.

Example 25B: LC-MS: (ES+H, m/z): [M+H]⁺=530.10. ¹H NMR (400 MHz, DMSO-d₆) δ 8.70 (s, 1H), 8.57 (d, 1H), 8.08-8.02 (m, 1H), 7.97 (s, 1H), 7.85 (d, 1H), 7.70 (d, 1H), 6.43 (t, 1H), 5.63-5.59 (m, 2H), 5.21 (s, 1H), 2.15 (s, 3H), 2.12 (s, 3H), 1.47 (s, 3H), 1.46 (s, 3H). ¹⁹F NMR (400 MHz, DMSO-d₆) δ −120.38, −120.40, −123.01, −123.03.

Example 26A, 26B

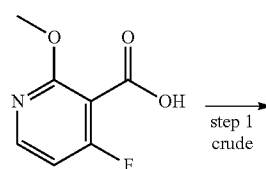

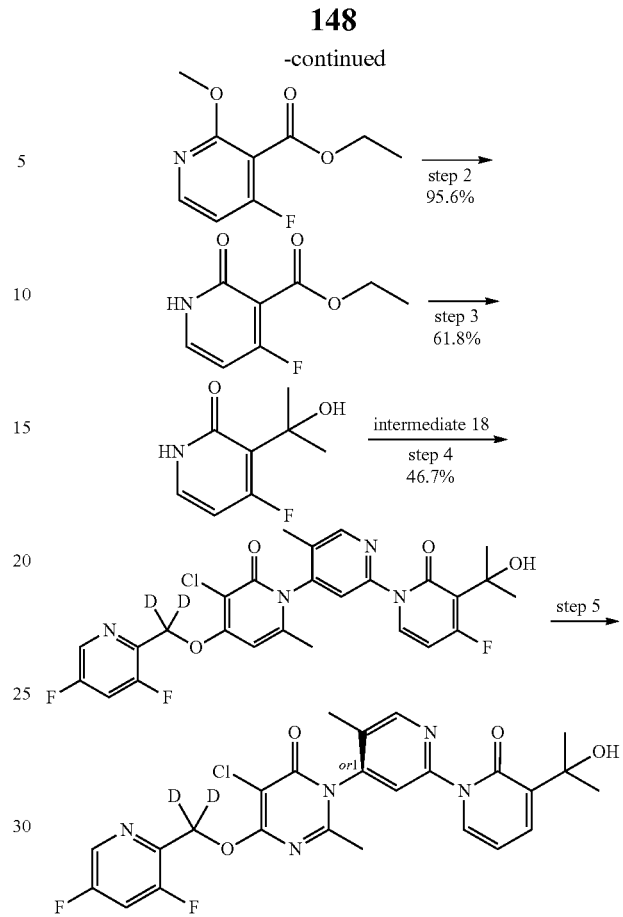

Example 26A

Example 26B

Step 1: Preparation of ethyl 4-fluoro-2-methoxypyridine-3-carboxylate

To a stirred mixture of 4-fluoro-2-methoxypyridine-3-carboxylic acid (1.00 g, 5.84 mmol, 1.00 equiv) in DMF (20 mL) was added iodoethane (1.37 g, 8.76 mmol, 1.50 equiv) and K₂CO₃ (1.62 g, 11.68 mmol, 2.00 equiv) at room temperature under nitrogen atmosphere. The resulting mixture was stirred for 2 h at 50° C. under nitrogen atmosphere. The mixture was allowed to cool down to room temperature. The resulting mixture was diluted with EtOAc (100 mL). The resulting mixture was washed with H₂O (5×60 mL) then brine (100 mL), dried over anhydrous Na₂SO₄. After filtration, the filtrate was concentrated under reduced pressure, to afford ethyl 4-fluoro-2-methoxypyridine-3-carboxylate (1.00 g, crude) as a yellow solid. LC-MS: (ES+H, m/z): [M+H]⁺=200.3

Step 2: Preparation of ethyl 4-fluoro-2-oxo-1H-pyridine-3-carboxylate

To a stirred solution of ethyl 4-fluoro-2-methoxypyridine-3-carboxylate (900 mg, 4.51 mmol, 1.00 equiv) in MeCN (15 ml) was added TMSI (3.62 g, 18.07 mmol, 4.00 equiv) at room temperature under nitrogen atmosphere. The resulting mixture was stirred for 2 h at room temperature under nitrogen atmosphere. The resulting mixture was concentrated under reduced pressure. The residue was purified by silica gel column chromatography to afford ethyl 4-fluoro-2-oxo-1H-pyridine-3-carboxylate (800 mg, 95.6%) as a yellow solid. LC-MS: (ES+H, m/z): [M+H]$^+$=186.3.

Step 3: Preparation of 4-fluoro-3-(2-hydroxypropan-2-yl)-1H-pyridin-2-one

To a stirred solution of ethyl 4-fluoro-2-oxo-1H-pyridine-3-carboxylate (700 mg, 3.78 mmol, 1.00 equiv) in THF (70.00 mL) was added MeMgBr (3.7 mL, 3M in 2-methyl-THF, 11.34 mmol, 3.00 equiv) dropwise at 0° C. under nitrogen atmosphere. The resulting mixture was stirred for 1 h at 0° C. under nitrogen atmosphere. The reaction was quenched by the addition of sat. NH$_4$Cl (aq.) (20 mL) at 0° C. The resulting mixture was extracted with EtOAc (3×100 mL). After filtration, the filtrate was concentrated under reduced pressure. The residue was purified by reverse flash chromatography. This resulted in 4-fluoro-3-(2-hydroxypropan-2-yl)-1H-pyridin-2-one (400 mg, 61.8%) as a white solid. LC-MS: (ES+H, m/z): [M+H]$^+$=172.3.

Step 4: Preparation of 3-chloro-4-[(3,5-difluoropyridin-2-yl)(2H2)methoxy]-2'-[4-fluoro-3-(2-hydroxypropan-2-yl)-2-oxopyridin-1-yl]-5',6-dimethyl-[1,4'-bipyridin]-2-one To a stirred mixture of 2'-bromo-3-chloro-4-[(3,5-difluoropyridin-2-yl)(2H2)methoxy]-5',6-dimethyl-[1,4'-bipyridin]-2-one (500 mg, 1.09 mmol, 1.00 equiv) and 4-fluoro-3-(2-hydroxypropan-2-yl)-1H-pyridin-2-one (373 mg, 2.180 mmol, 2.00 equiv) in dioxane (10 mL) was added CuI (41 mg, 0.21 mmol, 0.20 equiv), (1R,2R)-1-N,2-N-dimethylcyclohexane-1,2-diamine (62 mg, 0.43 mmol, 0.40 equiv) and K$_2$CO$_3$ (301 mg, 2.18 mmol, 2.00 equiv) at room temperature under nitrogen atmosphere. The resulting mixture was stirred for 3 h at room temperature under nitrogen atmosphere. The resulting mixture was diluted with EtOAc (50 mL). The combined organic layers were washed with brine (2×100 mL), dried over anhydrous Na$_2$SO$_4$. After filtration, the filtrate was concentrated under reduced pressure. The residue was purified by PREP-HPLC to afford 3-chloro-4-[(3,5-difluoropyridin-2-yl)(2H2)methoxy]-2'-[4-fluoro-3-(2-hydroxypropan-2-yl)-2-oxopyridin-1-yl]-5',6-dimethyl-[1,4'-bipyridin]-2-one (280 mg, 46.7%) as a white solid. LC-MS: (ES+H, m/z): [M+H]$^+$=549.2.

Step 5: Preparation of rel-3-chloro-4-[(3,5-difluoropyridin-2-yl)(2H2)methoxy]-2'-[4-fluoro-3-(2-hydroxypropan-2-yl)-2-oxopyridin-1-yl]-5',6-dimethyl-[1,4'-bipyridin]-2-one & rel-3-chloro-4-[(3,5-difluoropyridin-2-yl)(2H2)methoxy]-2'-[4-fluoro-3-(2-hydroxypropan-2-yl)-2-oxopyridin-1-yl]-5',6-dimethyl-[1,4'-bipyridin]-2-one 3-chloro-4-[(3,5-difluoropyridin-2-yl)(2H2)methoxy]-2'-[4-fluoro-3-(2-hydroxypropan-2-yl)-2-oxopyridin-1-yl]-5',6-dimethyl-[1,4'-bipyridin]-2-one (200 mg) was separated by prep-chiral-HPLC to afford Example 26A (80.6 mg, 99.4% purity, 97.3% deuterium purity, ee=100%) and Example 26B (82.5 mg, 97.7% purity, 97.1% deuterium purity, ee=99%) as a white solid.

Example 26A: LC-MS: (ES+H, m/z): [M+H]$^+$=549.05. $^1$H NMR (300 MHz, DMSO-d$_6$) δ 8.71 (s, 1H), 8.61 (d, 1H), 8.17-8.03 (m, 2H), 7.81 (s, 1H), 6.81 (d, 1H), 6.56-6.53 (m, 1H), 6.41 (s, 1H), 2.09 (s, 3H), 2.03 (s, 3H), 1.52 (s, 3H), 1.50 (s, 3H). $^{19}$F NMR (282 MHz, DMSO-d$_6$) δ−91.28, −120.25, −120.27, −122.32, −122.35.

Example 26B: LC-MS: (ES+H, m/z): [M+H]$^+$=549.1. $^1$H NMR (300 MHz, DMSO-d$_6$) δ 8.71 (s, 1H), 8.61 (d, 1H), 8.17-8.03 (m, 2H), 7.81 (s, 1H), 6.81 (d, 1H), 6.56-6.53 (m, 1H), 6.41 (s, 1H), 2.09 (s, 3H), 2.03 (s, 3H), 1.51 (s, 3H), 1.50 (s, 3H). $^{19}$F NMR (282 MHz, DMSO-d$_6$) δ−91.28, −120.25, −120.27, −122.32, −122.35.

Example 27A, 27B

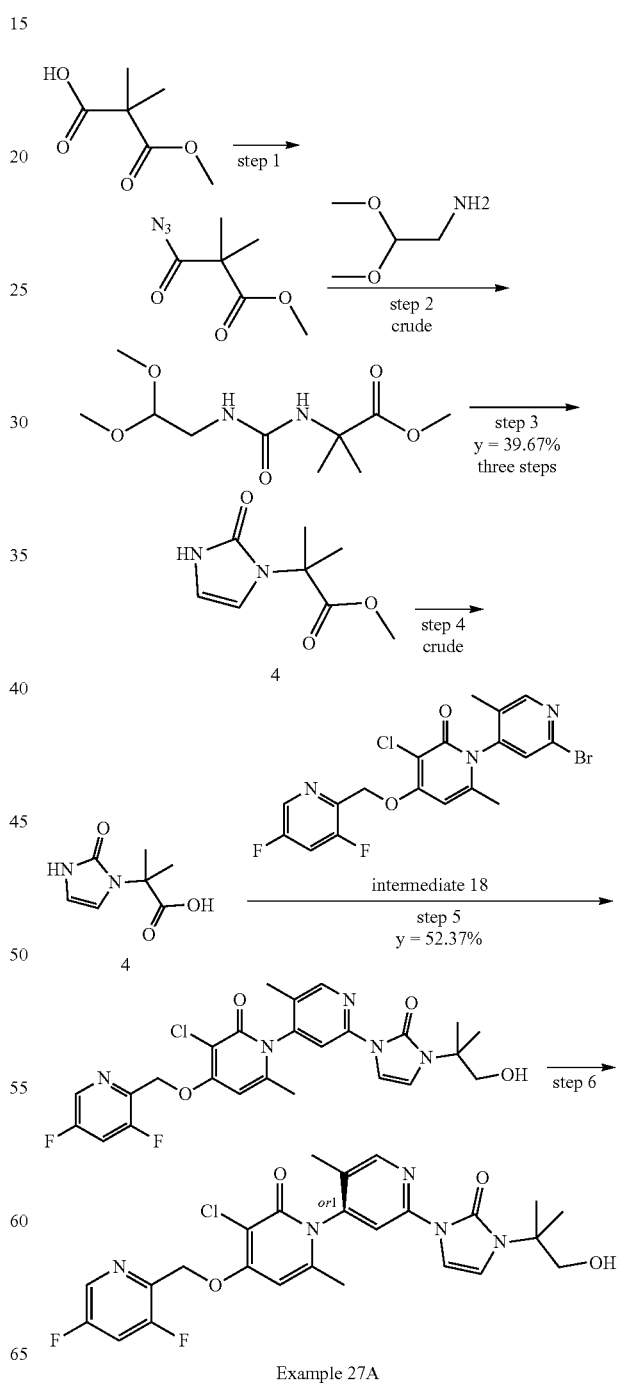

Example 27A

-continued

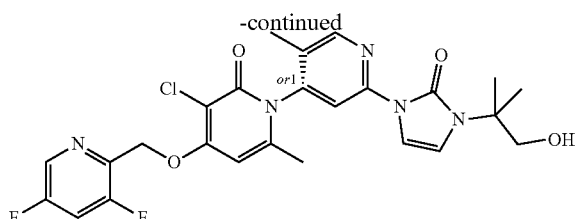

Example 27B

Step 1&2: Preparation of Methyl 2-{[(2,2-dimethoxyethyl)carbamoyl]amino}-2-methylpropanoate To a stirred mixture of 3-methoxy-2,2-dimethyl-3-oxopropanoic acid (2.00 g, 13.68 mmol, 1.00 equiv) and Et$_3$N (1.52 g, 15.05 mmol, 1.10 equiv) in DME (20 mL) was added DPPA (4.14 g, 15.05 mmol, 1.10 equiv) dropwise at 0° C. under nitrogen atmosphere. The resulting mixture was stirred for 30 min at room temperature under nitrogen atmosphere. The resulting mixture was stirred for additional 2 h at 90° C. under nitrogen atmosphere. To the above mixture was added 2,2-dimethoxyethanamine (2.88 g, 27.37 mmol, 2.00 equiv) at room temperature. The resulting mixture was stirred for additional 2 h at room temperature. The reaction was quenched by the addition of sat. NaHCO$_3$ (aq.) (20 mL) at room temperature. The resulting mixture was extracted with EtOAc (3×30 mL). The combined organic layers were washed with brine (50 mL), dried over anhydrous Na$_2$SO$_4$. After filtration, the filtrate was concentrated under reduced pressure to afford methyl 2-{[(2,2-dimethoxyethyl)carbamoyl]amino}-2-methylpropanoate (2.20 g, crude) as a colorless liquid. LC-MS: (ES+H, m/z): [M+H]$^+$=249.1.

Step 3: Preparation of methyl 2-methyl-2-(2-oxo-3H-imidazol-1-yl)propanoate

To a stirred mixture of methyl 2-{1[(2,2-dimethoxyethyl)carbamoyl]amino}-2-methylpropanoate (2.20 g, 8.86 mmol, 1.00 equiv) in THF (5 mL) was added TFA (2.5 mL) dropwise at room temperature under nitrogen atmosphere. The resulting mixture was stirred for 1 h at 70° C. under nitrogen atmosphere. The residue was purified by reverse flash chromatography to afford methyl 2-methyl-2-(2-oxo-3H-imidazol-1-yl)propanoate (1.00 g, 39.67%) as a white solid. LC-MS: (ES+H, m/z): [M+H]$^+$=185.1. $^1$H NMR (300 MHz, DMSO-d$_6$) δ 9.96 (s, 1H), 6.54 (dd, 1H), 6.35 (t, 1H), 3.59 (s, 3H), 1.52 (s, 6H).

Step 4: Preparation of 1-(1-hydroxy-2-methylpropan-2-yl)-3H-imidazol-2-one

To a stirred mixture of methyl 2-methyl-2-(2-oxo-3H-imidazol-1-yl)propanoate (600 mg, 3.25 mmol, 1.00 equiv) in THF (6 mL) was added LiAlH$_4$ (247 mg, 6.51 mmol, 2.00 equiv) in portions at 0° C. under nitrogen atmosphere. The resulting mixture was stirred for 30 min at room temperature under nitrogen atmosphere. The reaction was quenched with water at 0° C. The resulting mixture was extracted with EtOAc (3×10 mL). The combined organic layers were washed with brine (20 mL), dried over anhydrous Na$_2$SO$_4$. After filtration, the filtrate was concentrated under reduced pressure to afford 1-(1-hydroxy-2-methylpropan-2-yl)-3H-imidazol-2-one (360 mg, crude) as a white solid. $^1$H NMR (300 MHz, DMSO-d$_6$) δ 9.97 (s, 1H), 6.50 (dd, 1H), 6.35 (t, 1H), 5.28 (t, 1H), 3.68 (d, 2H), 1.42 (s, 6H).

Step 5: Preparation of 3-chloro-4-[(3,5-difluoropyridin-2-yl)methoxy]-2'-[3-(1-hydroxy-2-methylpropan-2-yl)-2-oxoimidazol-1-yl]-5',6-dimethyl-[1,4'-bipyridin]-2-one A mixture of 2'-bromo-3-chloro-4-[(3,5-difluoropyridin-2-yl)methoxy]-5',6-dimethyl-[1,4'-bipyridin]-2-one (500 mg, 1.09 mmol, 1.00 equiv), 1-(1-hydroxy-2-methylpropan-2-yl)-3H-imidazol-2-one (342 mg, 2.19 mmol, 2.00 equiv), (1R,2R)—N1,N2-dimethylcyclohexane-1,2-diamine (62 mg, 0.43 mmol, 0.40 equiv), K$_2$CO$_3$ (302 mg, 2.19 mmol, 2.00 equiv) and CuI (41 mg, 0.21 mmol, 0.20 equiv) in dioxane (5 ml) was stirred for 2 h at 80° C. under nitrogen atmosphere. The mixture was allowed to cool down to room temperature. The resulting mixture was diluted with EtOAc (20 mL). The resulting mixture was washed with water (10% NH$_3$.H$_2$O, 3×20 mL). The combined organic layers were washed with brine (50 mL), dried over anhydrous Na$_2$SO$_4$. After filtration, the filtrate was concentrated under reduced pressure. The crude product was purified by Prep-HPLC to afford 3-chloro-4-[(3,5-difluoropyridin-2-yl)methoxy]-2'-[3-(1-hydroxy-2-methylpropan-2-yl)-2-oxoimidazol-1-yl]-5',6-dimethyl-[1,4'-bipyridin]-2-one (305 mg, 52.37%) as a white solid. LC-MS: (ES+H, m/z): [M+H]$^+$=532.25.

Step 6: Preparation of rel-3-chloro-4-[(3,5-difluoropyridin-2-yl)methoxy]-2'-[3-(1-hydroxy-2-methylpropan-2-yl)-2-oxoimidazol-1-yl]-5',6-dimethyl-[1,4'-bipyridin]-2-one & rel-3-chloro-4-[(3,5-difluoropyridin-2-yl)methoxy]-2'-[3-(1-hydroxy-2-methylpropan-2-yl)-2-oxoimidazol-1-yl]-5',6-dimethyl-[1,4'-bipyridin]-2-one The racemate (300 mg) was separated by prep-SFC to afford Example 27A (91.3 mg, 98.1% purity, ee=100.0%) as a white solid and Example 27B (82.9 mg, 99.7% purity, ee=99.5%) as a white solid.

Example 27A: LC-MS: (ES+H, m/z): [M+H]$^+$=532.2. $^1$H NMR (400 MHz, DMSO-d$_6$) δ 8.60 (d, 1H), 8.52 (s, 1H), 8.20 (s, 1H), 8.14-8.01 (m, 1H), 7.30 (d, 1H), 6.80 (s, 1H), 6.79 (d, 1H), 5.49 (d, 2H), 4.99 (t, 1H), 3.77-3.61 (m, 2H), 1.99 (s, 3H), 1.98 (s, 3H), 1.43 (s, 6H). $^{19}$F NMR (377 MHz, DMSO-d$_6$) δ −120.20, −120.22, −122.42, −122.44.

Example 27B: LC-MS: (ES+H, m/z): [M+H]$^+$=532.1. $^1$H NMR (400 MHz, DMSO-d$_6$) δ 8.60 (d, 1H), 8.52 (s, 1H), 8.20 (s, 1H), 8.14-8.05 (m, 1H), 7.30 (d, 1H), 6.80 (s, 1H), 6.79 (d, 1H), 5.49 (d, 2H), 4.99 (t, 1H), 3.79-3.57 (m, 2H), 1.99 (s, 3H), 1.99 (s, 3H), 1.43 (s, 6H). $^{19}$F NMR (377 MHz, DMSO-d$_6$) δ −120.20, −120.22, −122.42, −122.44.

Example 28A, 28B

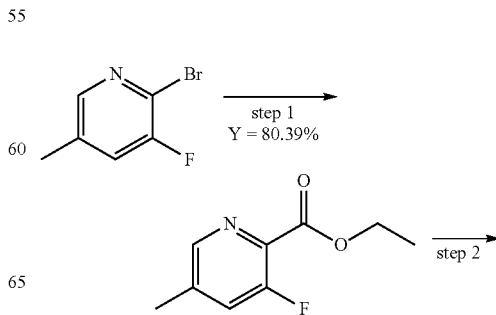

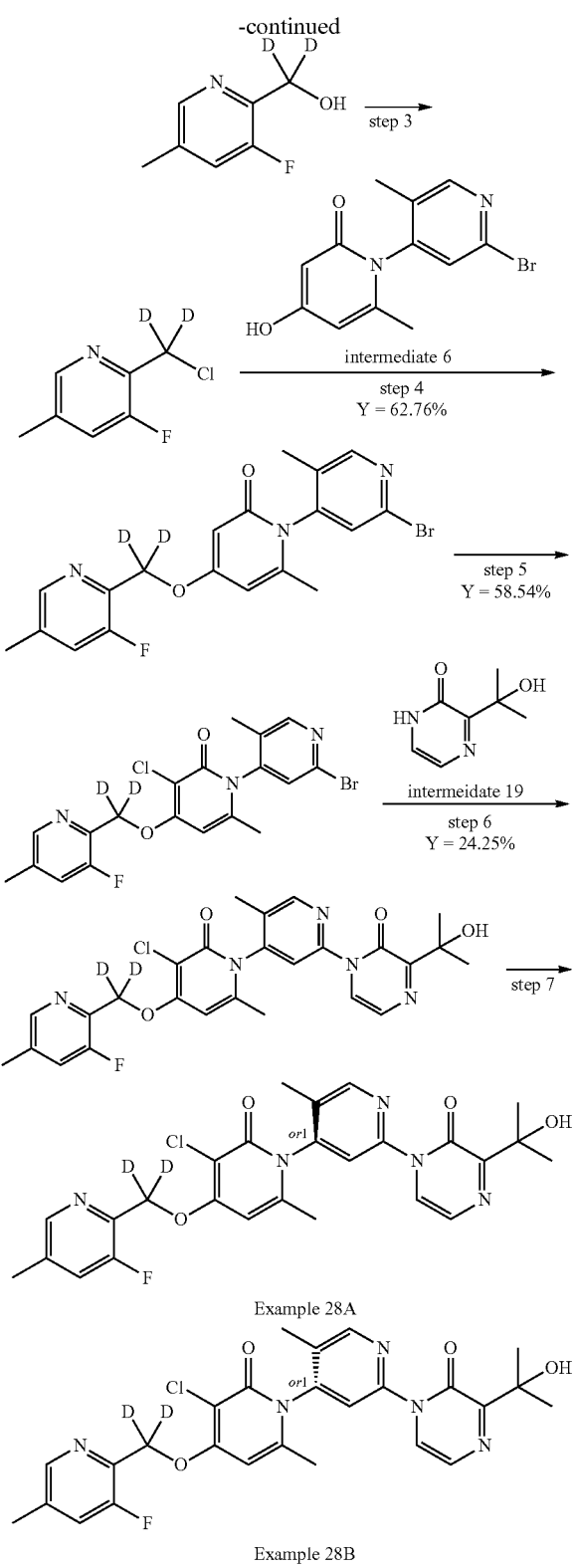

Example 28A

Example 28B

Step 1: Preparation of Ethyl 3-fluoro-5-methylpyridine-2-carboxylate

To a stirred mixture of 2-bromo-3-fluoro-5-methylpyridine (4.00 g, 21.05 mmol, 1.00 equiv) and Pd(dppf)C$l_2$ (1.54 g, 2.10 mmol, 0.10 equiv) in EtOH (40 mL) were added Et$_3$N (25.56 g, 252.61 mmol, 3.00 equiv) dropwise at room temperature. The resulting mixture was stirred for 18 h at 80° C. under carbon monoxide atmosphere (50 atm). The mixture was allowed to room temperature. The resulting mixture was concentrated under reduced pressure. The resulting mixture was diluted with CH$_2$Cl$_2$ (200 mL), washed with 3×100 mL of H$_2$O. The organic layers were concentrated under reduced pressure and purified by silica gel column chromatography to afford ethyl 3-fluoro-5-methylpyridine-2-carboxylate (3.10 g, 80.39%) as a white solid. LC-MS: (ES+H, m/z): [M+H]$^+$=184.1. $^1$H NMR (300 MHz, DMSO-d$_6$) δ 8.35 (d, 1H), 7.71-7.68 (m, 1H), 4.37-4.30 (m, 2H), 2.37 (s, 3H), 1.30 (t, 3H).

Step 2: Preparation of (3-fluoro-5-methylpyridin-2-yl)(2H2)methanol

To a stirred mixture of ethyl 3-fluoro-5-methylpyridine-2-carboxylate (3.00 g, 16.37 mmol, 1.00 equiv) in solution of CD$_3$OD (10 mL) and THF (20 mL) were added Sodium borodeuteride (1.86 g, 49.13 mmol, 3.00 equiv) in portions at 0° C. under nitrogen atmosphere. The resulting mixture was stirred for 2 h at room temperature under nitrogen atmosphere. The filtrate was quenched by the addition of D$_2$O (4 mL) at 0° C. The resulting mixture was diluted with ethyl acetate (300 mL), washed with 3×100 mL of H$_2$O. The organic layers were dried over anhydrous Na$_2$SO$_4$. After filtration, the filtrate was concentrated under reduced pressure. To afford (3-fluoro-5-methylpyridin-2-yl)(2H2)methanol (2.4 g, crude) as a yellow liquid. LC-MS: (ES+H, m/z): [M+H]$^+$=144.3. $^1$H NMR (300 MHz, DMSO-d$_6$) δ 8.23 (d, 1H), 7.55-7.50 (m, 1H), 5.20 (s, 1H), 2.32 (s, 3H).

Step 3: Preparation of 2-[chloro(2H2)methyl]-3-fluoro-5-methylpyridine

To a stirred mixture of (3-fluoro-5-methylpyridin-2-yl)(2H2)methanol (2.40 g, 16.76 mmol, 1.00 equiv) and DMF (0.1 mL, 1.67 mmol, 0.10 equiv) in DCM (24 mL) were added SOCl$_2$ (2.6 mL, 36.88 mmol, 2.20 equiv) dropwise at 0° C. under nitrogen atmosphere. The resulting mixture was stirred for 2 h at room temperature under nitrogen atmosphere. The resulting mixture was concentrated under vacuum to afford 2-[chloro(2H2)methyl]-3-fluoro-5-methylpyridine (3.30 g, crude) as a brown yellow liquid. LC-MS: (ES+H, m/z): [M+H]$^+$=162.1. $^1$H NMR (300 MHz, DMSO-d$_6$) δ 8.29 (d, 1H), 7.69-7.64 (m, 1H), 2.35 (s, 3H).

Step 4: Preparation of 2'-bromo-4-[(3-fluoro-5-methylpyridin-2-yl)(2H2)methoxy]-5',6-dimethyl-[1,4'-bipyridin]-2-one A mixture of 2'-bromo-4-hydroxy-5',6-dimethyl-[1,4'-bipyridin]-2-one (2.57 g, 8.72 mmol, 1.00 equiv), 2-[chloro (2H2)methyl]-3-fluoro-5-methylpyridine (3.10 g, 19.18 mmol, 2.20 equiv), 18-Crown-6 (691 mg, 2.61 mmol, 0.30 equiv) and K$_2$CO$_3$ (7.23 g, 52.31 mmol, 6.00 equiv) in DMF (25 mL) was stirred for 2 h at 60° C. under nitrogen atmosphere. The mixture was allowed to room temperature. The resulting mixture was diluted with ethyl acetate (200 mL). The resulting mixture was washed with brine (3×100 mL). The organic layer dried over anhydrous Na$_2$SO$_4$. After filtration, the filtrate was concentrated under reduced pressure. The residue was purified by silica gel column chromatography to afford 2'-bromo-4-[(3-fluoro-5-methylpyridin-2-yl)(2H2)methoxy]-5',6-dimethyl-[1,4'-bipyridin]-2-one (2.30 g, 62.76%) as a white solid. LC-MS: (ES+H, m/z):

[M+H]+=420.1. $^1$H NMR (300 MHz, DMSO-$d_6$) δ 8.48 (s, 1H), 8.34 (d, 1H), 7.73 (s, 1H), 7.70-7.67 (m, 1H), 6.12 (d, 1H), 6.02 (d, 1H), 2.37 (s, 3H), 1.96 (s, 3H), 1.85 (s, 3H).

Step 5: Preparation of 2'-bromo-3-chloro-4-[(3-fluoro-5-methylpyridin-2-yl)(2H2)methoxy]-5',6-dimethyl-[1,4'-bipyridin]-2-one To a stirred solution of 2'-bromo-4-[(3-fluoro-5-methylpyridin-2-yl)(2H2)methoxy]-5',6-dimethyl-[1,4'-bipyridin]-2-one (600 mg, 1.42 mmol, 1.00 equiv) and NCS (190 mg, 1.42 mmol, 1.00 equiv) in IPA (6 mL) was added 2,2-dichloroacetic acid (18 mg, 0.14 mmol, 0.10 equiv) at room temperature under air atmosphere. The resulting mixture was stirred for 1 h at 60° C. under nitrogen atmosphere. The mixture was allowed to cool down to 4° C. The precipitated solids were collected by filtration and washed with cold IPA (3×40 mL). To afford 2'-bromo-3-chloro-4-[(3-fluoro-5-methylpyridin-2-yl)(2H2)methoxy]-5',6-dimethyl-[1,4'-bipyridin]-2-one (380 mg, 58.54%) as a white solid. LC-MS: (ES+H, m/z): [M+H]+=455.90. $^1$H NMR (300 MHz, DMSO-$d_6$) δ 8.52 (s, 1H), 8.36 (d, 1H), 7.82 (s, 1H), 7.73-7.69 (m, 1H), 6.82 (s, 1H), 2.38 (s, 3H), 1.96 (s, 6H).

Step 6: Preparation of 3-chloro-4-[(3-fluoro-5-methylpyridin-2-yl)(2H2)methoxy]-2'-[3-(2-hydroxypropan-2-yl)-2-oxopyrazin-1-yl]-5',6-dimethyl-[1,4'-bipyridin]-2-one A mixture of 2'-bromo-3-chloro-4-[(3-fluoro-5-methylpyridin-2-yl)(2H2)methoxy]-5',6-dimethyl-[1,4'-bipyridin]-2-one (380 mg, 0.83 mmol, 1.00 equiv), 3-(2-hydroxypropan-2-yl)-1H-pyrazin-2-one (386 mg, 2.50 mmol, 3.00 equiv), (1S,2S)—N1,N2-dimethylcyclohexane-1,2-diamine (47 mg, 0.33 mmol, 0.40 equiv), CuI (31 mg, 0.16 mmol, 0.20 equiv) and $K_2CO_3$ (230 mg, 1.67 mmol, 2.00 equiv) in 1,4-dioxane (3 mL) was stirred for 2 h at 80° C. under nitrogen atmosphere. The mixture was allowed to room temperature. The resulting mixture was diluted with ethyl acetate (100 mL) and washed with water (10% $NH_3$, 3×50 mL). The organic layer was concentrated under reduced pressure to afford crude product, which was further purified by PREP-HPLC. This resulted in 3-chloro-4-[(3-fluoro-5-methylpyridin-2-yl)(2H2)methoxy]-2'-[3-(2-hydroxypropan-2-yl)-2-oxopyrazin-1-yl]-5',6-dimethyl-[1,4'-bipyridin]-2-one (107 mg, 24.25%) as a white solid. LC-MS: (ES+H, m/z): [M+H]+=528.20. $^1$H NMR (300 MHz, DMSO-$d_6$) δ 8.75 (s, 1H), 8.36 (d, 1H), 8.00 (d, 1H), 7.95 (s, 1H), 7.73-7.69 (m, 1H), 7.47 (d, 1H), 6.83 (s, 1H), 5.12 (s, 1H), 2.39 (s, 3H), 2.10 (s, 3H), 2.01 (s, 3H), 1.51 (s, 6H).

Step 7: Preparation of rel-3-chloro-4-[(3-fluoro-5-methylpyridin-2-yl)(2H2)methoxy]-2'-[3-(2-hydroxypropan-2-yl)-2-oxopyrazin-1-yl]-5',6-dimethyl-[1,4'-bipyridin]-2-one and rel-3-chloro-4-[(3-fluoro-5-methylpyridin-2-yl)(2H2)methoxy]-2'-[3-(2-hydroxypropan-2-yl)-2-oxopyrazin-1-yl]-5',6-dimethyl-[1,4'-bipyridin]-2-one The racemate (102 mg) was separated by Prep-Chiral-HPLC to afford Example 28A (35.4 mg, 99.6% purity, ee=100%) as a white solid and Example 28B (26.7 mg, 99.7% purity, ee=100%) as a white solid.

Example 28A: LC-MS: (ES+H, m/z): [M+H]+=528.20. $^1$H NMR (300 MHz, DMSO-$d_6$) δ 8.75 (s, 1H), 8.36 (d, 1H), 8.00 (d, 1H), 7.95 (s, 1H), 7.73-7.69 (m, 1H), 7.47 (d, 1H), 6.83 (s, 1H), 5.13 (s, 1H), 2.38 (s, 3H), 2.10 (s, 3H), 2.00 (s, 3H), 1.51 (s, 6H). $^{19}$F NMR (282 MHz, DMSO-$d_6$) δ–126.30.

Example 28B: LC-MS: (ES+H, m/z): [M+H]+=528.20. $^1$H NMR (300 MHz, DMSO-$d_6$) δ 8.75 (s, 1H), 8.36 (d, 1H), 8.00 (d, 1H), 7.95 (s, 1H), 7.73-7.69 (m, 1H), 7.47 (d, 1H), 6.83 (s, 1H), 5.13 (s, 1H), 2.38 (s, 3H), 2.10 (s, 3H), 2.00 (s, 3H), 1.51 (s, 6H). $^{19}$F NMR (282 MHz, DMSO-$d_6$) δ–126.30.

BIOLOGICAL EXAMPLES

Protein Expression and Purification

Expression vectors of the recombinant MK2 and PRAK kinases were constructed by cloning of the codon optimized gene sequences of MK2 (Uniprot ID P49137, amino acid fragment F46-H400), or PRAK (Uniprot ID Q81W41, amino acid fragment M1-Q471) into pGEX-4T1 (GE) for over expression of these kinases with N-terminal GST-tag. Protein expression was carried out in E. coli BL21 by growing the hosts in TB medium, induction of protein expression with 0.5 mM IPTG at approximate 0.8 $OD_{600}$, and incubation of the cultures at 18° C. for 14-20 hours afterwards. The harvested cells were resuspended in 100 ml of Lysis buffer (50 mM Tris-HCl, pH 8.0, 500 mM NaCl, 1 mM DTT, 5% glycerol, and 1 mM PMSF) per gram of wet cell mass and homogenized at 4° C. in a microfluidizer (ATS, Suzhou, China) at 14,000 psi pressure, 3 passes. The cell lysates were clarified by centrifugation and the supernatants containing the GST-fusion proteins were purified by affinity chromatography using GSH-Sepharose (GE) gravity flow columns pre-equilibrated in Buffer A (50 mM Tris-HCl, pH 8.0, 500 mM NaCl, 1 mM DTT, and 5% glycerol). After thorough washing of the columns with Buffer A, the bound GST-proteins were eluted by Buffer B (50 mM Tris, pH 8.0, 500 mM NaCl, 1 mM DTT, 5% glycerol, 10 mM glutathione), followed by size-exclusion purification on Superdex 200 column equilibrated in Buffer A. The purified proteins were concentrated to approximately 1 mg/ml and stored at –80° C.

Biochemical Assay

This study evaluates the inhibitory potency of invention compound on p38/MK2 pathway vs p38/PRAK pathway. More specially the compound concentration ($IC_{50}$) was determined that inhibited half of the maximal activation of MK2 or PRAK by p38. MK2 activation study was set up without or with a serial of 10-point 1:3 dilution of invention compound at top dose of 1 or 10 µM, and PRAK activation study was set up without or with a serial of 10-point 1:3 dilution of invention compound at top dose of 300 µM. The MIK2 and PRAK activity were determined by the phosphorylation level of HSP27 peptide conjugated with FITC.

A typical assay was conducted in 20 µL volume including 60 µM active p38α (Carna, cat #04-152), 10 µM ATP, 1 µM FITC-HSP27 peptide (Sangon, Cat #P22354), and 1 nM inactive MK2, or PRAK in 1× reaction buffer (20 mM HEPES, pH7.5, 10 mM $MgCl_2$, 1 mM DTT, 0.0100 Triton X-100, 0.01% BSA). After 2 h incubation of the reaction mixture with various concentration of invention compound (200 nL), 60 µL 1×IMAP solution Mixture (Molecular Devices, Cat #R8127) was added to the reaction mixture and incubated for another half hour. The signal was then read by Synergy™ Neo2 Multi-Mode Microplate Reader with filter setting (Ex/Em=485 nm/FITC FP-P pol 528 nm & FITC FP-S pol 528 nm)

The signal was then normalized to vehicle control and fitted in Xfit to generate IC$_{50}$. The selectivity of MK2 over PRAK was calculated by the formular Selectivity=IC$_{50}$ of PRAK/IC$_{50}$ of MK2.

The data from the above assays is found in table 2.

TABLE 2

| Ex. | p38a/MK2 (10 μM) Enzyme pIC$_{50}$ | p38a/MK2 (1 μM) Enzyme pIC$_{50}$ | p38a/PRAK Enzyme pIC$_{50}$ |
|---|---|---|---|
| 1A | 8.5 | 8.7 | 5.5 |
| 1B | 6.4 | | <3.5 |
| 2A | | 8.4 | 5.9 |
| 2B | | <6.0 | <3.5 |
| 3A | | 8.2 | 5.3 |
| 3B | | <6.0 | <3.5 |
| 4A | | 8.7 | 5.3 |
| 4B | | <6.0 | <3.5 |
| 5A | | 8.6 | 5.6 |
| 5B | | <6.0 | <3.5 |
| 6 | | 7.7 | 5.2 |
| 7A | | 9 | 5.1 |
| 7B | | <6.0 | <3.5 |
| 8A | | 9.1 | 5.6 |
| 8B | | <6.0 | <3.5 |
| 9A | | 7.9 | 5.7 |
| 9B | | <6.0 | <3.5 |
| 10A | | 7 | 5.4 |
| 10B | | <6.0 | <3.5 |
| 11A | | 8.4 | 5.3 |
| 11B | | <6.0 | <3.5 |
| 12A | | 7.9 | 5.1 |
| 12B | | <6.0 | <3.5 |
| 13A | | <6.0 | <3.5 |
| 13B | | <6.0 | 4.8 |
| 14A | | 8.8 | 5.5 |
| 14B | | 8.9 | 5.5 |
| 14C | | <6.0 | <3.5 |
| 14D | | <6.0 | <3.5 |
| 15A | | 8 | 5.6 |
| 15B | | <6.0 | <3.5 |
| 16A | | 6.7 | 5.1 |
| 16B | | <6.0 | <3.5 |
| 17A | | 8.8 | 5.2 |
| 17B | | <6.0 | <3.5 |
| 18A | | 8.8 | 5.5 |
| 18B | | <7.0 | <3.5 |
| 19A | | 9 | 5.8 |
| 19B | | 6.1 | <3.5 |
| 20A | | 9 | 5.5 |
| 20B | | 6.5 | <3.5 |
| 21A | | 8.9 | 5.3 |
| 21B | | <6.0 | <3.5 |
| 22A | | 8.7 | 5.4 |
| 22B | | <7.0 | <3.5 |
| 23A | | 8.6 | 5.2 |
| 23B | | <7.0 | <3.5 |
| 24A | | <6.0 | <3.5 |
| 24B | | 8.6 | 5.3 |
| 25A | | 8.4 | 5.2 |
| 25B | | 6.2 | <3.5 |
| 26A | | 8.6 | 5.5 |
| 26B | | <7.0 | <3.5 |
| 27A | | <7.0 | <3.5 |
| 27B | | 7.9 | 6.1 |
| 28A | | 9.0 | 5.5 |
| 28B | | <7.0 | <3.5 |

What is claimed is:

1. A compound of Formula (I), or a pharmaceutically acceptable salt, solvate, stereoisomer, or rotamer thereof:

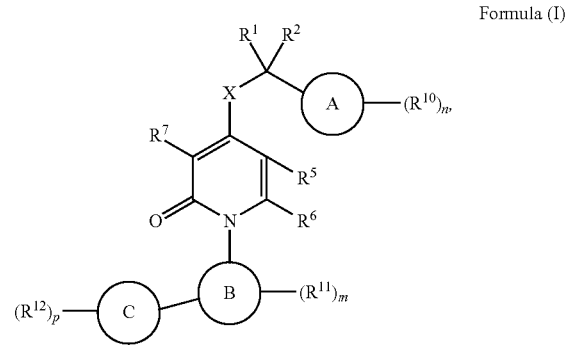

Formula (I)

wherein:
Ring A is cycloalkyl, heterocycloalkyl, aryl, or heteroaryl;
each $R^{10}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more Rina;
or two $R^{10}$ on the same atom are taken together to form an oxo;
each $R^{10a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;
or two $R^{10a}$ on the same atom are taken together to form an oxo;
n is 1-4;
$R^1$ and $R^2$ are independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;
or $R^1$ and $R^2$ are taken together to form an oxo;
or $R^1$ and $R^2$ are taken together to form a cycloalkyl or heterocycloalkyl; wherein the cycloalkyl and heterocycloalkyl is optionally substituted with deuterium, halogen, —CN, —OH, —OCH$_3$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

X is —C(R$^3$)$_2$—, —NR$^4$—, —O—, or —S—;

each R$^3$ are independently hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

or two R$^3$ are taken together to form an oxo;

R$^4$ is hydrogen, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

R$^5$ is hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

R$^6$ is hydrogen, deuterium, halogen, —CN, —NO$_2$, —OH, —OR$^a$, —NR$^c$R$^d$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, or heterocycloalkyl;

R$^7$ is hydrogen, deuterium, halogen, C$_1$-C$_6$alkyl, C$_1$-C$_6$haloalkyl, or C$_1$-C$_6$deuteroalkyl;

Ring B is cycloalkyl, heterocycloalkyl, aryl, or heteroaryl;

each R$^{11}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl; wherein the alkyl, alkenyl, alkynyl, cycloalkyl, heterocycloalkyl, aryl, and heteroaryl is optionally and independently substituted with one or more R$^{11a}$;

or two R$^{11}$ on the same atom are taken together to form an oxo;

each R$^{11a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{11a}$ on the same atom are taken together to form an oxo;

m is 1-4;

Ring C is N-linked pyridinone, N-linked pyrimidinone, N-linked pyrazinone, or N-linked pyridazinone;

each R$^{12}$ is independently hydrogen, deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —S(=O)(=NR$^b$)R$^a$, —SiR$^c$R$^d$OR$^b$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)OR$^b$, —C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein the alkyl, alkenyl, alkynyl, cycloalkyl, heterocycloalkyl, aryl, and heteroaryl is optionally and independently substituted with one or more R$^{12a}$;

each R$^{12a}$ is independently deuterium, halogen, —CN, —NO$_2$, —OH, —OR$^a$, —OC(=O)R$^a$, —OC(=O)OR$^b$, —OC(=O)NR$^c$R$^d$, —SH, —SR$^a$, —S(=O)R$^a$, —S(=O)$_2$R$^a$, —S(=O)$_2$NR$^c$R$^d$, —NR$^c$R$^d$, —NR$^b$C(=O)NR$^c$R$^d$, —NR$^b$C(=O)R$^a$, —NR$^b$C(=O)OR$^b$, —NR$^b$S(=O)$_2$R$^a$, —C(=O)R$^a$, —C(=O)C(=O)R$^a$, —C(=O)OR$^b$, —C(=O)NR$^c$R$^d$, —C(=O)C(=O)NR$^c$R$^d$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, or heteroaryl;

or two R$^{12a}$ on the same atom are taken together to form an oxo;

p is 1-4;

each R$^a$ is independently C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

each R$^b$ is independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocycloalkyl), C$_1$-C$_6$alkylene(aryl), or C$_1$-C$_6$alkylene(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl; and each R$^c$ and R$^d$ are independently hydrogen, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, C$_1$-C$_6$heteroalkyl, C$_2$-C$_6$alkenyl, C$_2$-C$_6$alkynyl, cycloalkyl, heterocycloalkyl, aryl, heteroaryl, C$_1$-C$_6$alkylene(cycloalkyl), C$_1$-C$_6$alkylene(heterocydoalkyl), C$_1$-C$_6$alkylene(aryl), or C$_1$-C$_6$alkylene(heteroaryl); wherein each alkyl, alkenyl, alkynyl, cycloalkyl, heterocycloalkyl, aryl, and heteroaryl is independently optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or R$^c$ and R$^d$ are taken together with the atom to which they are attached to form a heterocyclo alkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or R$^b$ and R$^c$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or R$^a$ and R$^b$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl;

or two R$^b$ are taken together with the atom to which they are attached to form a heterocycloalkyl optionally substituted with one or more oxo, deuterium, halogen, —CN, —OH, —OCH$_3$, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, C$_1$-C$_6$alkyl, C$_1$-C$_6$haloalkyl, C$_1$-C$_6$deuteroalkyl, C$_1$-C$_6$hydroxyalkyl, C$_1$-C$_6$aminoalkyl, or C$_1$-C$_6$heteroalkyl.

2. The compound of claim 1, or a pharmaceutically acceptable salt, solvate, stereoisomer, or rotamer thereof, wherein the compound of Formula (I) is a compound of Formula (Ia):

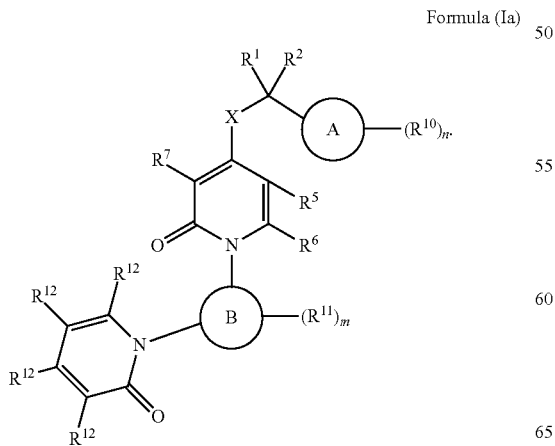

Formula (Ia)

3. The compound of claim 1, or a pharmaceutically acceptable salt, solvate, stereoisomer, or rotamer thereof, wherein the compound of Formula (I) is a compound of Formula (Ib):

Formula (Ib)

4. The compound of claim 1, or a pharmaceutically acceptable salt, solvate, stereoisomer, or rotamer thereof, wherein the compound of Formula (I) is a compound of Formula (Ic):

Formula (Ic)

5. The compound of claim 1, or a pharmaceutically acceptable salt, solvate, stereoisomer, or rotamer thereof, wherein the compound of Formula (I) is a compound of Formula (Id):

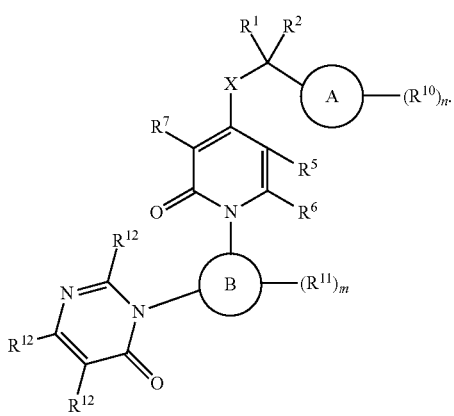

Formula (Id)

6. The compound of claim 1, or a pharmaceutically acceptable salt, solvate, stereoisomer, or rotamer thereof, wherein the compound of Formula (I) is a compound of Formula (Ie):

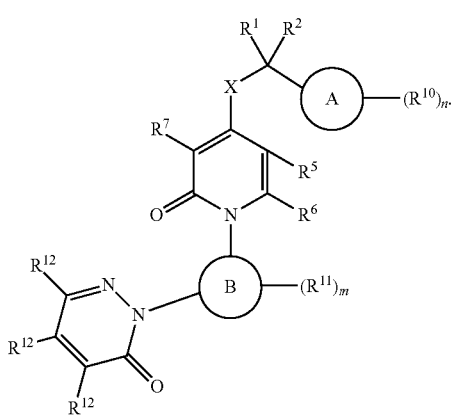

Formula (Ie)

7. The compound of claim 1, or a pharmaceutically acceptable salt, solvate, stereoisomer, or rotamer thereof, wherein Ring A is pyridyl.

8. The compound of claim 1, or a pharmaceutically acceptable salt, solvate, stereoisomer, or rotamer thereof, wherein each 10° is independently hydrogen or halogen.

9. The compound of claim 1, or a pharmaceutically acceptable salt, solvate, stereoisomer, or rotamer thereof, wherein n is 1 or 2.

10. The compound of claim 1, or a pharmaceutically acceptable salt, solvate, stereoisomer, or rotamer thereof, wherein $R^1$ and $R^2$ are hydrogen or deuterium.

11. The compound of claim 1, or a pharmaceutically acceptable salt, solvate, stereoisomer, or rotamer thereof, wherein X is —O—.

12. The compound of claim 1, or a pharmaceutically acceptable salt, solvate, stereoisomer, or rotamer thereof, wherein $R^5$ is hydrogen, deuterium, halogen, —CN, or $C_1$-$C_6$alkyl.

13. The compound of claim 1, or a pharmaceutically acceptable salt, solvate, stereoisomer, or rotamer thereof, wherein $R^6$ is hydrogen, deuterium, halogen, —CN, or $C_1$-$C_6$alkyl.

14. The compound of claim 1, or a pharmaceutically acceptable salt, solvate, stereoisomer, or rotamer thereof, wherein $R^7$ is hydrogen, deuterium, or halogen.

15. The compound of claim 1, or a pharmaceutically acceptable salt, solvate, stereoisomer, or rotamer thereof, wherein Ring B is a phenyl or a 6-membered heteroaryl.

16. The compound of claim 1, or a pharmaceutically acceptable salt, solvate, stereoisomer, or rotamer thereof, wherein each $R^{11}$ is independently hydrogen or $C_1$-$C_6$alkyl.

17. The compound of claim 1, or a pharmaceutically acceptable salt, solvate, stereoisomer, or rotamer thereof, wherein m is 1 or 2.

18. The compound of claim 1, or a pharmaceutically acceptable salt, solvate, stereoisomer, or rotamer thereof, wherein each $R^{12}$ is independently hydrogen, deuterium, halogen, $C_1$-$C_6$alkyl, $C_1$-$C_6$haloalkyl, $C_1$-$C_6$hydroxyalkyl, cycloalkyl, heterocycloalkyl, $C_1$-$C_6$alkylene(cycloalkyl), or $C_1$-$C_6$alkylene(heterocycloalkyl); wherein the alkyl, cycloalkyl, and heterocycloalkyl is optionally and independently substituted with one or more $R^{12a}$.

19. The compound of claim 1, or a pharmaceutically acceptable salt, solvate, stereoisomer, or rotamer thereof, wherein each $R^{12}$ is independently hydrogen, deuterium, halogen, $C_1$-$C_6$alkyl, $C_1$-$C_6$haloalkyl, $C_1$-$C_6$hydroxyalkyl, cycloalkyl, or heterocycloalkyl; wherein the alkyl, cycloalkyl, and heterocycloalkyl is optionally and independently substituted with one or more $R^{12a}$.

20. The compound claim 1, or a pharmaceutically acceptable salt, solvate, stereoisomer, or rotamer thereof, wherein p is 1 or 2.

21. The compound of claim 1 selected from the group consisting of:

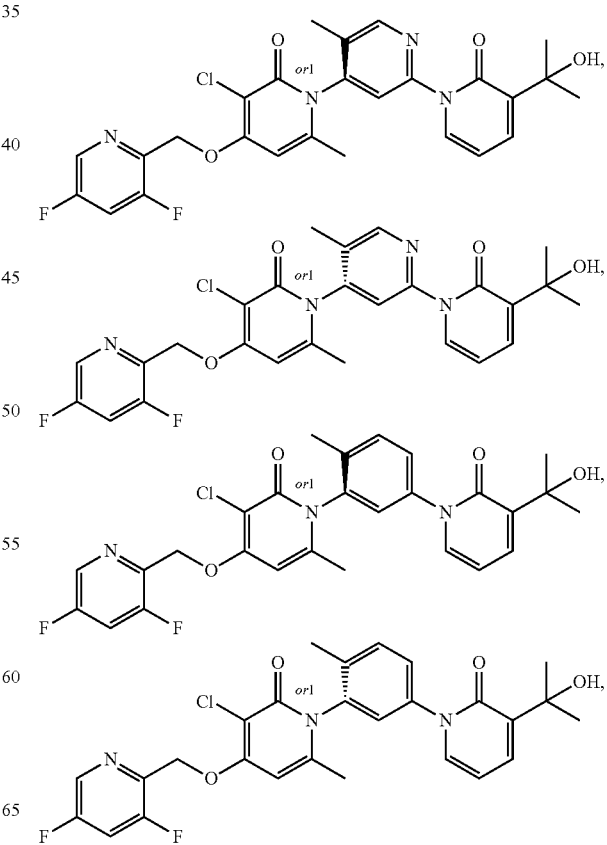

-continued
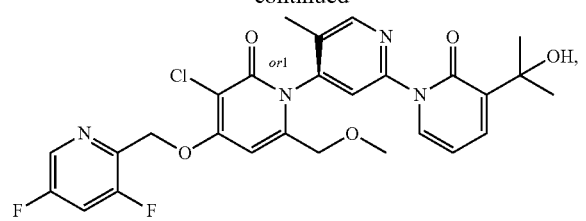
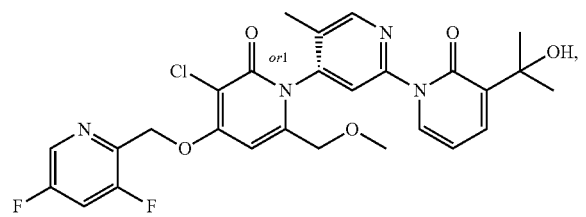
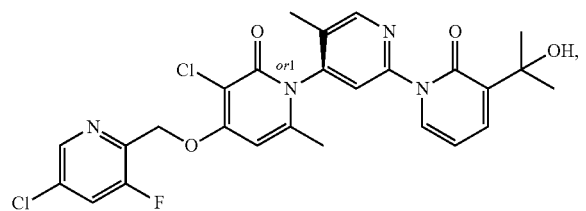
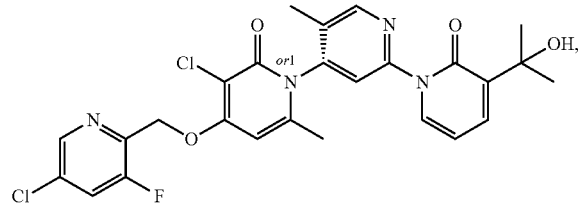
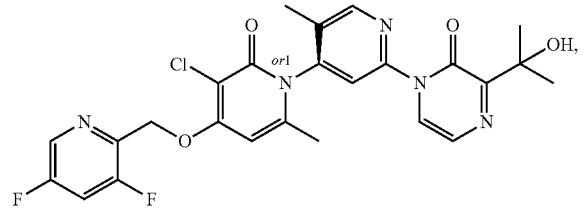
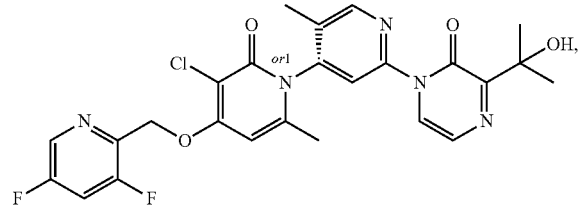
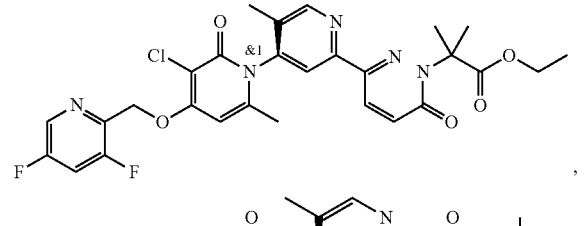
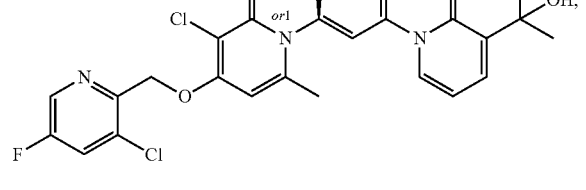
-continued
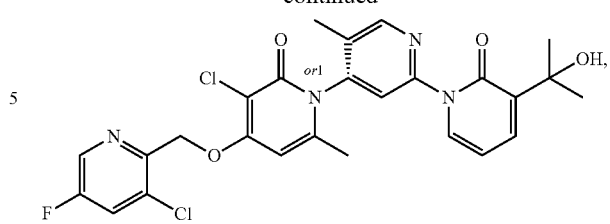
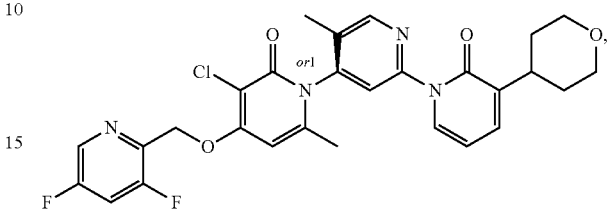
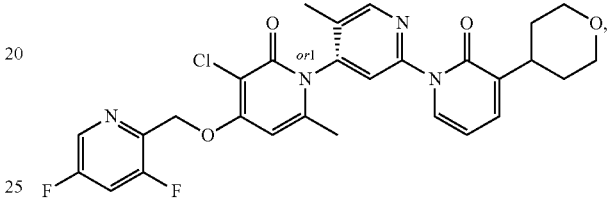
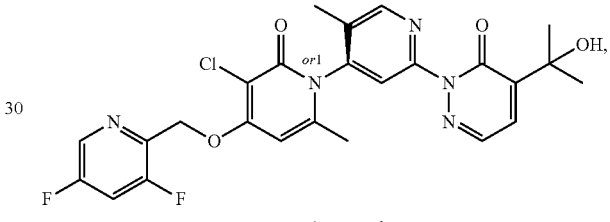
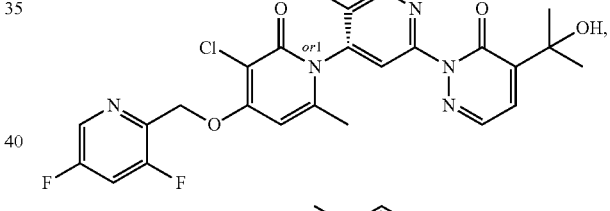
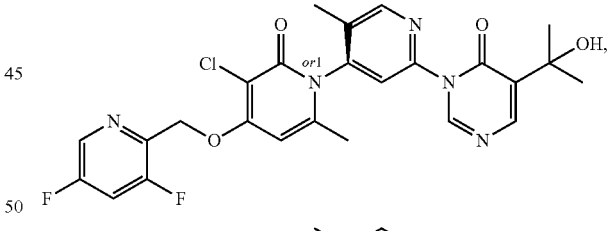
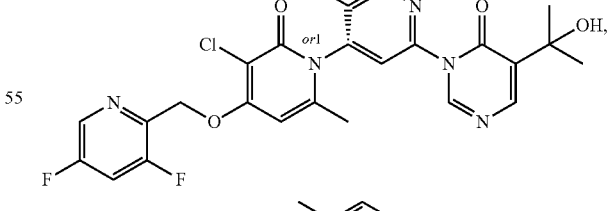
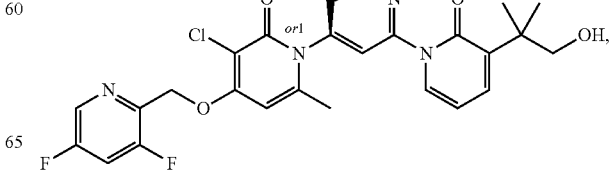

167
-continued
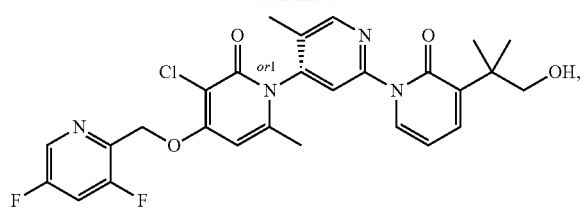
,
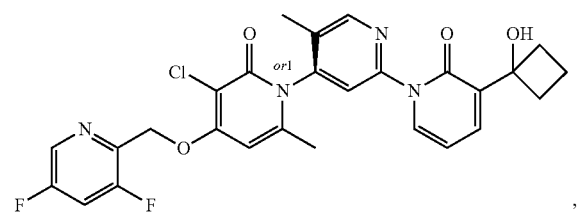
,
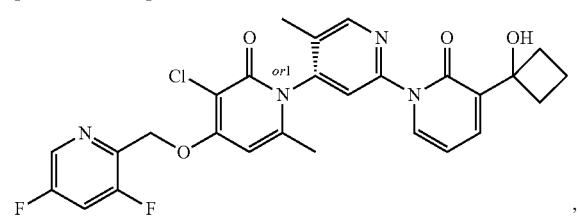
,
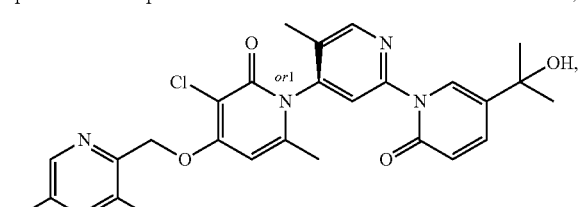
,
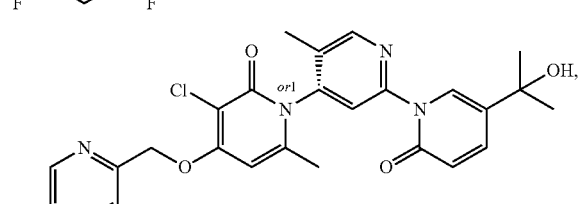
,
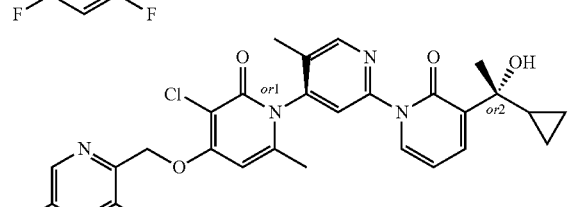
,
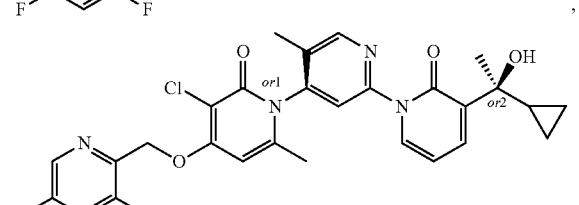
,
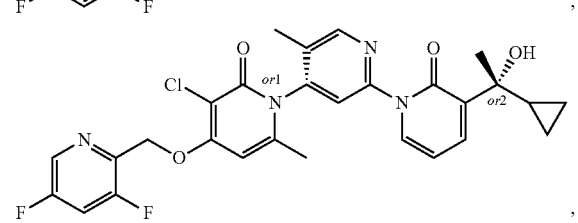
,
168
-continued
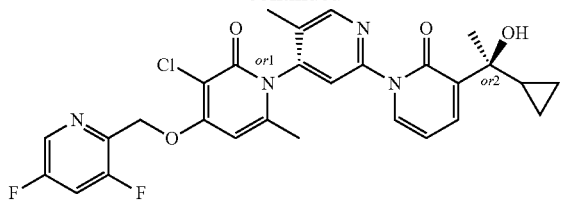
,
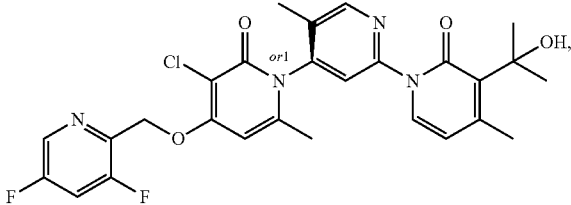
,
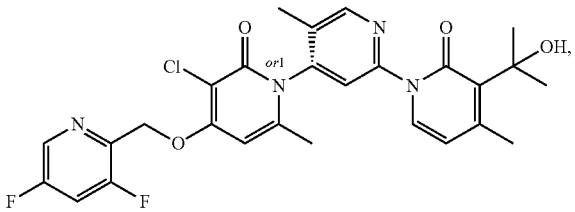
,
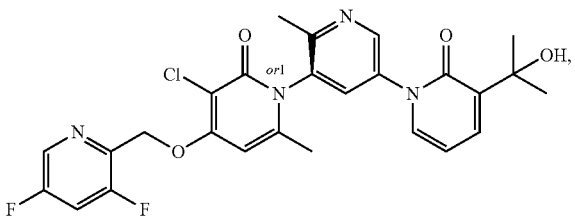
,
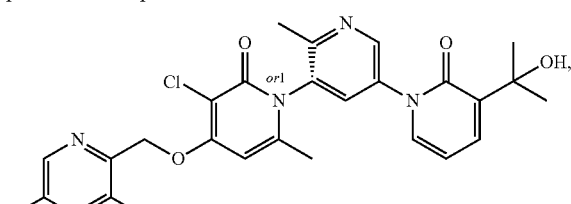
,
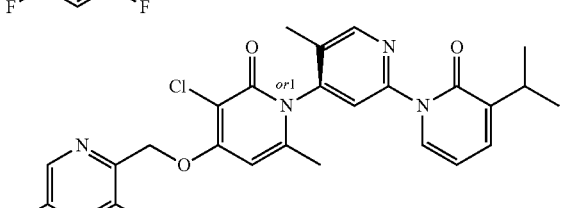
,
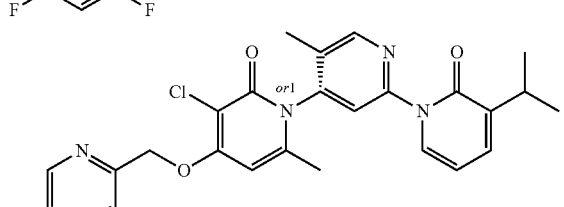
,
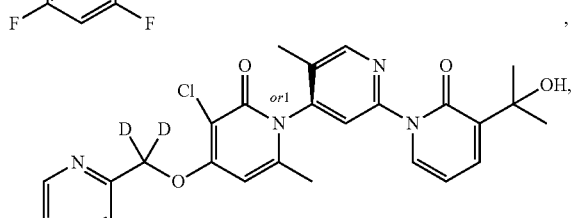

-continued
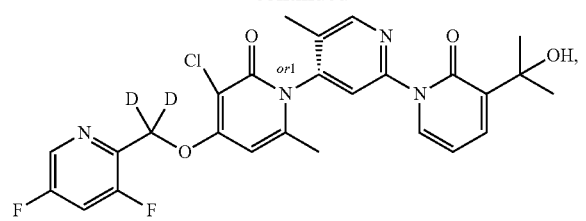
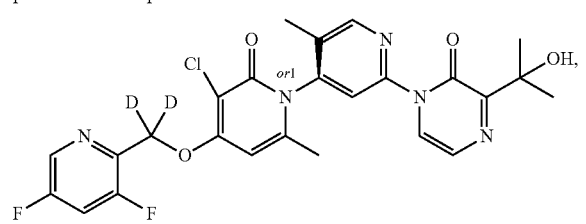
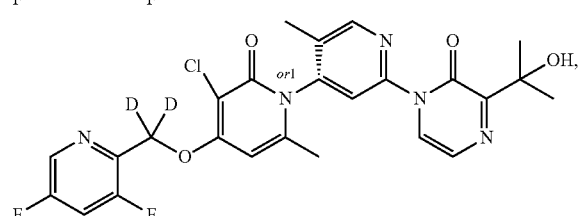
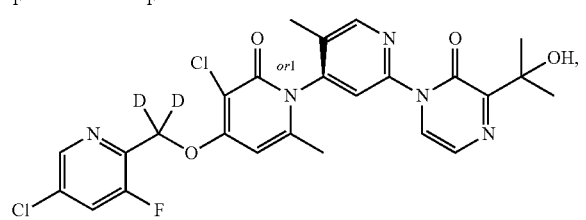
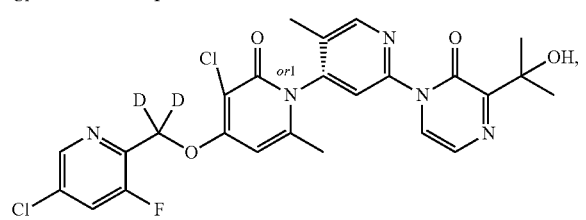
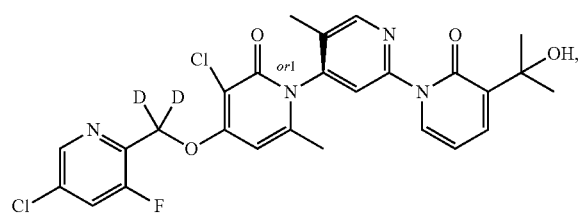
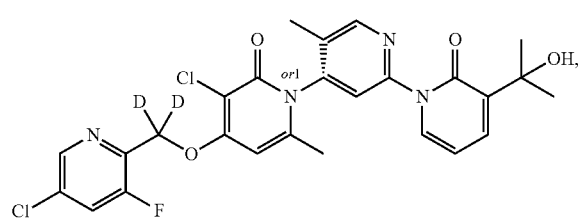
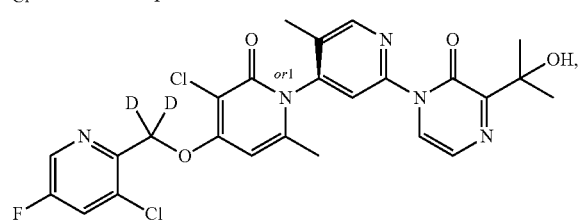
-continued
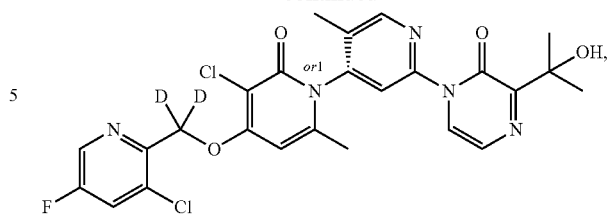
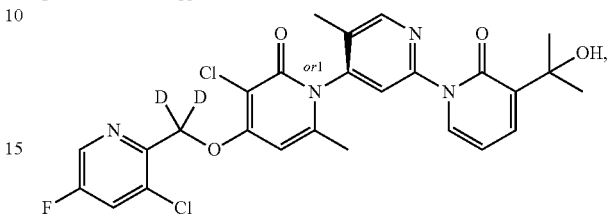
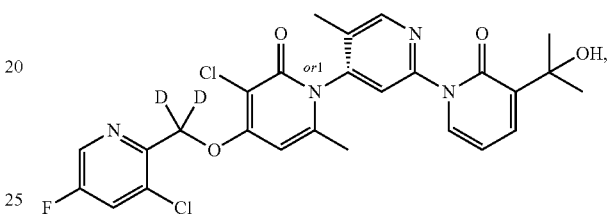
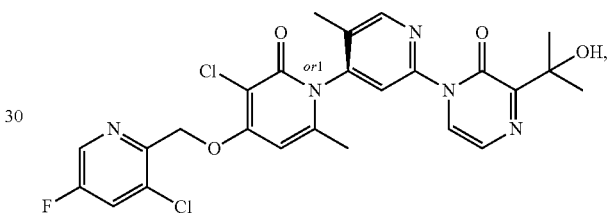
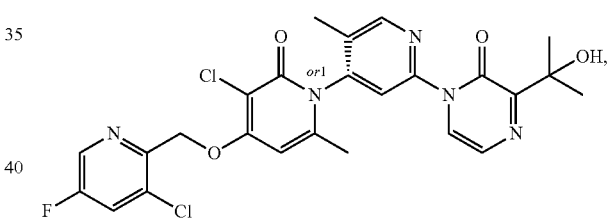
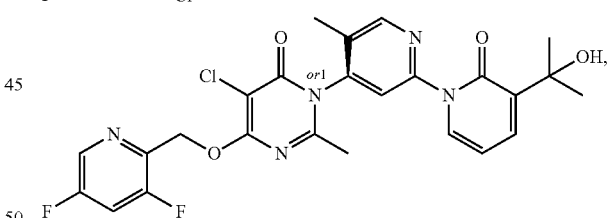
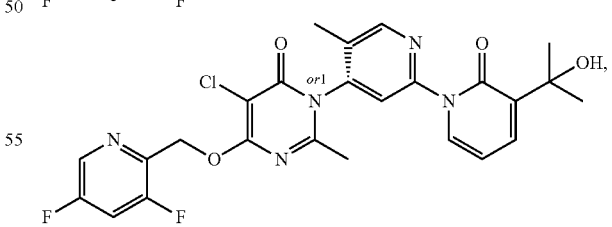
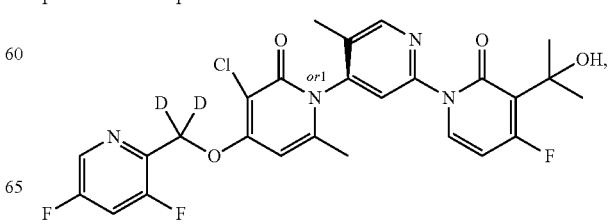

-continued

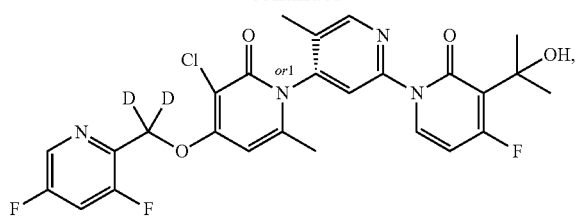

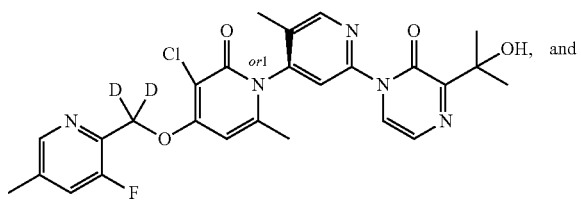

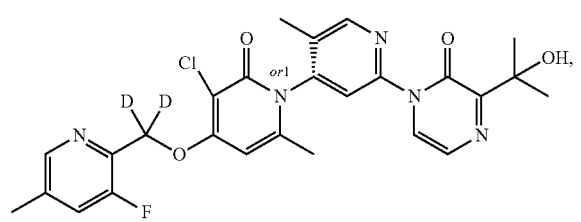

or a pharmaceutically acceptable salt, solvate, stereoisomer, or rotamer thereof; wherein the "or1" or "or2" labels denote pure substances but the absolute configuration of the stereochemical centers are unknown and the "&1" label denotes both isomers are present at the depicted stereochemical center.

22. The compound of claim 1 that is:

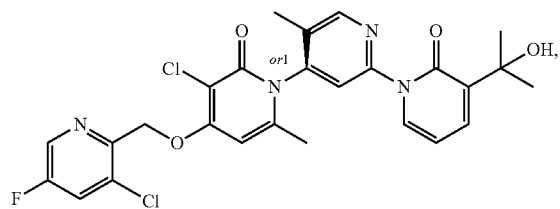

or a pharmaceutically acceptable salt, solvate, stereoisomer, or rotamer thereof, wherein the "or1" label denotes a pure substance but the absolute configuration of the stereochemical center is unknown.

23. The compound of claim 1 that is:

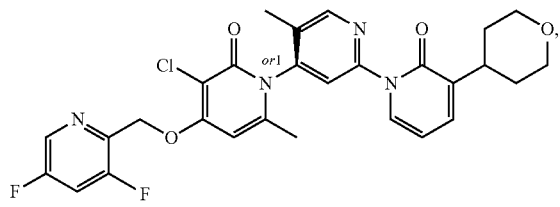

or a pharmaceutically acceptable salt, solvate, stereoisomer, or rotamer thereof, wherein the "or1" label denotes a pure substance but the absolute configuration of the stereochemical center is unknown.

24. The compound of claim 1 that is:

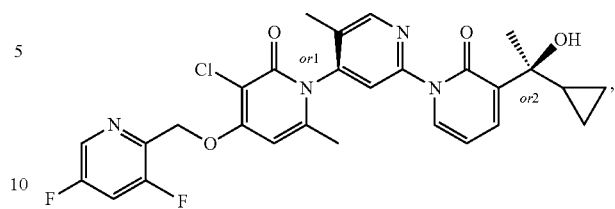

or a pharmaceutically acceptable salt, solvate, stereoisomer, or rotamer thereof, wherein the "or1" and "or2" label denote a pure substance but the absolute configuration of the stereochemical center is unknown.

25. The compound of claim 1 that is:

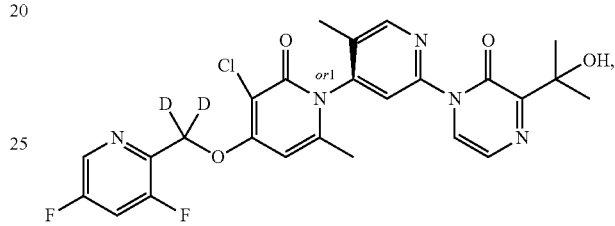

or a pharmaceutically acceptable salt, solvate, stereoisomer, or rotamer thereof, wherein the "or1" label denotes a pure substance but the absolute configuration of the stereochemical center is unknown.

26. The compound of claim 1 that is:

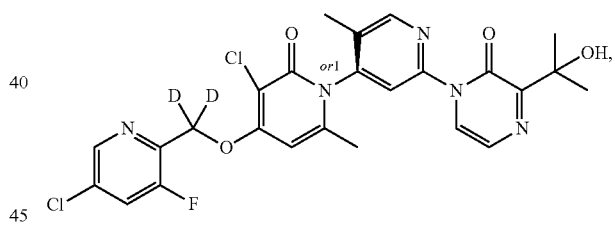

or a pharmaceutically acceptable salt, solvate, stereoisomer, or rotamer thereof, wherein the "or1" label denotes a pure substance but the absolute configuration of the stereochemical center is unknown.

27. The compound of claim 1 that is:

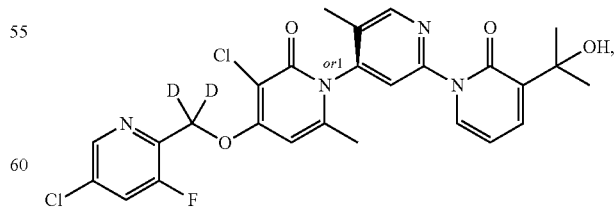

or a pharmaceutically acceptable salt, solvate, stereoisomer, or rotamer thereof, wherein the "or1" label denotes a pure substance but the absolute configuration of the stereochemical center is unknown.

28. The compound of claim 1 that is:

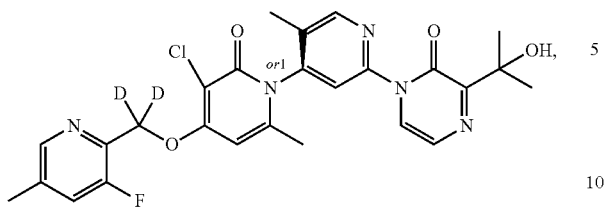

or a pharmaceutically acceptable salt, solvate, stereoisomer, or rotamer thereof, wherein the "or1" label denotes a pure substance but the absolute configuration of the stereochemical center is unknown.

29. A pharmaceutical composition comprising a therapeutically effective amount of a compound of claim 1, or a pharmaceutically acceptable salt, solvate, stereoisomer, or rotamer thereof, and a pharmaceutically acceptable excipient.

30. A method for treating a condition comprising administering to a subject in need thereof a therapeutically effective amount of a compound of claim 1, or a pharmaceutically acceptable salt, solvate, stereoisomer, or rotamer thereof, wherein the condition is selected from the group consisting of an autoimmune disorder, a chronic inflammatory disorder, an acute inflammatory disorder, an auto-inflammatory disorder, a fibrotic disorder, a metabolic disorder, a neoplastic disorder, and a cardiovascular or a cerebrovascular disorder.

\* \* \* \* \*